United States Patent
Reddy et al.

(10) Patent No.: US 12,145,939 B2
(45) Date of Patent: Nov. 19, 2024

(54) SUBSTITUTED [1,2,4]TRIAZOLO[4,3-A]PYRAZINES AS ION CHANNEL MODULATORS

(71) Applicant: PRAXIS PRECISION MEDICINES, INC., Boston, MA (US)

(72) Inventors: Kiran Reddy, Boston, MA (US); Gabriel Martinez Botella, Wayland, MA (US); Andrew Mark Griffin, Montreal (CA); Brian Edward Marron, Ada, MI (US); Carlos Loya, Cambridge, MA (US)

(73) Assignee: Praxis Precision Medicines, Inc., Boston, MA (US)

( * ) Notice: Subject to any disclaimer, the term of this patent is extended or adjusted under 35 U.S.C. 154(b) by 0 days.

(21) Appl. No.: 18/365,695

(22) Filed: Aug. 4, 2023

(65) Prior Publication Data

US 2024/0043433 A1 Feb. 8, 2024

Related U.S. Application Data

(62) Division of application No. 17/104,512, filed on Nov. 25, 2020, now Pat. No. 11,767,325.

(60) Provisional application No. 62/940,489, filed on Nov. 26, 2019, provisional application No. 62/940,502, filed on Nov. 26, 2019, provisional application No. 62/940,503, filed on Nov. 26, 2019.

(51) Int. Cl.
*A61K 31/4985* (2006.01)
*A61P 25/00* (2006.01)
*C07D 487/04* (2006.01)

(52) U.S. Cl.
CPC ............ *C07D 487/04* (2013.01); *A61P 25/00* (2018.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| | | | |
|---|---|---|---|
| 4,112,095 A | 9/1978 | Allen, Jr. et al. | |
| 4,230,705 A | 10/1980 | Allen, Jr. et al. | |
| 4,242,515 A | 12/1980 | Trust et al. | |
| 5,905,079 A | 5/1999 | Sargent et al. | |
| 6,589,952 B2 | 7/2003 | Bakthavatchalam et al. | |
| 7,863,279 B2 | 1/2011 | Even et al. | |
| 8,030,305 B2 | 10/2011 | Lu et al. | |
| 8,173,654 B2 | 5/2012 | Lu et al. | |
| 8,198,448 B2 | 6/2012 | Albrecht et al. | |
| 8,212,041 B2 | 7/2012 | Albrecht et al. | |
| 8,217,177 B2 | 7/2012 | Albrecht et al. | |
| 8,524,900 B2 | 9/2013 | Albrecht et al. | |
| 8,937,060 B2 | 1/2015 | Cid-Nunez et al. | |
| 8,952,034 B2 | 2/2015 | Corkey et al. | |
| 9,066,954 B2 | 6/2015 | Albrecht et al. | |
| 9,371,329 B2 | 6/2016 | Corkey et al. | |
| 10,280,184 B2 | 5/2019 | Friedman et al. | |
| 11,767,325 B2 | 9/2023 | Reddy et al. | |
| 2002/0049208 A1 | 4/2002 | Bakthavatchalam et al. | |
| 2009/0124609 A1 | 5/2009 | Albrecht et al. | |
| 2010/0088778 A1 | 4/2010 | Mulley et al. | |
| 2011/0021521 A1 | 1/2011 | Corkey et al. | |
| 2012/0010192 A1 | 1/2012 | Kobayashi et al. | |
| 2012/0065191 A1 | 3/2012 | Kiss et al. | |
| 2012/0245164 A1 | 9/2012 | Auger et al. | |
| 2013/0315895 A1 | 11/2013 | Farrell et al. | |
| 2014/0066443 A1 | 3/2014 | Beshore et al. | |
| 2014/0303158 A1 | 10/2014 | Corkey et al. | |
| 2015/0038503 A1 | 2/2015 | Bourotte et al. | |
| 2016/0159801 A1 | 6/2016 | Quinn et al. | |
| 2016/0235718 A1 | 8/2016 | Baraban | |
| 2016/0297799 A1 | 10/2016 | Brookings et al. | |
| 2016/0317536 A1 | 11/2016 | Reich et al. | |
| 2019/0389868 A1 | 12/2019 | Reddy et al. | |
| 2020/0179358 A1 | 6/2020 | Reddy et al. | |
| 2020/0247793 A1 | 8/2020 | Reddy et al. | |

(Continued)

FOREIGN PATENT DOCUMENTS

| | | |
|---|---|---|
| JP | 2017-1991 A | 1/2017 |
| WO | WO-2006/061428 A2 | 6/2006 |

(Continued)

OTHER PUBLICATIONS

US 8,754,103 B2, 06/2014, Corkey et al. (withdrawn)

(Continued)

*Primary Examiner* — Douglas M Willis
(74) *Attorney, Agent, or Firm* — McCarter & English, LLP; Jonathan M. Sparks; Yelena Margolin

(57) ABSTRACT

The present invention is directed to, in part, fused heteroaryl compounds of Formula (III-II):

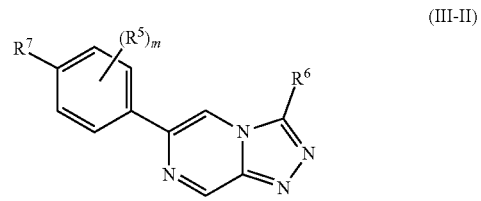

and compositions thereof, useful for preventing and/or treating a disease or condition relating to aberrant function of a voltage-gated, sodium ion channel, for example, abnormal late/persistent sodium current. Methods of treating a disease or condition relating to aberrant function of a sodium ion channel including neurological disorders (e.g., Dravet syndrome, epilepsy), pain, and neuromuscular disorders are also provided herein.

19 Claims, No Drawings

(56) References Cited

U.S. PATENT DOCUMENTS

| | | |
|---|---|---|
| 2020/0377499 A1 | 12/2020 | Griffin et al. |
| 2020/0377506 A1 | 12/2020 | Reddy et al. |
| 2020/0377507 A1 | 12/2020 | Griffin et al. |
| 2021/0171530 A1 | 6/2021 | Reddy et al. |

FOREIGN PATENT DOCUMENTS

| | | |
|---|---|---|
| WO | WO-2007/075567 A1 | 7/2007 |
| WO | WO-2008/008539 A2 | 1/2008 |
| WO | WO-2010/053757 A1 | 5/2010 |
| WO | WO-2010/056865 A1 | 5/2010 |
| WO | WO-2010/074807 A1 | 7/2010 |
| WO | WO-2011/014462 A1 | 2/2011 |
| WO | WO-2011/056985 A2 | 5/2011 |
| WO | WO-2012/003392 A1 | 1/2012 |
| WO | WO-2012/065546 A1 | 5/2012 |
| WO | WO-2012/154760 A1 | 11/2012 |
| WO | WO-2013/006463 A1 | 1/2013 |
| WO | WO-2013/043925 A1 | 3/2013 |
| WO | WO-2014/179492 A1 | 11/2014 |
| WO | WO-2015/095370 A1 | 6/2015 |
| WO | WO-2015/158283 A1 | 10/2015 |
| WO | WO-2015/194670 A1 | 12/2015 |
| WO | WO-2015/197567 A1 | 12/2015 |
| WO | WO-2018/098491 A1 | 5/2018 |
| WO | WO-2018/098499 A1 | 5/2018 |
| WO | WO-2018/098500 A1 | 5/2018 |
| WO | WO-2018/148745 A1 | 8/2018 |
| WO | WO-2018/187480 A1 | 10/2018 |
| WO | WO-2019/035951 A1 | 2/2019 |
| WO | WO-2019/232209 A1 | 12/2019 |
| WO | WO-2020/069322 A1 | 4/2020 |

OTHER PUBLICATIONS

Albright et al., Synthesis and anxiolytic activity of 6-(substituted-phenyl)-1,2,4-triazolo[4,3-b]pyridazines. J Med Chem. May 1981;24(5):592-600.

Anderson et al., Antiepileptic activity of preferential inhibitors of persistent sodium current. Epilepsia. Aug. 2014;55(8):1274-83.

Anderson et al., Unexpected Efficacy of a Novel Sodium Channel Modulator in Dravet Syndrome. Sci Rep. May 10, 2017;7(1):1682, 9 pages.

Baker et al., The novel sodium channel modulator GS-458967 (GS967) is an effective treatment in a mouse model of SCN8A encephalopathy. Epilepsia. Jun. 2018;59(6):1166-1176.

Barbieri et al., Late sodium current blocker GS967 inhibits persistent currents induced by familial hemiplegic migraine type 3 mutations of the SCN1A gene. J Headache Pain. Nov. 15, 2019;20(1):107, 13 pages.

Belardinelli et al., A novel, potent, and selective inhibitor of cardiac late sodium current suppresses experimental arrhythmias. J Pharmacol Exp Ther. Jan. 2013;344(1):23-32.

Guan et al., Synthesis and anticonvulsant activity of a new 6-alkoxy-[1,2,4]triazolo[4,3-b]pyridazine. Eur J Med Chem. May 2010;45(5):1746-52.

Hackam et al., Translation of research evidence from animals to humans. JAMA. Oct. 11, 2006;296(14):1731-2.

Jordan, Tamoxifen: a most unlikely pioneering medicine. Nat Rev Drug Discov. Mar. 2003;2(3):205-13.

Koltun et al., Discovery of triazolopyridinone GS-462808, a late sodium current inhibitor (Late INai) of the cardiac Nav1.5 channel with improved efficacy and potency relative to ranolazine. Bioorg Med Chem Lett. Jul. 1, 2016;26(13):3207-3211.

PubChem CID 58763997, 5-Phenylpyrazolo[1,5-A]pyridine. 14 pages, Aug. 19, 2012.

PubChem CID 597467, 5-Phenyl-2H-benzotriazole, 15 pages, May 12, 2018.

PubChem CID 82381512, Tuijeduithxzgl-Uhfffaoysa-N, 10 pages, Sep. 29, 2018.

PubChem CID 89077556, SCHEMBL13387345, 11 pages, Jan. 6, 2018.

STN Chemical Structure Search Results, 102 pages, May 18, 2016.
STN Chemical Structure Search Results, 107 pages, Nov. 1, 2017.
STN Chemical Structure Search Results, 123 pages, Nov. 6, 2017.
STN Chemical Structure Search Results, 22 pages, Jan. 15, 2020.
STN Chemical Structure Search Results, 23 pages, Jan. 2018.
STN Chemical Structure Search Results, 264 pages, Mar. 20, 2018.
STN Chemical Structure Search Results, 29 pages, Feb. 2018.
STN Chemical Structure Search Results, 36 pages, Apr. 14, 2019.
STN Chemical Structure Search Results, 45 pages, Apr. 23, 2019.
STN Chemical Structure Search Results, 480 pages, Mar. 6, 2017.
STN Chemical Structure Search Results, 511 pages, Mar. 6, 2017.
STN Chemical Structure Search Results, 55 pages, Apr. 2018.
STN Chemical Structure Search Results, 57 pages, Nov. 3, 2017.
STN Chemical Structure Search Results, 7 pages, Nov. 6, 2017.
STN Chemical Structure Search Results, 83 pages, Mar. 20, 2018.
STN Chemical Structure Search Results, 85 pages, Nov. 21, 2017.

Wengert et al., Prax330 reduces persistent and resurgent sodium channel currents and neuronal hyperexcitability of subiculum neurons in a mouse model of SCN8A epileptic encephalopathy. Neuropharmacology. Nov. 1, 2019;158:107699, 26 pages.

Zablocki et al., Discovery of Dihydrobenzoxazepinone (GS-6615) Late Sodium Current Inhibitor (Late INai), a Phase II Agent with Demonstrated Preclinical Anti-Ischemic and Antiarrhythmic Properties. J Med Chem. Oct. 13, 2016;59(19):9005-9017.

International Search Report and Written Opinion for Application No. PCT/US2017/063507, dated Mar. 29, 2019, 9 pages.

International Search Report and Written Opinion for Application No. PCT/US2017/063533, dated Mar. 29, 2019, 10 pages.

International Search Report and Written Opinion for Application No. PCT/US2017/063534, dated Mar. 29, 2019, 11 pages.

International Search Report and Written Opinion for Application No. PCT/US2018/000224, dated Nov. 5, 2018, 8 pages.

International Search Report and Written Opinion for Application No. PCT/US2018/018044, dated May 24, 2018, 10 pages.

International Search Report and Written Opinion for Application No. PCT/US2018/026099, dated Aug. 10, 2018, 9 pages.

International Search Report and Written Opinion for Application No. PCT/US2019/034653, dated Aug. 9, 2019, 9 pages.

International Search Report and Written Opinion for Application No. PCT/US2019/053467, dated Jan. 14, 2020, 9 pages.

U.S. Appl. No. 17/104,512, filed Nov. 25, 2020, U.S. Pat. No. 11,767,325, Issued.

SUBSTITUTED [1,2,4]TRIAZOLO[4,3-A]PYRAZINES AS ION CHANNEL MODULATORS

CROSS-REFERENCE TO RELATED APPLICATIONS

This application is a divisional application of U.S. patent application Ser. No. 17/104,512, filed on Nov. 25, 2020; which, in turn, claims the benefit of U.S. Provisional Patent Application No. 62/940,489, filed on Nov. 26, 2019, U.S. Provisional Patent Application No. 62/940,502, filed on Nov. 26, 2019, and U.S. Provisional Patent Application No. 62/940,503, filed on Nov. 26, 2019. The entire contents of each of the foregoing applications are hereby incorporated by reference.

BACKGROUND

Sodium ion (Na+) channels primarily open in a transient manner and are quickly inactivated, thereby generating a fast Na+ current to initiate the action potential. The late or persistent sodium current (INaL) is a sustained component of the fast Na+ current of cardiac myocytes and neurons. Many common neurological and cardiac conditions are associated with abnormal INaL enhancement, which contributes to the pathogenesis of both electrical and contractile dysfunction in mammals (see, e.g., *Pharmacol Ther* (2008) 119:326-339).

Accordingly, pharmaceutical compounds that selectively modulate sodium channel activity, e.g., abnormal INaL, are useful in treating such disease states.

SUMMARY

Described herein are fused heteroaryl compounds and compositions useful for preventing and/or treating a disease, disorder, or condition, e.g., a disease, disorder, or condition relating to aberrant function of a sodium ion channel, e.g., abnormal late/persistent sodium current (INaL).

Thus, in one aspect, provided herein is a compound having the Formula I-I:

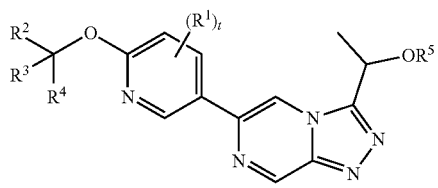
(I-I)

or a pharmaceutically acceptable salt thereof, wherein
$R^1$ is halo;
$R^2$ is $C_{1-4}$haloalkyl;
$R^3$ and $R^4$ are each independently selected from the group consisting of hydrogen, $C_{1-4}$alkyl, and $C_{3-6}$carbocyclyl; or $R^3$ and $R^4$ together with the carbon attached to $R^3$ and $R^4$ form a $C_{3-6}$carbocyclyl;
$R^5$ is $C_{1-4}$alkyl; and
t is 0 or 1.

In another aspect, provided herein is a compound having the Formula II-I:

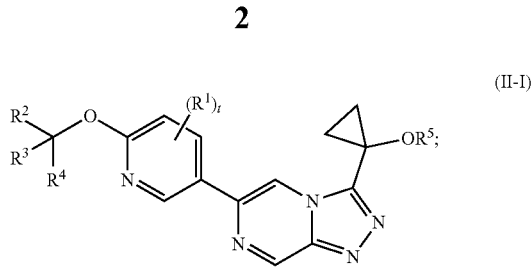
(II-I)

or a pharmaceutically acceptable salt thereof, wherein
$R^1$ is halo;
$R^2$ is $C_{1-4}$haloalkyl;
$R^3$ and $R^4$ are each independently hydrogen or $C_{1-4}$alkyl; or $R^3$ and $R^4$ together with the carbon attached to $R^3$ and $R^4$ form a $C_{3-6}$carbocyclyl;
$R^5$ is $C_{1-4}$alkyl; and
t is 0 or 1.

In another aspect, provided herein is a compound having the Formula II-II:

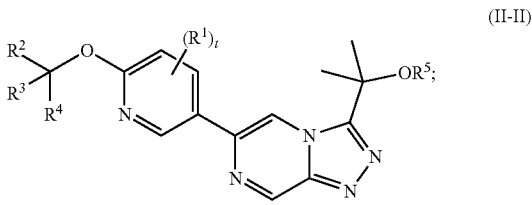
(II-II)

or a pharmaceutically acceptable salt thereof, wherein
$R^1$ is halo;
$R^2$ is $C_{1-4}$haloalkyl;
$R^3$ and $R^4$ are each independently hydrogen or $C_{1-4}$alkyl; or $R^3$ and $R^4$ together with the carbon attached to $R^3$ and $R^4$ form a $C_{3-6}$carbocyclyl;
$R^5$ is $C_{1-4}$alkyl; and
t is 0 or 1.

In another aspect, provided herein is a compound of Formula (III-I):

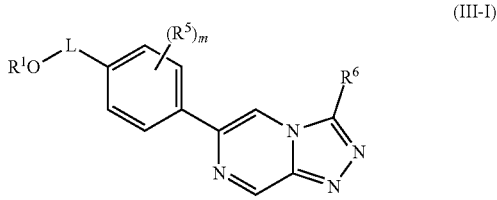
(III-I)

or a pharmaceutically acceptable salt thereof, wherein:
L is $C_{1-6}$alkyl;
$R^1$ is selected from the group consisting of

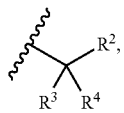

$CF_3$, monocyclic $C_{3-6}$ cycloalkyl, and 4- to 7-membered monocyclic heterocyclyl, wherein the cycloalkyl and heterocyclyl are optionally substituted with one or more $R^a$;

R² is selected from the group consisting of hydrogen, $C_{1-4}$haloalkyl, and monocyclic $C_{3-6}$ cycloalkyl optionally substituted with one or more $R^b$;

R³ is selected from the group consisting of hydrogen, $C_{1-4}$alkyl, and $C_{1-4}$haloalkyl;

R⁴ is hydrogen or $C_{1-4}$alkyl;

R⁵ is selected from the group consisting of halo, $C_{3-6}$ cycloalkyl, and $C_{1-4}$alkyl optionally substituted with O—$C_{1-4}$alkyl or O—$C_{3-6}$ cycloalkyl;

R⁶ is $C_{1-4}$alkyl or $C_{1-4}$haloalkyl, wherein the $C_{1-4}$alkyl or $C_{1-4}$haloalkyl is each substituted with $OR^c$;

m is 0, 1, or 2;

$R^a$ and $R^b$ are each independently selected from the group consisting of halo, $C_{1-4}$alkyl, $C_{1-4}$haloalkyl, $C_{1-4}$alkoxy, and $C_{1-4}$haloalkoxy; and $R^c$ is $C_{1-4}$alkyl optionally substituted with $C_{3-6}$ cycloalkyl or phenyl, or $C_{3-6}$ cycloalkyl.

In another aspect, provided herein is a compound of Formula (III-II):

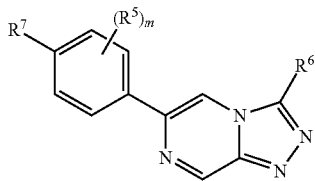

(III-II)

or a pharmaceutically acceptable salt thereof, wherein:

R⁷ is a monocyclic $C_{3-6}$ cycloalkyl substituted with one or more $R^a$;

R⁵ is selected from the group consisting of halo, $C_{3-6}$ cycloalkyl, and $C_{1-4}$alkyl optionally substituted with O—$C_{1-4}$alkyl or O—$C_{3-6}$ cycloalkyl;

R⁶ is $C_{1-4}$alkyl or $C_{1-4}$haloalkyl, wherein the $C_{1-4}$alkyl or $C_{1-4}$haloalkyl is each substituted with $OR^c$;

m is 0, 1, or 2;

$R^a$ is selected from the group consisting of halo, $C_{1-4}$alkyl, $C_{1-4}$haloalkyl, $C_{1-4}$alkoxy, and $C_{1-4}$haloalkoxy; and $R^c$ is $C_{1-4}$alkyl optionally substituted with $C_{3-6}$ cycloalkyl or phenyl, or $C_{3-6}$ cycloalkyl.

In another aspect, provided herein is a pharmaceutical composition comprising a compound described herein (e.g., a compound of Formula I-I, II-I, II-II, III-I, III-II), or a pharmaceutically acceptable salt thereof; and a pharmaceutically acceptable carrier.

In one aspect, provided herein is a method of treating a condition relating to aberrant function of a sodium ion channel in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein. In some embodiments, the condition is a neurological or psychiatric disorder. In some embodiments, the condition is epilepsy or an epilepsy syndrome. In some embodiments, the condition is a genetic epilepsy or a genetic epilepsy syndrome. In some embodiments, the condition is a pediatric epilepsy or a pediatric epilepsy syndrome. In some embodiments, the condition is epileptic encephalopathy.

In some embodiments, the epileptic encephalopathy is selected from the group consisting of Dravet syndrome, infantile spasms, or Lennox-Gastaut syndrome. In some embodiments, the condition is selected from the group consisting of epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

In another aspect, provided herein is a method of treating a neurological disorder or a psychiatric disorder, wherein the method comprises administering to a subject in need thereof a compound described herein (e.g., a compound of Formula I-I, II-I, II-II, III-I, III-II), or a pharmaceutically acceptable salt thereof, or a pharmaceutical composition described herein.

Also provided herein is a method of treating a pain, wherein the method comprises administering to a subject in need thereof a compound described herein (e.g., a compound of Formula I-I, II-I, II-II, III-I, III-II), or a pharmaceutically acceptable salt thereof, or a pharmaceutical composition described herein.

In another aspect, methods of preventing or treating trigeminal autonomic cephalalgia (e.g., paroxysmal hemicrania, hemicrania continua, short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania) are provided. Also provided herein are methods of preventing or treating a cranial neuropathy (e.g., bell palsy, microvascular cranial nerve palsy, third nerve palsy, fourth nerve palsy, and sixth nerve palsy) or multiple cranial neuropathies (MCN). In certain embodiments, methods of preventing or treating a migraine (e.g., migraine without aura, migraine with aura, familial hemiplegic migraine type 1 (FHM1), familial hemiplegic migraine type 2 (FHM2), familial hemiplegic migraine type 4 (FHM4), and sporadic hemiplegic migraine (SHM)) are provided. In some other embodiments, provided herein are methods of preventing or treating cortical spreading depression (CDC).

In one aspect, the present disclosure provides a method of treating or preventing trigeminal autonomic cephalalgia (TAC) in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein, wherein the TAC is selected from the group consisting of paroxysmal hemicrania, hemicrania continua, short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania.

In another aspect, provided herein is a method of treating or preventing a migraine in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein, wherein the migraine is selected from the group consisting of migraine without aura, migraine with aura, familial hemiplegic migraine type 1 (FHM1), familial hemiplegic migraine type 2 (FHM2), familial hemiplegic migraine type 4 (FHM4), and sporadic hemiplegic migraine (SHM).

In another aspect, the present disclosure provides a method of treating or preventing cortical spreading depression (CSD) in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein.

In another aspect, the present disclosure provides a method of treating or preventing a cranial neuropathy or multiple cranial neuropathies (MCN) in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein.

Other objects and advantages will become apparent to those skilled in the art from consideration of the ensuing Detailed Description, Examples, and Claims.

DETAILED DESCRIPTION

As generally described herein, the present invention provides compounds and compositions useful for preventing and/or treating a disease, disorder, or condition described herein, e.g., a disease, disorder, or condition relating to aberrant function of a sodium ion channel, such as abnormal late sodium current (INaL). Exemplary diseases, disorders, or conditions include a neurological disorder (e.g., epilepsy or an epilepsy syndrome, a neurodevelopmental disorder or a neuromuscular disorder), a psychiatric disorder, pain, or a gastrointestinal disorder.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkylene" refers to a divalent radical of an alkyl group. When a range or number of carbons is provided for a particular "alkylene" group, it is understood that the range or number refers to the range or number of carbons in the linear carbon divalent chain. "Alkylene" groups may be substituted or unsubstituted with one or more substituents as described herein.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes.

As used herein, "$C_{3-6}$ monocyclic cycloalkyl" or "monocyclic $C_{3-6}$ cycloalkyl" refers to a 3- to 7-membered monocyclic hydrocarbon ring system that is saturated. 3- to 7-membered monocyclic cycloalkyl groups include, without limitation, cyclopropyl, cyclobutyl, cyclopentyl, and cyclohexyl. Where specified as being optionally substituted or substituted, substituents on a cycloalkyl (e.g., in the case of an optionally substituted cycloalkyl) may be present on any substitutable position and, include, e.g., the position at which the cycloalkyl group is attached.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms "heterocycle," "heterocyclyl," "heterocyclyl ring," "heterocyclic group," "heterocyclic moiety," and "heterocyclic radical," may be used interchangeably.

In some embodiments, a heterocyclyl group is a 4-7 membered non-aromatic ring system having ring carbon atoms and 1-4 ring heteroatoms, wherein each heteroatom is independently selected from nitrogen, oxygen, and sulfur ("4-7 membered heterocyclyl"). In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Examples of saturated or partially unsaturated heterocyclic radicals include, without limitation, tetrahydrofuranyl, tetrahydrothienyl, tetrahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. Where specified as being optionally substituted or substituted, substituents on a heterocyclyl (e.g., in the case of an optionally substituted heterocyclyl) may be present on any substitutable position and, include, e.g., the position at which the heterocyclyl group is attached.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g., heteroaryl; and the like having from 1 to 5, and particularly from 1 to 3 heteroatoms.

The terms "halo" and "halogen" as used herein refer to an atom selected from fluorine (fluoro, —F), chlorine (chloro, —Cl), bromine (bromo, —Br), and iodine (iodo, —I). In certain embodiments, the halo group is either fluoro or chloro.

The term "haloalkyl" includes mono, poly, and perhaloalkyl groups substituted with one or more halogen atoms where the halogens are independently selected from fluorine, chlorine, bromine, and iodine.

The term "alkoxy," as used herein, refers to an alkyl group which is attached to another moiety via an oxygen atom (—O(alkyl)). Non-limiting examples include e.g., methoxy, ethoxy, propoxy, and butoxy.

"Haloalkoxy" is a haloalkyl group which is attached to another moiety via an oxygen atom such as, e.g., but are not limited to —OCHCF$_2$ or —OCF$_3$.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Compounds

In one aspect, provided herein is a compound having the Formula I-I:

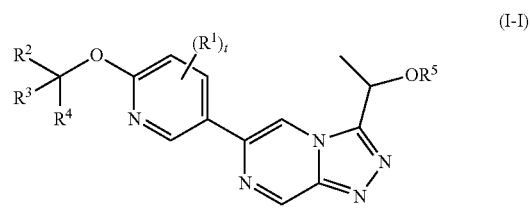

(I-I)

or a pharmaceutically acceptable salt thereof, wherein $R^1$ is halo;

$R^2$ is $C_{1-4}$haloalkyl;

$R^3$ and $R^4$ are each independently selected from the group consisting of hydrogen, $C_{1-4}$alkyl, and $C_{3-6}$carbocyclyl; or $R^3$ and $R^4$ together with the carbon attached to $R^3$ and $R^4$ form a $C_{3-6}$carbocyclyl;

$R^5$ is $C_{1-4}$alkyl; and t is 0 or 1.

In some embodiments, the compound is a compound of Formula I-I-a:

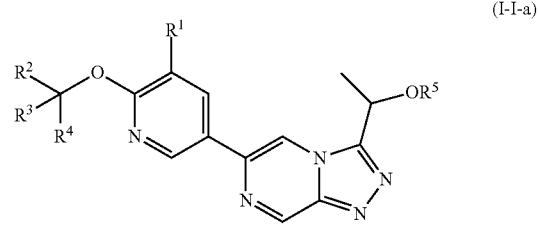

(I-I-a)

or a pharmaceutically acceptable salt thereof.

In some embodiments, the compound is a compound of Formula I-I-a1 or Formula I-I-a2:

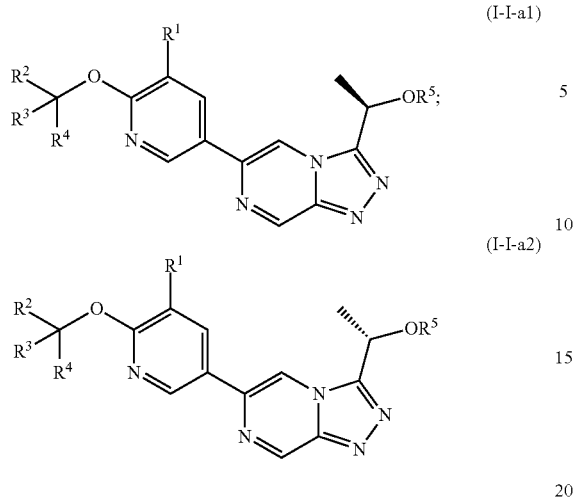

or a pharmaceutically acceptable salt thereof.

In some embodiments, the compound is a compound of Formula I-I-b:

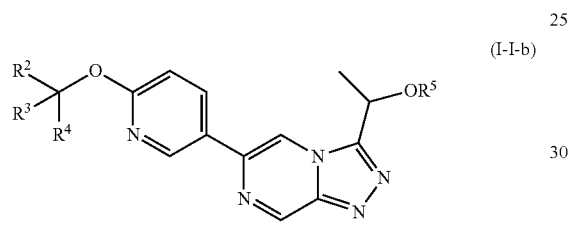

or a pharmaceutically acceptable salt thereof.

In some embodiments, the compound is a compound of Formula I-I-b1 or Formula I-I-b2:

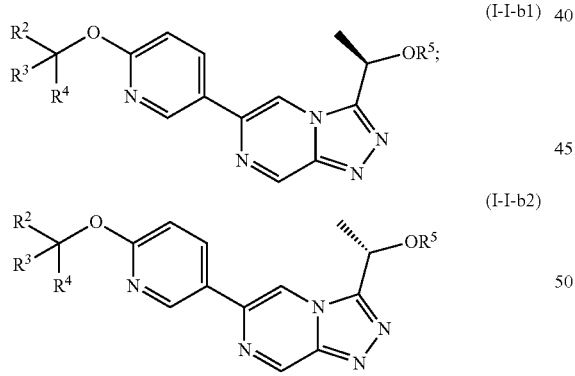

or a pharmaceutically acceptable salt thereof.

In some embodiments, $R^1$ is fluoro. In some embodiments, $R^2$ is $CF_3$. In some embodiments, $R^3$ and $R^4$ are each $C_{1-4}$alkyl. In some embodiments, $R^3$ and $R^4$ are each methyl. In some embodiments, $R^3$ is hydrogen and $R^4$ is $C_{3-6}$carbocyclyl. In some embodiments, $R^3$ is hydrogen and $R^4$ is cyclopropyl. In some embodiments, $R^3$ and $R^4$ together with the carbon attached to $R^3$ and $R^4$ form cyclobutyl. In some embodiments, $R^5$ is methyl or ethyl. In some embodiments, t is 1. In some embodiments, t is 0.

In some embodiments, the compound of Formula I-I is selected from the group consisting of:

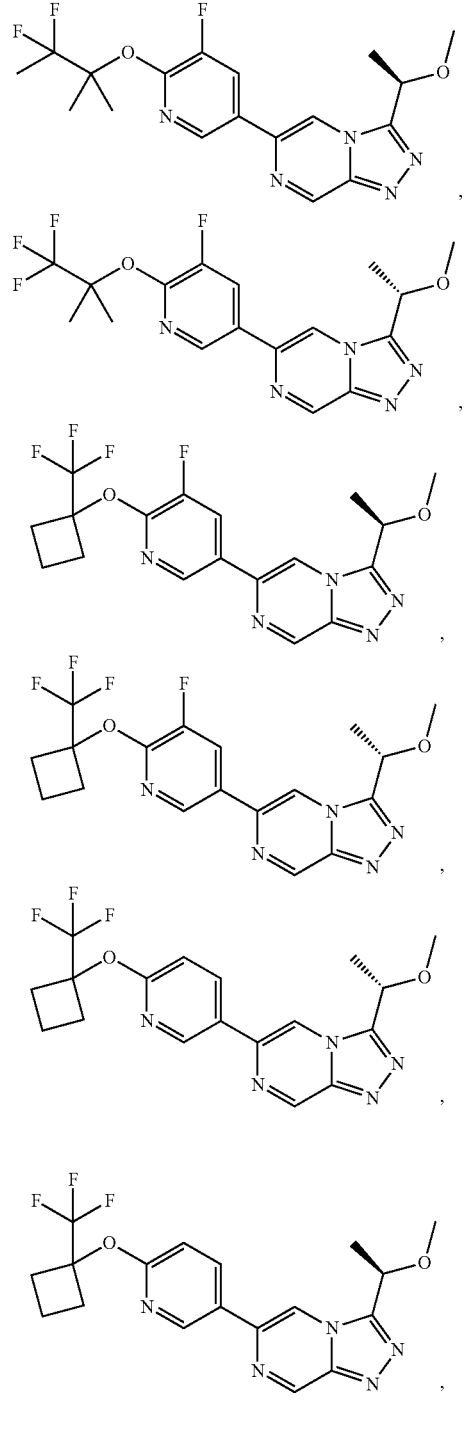

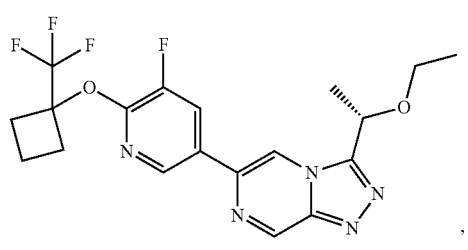

-continued
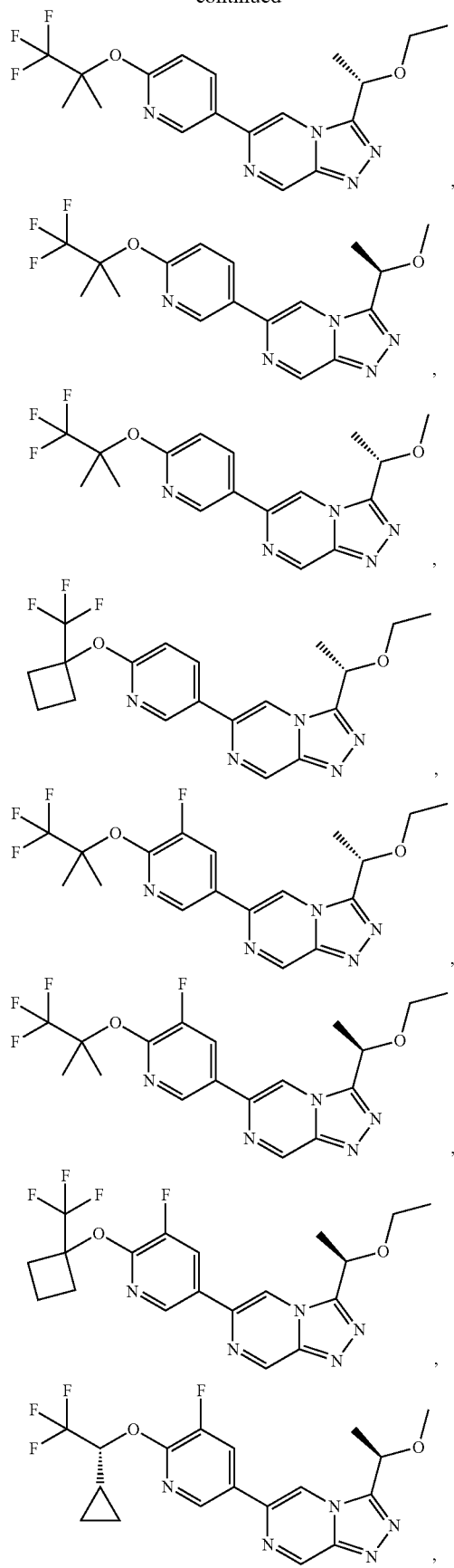
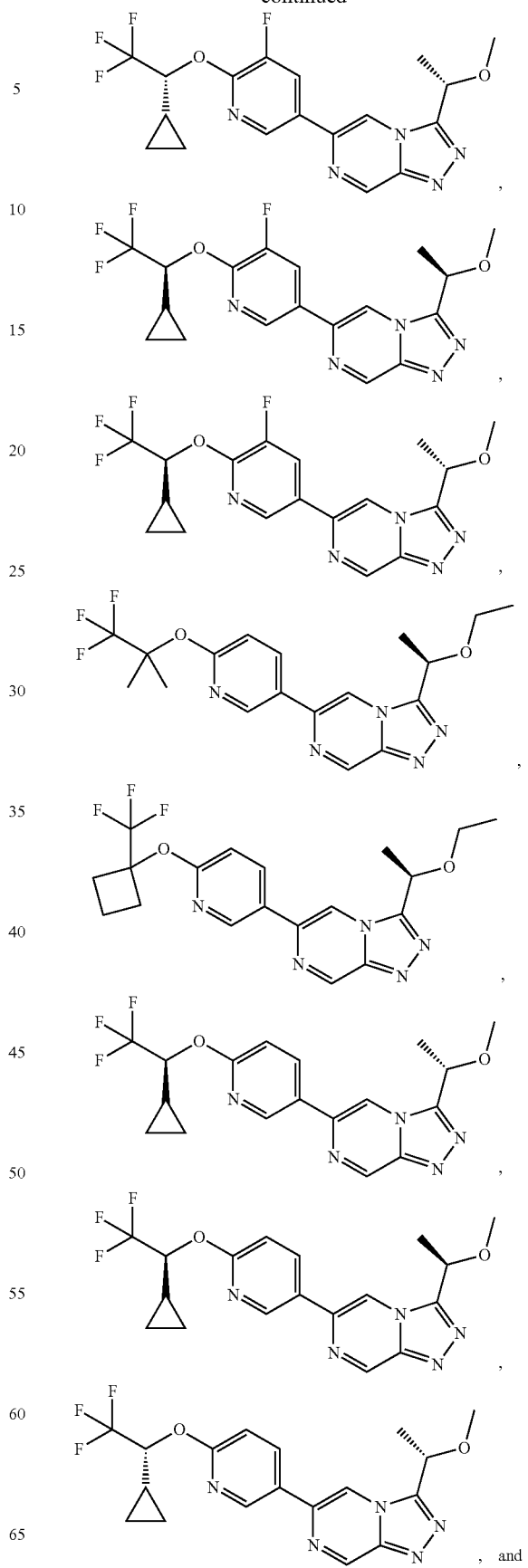
, and

17

-continued

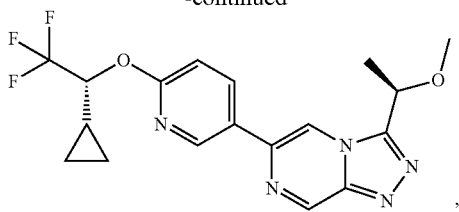

or a pharmaceutically acceptable salt thereof.

In another aspect, provided herein is a compound having the Formula II-I:

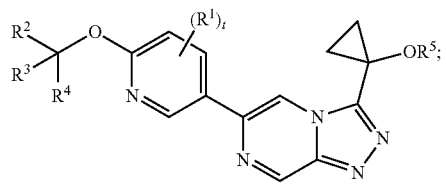
(II-I)

or a pharmaceutically acceptable salt thereof, wherein
$R^1$ is halo;
$R^2$ is $C_{1-4}$haloalkyl;
$R^3$ and $R^4$ are each independently hydrogen or $C_{1-4}$alkyl; or $R^3$ and $R^4$ together with the carbon attached to $R^3$ and $R^4$ form a $C_{3-6}$carbocyclyl;
$R^5$ is $C_{1-4}$alkyl; and
t is 0 or 1.

In some embodiments, the compound is a compound of Formula II-I-a:

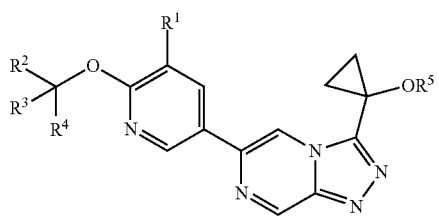
(II-I-a)

or a pharmaceutically acceptable salt thereof.

In some embodiments, $R^1$ is fluoro. In some embodiments, $R^2$ is $CF_3$. In some embodiments, $R^3$ and $R^4$ are each hydrogen. In some embodiments, $R^3$ is hydrogen and $R^4$ is methyl. In some embodiments, $R^5$ is methyl. In some embodiments, t is 1.

In some embodiments, the compound of Formula II-I is selected from the group consisting of:

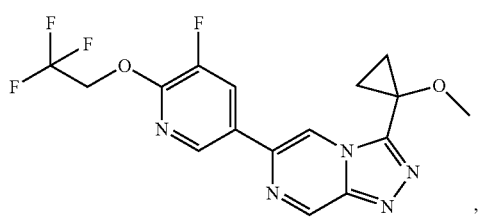

18

-continued

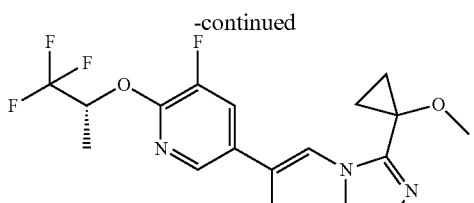

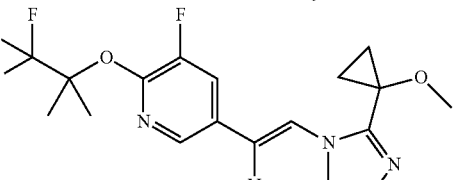
, and

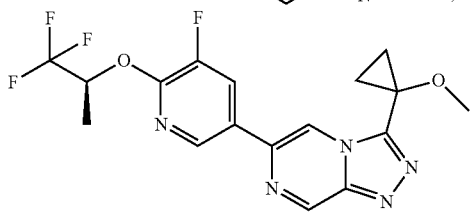
, or a pharmaceutically acceptable salt thereof.

In another aspect, provided herein is a compound having the Formula II-II:

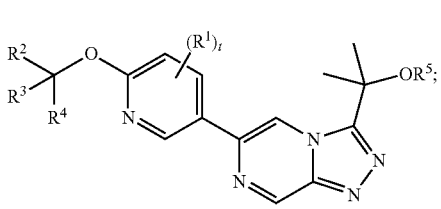
(II-II)

or a pharmaceutically acceptable salt thereof, wherein
$R^1$ is halo;
$R^2$ is $C_{1-4}$haloalkyl;
$R^3$ and $R^4$ are each independently hydrogen or $C_{1-4}$alkyl; or $R^3$ and $R^4$ together with the carbon attached to $R^3$ and $R^4$ form a $C_{3-6}$carbocyclyl;
$R^5$ is $C_{1-4}$alkyl; and
t is 0 or 1.

In some embodiments, the compound is a compound of Formula II-II-a:

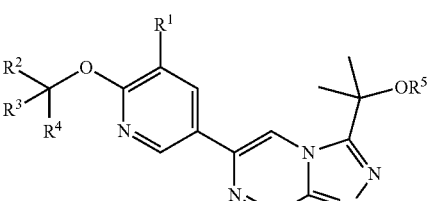
(II-II-a)

or a pharmaceutically acceptable salt thereof.

In some embodiments, the compound is a compound of Formula II-II-b:

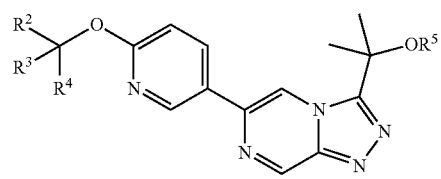

(II-II-b)

or a pharmaceutically acceptable salt thereof.

In some embodiments, $R^1$ is fluoro. In some embodiments, $R^2$ is $CF_3$. In some embodiments, $R^3$ and $R^4$ are each hydrogen. In some embodiments, $R^3$ is hydrogen and $R^4$ is methyl. In some embodiments, $R^3$ and $R^4$ are each methyl. In some embodiments, $R^3$ and $R^4$ together with the carbon attached to $R^3$ and $R^4$ form cyclobutyl. In some embodiments, $R^5$ is methyl or ethyl. In some embodiments, t is 1. In some embodiments, t is 0.

In some embodiments, the compound of Formula II-II is selected from the group consisting of:

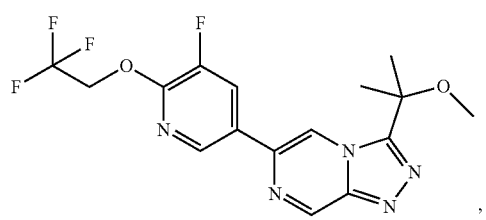

,

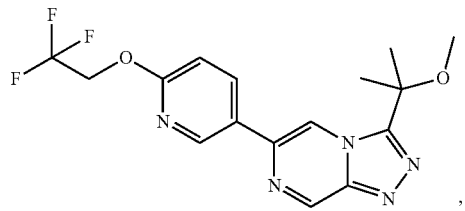

,

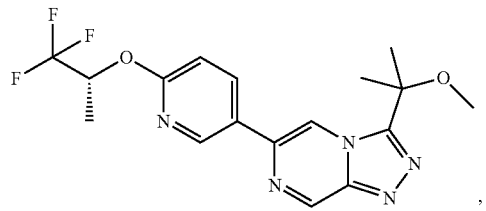

,

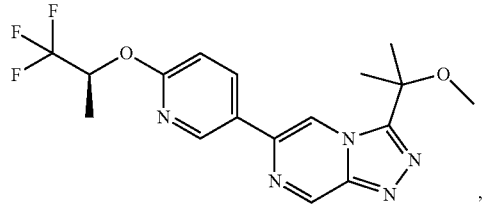

,

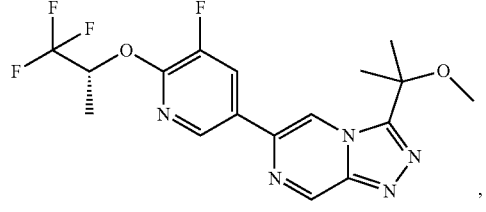

,

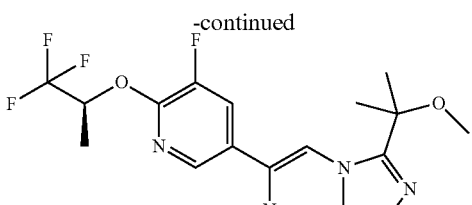

,

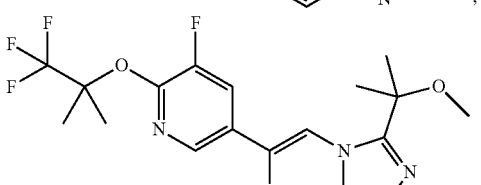

,

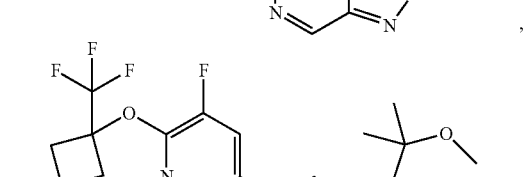

,

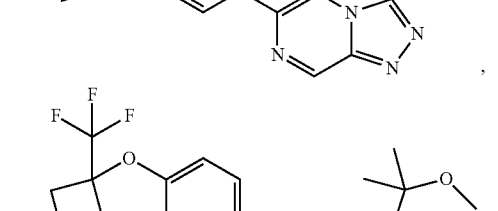

,

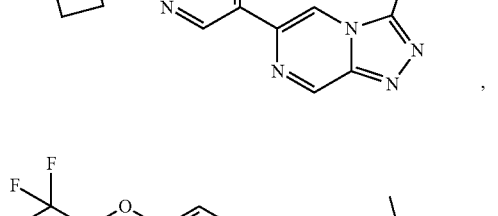

,

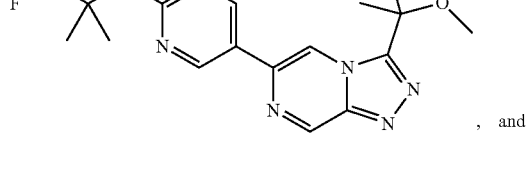

, and

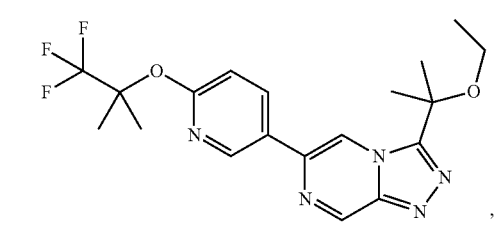

, or a pharmaceutically acceptable salt thereof.

In another aspect, provided herein is a compound of Formula (III-I):

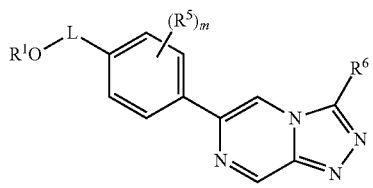

or a pharmaceutically acceptable salt thereof, wherein:
L is $C_{1-6}$alkyl;
$R^1$ is selected from the group consisting of

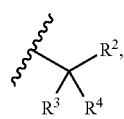

$CF_3$, monocyclic $C_{3-6}$ cycloalkyl, and 4- to 7-membered monocyclic heterocyclyl, wherein the cycloalkyl and heterocyclyl are optionally substituted with one or more $R^a$;
$R^2$ is selected from the group consisting of hydrogen, $C_{1-4}$haloalkyl, and monocyclic $C_{3-6}$ cycloalkyl optionally substituted with one or more $R^b$;
$R^3$ is selected from the group consisting of hydrogen, $C_{1-4}$alkyl, and $C_{1-4}$haloalkyl;
$R^4$ is hydrogen or $C_{1-4}$alkyl;
$R^5$ is selected from the group consisting of halo, $C_{3-6}$ cycloalkyl, and $C_{1-4}$alkyl optionally substituted with O—$C_{1-4}$alkyl or O—$C_{3-6}$ cycloalkyl;
$R^6$ is $C_{1-4}$alkyl or $C_{1-4}$haloalkyl, wherein the $C_{1-4}$alkyl or $C_{1-4}$haloalkyl is each substituted with $OR^c$;
m is 0, 1, or 2;
$R^a$ and $R^b$ are each independently selected from the group consisting of halo, $C_{1-4}$alkyl, $C_{1-4}$haloalkyl, $C_{1-4}$alkoxy, and $C_{1-4}$haloalkoxy; and
$R^c$ is $C_{1-4}$alkyl optionally substituted with $C_{3-6}$ cycloalkyl or phenyl, or $C_{3-6}$ cycloalkyl.

In some embodiments, the compound is a compound of Formula (III-I-a):

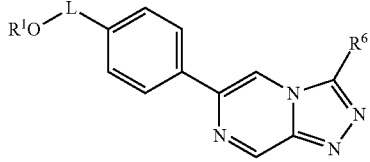

or a pharmaceutically acceptable salt thereof.

In some embodiments, the compound is a compound of Formula (III-I-b):

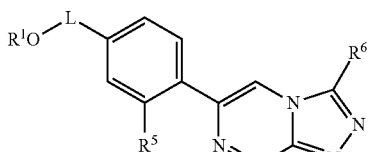

or a pharmaceutically acceptable salt thereof.

In some embodiments, the compound is a compound of Formula (III-I-c):

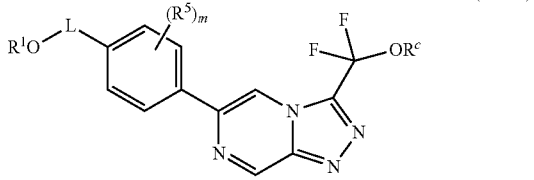

or a pharmaceutically acceptable salt thereof.

In some embodiments, the compound is a compound of Formula (III-I-d):

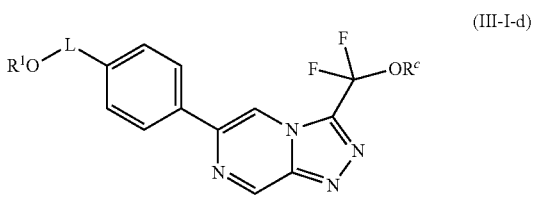

or a pharmaceutically acceptable salt thereof.

In some embodiments, the compound is a compound of Formula (III-I-e):

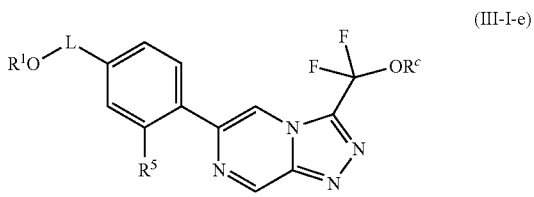

or a pharmaceutically acceptable salt thereof.

In some embodiments, L is —$CH_2$— or —$CHCH_3$—.
In some embodiments, $R^2$ is $C_{1-4}$haloalkyl. In some embodiments, $R^2$ is $CF_3$.
In some embodiments, $R^3$ and $R^4$ are both hydrogen.
In some embodiments, $R^5$ is $C_{1-4}$alkyl. In some embodiments, $R^5$ is methyl.
In some embodiments, m is 1.
In some embodiments, $R^6$ is $C_{1-4}$haloalkyl substituted with $OR^c$. In some embodiments, $R^6$ is $CF_2OR^c$. In some embodiments, $R^c$ is $C_{1-4}$alkyl. In some embodiments, $R^c$ is methyl or ethyl.

In some embodiments, the compound of Formula III-I is selected from the group consisting of:

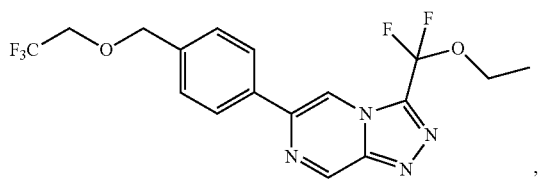

-continued

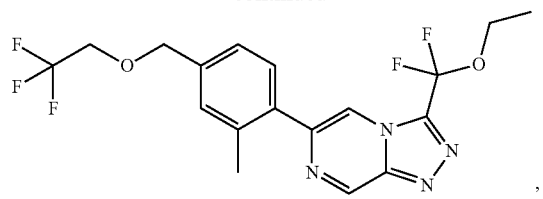

,

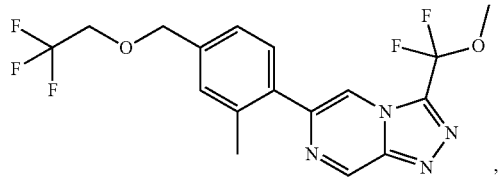

,

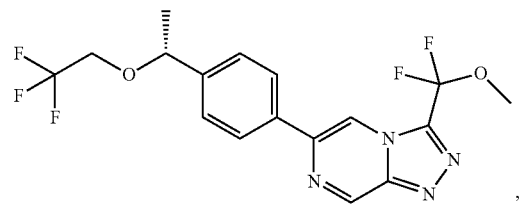

,

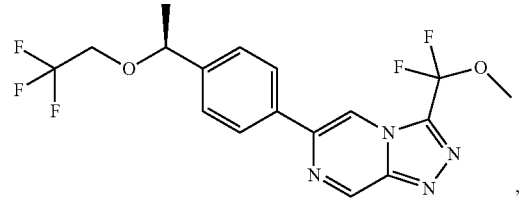

,

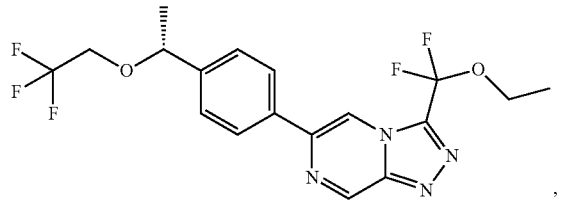

,

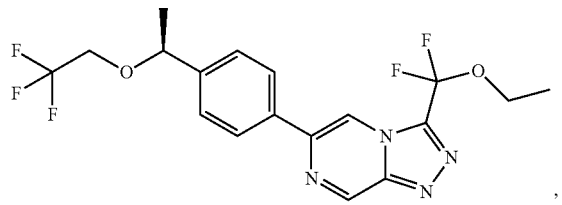

,

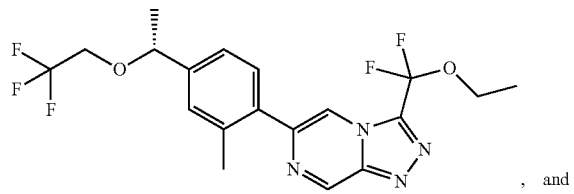

, and

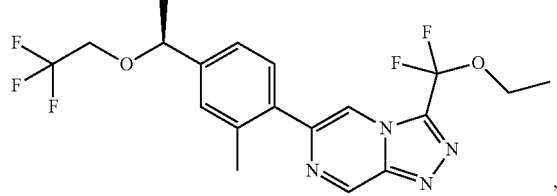

, or a pharmaceutically acceptable salt thereof.

In another aspect, provided herein is a compound of Formula (III-II):

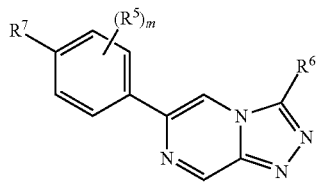

(III-II)

or a pharmaceutically acceptable salt thereof, wherein:
$R^7$ is a monocyclic $C_{3-6}$ cycloalkyl substituted with one or more $R^a$;
$R^5$ is selected from the group consisting of halo, $C_{3-6}$ cycloalkyl, and $C_{1-4}$alkyl optionally substituted with O—$C_{1-4}$alkyl or O—$C_{3-6}$ cycloalkyl;
$R^6$ is $C_{1-4}$alkyl or $C_{1-4}$haloalkyl, wherein the $C_{1-4}$alkyl or $C_{1-4}$haloalkyl is each substituted with $OR^c$;
m is 0, 1, or 2;
$R^a$ is selected from the group consisting of halo, $C_{1-4}$alkyl, $C_{1-4}$haloalkyl, $C_{1-4}$alkoxy, and $C_{1-4}$haloalkoxy; and
$R^c$ is $C_{1-4}$alkyl optionally substituted with $C_{3-6}$ cycloalkyl or phenyl, or $C_{3-6}$ cycloalkyl.

In some embodiments, the compound is a compound of Formula (III-II-a):

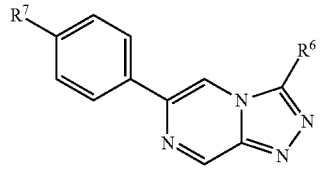

(III-II-a)

or a pharmaceutically acceptable salt thereof.

In some embodiments, the compound is a compound of Formula (III-I-b):

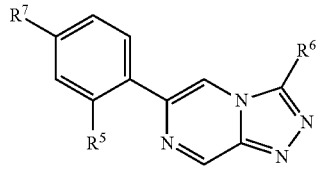

(III-II-b)

or a pharmaceutically acceptable salt thereof.

In some embodiments, the compound is a compound of Formula (III-II-c):

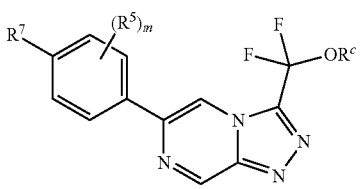

(III-II-c)

or a pharmaceutically acceptable salt thereof.

In some embodiments, the compound is a compound of Formula (III-II-d):

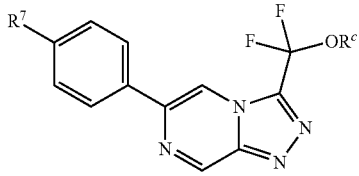
(III-II-d)

or a pharmaceutically acceptable salt thereof.

In some embodiments, the compound is a compound of Formula (III-II-e):

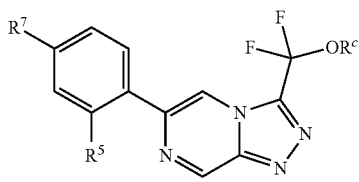
(III-II-e)

or a pharmaceutically acceptable salt thereof.

In some embodiments, the compound is a compound of Formula (III-II-f):

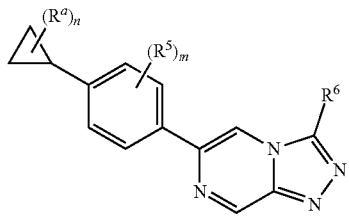
(III-II-f)

wherein n is 0, 1, 2, 3, 4, or 5; or a pharmaceutically acceptable salt thereof.

In some embodiments, $R^7$ is cyclopropyl.

In some embodiments, $R^5$ is $C_{1-4}$alkyl. In some embodiments, $R^5$ is methyl.

In some embodiments, m is 1.

In some embodiments, $R^6$ is $C_{1-4}$haloalkyl substituted with $OR^c$. In some embodiments, $R^6$ is $CF_2OR^c$. In some embodiments, $R^c$ is $C_{1-4}$alkyl. In some embodiments, $R^c$ is methyl.

In some embodiments, the compound of Formula III-II is selected the group consisting of:

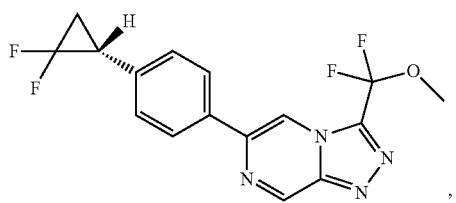

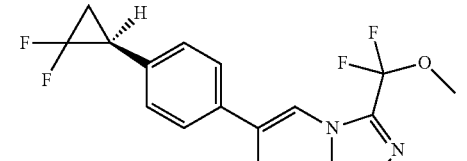

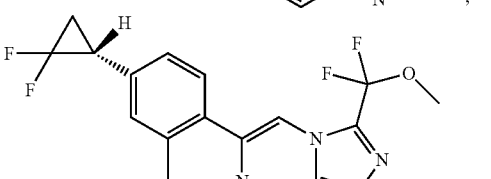

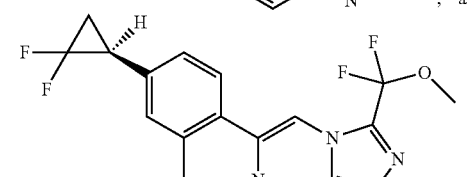

, or a pharmaceutically acceptable salt thereof.

Also provided herein is a compound selected from the group consisting of:

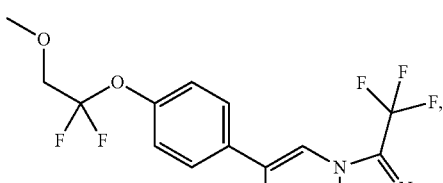

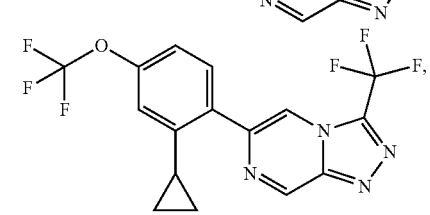

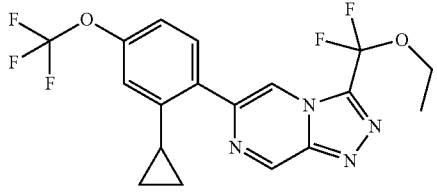

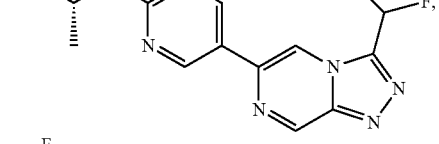

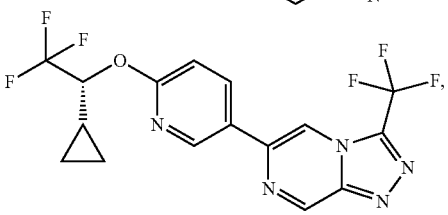

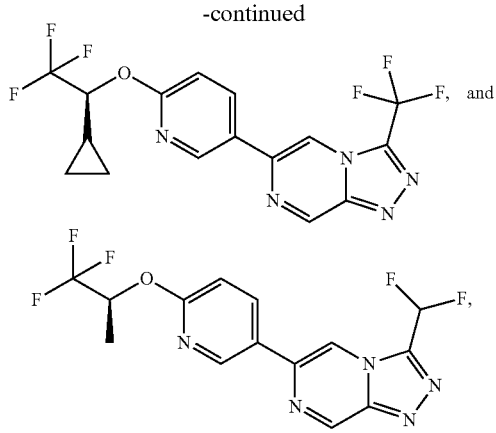

or a pharmaceutically acceptable salt thereof.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described herein, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modem Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule).

The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprises a disclosed compound, or pharmaceutically acceptable salt thereof, and a pharmaceutically acceptable carrier.

Methods of Treatment

Compounds and compositions described herein are generally useful for the modulating the activity of sodium channels and are useful in treating conditions relating to aberrant function of a sodium channel ion channel, e.g., abnormal late sodium (INaL) current. In some embodiments, a compound provided by the present invention is effective in the treatment of epilepsy or an epilepsy syndrome, a neurodevelopmental disorder, pain, or a neuromuscular disorder. In some embodiments, a compound provided by the present invention is effective in the treatment of neuropathy such as cranial neuropathy and pain such as migraines, trigeminal autonomic cephalalgias, and cortical spreading depression. A provided compound, pharmaceutically acceptable salt thereof, or composition may also modulate all sodium ion channels, or may be specific to only one or a plurality of sodium ion channels, e.g., Nav 1.1, 1.2, 1.3, 1.4, 1.5, 1.6, 1.7, 1.8, and/or 1.9.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein (e.g., a compound of Formula I-I, II-I, II-II, III-I, III-II).

Epilepsy and Epilepsy Syndromes

The compounds described herein are useful in the treatment of epilepsy and epilepsy syndromes. Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and may actually turn blue. The return to consciousness is gradual and the person may be confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

The compounds described herein (e.g., a compound of Formula I-I, II-I, II-II, III-I, III-II) may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden unexpected death in epilepsy (SUDEP), KCNQ2 epileptic encephalopathy, or KCNT1 epileptic encephalopathy) prior to administration of a compound described herein (e.g., a compound of Formula I-I, II-I, II-II, III-I, III-II).

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) comprising administering to a subject in need thereof a compound described herein (e.g., a compound of Formula I-I, II-I, II-II, III-I, III-II).

or a pharmaceutically acceptable salt thereof, wherein the variables are as defined herein.

A compound of the present invention (e.g., a compound of Formula I-I, II-I, II-II, III-I, III-II) may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX prior to administration of a compound described herein (e.g., a compound of Formula I-I, II-I, II-II, III-I, III-II).

Neurodevelopmental Disorders

The compounds described herein may be useful in the treatment of a neurodevelopmental disorder. In some embodiments, the neurodevelopmental disorder comprises autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy. In some embodiments, the methods described herein further comprise identifying a subject having a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) prior to administration of a compound described herein (e.g., a compound of Formula I-I, II-I, II-II, III-I, III-II).

In one aspect, the present invention features a method of treating a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) comprising administering to a subject in need thereof a compound described herein (e.g., a compound of Formula I-I, II-I, II-II, III-I, III-II).

Pain

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, or a related headache disorder) prior to administration of a compound described herein (e.g., a compound of Formula I-I, II-I, II-II, III-I, III-II).

In one aspect, the present invention features a method of treating pain (e.g., neuropathic pain, trigeminal neuralgia, migraine, hemiplegic migraine, familial hemiplegic migraine, familial hemiplegic migraine type 3, cluster headache, trigeminal neuralgia, or a related headache disorder)

comprising administering to a subject in need thereof a compound described herein (e.g., a compound of Formula I-I, II-I, II-II, III-I, III-II).

Neuromuscular Disorders

The compounds described herein may be useful in the treatment of a neuromuscular disorder. In some embodiments, the neuromuscular disorder comprises amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation. In some embodiments, the methods described herein further comprise identifying a subject having a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) prior to administration of a compound described herein (e.g., a compound of Formula I-I, II-I, II-II, III-I, III-II).

In one aspect, the present invention features a method of treating a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) comprising administering to a subject in need thereof a compound described herein (e.g., a compound of Formula I-I, II-I, II-II, III-I, III-II).

Trigeminal Autonomic Cephalalgia

The compounds described herein are useful in the treatment of trigeminal autonomic cephalalgias (TACs). TACs are a group of primary headaches characterized by unilaterality of pain, a relatively short duration of symptoms, and associated ipsilateral cranial autonomic signs. TACs may include cluster headache (CH), paroxysmal hemicrania (PH), hemicrania continua (HC), short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania (LASH). Despite their common elements, the trigeminal autonomic cephalalgias differ, e.g., in attack duration and frequency and in the response to therapy.

In some embodiments, the present invention provides a method of treating PH, HC, SUNCT, SUNA, and/or LASH using a compound described herein (e.g., a compound of Formula I-I, II-I, II-II, III-I, III-II), or a pharmaceutically acceptable salt thereof, or a pharmaceutical composition described herein. In some embodiments, the present invention provides a method of treating SUNCT using a compound described herein (e.g., a compound of Formula I-I, II-I, II-II, III-I, III-II), or a pharmaceutically acceptable salt thereof, or a pharmaceutical composition described herein. In some embodiments, the present invention provides a method of treating SUNA using a compound described herein (e.g., a compound of Formula I-I, II-I, II-II, III-I, III-II), or a pharmaceutically acceptable salt thereof, or a pharmaceutical composition described herein.

In some embodiments, the present invention provides a method of treating TAC (e.g., PH, HC, SUNCT, SUNA, or LASH) comprising administering to a subject in need thereof a therapeutically effective amount of a compound described herein (e.g., a compound of Formula I-I, II-I, II-II, III-I, III-II), or a pharmaceutically acceptable salt thereof, or a pharmaceutical composition described herein.

In one aspect, provided herein is a method of treating or preventing trigeminal autonomic cephalalgia (TAC) in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein, wherein the TAC is selected from the group consisting of paroxysmal hemicrania, hemicrania continua, short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania.

In some embodiments, the subject may have an inadequate response to at least one medication (e.g., lidocaine, triptans, lamotrigine, topiramate, or gabapentin, or any combinations thereof) used for the treatment of a TAC (e.g., PH, HC, SUNCT, SUNA, or LASH).

In some embodiments, the methods described herein further comprise identifying a subject having a TAC (e.g., PH, CH, SUNCT, SUNA, or LASH) prior to the administration of a compound described herein (e.g., a compound of Formula I-I, II-I, II-II, III-I, III-II), or a pharmaceutically acceptable salt thereof, or a pharmaceutical composition described herein.

Migraines

The compounds described herein are useful in the treatment of migraines. Migraine is a primary headache disorder characterized by recurrent headaches that are moderate to severe. As described herein, a migraine may be migraine without aura, migraine with aura, hemiplegic migraine, familial hemiplegic migraine (FHM), familial hemiplegic migraine type 1 (FHM1), familial hemiplegic migraine type 2 (FHM2), familial hemiplegic migraine type 3 (FHM3), familial hemiplegic migraine type 4 (FHM4), and sporadic hemiplegic migraine (SHM).

In some embodiments, the present invention provides a method of treating migraine without aura, migraine with aura, hemiplegic migraine, FHM, FHM1, FHM2, FHM3, FHM4, and/or SHM using a compound described herein (e.g., a compound of Formula I-I, II-I, II-II, III-I, III-II), or a pharmaceutically acceptable salt thereof, or a pharmaceutical composition described herein. In some embodiments, the present invention provides a method of treating migraine without aura, migraine with aura, FHM1, FHM2, FHM4, and/or SHM using a compound described herein (e.g., a compound of Formula I-I, II-I, II-II, III-I, III-II), or a pharmaceutically acceptable salt thereof, or a pharmaceutical composition described herein. In some embodiments, the present invention provides a method of treating migraine without aura using a compound described herein (e.g., a compound of Formula I-I, II-I, II-II, III-I, III-II), or a pharmaceutically acceptable salt thereof, or a pharmaceutical composition described herein. In some embodiments, the present invention provides a method of treating migraine with aura using a compound described herein (e.g., a compound of Formula I-I, II-I, II-II, III-I, III-II), or a pharmaceutically acceptable salt thereof, or a pharmaceutical composition described herein. In some embodiments, the present invention provides a method of treating FHM1, FHM2, and/or FHM4 using a compound described herein (e.g., a compound of Formula I-I, II-I, II-II, III-I, III-II), or a pharmaceutically acceptable salt thereof, or a pharmaceutical composition described herein. In some embodiments, the present invention provides a method of treating SHM using a a compound described herein (e.g., a compound of Formula I-I, II-I, II-II, III-I, III-II), or a pharmaceutically acceptable salt thereof, or a pharmaceutical composition described herein.

In some embodiments, the present invention provides a method of treating migraine (e.g., migraine without aura, migraine with aura, FHM1, FHM2, FHM4, or SHM) comprising administering to a subject in need thereof a therapeutically effective amount of a compound described herein (e.g., a compound of Formula I-I, II-I, II-II, III-I, III-II), or a pharmaceutically acceptable salt thereof, or a pharmaceutical composition described herein.

In another aspect, the present disclosure provides a method of treating or preventing a migraine in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein, wherein the migraine is selected from the group consisting of migraine without aura, migraine with aura, familial hemiplegic migraine type 1 (FHM1), familial hemiplegic migraine type 2 (FHM2), familial hemiplegic migraine type 4 (FHM4), and sporadic hemiplegic migraine (SHM).

In some embodiments, the subject has an inadequate response to at least one medication for the treatment of a migraine (e.g., migraine without aura, migraine with aura, FHM1, FHM2, FHM4, or SHM).

In some embodiments, the methods described herein further comprise identifying a subject having a migraine (e.g., migraine without aura, migraine with aura, FHM1, FHM2, FHM4, or SHM) prior to the administration of a compound described herein (e.g., a compound of Formula I-I, II-I, II-II, III-I, III-II), or a pharmaceutically acceptable salt thereof, or a pharmaceutical composition described herein.

Cortical Spreading Depression

The compounds described herein (e.g., a compound of Formula I-I, II-I, II-II, III-I, III-II), or a pharmaceutically acceptable salt thereof, or a pharmaceutical composition described herein, are useful in the treatment of cortical spreading depression (CSD). CSD is a wave of sustained depolarization (neuronal inactivation) moving through intact brain tissue and involved in, for example, brain ischemia, migraine aura, and seizures.

In some embodiments, the present invention provides a method of treating CSD using a compound described herein (e.g., a compound of Formula I-I, II-I, II-II, III-I, III-II), or a pharmaceutically acceptable salt thereof, or a pharmaceutical composition described herein. In some embodiments, the present invention provides a method of treating CSD comprising administering to a subject in need thereof a therapeutically effective amount of a compound described herein (e.g., a compound of Formula I-I, II-I, II-II, III-I, III-II), or a pharmaceutically acceptable salt thereof, or a pharmaceutical composition described herein.

In another aspect, provided herein is a method of treating or preventing cortical spreading depression (CSD) in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein In some embodiments, the subject may have an inadequate response to at least one medication for the treatment of CSD.

In some embodiments, the methods described herein further comprise identifying a subject having a CSD prior to the administration of a compound described herein.

Cranial Neuropathy

The compounds described herein are useful in the treatment of cranial neuropathy. Neuropathy is a disorder of nerve damage and affects the ability to feel and move. When nerves in the brain or brainstem are affected, it is called cranial neuropathy. The cranial nerves are those that arise directly from the brain or brainstem and often affect areas like the face and eyes. Cranial neuropathies include Bell's palsy, microvascular cranial nerve palsy, third nerve palsy, fourth nerve palsy, and sixth nerve palsy. When several different cranial nerves are affected, it is called multiple cranial neuropathies (MCN).

In some embodiments, the present invention provides a method of treating cranial neuropathy (e.g., Bell's palsy, microvascular cranial nerve palsy, third nerve palsy, fourth nerve palsy, or sixth nerve palsy) or MCN comprising administering to a subject in need thereof a therapeutically effective amount of a compound described herein (e.g., a compound of Formula I-I, II-I, II-II, III-I, III-II), or a pharmaceutically acceptable salt thereof, or a pharmaceutical composition described herein.

Also provided herein is a method of treating or preventing cranial neuropathy in a subject in need thereof, comprising administering to the subject a therapeutically effective amount of a compound described herein (e.g., a compound of Formula I-I, II-I, II-II, III-I, III-II), or a pharmaceutically acceptable salt thereof, or a pharmaceutical composition described herein, wherein the cranial neuropathy is selected from the group consisting of bell palsy, microvascular cranial nerve palsy, third nerve palsy, fourth nerve palsy, and sixth nerve palsy.

In some embodiments, the subject may have an inadequate response to at least one medication for the treatment of cranial neuropathy (e.g., Bell's palsy, microvascular cranial nerve palsy, third nerve palsy, fourth nerve palsy, or sixth nerve palsy) or MCN.

In some embodiments, the methods described herein further comprise identifying a subject having a cranial neuropathy (e.g., Bell's palsy, microvascular cranial nerve palsy, third nerve palsy, fourth nerve palsy, or sixth nerve palsy) or MCN prior to the administration of a compound described herein (e.g., a compound of Formula I-I, II-I, II-II, III-I, III-II), or a pharmaceutically acceptable salt thereof, or a pharmaceutical composition described herein.

Other Disorders

In some embodiments, a compound of the present invention (e.g., a compound of Formula I-I, II-I, II-II, III-I, III-II) may have appropriate pharmacokinetic properties such that they may be active with regard to the central and/or peripheral nervous system. In some embodiments, the compounds provided herein are used to treat a cardiovascular disease such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, recurrent ischemia, cerebral ischemia, stroke, renal ischemia, ischemia associated with organ transplant, acute coronary syndrome, peripheral arterial disease, intermittent claudication, and myocardial infarction. In some embodiments, the compounds provided herein may be used in the treatment of diseases affecting the neuromuscular system resulting in itching, seizures, or paralysis, or in the treatment of diabetes or reduced insulin sensitivity, and disease states related to diabetes, such as diabetic peripheral neuropathy. In some embodiments, a disclosed method comprises administering the pharmaceutical composition.

In some embodiments, provided herein is a method of treating a neurological disorder or a psychiatric disorder, wherein the method comprises administering to a subject in need thereof a compound disclosed herein, or a pharmaceutically acceptable salt thereof or a pharmaceutical composition disclosed herein.

Combination Therapy

A compound or composition described herein (e.g., for use in modulating a sodium ion channel, e.g., the late sodium (INaL) current) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome, a neurodevelopmental disorder, pain, or a neuromuscular disorder.

Antiepilepsy Agents Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide, and cannabidiol.

Cardiovascular Agent Combination Therapy

Cardiovascular related diseases or conditions that can benefit from a combination treatment of the sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the sodium channel blockers of the invention with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics-platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the sodium channel blocker ranolazine and amiodarone and dronedarone.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include .beta.-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the sodium channel blockers of the invention to treat neuropathic pain via inhibition of the Nav 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillizers. Examples of antidepressant and anti-anxiety agents include benzodiazepines, such as diazepam, lorazepam, and midazolam; benzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban). Antidepressant and anti-anxiety agents may include neuroactive steroid and ketamine and related NMDA receptor antagonists.

Accordingly, one aspect of the invention provides for a composition comprising the sodium channel blockers of the invention and at least one therapeutic agent. In an alternative embodiment, the composition comprises the sodium channel blockers of the invention and at least two therapeutic agents. In further alternative embodiments, the composition comprises the sodium channel blockers of the invention and at least three therapeutic agents, the sodium channel blockers of the invention and at least four therapeutic agents, or the sodium channel blockers of the invention and at least five therapeutic agents.

The methods of combination therapy include co-administration of a single formulation containing the sodium channel blockers of the invention and therapeutic agent or agents, essentially contemporaneous administration of more than one formulation comprising the sodium channel blocker of the invention and therapeutic agent or agents, and consecutive administration of a sodium channel blocker of the invention and therapeutic agent or agents, in any order, wherein preferably there is a time period where the sodium channel blocker of the invention and therapeutic agent or agents simultaneously exert their therapeutic effect.

EXEMPLIFICATION

The representative examples that follow are intended to help illustrate the invention, and are not intended to, nor should they be construed to, limit the scope of the invention.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

Exemplary general methods for analytical LCMS include Method A (Xtimate $C_{18}$ (2.1 mm×30 mm, 3 μm); A=$H_2O$ (0.04% TFA) and B=$CH_3CN$ (0.02% TFA); 50° C.; 1.2 mL/min; 10-80% B over 0.9 minutes, then 80% B for 0.6 minutes) and Method B (Chromolith Flash RP-18 end-capped $C_{18}$ (2 mm×25 mm); A=$H_2O$ (0.04% TFA) and B=$CH_3CN$ (0.02% TFA); 50° C.; 1.5 mL/min; 5-95% B over 0.7 minutes, then 95% B for 0.4 minutes)

LIST OF ABBREVIATIONS

Pd(dppf)$Cl_2$ [1,1'-bis(diphenylphosphino)ferrocene]palladium(II) dichloride $PdCl_2(PPh_3)_2$ bis(triphenylphosphine)palladium(II) dichloride $Pd_2(dba)_3$ tris(dibenzylideneacetone)dipalladium(0)

PyBOP (benzotriazol-1-yloxy)tripyrrolidinophosphonium hexafluorophosphate

DMF N,N-dimethylformamide

MeOH methanol

EtOH ethanol

THF tetrahydrofuran

EtOAc ethyl acetate

PE petroleum ether

MeCN or ACN acetonitrile

DMF N,N-dimethylformamide

DCM dichloromethane

EtOAc ethyl acetate

DMSO dimethyl sulfoxide

TFA trifluoroacetic acid

DIPEA N,N-diisopropylethylamine

DEA diethanolamine

KOAc potassium acetate

TsOH p-toluenesulfonic acid n-BuLi n-butyllithium

KOAc potassium acetate

TBAB tetrabutylammonium bromide

MeMgBr methyl magnesium bromide $PCy_3$ tricyclohexylphosphine

XPhos 2-dicyclohexylphosphino-2',4',6'-triisopropylbiphenyl

Example I-1. Syntheses of Compound I-1: 6-[5-fluoro-6-(2,2,2-trifluoro-1,1-dimethyl-ethoxy)-3-pyridyl]-3-[(1R)-1-methoxyethyl]-[1,2,4]triazolo[4,3-a]pyrazine & Compound I-2: 6-[5-fluoro-6-(2,2,2-trifluoro-1,1-dimethyl-ethoxy)-3-pyridyl]-3-[(1S)-1-methoxyethyl]-[1,2,4]triazolo[4,3-a]pyrazine
Note stereochemistry is randomly assigned.
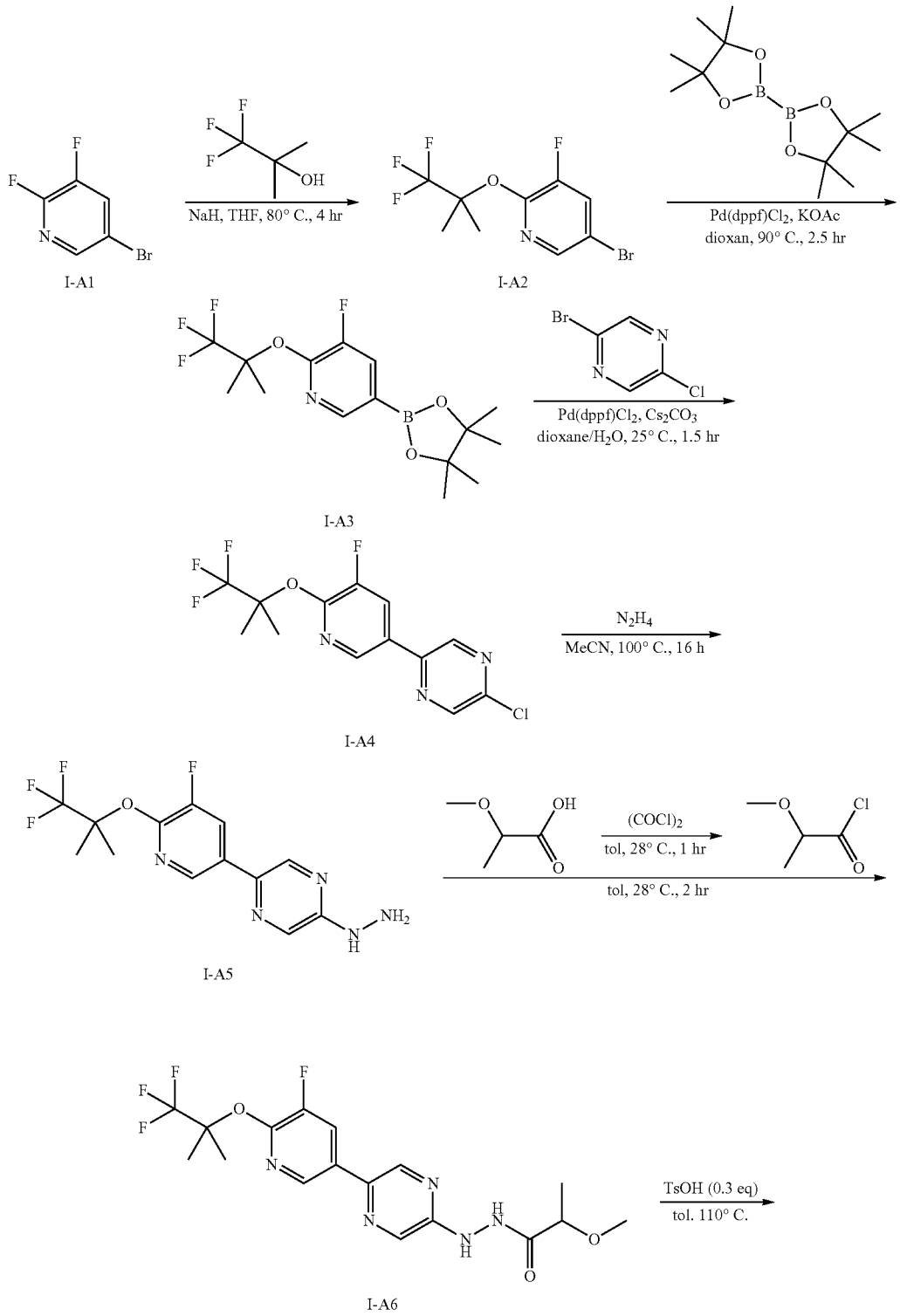

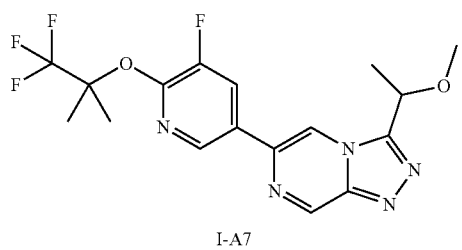

I-A7

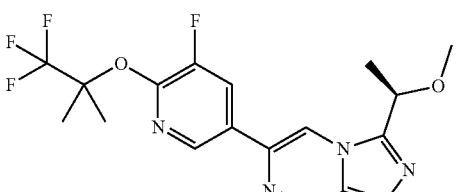

I-1

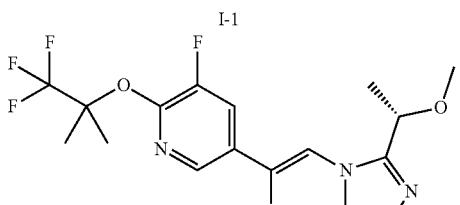

I-2

I-A2: 5-bromo-3-fluoro-2-(2,2,2-trifluoro-1,1-dimethyl-ethoxy)pyridine

To a solution of 1,1,1-trifluoro-2-methyl-propan-2-ol (5.08 g, 39.69 mmol) in THF (50 mL) was added NaH (1.59 g, 39.69 mmol, 60% in oil) in portions at 0° C. The mixture was stirred at 25° C. for 30 mins. Then, 5-bromo-2,3-difluoro-pyridine (7 g, 36.09 mmol) was added and the mixture was stirred at 50° C. for 16 hours and at 80° C. for 4 hours. After cooling to 25° C., the mixture was quenched with H$_2$O (100 mL). The aqueous layer was extracted with EtOAc (150 mL×2). The combined organic layers were washed with brine (300 mL), dried over anhydrous Na$_2$SO$_4$, filtered, and concentrated to give a crude product. The crude product was purified by flash chromatography on silica gel (EtOAc in PE=0% to 15%) to give the product (6.3 g, 20.86 mmol, 57% yield) as an oil. $^1$H NMR (400 MHz, CDCl$_3$) $\delta_H$=7.99 (d, 1H), 7.54 (dd, 1H), 1.80 (s, 6H). LCMS R$_t$=0.98 min in 1.5 min chromatography, 5-95AB, MS ESI calcd. for C$_9$H$_9$BrF$_4$NO [M+H]$^+$ 304, found 303.7.

I-A3: 3-fluoro-5-(4,4,5,5-tetramethyl-1,3,2-dioxaborolan-2-yl)-2-(2,2,2-trifluoro-1,1-dimethyl-ethoxy)pyridine A mixture of 5-bromo-3-fluoro-2-(2,2,2-trifluoro-1,1-dimethyl-ethoxy)pyridine (6.3 g, 20.86 mmol), 4,4,5,5-tetramethyl-2-(4,4,5,5-tetramethyl-1,3,2-dioxaborolan-2-yl)-1,3,2-dioxaborolane (5.83 g, 22.94 mmol), Pd(dppf)Cl$_2$ (1.53 g, 2.09 mmol) and KOAc (4.09 g, 41.71 mmol) in 1,4-dioxane (100 mL) was stirred at 90° C. for 2.5 hours. After cooling to 25° C., the suspension was diluted with EtOAc (50 mL), filtered through silica gel and eluted with EtOAc (50 mL). The combined filtrates were concentrated to give a crude product. The crude product was purified by flash chromatography on silica gel (EtOAc in PE=0% to 10%) to give the product (5.7 g, 16.33 mmol, 78% yield) as an oil. $^1$H NMR (400 MHz, CDCl$_3$) $\delta_H$=8.26 (s, 1H), 7.67 (d, 1H), 1.83 (s, 6H), 1.34 (s, 12H). LCMS R$_t$=1.06 min in 1.5 min chromatography, 5-95AB, MS ESI calcd. for C$_{15}$H$_{21}$BF$_4$NO$_3$ [M+H]$^+$ 350.1, found 350.0.

I-A4: 2-chloro-5-[5-fluoro-6-(2,2,2-trifluoro-1,1-dimethyl-ethoxy)-3-pyridyl]pyrazine A mixture of Pd(dppf)Cl$_2$ (0.6 g, 0.82 mmol), Cs$_2$CO$_3$ (10.64 g, 32.65 mmol), 3-fluoro-5-(4,4,5,5-tetramethyl-1,3,2-dioxaborolan-2-yl)-2-(2,2,2-trifluoro-1,1-dimethyl-ethoxy)pyridine (5.7 g, 16.33 mmol) and 2-bromo-5-chloro-pyrazine (3.47 g, 17.96 mmol) in 1,4-dioxane (60 mL) and water (6 mL) under N$_2$ was stirred at 25° C. for 1.5 hours. Water (150 mL) was added and the aqueous layer was extracted with EtOAc (50 mL×2). The combined organic layers were washed with brine (300 mL), dried over anhydrous Na$_2$SO$_4$, filtered, and concentrated to give a crude product. The crude product was purified by flash chromatography on silica gel (EtOAc in PE=0% to 2% to 5%) to give the product (4.6 g, 13.70 mmol, 83% yield) as a solid. $^1$H NMR (400 MHz, CDCl$_3$) $\delta_H$=8.77 (s, 1H), 8.64 (s, 1H), 8.53 (d, 1H), 8.05 (dd, 1H), 1.88 (s, 6H). LCMS R$_t$=1.00 min in 1.5 min chromatography, 5-95AB, MS ESI calcd. for C$_{13}$H$_{11}$ClF$_4$N$_3$O [M+H]$^+$ 336.0, found 335.8.

I-A5: [5-[5-fluoro-6-(2,2,2-trifluoro-1,1-dimethyl-ethoxy)-3-pyridyl]pyrazin-2-yl]hydrazine To a solution of 2-chloro-5-[5-fluoro-6-(2,2,2-trifluoro-1,1-dimethyl-ethoxy)-3-pyridyl]pyrazine (4.6 g, 13.70 mmol) in MeCN (50 mL) was added N$_2$H$_4$·H$_2$O (3.43 g, 68.52 mmol) at 25° C. The mixture was stirred at 100° C. for 16 hours. After cooling to 25° C., the reaction was poured into water (150 mL). The mixture was extracted with EtOAc (30 mL×2). The combined organic layers was washed with brine (100 mL), dried over anhydrous Na$_2$SO$_4$, filtered, and concentrated. The crude product was triturated from EtOAc/PE=⅕ (60 mL) to give the product (3.8 g, 11.47 mmol, 83% yield) as a solid. $^1$H NMR (400 MHz, CDCl$_3$) $\delta_H$=8.43-8.41 (m, 2H), 8.29 (s, 1H), 7.94 (dd, 1H), 6.09 (brs, 1H), 3.92 (brs, 2H), 1.84 (s, 6H). LCMS R$_t$=0.78 min in 1.5 min chromatography, 5-95AB, MS ESI calcd. for C$_{13}$H$_{14}$F$_4$N$_5$O [M+H]$^+$ 332.1, found 331.9.

I-A7: 6-[5-fluoro-6-(2,2,2-trifluoro-1,1-dimethyl-ethoxy)-3-pyridyl]-3-(1-methoxyethyl)-[1,2,4]triazolo[4,3-a]pyrazine To a solution of 2-methoxypropanoic acid (190 mg, 1.83 mmol) in toluene (5 mL) was added (COCl)$_2$ (0.19 mL, 2.19 mmol) and 1 drop of DMF. The mixture was stirred at 28° C. for 1 hour. A solution of [5-[5-fluoro-6-(2,2,2-trifluoro-1,1-dimethyl-ethoxy)-3-pyridyl]pyrazin-2-yl]hydrazine (500 mg, 1.51 mmol) in toluene (2 mL) was added to the mixture. The mixture was stirred at 28° C. for 2 hours. To the above mixture was added TsOH (77.36 mg, 0.45 mmol). The mixture was stirred at 110° C. for 12 hours. After cooling to room temperature, H$_2$O (30 mL) was added. The mixture was extracted with EtOAc (20 mL×2). The combined organic layers were washed with brine (40 mL), dried over anhydrous Na$_2$SO$_4$, filtered, and concentrated to give a crude product. The crude product was purified by flash chromatography on silica gel (EtOAc in PE=0% to 40% to 70%) to give the product (60 mg, 0.15 mmol) as an oil. $^1$H NMR (400 MHz, CDCl$_3$) $\delta_H$=9.42 (s, 1H), 8.59 (s, 1H), 8.49 (d, 1H), 8.01 (d, 1H), 5.23 (q, 1H), 3.38 (s, 3H), 1.88 (s, 6H), 1.79 (d, 3H). LCMS R$_t$=0.89 min in 1.5 min chromatography, 5-95AB, MS ESI calcd. for C$_{17}$H$_{18}$F$_4$N$_5$O$_2$[M+H]$^+$ 400.1, found 400.1.

Compounds I-1 and I-2: 6-[5-fluoro-6-(2,2,2-trifluoro-1,1-dimethyl-ethoxy)-3-pyridyl]-3-[(1R)-1-methoxyethyl]-[1,2,4]triazolo[4,3-a]pyrazine & 6-[5-fluoro-6-(2,2,2-trifluoro-1,1-dimethyl-ethoxy)-3-pyridyl]-3-[(1S)-1-methoxyethyl]-[1,2,4]triazolo[4,3-a]pyrazine 6-[5-fluoro-6-(2,2,2-trifluoro-1,1-dimethyl-ethoxy)-3-pyridyl]-3-(1-methoxyethyl)-[1,2,4]triazolo[4,3-a]pyrazine (60 mg, 0.15 mmol) was purified by prep-HPLC [YMC Triart C18 (150 mm×25 mm, 5 μm) A=H$_2$O (10 mM NH$_4$HCO$_3$) and B=CH$_3$CN; 47-77% B over 9.5 minutes] to give the product (50 mg, 0.13 mmol) as a solid. Analysis SFC: (Chiralcel OJ-3 100×4.6 mm I.D., 3 μm. Mobile phase: A: CO$_2$, B: ethanol (0.05% DEA). Gradient: from 5% to 40% of B in 4 min and hold 40% for 2.5 min, then 5% of B for 1.5 min. Flow rate: 2.8 mL/min. Column temperature: 35° C. ABPR: 1500 psi) showed two peaks at 1.35 min (50%) and 1.42 min (50%). The stereochemistry of the compounds was randomly assigned.

6-[5-fluoro-6-(2,2,2-trifluoro-1,1-dimethyl-ethoxy)-3-pyridyl]-3-(1-methoxyethyl)-[1,2,4]triazolo[4,3-a]pyrazine (50 mg, 0.13 mmol) was purified by SFC (DAICEL CHIRALCEL OJ-H (250 mm×30 mm, 5 μm); A: CO$_2$, B=0.1% NH$_3$H$_2$O EtOH; 38° C.; 60 mL/min; 10% B; 11 min run; 40 injections) to give the Enantiomer 1, randomly assigned as 6-[5-fluoro-6-(2,2,2-trifluoro-1,1-dimethyl-ethoxy)-3-pyridyl]-3-[(1R)-1-methoxyethyl]-[1,2,4]triazolo[4,3-a]pyrazine (6.17 mg, 15.2 μmol, 12% yield) (Rt of Peak 1=1.35 min) as a solid and 6-[5-fluoro-6-(2,2,2-trifluoro-1,1-dimethyl-ethoxy)-3-pyridyl]-3-[(1S)-1-methoxyethyl]-[1,2,4]triazolo[4,3-a]pyrazine (20 mg, 58.9 μmol) as a solid. 6-[5-fluoro-6-(2,2,2-trifluoro-1,1-dimethyl-ethoxy)-3-pyridyl]-3-[(1S)-1-methoxyethyl]-[1,2,4]triazolo[4,3-a]pyrazine (20 mg, 58.9 μmol) was further purified by SFC (DAICEL CHIRALPAK IG (250 mm×30 mm, 10 μm); A: CO$_2$, B=0.1% NH$_3$H$_2$O MeOH; 38° C.; 60 mL/min; 15% B; 15 min run; 8 injections) to give Enantiomer 2, randomly assigned as 6-[5-fluoro-6-(2,2,2-trifluoro-1,1-dimethyl-ethoxy)-3-pyridyl]-3-[(1S)-1-methoxyethyl]-[1,2,4]triazolo[4,3-a]pyrazine (13.4 mg, 33.6 μmol, 27% yield) (Rt of Peak 1=2.20 min) as a solid.

Compound I-1: $^1$H NMR (400 MHz, CDCl$_3$) $\delta_H$=9.42 (s, 1H), 8.59 (s, 1H), 8.49 (d, 1H), 8.00 (dd, 1H), 5.23 (q, 1H), 3.37 (s, 3H), 1.88 (s, 6H), 1.79 (d, 3H). LCMS R$_t$=1.20 min in 2.0 min chromatography, 10-80AB, MS ESI calcd. for C$_{17}$H$_{18}$F$_4$N$_5$O$_2$[M+H]$^+$ 400.1, found 400.1.

Compound I-2: $^1$H NMR (400 MHz, CDCl$_3$) $\delta_H$=9.42 (s, 1H), 8.59 (s, 1H), 8.49 (d, 1H), 8.00 (dd, 1H), 5.23 (q, 1H), 3.37 (s, 3H), 1.88 (s, 6H), 1.79 (d, 3H). LCMS R$_t$=1.18 min in 2.0 min chromatography, 10-80AB, MS ESI calcd. for C$_{17}$H$_{18}$F$_4$N$_5$O$_2$[M+H]$^+$ 400.1, found 400.1.

Example I-2. Syntheses of Compound I-3 & Compound I-4: (R)-6-(5-fluoro-6-(1-(trifluoromethyl)cyclobutoxy)pyridin-3-yl)-3-(1-methoxyethyl)-[1,2,4]triazolo[4,3-a]pyrazine & (S)-6-(5-fluoro-6-(1-(trifluoromethyl)cyclobutoxy)pyridin-3-yl)-3-(1-methoxyethyl)-[1,2,4]triazolo[4,3-a]pyrazine Note stereochemistry is randomly assigned.

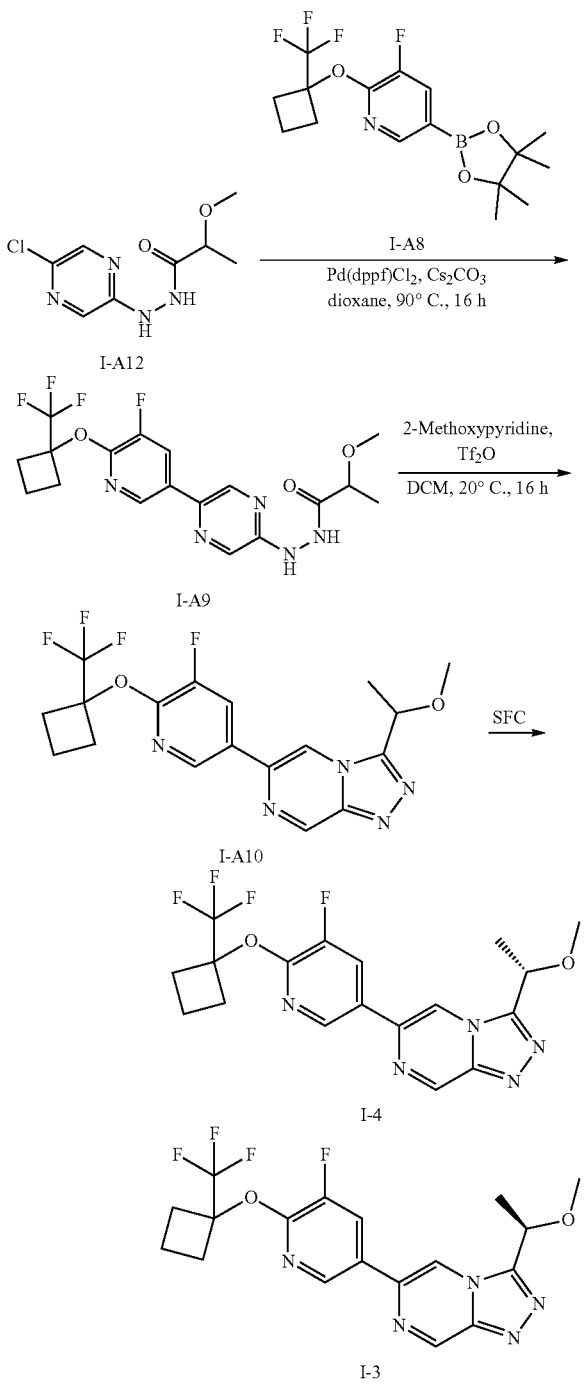

I-A9: N'-(5-(5-fluoro-6-(1-(trifluoromethyl)cyclobutoxy)pyridin-3-yl)pyrazin-2-yl)-2-methoxypropanehydrazide To a mixture of 3-fluoro-5-(4,4,5,5-tetramethyl-1,3,2-dioxaborolan-2-yl)-2-[1-(trifluoromethyl)cyclobutoxy]pyridine (500 mg, 1.38 mmol) and N'-(5-chloropyrazin-2-yl)-2-methoxy-propanehydrazide (351.27 mg, 1.52 mmol) and $Cs_2CO_3$ (902.14 mg, 2.77 mmol) in 1,4-dioxane (10 mL) and water (1 mL) was added Pd(dppf)Cl$_2$ (101.3 mg, 0.14 mmol) under N$_2$. The mixture was stirred at 90° C. for 16 hours. The mixture was filtered, and the filtrate was concentrated to remove dioxane. The aqueous layer was extracted with EtOAc (30 mL×3). The combined organic layers were washed with brine (30 mL), dried over anhydrous Na$_2$SO$_4$, filtered, and concentrated to afford the product (594 mg, 1.38 mmol, 99% yield) as an oil. LCMS R$_t$=0.89 min in 1.5 min chromatography, 5-95AB, MS ESI calcd. for $C_{18}H_{20}F_4N_5O_3[M+H]^+$ 430.1, found 430.0.

I-A10: 6-(5-fluoro-6-(1-(trifluoromethyl)cyclobutoxy)pyridin-3-yl)-3-(1-methoxyethyl)-[1,2,4]triazolo[4,3-a]pyrazine To a mixture of N'-[5-[5-fluoro-6-[1-(trifluoromethyl)cyclobutoxy]-3-pyridyl]pyrazin-2-yl]-2-methoxy-propanehydrazide (594 mg, 1.38 mmol) in DCM (20 mL) was added 2-methoxypyridine (1.21 g, 11.07 mmol) and Tf$_2$O (0.93 mL, 5.53 mmol). The mixture was stirred at 20° C. for 2 hours, quenched by adding water (50 mL), and extracted with EtOAc (50 mL×2). The combined organic phase was washed with saturated NaHCO$_3$ aqueous solution (30 mL), brine (30 mL), dried over anhydrous Na$_2$SO$_4$, filtered, and concentrated to give the crude product. The residue was purified by flash chromatography (0 to 50% of EtOAc in PE) to give 6-[5-fluoro-6-[1-(trifluoromethyl)cyclobutoxy]-3-pyridyl]-3-(1-methoxyethyl)-[1,2,4]triazolo[4,3-a]pyrazine (130 mg) as a solid. $^1$H NMR (400 MHz, CDCl$_3$) $\delta_H$=9.41 (d, 1H), 8.59 (d, 1H), 8.46 (d, 1H), 8.07-7.99 (m, 1H), 5.26-5.15 (m, 1H), 3.36 (s, 3H), 3.02-2.83 (m, 2H), 2.81-2.67 (m, 3H), 2.09-1.91 (m, 3H), 1.77 (d, 3H).

Compounds I-3 and I-4: (S)-6-(5-fluoro-6-(1-(trifluoromethyl)cyclobutoxy)pyridin-3-yl)-3-(1-methoxyethyl)-[1,2,4]triazolo[4,3-a]pyrazine & (R)-6-(5-fluoro-6-(1-(trifluoromethyl)cyclobutoxy)pyridin-3-yl)-3-(1-methoxyethyl)-[1,2,4]triazolo[4,3-a]pyrazine The mixture of 6-[5-fluoro-6-[1-(trifluoromethyl)cyclobutoxy]-3-pyridyl]-3-(1-methoxyethyl)-[1,2,4]triazolo[4,3-a]pyrazine (160 mg, 0.39 mmol) was purified by SFC (DAICEL CHIRALCEL OJ-H (250 mm×30 mm, 5 μm); A: CO$_2$ and B=EtOH 0.1% NH$_3$·H$_2$O, 10% B); to give 6-[5-fluoro-6-[1-(trifluoromethyl)cyclobutoxy]-3-pyridyl]-3-[(1R)-1-methoxyethyl]-[1,2,4]triazolo[4,3-a]pyrazine (32.34 mg) (Rt of Peak 1=3.004 mins) as a solid, and 6-[5-fluoro-6-[1-(trifluoromethyl)cyclobutoxy]-3-pyridyl]-3-[(1S)-1-methoxyethyl]-[1,2,4]triazolo[4,3-a]pyrazine (36.04 mg) (Rt of Peak 2=3.145 mins) as a solid.

Compound I-3: $^1$H NMR (400 MHz, CDCl$_3$) $\delta_H$=9.40 (d, 1H), 8.59 (d, 1H), 8.46 (d, 1H), 8.02 (dd, 1H), 5.21 (q, 1H), 3.36 (s, 3H), 2.99-2.82 (m, 2H), 2.81-2.67 (m, 2H), 2.11-1.87 (m, 3H), 1.77 (d, 3H). LCMS R$_t$=1.57 min in 2.0 min chromatography, 10-80AB, MS ESI calcd. for $C_{18}H_{18}F_4N_5O_2[M+H]^+$ 412.1, found 412.2.

Compound I-4: $^1$H NMR (400 MHz, CDCl$_3$) $\delta_H$=9.41 (d, 1H), 8.59 (d, 1H), 8.46 (d, 1H), 8.03 (dd, 10.4 Hz, 1H), 5.21 (q, 1H), 3.36 (s, 3H), 2.97-2.83 (m, 2H), 2.81-2.69 (m, 2H), 2.11-1.90 (m, 2H), 1.77 (d, 3H). LCMS R$_t$=1.57 min in 2.0 min chromatography, 10-80AB, MS ESI calcd. for $C_{18}H_{18}F_4N_5O_2[M+H]^+$ 412.1, found 412.3.

Example I-3. Syntheses of Compound I-5 & Compound I-6: (S)-3-(1-methoxyethyl)-6-(6-(1-(trifluoromethyl)cyclobutoxy)pyridin-3-yl)-[1,2,4]triazolo[4,3-a]pyrazine & (R)-3-(1-methoxyethyl)-6-(6-(1-(trifluoromethyl)cyclobutoxy)pyridin-3-yl)-[1,2,4]triazolo[4,3-a]pyrazine Note stereochemistry is randomly assigned.

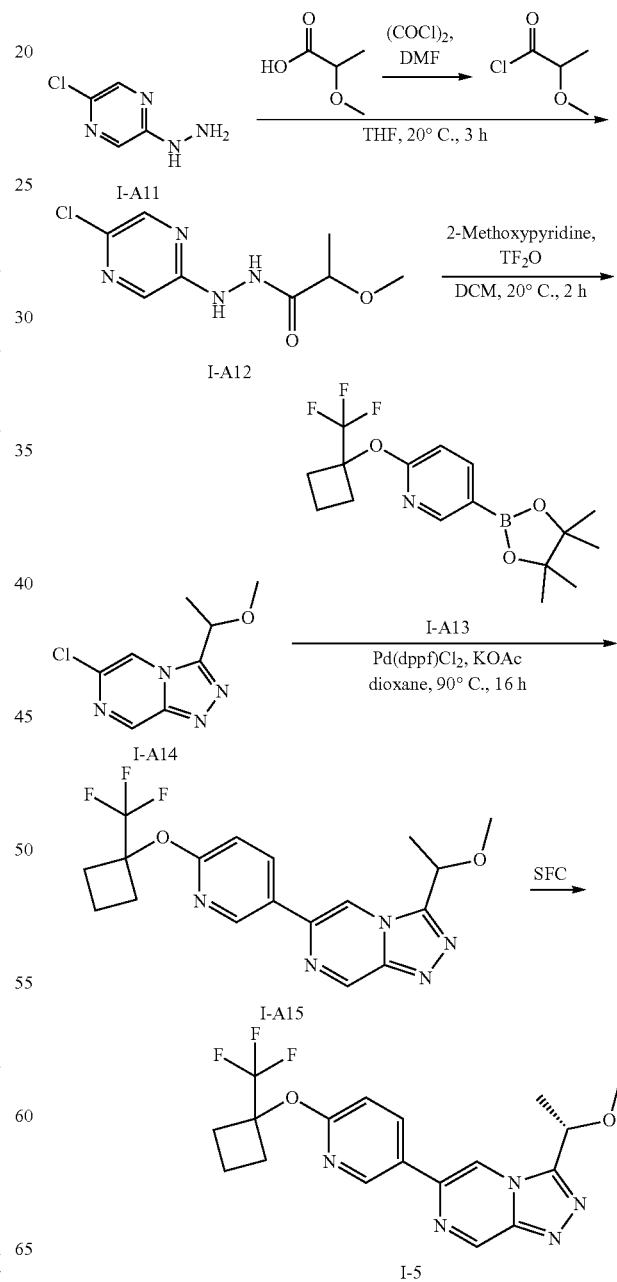

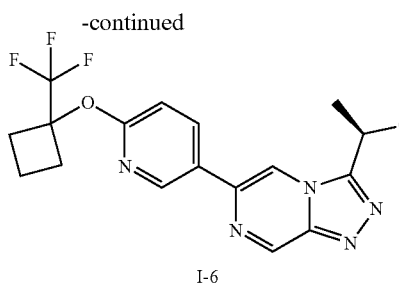

I-6

I-A12: N'-(5-chloropyrazin-2-yl)-2-methoxypropanehydrazide

To a solution of (5-chloropyrazin-2-yl)hydrazine (10 g, 69.2 mmol) in THF (100 mL) was added 2-methoxypropanoyl chloride (10.4 g, 76.1 mmol) at 0° C. The mixture was stirred at 25° C. for 1 hour. To the mixture was added water (100 mL), and the mixture was extracted with EtOAc (100 mL×2). The combined organic phase was washed with brine (100 mL), dried over anhydrous $Na_2SO_4$, filtered, and concentrated to give the crude product (10 g, 28.6 mmol, 41% yield) as an oil. $^1$H NMR (400 MHz, $CDCl_3$) $\delta_H$=8.63 (s, 1H), 8.19-8.01 (m, 1H), 7.94-7.80 (m, 1H), 7.70-7.35 (m, 1H), 3.98-3.89 (m, 1H), 3.48-3.45 (m, 3H), 1.49-1.38 (m, 3H).

I-A14: 6-chloro-3-(1-methoxyethyl)-[1,2,4]triazolo[4,3-a]pyrazine

To a mixture of N'-(5-chloropyrazin-2-yl)-2-methoxypropanehydrazide (3 g, 13.0 mmol) in DCM (30 mL) was added 2-methoxypyridine (7.1 g, 65.0 mmol) and $Tf_2O$ (5.49 mL, 32.5 mmol), and the mixture was stirred at 20° C. for 1 hour. To the mixture was added water (30 mL), and the aqueous phase was extracted with EtOAc (50 mL×2). The combined organic phase was washed with saturated $NaHCO_3$ aqueous solution (30 mL), brine (30 mL), dried over anhydrous $Na_2SO_4$, filtered, and concentrated to give the crude product (1.2 g, 3.95 mmol) as a solid. $^1$H NMR (400 MHz, $CDCl_3$) $\delta_H$=9.20-9.14 (m, 1H), 8.57-8.31 (m, 1H), 5.22-5.09 (m, 1H), 3.34 (s, 3H), 1.77-1.70 (m, 3H).

I-A15: 3-(1-methoxyethyl)-6-(6-(1-(trifluoromethyl)cyclobutoxy)pyridin-3-yl)-[1,2,4]triazolo[4,3-a]pyrazine To a mixture of 6-chloro-3-(1-methoxyethyl)-[1,2,4]triazolo[4,3-a]pyrazine (300 mg, 1.41 mmol) and 5-(4,4,5,5-tetramethyl-1,3,2-dioxaborolan-2-yl)-2-[1-(trifluoromethyl)cyclobutoxy]pyridine (532.5 mg, 1.55 mmol) and $Cs_2CO_3$ (919.3 mg, 2.82 mmol) in 1,4-dioxane (5 mL) and water (0.50 mL) was added $Pd(dppf)Cl_2$ (103.2 mg, 0.14 mmol) under $N_2$. The mixture was stirred at 90° C. for 2 hours. The mixture was filtered, and the filtrate was concentrated to remove dioxane. The aqueous layer was extracted with EtOAc (30 mL×3). The combined organic layers were washed with brine (30 mL), dried over anhydrous $Na_2SO_4$, filtered, and concentrated to give 3-(1-methoxyethyl)-6-(6-(1-(trifluoromethyl)cyclobutoxy)pyridin-3-yl)-[1,2,4]triazolo[4,3-a]pyrazine (300 mg, 0.61 mmol, 43% yield) $^1$H NMR (400 MHz, $CDCl_3$) $\delta_H$=9.47-9.37 (m, 1H), 8.59-8.52 (m, 1H), 8.25-8.17 (m, 1H), 6.97-6.87 (m, 1H), 5.26-5.15 (m, 1H), 3.35 (s, 3H), 2.98-2.84 (m, 2H), 2.77-2.62 (m, 2H), 2.0-1.87 (m, 3H), 1.82-1.72 (m, 3H).

Compounds I-5 & I-6: (S)-3-(1-methoxyethyl)-6-(6-(1-(trifluoromethyl)cyclobutoxy)pyridin-3-yl)-[1,2,4]triazolo[4,3-a]pyrazine & (R)-3-(1-methoxyethyl)-6-(6-(1-(trifluoromethyl)cyclobutoxy)pyridin-3-yl)-[1,2,4]triazolo[4,3-a]pyrazine The mixture of 3-(1-methoxyethyl)-6-(6-(1-(trifluoromethyl)cyclobutoxy)pyridin-3-yl)-[1,2,4]triazolo[4,3-a]pyrazine (100 mg, 0.25 mmol) was purified by SFC (DAICEL CHIRALCEL OJ-H (250 mm×30 mm, 5 μm), A: $CO_2$ and B=MeOH 0.1% $NH_3 \cdot H_2O$, 10% B; to give (S)-3-(1-methoxyethyl)-6-(6-(1-(trifluoromethyl)cyclobutoxy)pyridin-3-yl)-[1,2,4]triazolo[4,3-a]pyrazine (49.2 mg, 0.13 mmol) as a solid and (R)-3-(1-methoxyethyl)-6-(6-(1-(trifluoromethyl)cyclobutoxy)pyridin-3-yl)-[1,2,4]triazolo[4,3-a]pyrazine (55.0 mg, 0.14 mmol) as a solid.

Compound I-5: $^1$H NMR (400 MHz, $CDCl_3$) $\delta_H$=9.42 (d, 1H), 8.70 (d, 1H), 8.56 (d, 1H), 8.20 (dd, 1H), 6.92 (d, 1H), 5.21 (d, 1H), 3.36 (s, 3H), 2.98-2.85 (m, 2H), 2.77-2.65 (m, 2H), 2.08-1.89 (m, 2H), 1.77 (d, 3H). LCMS $R_t$=1.544 min in 2.0 min chromatography, 10-80AB, MS ESI calcd. for $C_{18}H_{19}F_3N_5O_2[M+H]^+$ 394.2, found 394.2.

Compound I-6: $^1$H NMR (400 MHz, $CDCl_3$) $\delta_H$=9.42 (d, 1H), 8.70 (d, 1H), 8.56 (d, 1H), 8.21 (dd, 1H), 6.92 (d, 1H), 5.21 (d, 1H), 3.36 (s, 3H), 2.92 (br d, 2H), 2.76-2.66 (m, 2H), 2.07-1.90 (m, 2H), 1.77 (d, 3H). LCMS $R_t$=1.539 min in 2.0 min chromatography, 10-80AB, MS ESI calcd. for $C_{18}H_{19}F_3N_5O_2[M+H]^+$ 394.2, found 394.2.

Example I-4. Synthesis of Compound I-7: (S)-3-(1-ethoxyethyl)-6-(5-fluoro-6-(1-(trifluoromethyl)cyclobutoxy)pyridin-3-yl)-[1,2,4]triazolo[4,3-a]pyrazine

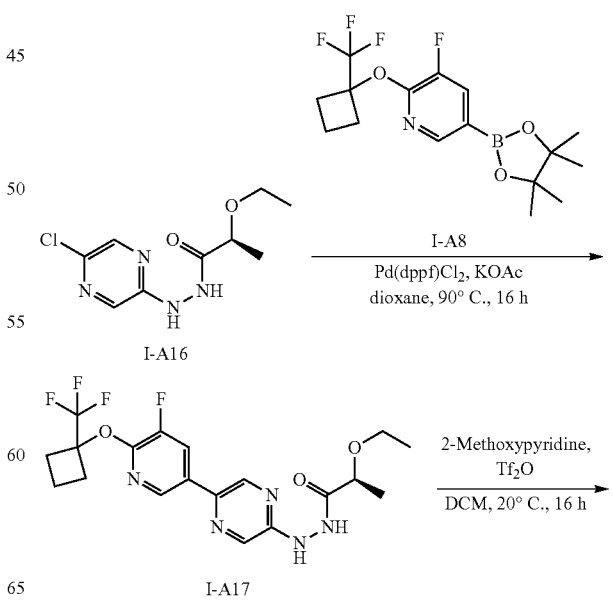

-continued

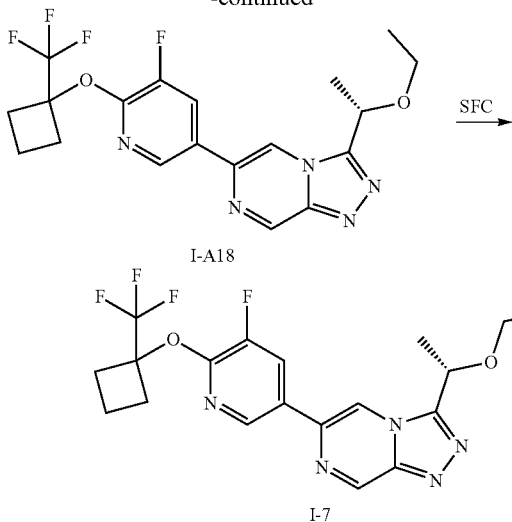

I-A17: (S)-2-ethoxy-N'-(5-(5-fluoro-6-(1-(trifluoromethyl)cyclobutoxy)pyridin-3-yl)pyrazin-2-yl)propanehydrazide To a mixture of 3-fluoro-5-(4,4,5,5-tetramethyl-1,3,2-dioxaborolan-2-yl)-2-[1-(trifluoromethyl)cyclobutoxy]pyridine (400 mg, 1.11 mmol) and (S)—N'-(5-chloropyrazin-2-yl)-2-ethoxypropanehydrazide (298.1 mg, 1.22 mmol) and $Cs_2CO_3$ (721.7 mg, 2.22 mmol) in 1,4-dioxane (10 mL) and water (1 mL) was added Pd(dppf)Cl$_2$ (81.0 mg, 0.11 mmol) under $N_2$. After stirring at 90° C. for 16 hours, the mixture was filtered, and the filtrate was concentrated to remove dioxane. The aqueous layer was extracted with EtOAc (30 mL×2). The combined organic layers were washed with brine (30 mL), dried over anhydrous $Na_2SO_4$, filtered, and concentrated to afford the product (500 mg, crude) as an oil. LCMS $R_t$=0.92 min in 1.5 min chromatography, 5-95AB, MS ESI calcd. for $C_{19}H_{22}F_4N_5O_3[M+H]^+$ 444.2, found 444.0.

I-A18: (S)-3-(1-ethoxyethyl)-6-(5-fluoro-6-(1-(trifluoromethyl)cyclobutoxy)pyridin-3-yl)-[1,2,4]triazolo[4,3-a]pyrazine To a mixture of (S)-2-ethoxy-N'-(5-(5-fluoro-6-(1-(trifluoromethyl)cyclobutoxy)pyridin-3-yl)pyrazin-2-yl)propanehydrazide (500 mg, crude) in DCM (20 mL) was added 2-methoxypyridine (513.1 mg, 4.70 mmol) and Tf$_2$O (0.40 mL, 2.35 mmol), and the mixture was stirred at 20° C. for 2 hours. The mixture was diluted with water (20 mL), and the aqueous phase was extracted with EtOAc (20 mL×2). The combined organic phase was washed with saturated NaHCO$_3$ aqueous solution (15 mL), brine (15 mL), dried over anhydrous Na$_2$SO$_4$, filtered, and concentrated. The residue was purified by flash column chromatography (0 to 30% of EtOAc in PE) to give the product (200 mg, 0.49 mmol, 42% yield) as a solid. $^1$H NMR (400 MHz, CDCl$_3$) $δ_H$=9.40 (d, 1H), 8.65 (d, 1H), 8.44 (d, 1H), 8.02 (dd, 1H), 5.36-5.25 (m, 1H), 3.68-3.53 (m, 1H), 3.47-3.32 (m, 1H), 2.98-2.85 (m, 2H), 2.82-2.70 (m, 2H), 2.03-1.91 (m, 2H), 1.76 (d, 3H), 1.25-1.22 (m, 3H).

Compound I-7: (S)-3-(1-ethoxyethyl)-6-(5-fluoro-6-(1-(trifluoromethyl)cyclobutoxy)pyridin-3-yl)-[1,2,4]triazolo[4,3-a]pyrazine The mixture of (S)-3-(1-ethoxyethyl)-6-(5-fluoro-6-(1-(trifluoromethyl) cyclobutoxy)pyridin-3-yl)-[1,2,4]triazolo[4,3-a]pyrazine (200 mg, 0.47 mmol) was purified by SFC (DAICEL CHIRALCEL OJ-H (250 mm×30 mm, 5 μm); A: CO$_2$, B=EtOH 0.1% NH$_3$·H$_2$O; 10% B; 60 mL/min; to afford (S)-3-(1-ethoxyethyl)-6-(5-fluoro-6-(1-(trifluoromethyl)cyclobutoxy)pyridin-3-yl)-[1,2,4]triazolo [4,3-a]pyrazine (87.9 mg, 0.21 mmol) as an oil. $^1$H NMR (400 MHz, CDCl$_3$) $δ_H$=9.40 (d, 1H), 8.65 (d, 1H), 8.44 (d, 1H), 8.02 (dd, 1H), 5.31 (q, 1H), 3.66-3.53 (m, 1H), 3.47-3.35 (m, 1H), 2.98-2.86 (m, 2H), 2.81-2.70 (m, 2H), 2.09-1.90 (m, 2H), 1.76 (d, 3H), 1.24 (t, 3H). LCMS $R_t$=1.63 min in 2.0 min chromatography, 10-80AB, MS ESI calcd. for $C_{19}H_{20}F_4N_5O_2$ [M+H]$^+$ 426.1, found 426.3.

Example I-5. Synthesis of Compound I-8: (S)-3-(1-ethoxyethyl)-6-(6-((1,1,1-trifluoro-2-methylpropan-2-yl)oxy)pyridin-3-yl)-[1,2,4]triazolo[4,3-a]pyrazine

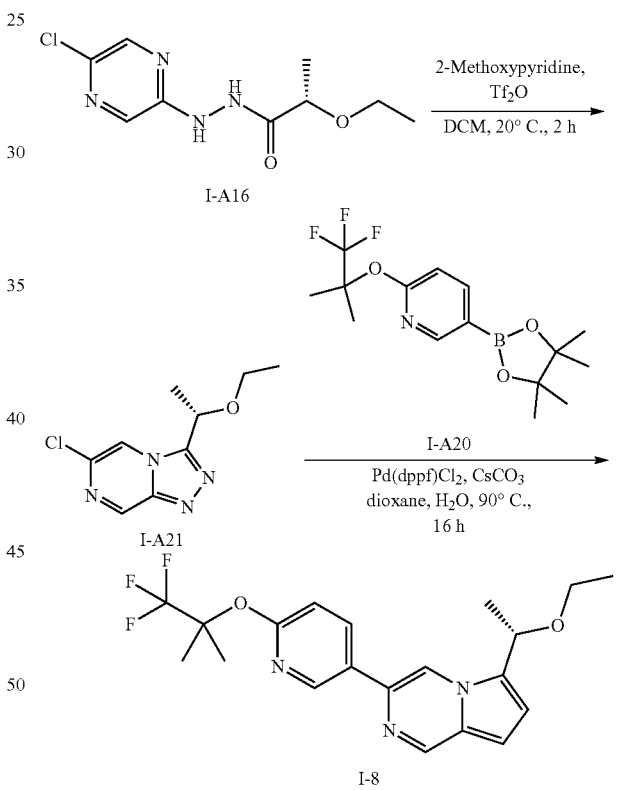

I-A21: (S)-6-chloro-3-(1-ethoxyethyl)-[1,2,4]triazolo[4,3-a]pyrazine To a mixture of (S)—N'-(5-chloropyrazin-2-yl)-2-ethoxypropanehydrazide (1 g, 4.09 mmol) in DCM (10 mL) was added 2-methoxypyridine (2.23 g, 20.4 mmol) and Tf$_2$O (1.73 mL, 10.2 mmol). The mixture was stirred at 20° C. for 2 hours. To the mixture was added water (50 mL), and the aqueous phase was extracted with EtOAc (50 mL×2). The combined organic phase was washed with saturated NaHCO$_3$ aqueous solution (30 mL), brine (30 mL), dried over anhydrous Na$_2$SO$_4$, filtered, and concentrated to give the crude product of 6-chloro-3-(1-ethoxyethyl)-[1,2,4]triazolo[4,3-a]pyrazine (500 mg, 1.54 mmol, 38% yield) as a solid. ¹H NMR (400 MHz, CDCl₃) δ$_H$=9.25-9.10 (m, 1H), 8.59-8.37 (m, 1H), 5.33-5.18 (m, 1H), 3.68-3.51 (m, 1H), 3.44-3.23 (m, 1H), 1.76-1.69 (m, 3H), 1.25-1.20 (m, 3H).

Compound I-8: (S)-3-(1-ethoxyethyl)-6-(6-((1,1,1-trifluoro-2-methylpropan-2-yl)oxy)pyridin-3-yl)-[1,2,4]triazolo[4,3-a]pyrazine To a mixture of (S)-6-chloro-3-(1-ethoxyethyl)-[1,2,4]triazolo[4,3-a]pyrazine (400 mg, 1.76 mmol) and 5-(4,4,5,5-tetramethyl-1,3,2-dioxaborolan-2-yl)-2-(2,2,2-trifluoro-1,1-dimethyl-ethoxy)pyridine (666.13 mg, 2.01 mmol) and Cs₂CO₃ (1149.92 mg, 3.53 mmol) in 1,4-dioxane (15 mL) and water (3 mL) was added Pd(dppf)Cl₂ (129.13 mg, 0.18 mmol) under N₂. The mixture was stirred at 90° C. for 2 hours. The mixture was filtered, and the filtrate was concentrated to remove dioxane. The aqueous layer was extracted with EtOAc (30 mL×3). The combined organic layers were washed with brine (30 mL), dried over anhydrous Na₂SO₄, filtered, and concentrated. The mixture of (300 mg, 0.76 mmol) was purified by SFC (DAICEL CHIRALPAK AD (250 mm×30 mm, 10 μm; A: CO₂ and B=EtOH 0.1% NH₃·H₂O; 10% B) to give the product (117.4 mg, 0.30 mmol, 39% yield) as a solid. ¹H NMR (400 MHz, CDCl₃) δ$_H$=9.41 (d, 1H), 8.68 (d, 1H), 8.61 (d, 1H), 8.15 (dd, 1H), 6.91 (d, 1H), 5.31 (d, 1H), 3.59 (br d, 1H), 3.48-3.35 (m, 1H), 1.86 (s, 6H), 1.77 (d, 3H), 1.24 (t, 3H). LCMS R$_t$=2.292 min in 3.0 min chromatography, 10-80AB, MS ESI calcd. for C₁₈H₂₁F₃N₅O₂[M+H]⁺ 395.16, found 396.2.

Example I-6. Syntheses of Compound I-9 and I-10: (R)-3-(1-methoxyethyl)-6-(6-((1,1,1-trifluoro-2-methylpropan-2-yl)oxy)pyridin-3-yl)-[1,2,4]triazolo[4,3-a]pyrazine & (S)-3-(1-methoxyethyl)-6-(6-((1,1,1-trifluoro-2-methylpropan-2-yl)oxy)pyridin-3-yl)-[1,2,4]triazolo[4,3-a]pyrazine Note stereochemistry is randomly assigned.

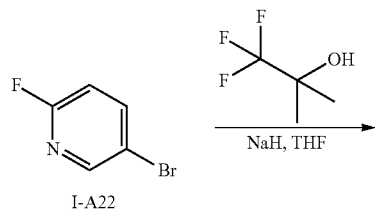

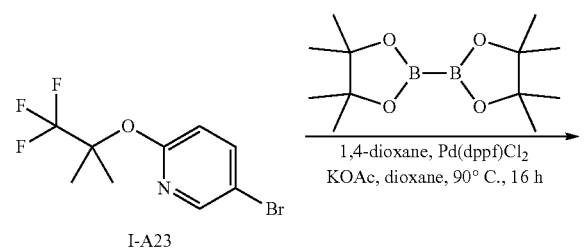

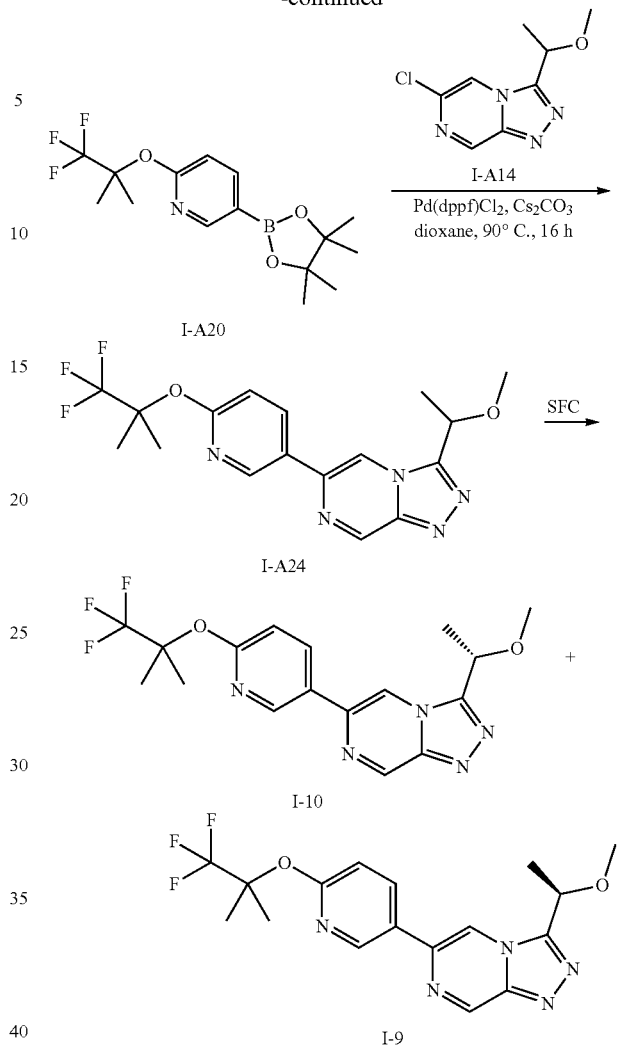

I-A23: 5-bromo-2-(2,2,2-trifluoro-1,1-dimethyl-ethoxy)pyridine

To a solution of 1,1,1-trifluoro-2-methyl-propan-2-ol (5.46 g, 42.6 mmol) in THF (80 mL) was added NaH (1.7 g, 42.6 mmol) (60% in oil) in portions at 0° C. After stirring at 25° C. for 30 minutes, 5-bromo-2-fluoro-pyridine (5.0 g, 28.4 mmol) was added. After stirring at 80° C. for another 48 hours, the mixture was cooled to 25° C. and quenched with H₂O (100 mL). The aqueous layer was extracted with EtOAc (50 mL×2). The combined organic layers were washed with brine (100 mL), dried over anhydrous Na₂SO₄, filtered, and concentrated. The crude product was purified by column chromatography on silica pad (0 to 2% of EtOAc in PE) to give the product (4.2 g, 14.8 mmol, 52% yield) as an oil. ¹H NMR (400 MHz, CDCl₃) δ$_H$=8.17 (d, 1H), 7.66 (dd, 1H), 6.68 (d, 1H), 1.77 (d, 6H).

I-A20: 5-(4,4,5,5-tetramethyl-1,3,2-dioxaborolan-2-yl)-2-(2,2,2-trifluoro-1,1-dimethyl-ethoxy)pyridine A mixture of 4,4,5,5-tetramethyl-2-(4,4,5,5-tetramethyl-1,3,2-dioxaborolan-2-yl)-1,3,2-dioxaborolane (5.63 g, 22.18 mmol), 5-bromo-2-(2,2,2-trifluoro-1,1-dimethyl-ethoxy)

pyridine (4.2 g, 14.8 mmol), KOAc (2.9 g, 29.6 mmol) and Pd(dppf)Cl$_2$ (1.08 g, 1.48 mmol) in 1,4-dioxane (70 mL) was stirred at 80° C. for 16 hours under N$_2$ atmosphere. After cooling to 25° C., the reaction was concentrated and diluted with H$_2$O (100 mL), then extracted with EtOAc (50 mL×3). The combined organic phase was washed with brine (200 mL), dried over Na$_2$SO$_4$, filtered, and concentrated to give the crude product, which was purified with flash chromatography on silica gel (EtOAc in PE=0% to 2%) to give the product (3.2 g, 7.73 mmol, 52% yield) as a solid. $^1$H NMR (400 MHz, CDCl$_3$) δ$_H$=8.51 (d, 1H), 7.94 (dd, 1H), 6.74 (dd, 1H), 1.82 (d, 6H), 1.34 (s, 12H).

Compound I-9 & I-10: (R)-3-(1-methoxyethyl)-6-(6-((1,1,1-trifluoro-2-methylpropan-2-yl)oxy)pyridin-3-yl)-[1,2,4]triazolo[4,3-a]pyrazine & (S)-3-(1-methoxyethyl)-6-(6-((1,1,1-trifluoro-2-methylpropan-2-yl)oxy)pyridin-3-yl)-[1,2,4]triazolo[4,3-a]pyrazine To a mixture of 6-chloro-3-(1-methoxyethyl)-[1,2,4]triazolo[4,3-a]pyrazine (300 mg, 1.41 mmol) and 5-(4,4,5,5-tetramethyl-1,3,2-dioxaborolan-2-yl)-2-(2,2,2-trifluoro-1,1-dimethyl-ethoxy)pyridine (513.9 mg, 1.55 mmol) and Cs$_2$CO$_3$ (919.3 mg, 2.82 mmol) in 1,4-dioxane (15 mL) and water (1.5 mL) was added Pd(dppf)Cl$_2$ (103.2 mg, 0.14 mmol) under N$_2$. After stirring at 90° C. for 16 hours, the mixture was filtered and water (30 mL) was added. The aqueous layer was extracted with EtOAc (20 mL×2). The combined organic layers were washed with brine (50 mL), dried over anhydrous Na$_2$SO$_4$, filtered, and concentrated. The residue was purified by flash column chromatography (0 to 50% of EtOAc in PE) to give the product (120 mg, 0.25 mmol) as a crude product, which was purified by SFC (DAICEL CHIRALPAK AD (250 mm×30 mm, 10 μm); A: CO$_2$ and B=EtOH 0.1% NH$_3$·H$_2$O; 20% B; 100% B; 60 mL/min; 80 injections) to afford (S)-3-(1-methoxyethyl)-6-(6-((1,1,1-trifluoro-2-methylpropan-2-yl)oxy)pyridin-3-yl)-[1,2,4]triazolo[4,3-a]pyrazine (15 mg, 0.04 mmol) as a solid and (R)-3-(1-methoxyethyl)-6-(6-((1,1,1-trifluoro-2-methylpropan-2-yl)oxy)pyridin-3-yl)-[1,2,4]triazolo[4,3-a]pyrazine (17.1 mg, 0.04 mmol) as a solid.

Compound I-9 $^1$H NMR (400 MHz, CDCl$_3$) δ$_H$=9.42 (d, 1H), 8.69 (d, 1H), 8.54 (d, 1H), 8.16 (dd, 1H), 6.91 (d, 1H), 5.22 (q, 1H), 3.36 (s, 3H), 1.85 (s, 6H), 1.77 (d, 3H). LCMS R$_t$=1.003 min in 1.5 min chromatography, 5-95AB, MS ESI calcd. for C$_{17}$H$_{19}$F$_3$N$_5$O$_2$[M+H]$^+$ 382.2, found 382.2. Compound I-10 $^1$H NMR (400 MHz, CDCl$_3$) δ$_H$=9.42 (d, 1H), 8.70 (d, 1H), 8.55 (d, 1H), 8.16 (dd, 1H), 6.91 (d, 1H), 5.22 (q, 1H), 3.36 (s, 3H), 1.86 (s, 6H), 1.78 (d, 3H). LCMS R$_t$=0.994 min in 1.5 min chromatography, 5-95AB, MS ESI calcd. for C$_{17}$H$_{19}$F$_3$N$_5$O$_2$ [M+H]$^+$ 382.2, found 382.2.

Example I-7. Synthesis of Compound I-11: (S)-3-(1-ethoxyethyl)-6-(6-(1-(trifluoromethyl)cyclobutoxy)pyridin-3-yl)-[1,2,4]triazolo[4,3-a]pyrazine

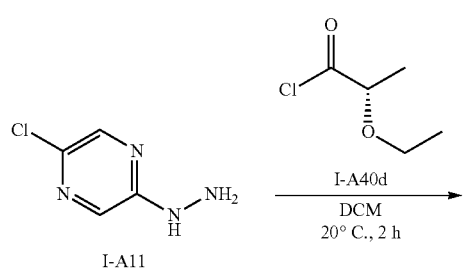

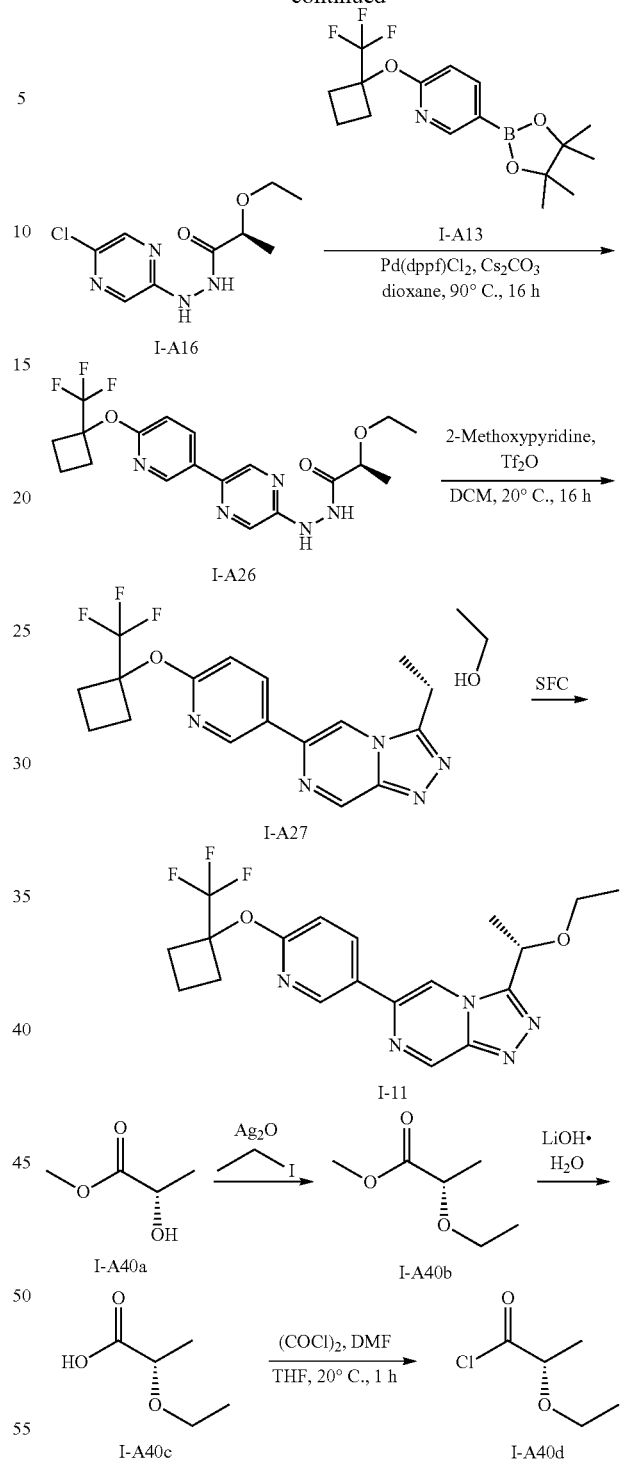

I-A40b: (S)-2-ethoxypropanoate

To a solution of iodoethane (45.0 g, 288.2 mmol), Ag$_2$O (66.8 g, 288.2 mmol) in Et$_2$O (300 mL) under N$_2$, shielded from the light was added methyl (S)-(−)-lactate (13.8 mL, 144.1 mmol). The reaction mixture was stirred at 20° C. for 16 hours under N$_2$. Then the reaction mixture was filtered, and the filter cake was washed with DCM. The filtrate was concentrated to give methyl (S)-2-ethoxypropanoate (22 g, 164.8 mmol, 50% yield) as an oil. 1H NMR (400 MHz, CDCl$_3$) $\delta_H$=4.01-3.94 (m, 1H), 3.75 (s, 3H), 3.52-3.35 (m, 1H), 1.43-1.39 (m, 4H), 1.25-1.18 (m, 3H).

I-A40c: (S)-2-ethoxypropanoic acid

To a solution of methyl (2S)-2-ethoxypropanoate (22 g, 166.5 mmol) in THF/MeOH/H$_2$O (350 mL), was added LiOH·H$_2$O (39.9 g, 1664.7 mmol). After stirring at 20° C. for 4 hours, HCl (2 M) (500 mL) was added, and the aqueous phase was extracted with DCM (2×200 mL). The combined organic phase was concentrated to give (S)-2-ethoxypropanoic acid (19 g, 159.2 mmol, 96% yield) as an oil. $^1$H NMR (400 MHz, CDCl$_3$) $\delta_H$=4.05-3.95 (m, 1H), 3.68-3.48 (m, 2H), 1.48-1.42 (m, 3H), 1.22-1.29 (m, 3H).

I-A40d: (S)-2-ethoxypropanoyl chloride

To a solution of 2-ethoxypropanoic acid (4.2 g, 35.6 mmol) in THF (80 mL) was added oxalyl chloride (5.42 g, 42.7 mmol) and DMF (1.0 mL, 35.6 mmol). The mixture was stirred at 25° C. for 1 hour. The solution was used for the next step directly without further purification.

I-A16: (S)—N'-(5-chloropyrazin-2-yl)-2-ethoxypropanehydrazide

To a solution of (S)-2-ethoxypropanoyl chloride (4.82 g, 35.3 mmol) in THF (80 mL) was added (5-chloropyrazin-2-yl)hydrazine (3.0 g, 20.8 mmol) at 0° C. After stirring at 25° C. for 1 hour, water (100 mL) was added to the mixture, and the aqueous phase was extracted with DCM (100 mL×2). The combined organic phase was washed with brine (200 mL), dried over anhydrous Na$_2$SO$_4$, filtered, and concentrated to give the crude product (6.2 g) as a solid, which was triturated from (PE:EtOAc=6:1, 60 ml) at 25° C. to give to give N'-(5-chloropyrazin-2-yl)-2-ethoxy-propanehydrazide (3.3 g, 13.5 mmol, 53% yield) as a solid. $^1$H NMR (400 MHz, CDCl$_3$) $\delta_H$=8.53 (s, 1H), 8.31-8.06 (m, 1H), 7.89 (s, 1H), 6.97 (br s, 1H), 4.04 (q, 1H), 3.80-3.47 (m, 2H), 1.45 (d, 3H), 1.32-1.23 (m, 3H).

I-A26: (S)-2-ethoxy-N'-(5-(6-(1-(trifluoromethyl)cyclobutoxy)pyridin-3-yl)pyrazin-2-yl)propanehydrazide To a mixture of 5-(4,4,5,5-tetramethyl-1,3,2-dioxaborolan-2-yl)-2-[1-(trifluoromethyl) cyclobutoxy]pyridine (400 mg, 1.17 mmol) and N'-(5-chloropyrazin-2-yl)-2-ethoxypropanehydrazide (313.7 mg, 1.28 mmol) and Cs$_2$CO$_3$ (759.6 mg, 2.33 mmol) in 1,4-dioxane (10 mL) and water (1 mL) was added Pd(dppf)Cl$_2$ (85.3 mg, 0.12 mmol) under N$_2$. After stirring at 90° C. for 16 hours, the mixture was filtered water (50 ml) was added. The aqueous layer was extracted with EtOAc (30 mL×3). The combined organic layers were washed with brine (100 mL), dried over anhydrous Na$_2$SO$_4$, filtered, and concentrated to afford the product (1.0 g) as a solid, which was used for the next step directly without further purification.

Compound I-11: (S)-3-(1-ethoxyethyl)-6-(6-(1-(trifluoromethyl)cyclobutoxy)pyridin-3-yl)-[1,2,4]triazolo[4,3-a]pyrazine To a mixture of (S)-2-ethoxy-N'-(5-(6-(1-(trifluoromethyl)cyclobutoxy)pyridin-3-yl) pyrazin-2-yl)propanehydrazide (1.0 g, 2.35 mmol) in DCM (15 mL) was added 2-methoxypyridine (0.54 g, 4.94 mmol) and Tf$_2$O (0.66 g, 2.35 mmol). After stirring at 20° C. for 16 hours, the mixture was diluted with water (30 mL) and extracted with EtOAc (30 mL×2). The combined organic phase was washed with saturated NaHCO$_3$ aqueous solution (30 mL), brine (30 mL), dried over anhydrous Na$_2$SO$_4$, filtered, and concentrated. The residue was purified by flash column chromatography (0 to 40% of EtOAc in PE) to give crude product, which was purified by prep-HPLC (Phenomenex Gemini-NX 80×30 mm, 3 μm) Mobile phase: A: water (10 mM NH$_4$HCO$_3$), B: acetonitrile, Gradient: from 53% to 83% B in 9 min, then 100% of B for 1.5 min; 30 mL/min, to give (S)-3-(1-ethoxyethyl)-6-(6-(1-(trifluoromethyl)cyclobutoxy)pyridin-3-yl)-[1,2,4]triazolo[4,3-a]pyrazine (55 mg, 0.14 mmol) as impure product. The impure product (55 mg, 0.14 mmol) was further purified by SFC (DAICEL CHIRALPAK AD (250 mm×30 mm, 10 μm) A: CO$_2$ and B=EtOH 0.1% NH$_3$·H$_2$O; Gradient: from 20% B to 100% B; 60 mL/min; 70 injections); to give the product (34.4 mg, 0.08 mmol, 63% yield) as a solid. $^1$H NMR (400 MHz, CDCl$_3$) $\delta_H$=9.41 (d, 1H), 8.69 (d, 1H), 8.62 (d, 1H), 8.19 (dd, 1H), 6.92 (d, 1H), 5.31 (q, 1H), 3.70-3.51 (m, 1H), 3.48-3.32 (m, 1H), 2.98-2.86 (m, 2H), 2.76-2.65 (m, 2H), 2.10-1.90 (m, 2H), 1.76 (d, 3H), 1.24 (t, 3H). LCMS R$_t$=1.033 min in 1.5 min chromatography, 5-95AB, MS ESI calcd. for C$_{19}$H$_{21}$F$_3$N$_5$O$_2$[M+H]$^+$ 408.3, found 408.3.

Example I-8. Synthesis of Compound I-12: 6-[5-fluoro-6-(2,2,2-trifluoro-1,1-dimethyl-ethoxy)-3-pyridyl]-3-[(1S)-1-ethoxyethyl]-[1,2,4]triazolo[4,3-a]pyrazine

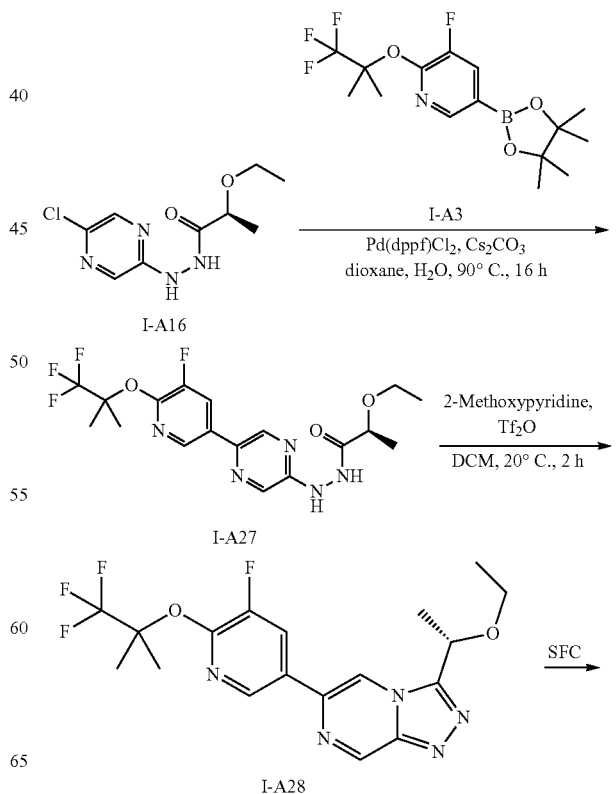

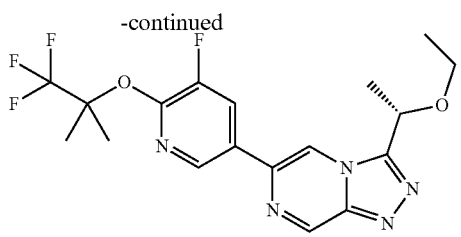

I-12

I-A27: (S)-2-ethoxy-N'-(5-(5-fluoro-6-((1,1,1-trifluoro-2-methylpropan-2-yl)oxy)pyridin-3-yl)pyrazin-2-yl)propanehydrazide To a mixture of (S)—N'-(5-chloropyrazin-2-yl)-2-ethoxypropanehydrazide (353.29 mg, 1.44 mmol) (353.3 mg, 1.44 mmol) and 3-fluoro-5-(4,4,5,5-tetramethyl-1,3,2-dioxaborolan-2-yl)-2-(2,2,2-trifluoro-1,1-dimethyl-ethoxy)pyridine (500 mg, 1.43 mmol) and $Cs_2CO_3$ (933.2 mg, 2.86 mmol) in 1,4-dioxane (5 mL) and water (0.50 mL) was added $Pd(dppf)Cl_2$ (104.8 mg, 0.14 mmol) under $N_2$. The mixture was stirred at 90° C. for 16 hours. The mixture was filtered, and the filtrate was concentrated to remove dioxane. The aqueous layer was extracted with EtOAc (30 mL×3). The combined organic layers were washed with brine (30 mL), dried over anhydrous $Na_2SO_4$, filtered, and concentrated to afford the product (617.8 mg, 1.43 mmol, 100% yield) as a solid. LCMS $R_t$=0.944 min in 1.5 min chromatography, 5-95AB, MS ESI calcd. for $C_{18}H_{22}F_4N_5O_3$ [M+H]$^+$ 432.1, found 432.1.

I-A28: 3-(1-ethoxyethyl)-6-[5-fluoro-6-(2,2,2-trifluoro-1,1-dimethyl-ethoxy)-3-pyridyl]-[1,2,4]triazolo[4,3-a]pyrazine To a mixture of (S)-2-ethoxy-N'-(5-(5-fluoro-6-((1,1,1-trifluoro-2-methylpropan-2-yl)oxy)pyridin-3-yl)pyrazin-2-yl)propanehydrazide (600 mg, 1.39 mmol) in DCM (2 mL) was added 2-methoxypyridine (607.2 mg, 5.56 mmol) and $Tf_2O$ (0.47 mL, 2.78 mmol). The mixture was stirred at 20° C. under $N_2$ for 2 hours, quenched with water (5 mL), extracted with DCM (5 mL×2), dried over anhydrous $Na_2SO_4$, filtered, and concentrated. The residue was purified by silica gel chromatography (EtOAc in PE=30% to 50%) to afford the product (220 mg, 0.53 mmol, 38% yield) as a solid. LCMS $R_t$=0.946 min in 1.5 min chromatography, 5-95AB, MS ESI calcd. for $C_{18}H_{20}F_4N_5O_2$ [M+H]$^+$ 414.0, found 414.0.

Compound I-12

(S)-3-(1-ethoxyethyl)-6-(5-fluoro-6-((1,1,1-trifluoro-2-methylpropan-2-yl)oxy)pyridin-3-yl)-[1,2,4]triazolo[4,3-a]pyrazine The residue of (S)-3-(1-ethoxyethyl)-6-(5-fluoro-6-((1,1,1-trifluoro-2-methylpropan-2-yl)oxy)pyridin-3-yl)-[1,2,4]triazolo[4,3-a]pyrazine (100 mg, 0.24 mmol) was purified by SFC (DAICEL CHIRALCEL OD-H (250 mm×30 mm, 5 µm); A: $CO_2$ and B=EtOH 0.1% $NH_3·H_2O$; 25% B; 60 mL/min); to the product (13.1 mg, 0.03 mmol, 12% yield) as a solid and as an oil. $^1$H NMR (400 MHz, $CDCl_3$) $\delta_H$=9.40 (d, 1H), 8.65 (d, 1H), 8.46 (d, 1H), 8.03-7.95 (m, 1H), 5.36-5.27 (m, 1H), 3.66-3.56 (m, 1H), 3.47-3.35 (m, 1H), 1.87 (s, 6H), 1.77 (d, 3H), 1.25 (t, 3H) LCMS $R_t$=1.287 min in 2.0 min chromatography, 10-80AB, MS ESI calcd for $C_{18}H_{20}F_4N_5O_2$ [M+H]$^+$ 414.1, found 414.1.

Example I-9. Synthesis of Compound I-13: (R)-3-(1-ethoxyethyl)-6-(5-fluoro-6-((1,1,1-trifluoro-2-methylpropan-2-yl)oxy)pyridin-3-yl)-[1,2,4]triazolo[4,3-a]pyrazine

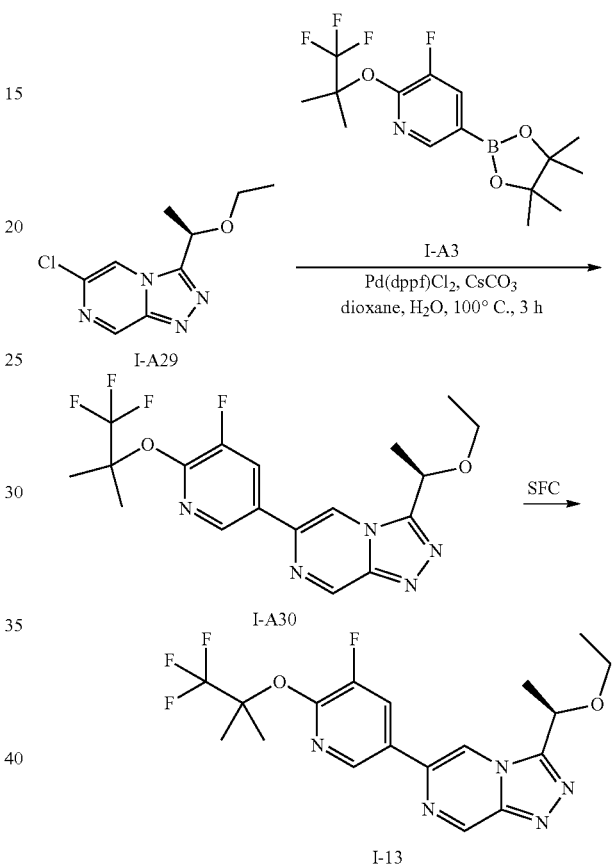

I-A30: (R)-3-[1-ethoxyethyl]-6-[5-fluoro-6-(2,2,2-trifluoro-1,1-dimethyl-ethoxy)-3-pyridyl]-[1,2,4]triazolo[4,3-a]pyrazine To a mixture of (R)-6-chloro-3-(1-ethoxyethyl)-[1,2,4]triazolo[4,3-a]pyrazine (200 mg, 0.88 mmol) and 3-fluoro-5-(4,4,5,5-tetramethyl-1,3,2-dioxaborolan-2-yl)-2-(2,2,2-trifluoro-1,1-dimethyl-ethoxy)pyridine (400.5 mg, 1.15 mmol) and $Cs_2CO_3$ (575.0 mg, 1.76 mmol) in 1,4-dioxane (5 mL) was added $Pd(dppf)Cl_2$ (83.9 mg, 0.11 mmol) under $N_2$. The mixture was stirred at 100° C. for 3 hours. After cooling, the mixture was filtered, and the filtrate was concentrated to remove dioxane. The aqueous layer was extracted with EtOAc (30 mL×3). The combined organic layers were washed with brine (30 mL), dried over anhydrous $Na_2SO_4$, filtered, and concentrated. The residue was purified by silica gel chromatography (PE:EtOAc=1:1) to afford the product (200 mg, 0.48 mmol, 55% yield) as a solid. LCMS $R_t$=1.011 min in 1.5 min chromatography, 5-95AB, MS ESI calcd. for $C_{18}H_{20}F_4N_5O_2$ [M+H]$^+$ 414.0, found 414.0.

Compound I-13: (R)-3-(1-ethoxyethyl)-6-(5-fluoro-6-((1,1,1-trifluoro-2-methylpropan-2-yl) oxy)pyridin-3-yl)-[1,2,4]triazolo[4,3-a]pyrazine The residue was purified by SFC (DAICEL CHIRALCEL OD-H (250 mm×30 mm, 5 μm); A: $CO_2$ and B=EtOH 0.1% $NH_3·H_2O$); 15% B; 60 mL/min; to afford the product (97.8 mg, 0.24 mmol, 49% yield) as a solid. $^1$H NMR (400 MHz, $CDCl_3$) $\delta_H$=9.41 (d, 1H), 8.65 (d, 1H), 8.46 (d, 1H), 8.03-7.94 (m, 1H), 5.37-5.25 (m, 1H), 3.65-3.56 (m, 1H), 3.46-3.37 (m, 1H), 1.87 (s, 6H), 1.77 (d, 3H), 1.25 (t, 3H) LCMS $R_t$=1.007 min in 1.5 min chromatography, 5-95AB, MS ESI calcd for $C_{18}H_{20}F_4N_5O_2$ [M+H]$^+$ 414.0, found 414.0.

Example I-10. Synthesis of Compound I-14: (R)-3-(1-ethoxyethyl)-6-(5-fluoro-6-(1-(trifluoromethyl)cyclobutoxy)pyridin-3-yl)-[1,2,4]triazolo[4,3-a]pyrazine

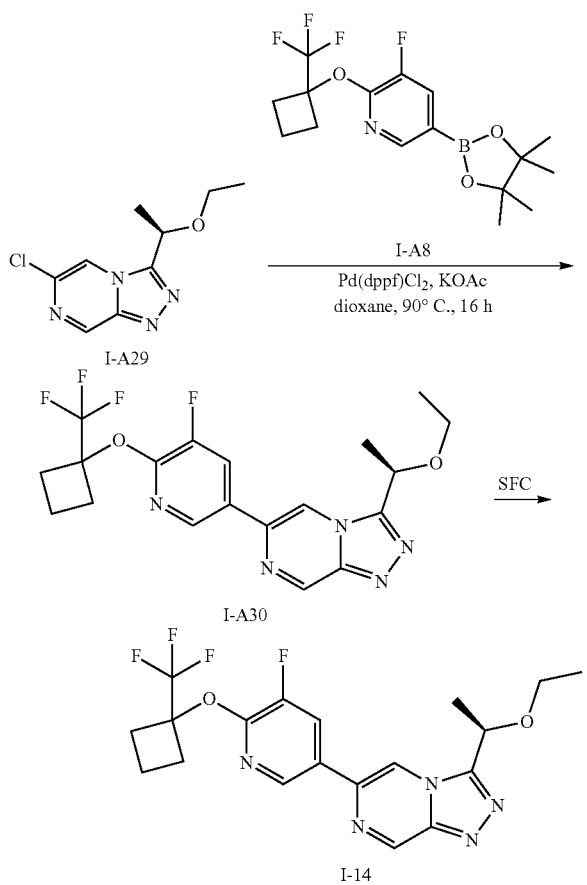

To a mixture of 3-fluoro-5-(4,4,5,5-tetramethyl-1,3,2-dioxaborolan-2-yl)-2-[1-(trifluoromethyl)cyclobutoxy]pyridine (350.5 mg, 0.97 mmol) and 6-chloro-3-[(1R)-1-ethoxyethyl]-[1,2,4]triazolo[4,3-a]pyrazine (200 mg, 0.88 mmol) and $Cs_2CO_3$ (575.0 mg, 1.76 mmol) in 1,4-dioxane (10 mL) and water (1 mL) was added Pd(dppf)$Cl_2$ (64.6 mg, 0.09 mmol) under $N_2$. The mixture was stirred at 90° C. for 3 hours. The mixture was filtered, and the filtrate was concentrated to remove dioxane. The aqueous layer was extracted with EtOAc (30 mL×3). The combined organic layers were washed with brine (30 mL), dried over anhydrous $Na_2SO_4$, filtered, and concentrated. The crude was purified by flash column (0 to 30% to 50% of EtOAc in PE) to give the product (200 mg, 0.47 mmol, 53% yield) as a solid. $^1$H NMR (400 MHz, $CDCl_3$) $\delta_H$=9.40 (d, 1H), 8.65 (d, 1H), 8.44 (d, 1H), 8.02 (dd, 1H), 5.40-5.21 (m, 1H), 3.67-3.55 (m, 1H), 3.49-3.27 (m, 1H), 2.98-2.85 (m, 2H), 2.82-2.68 (m, 2H), 2.11-1.89 (m, 2H), 1.76 (d, 3H), 1.24 (t, 3H).

The above solid (200 mg) was purified by SFC (DAICEL CHIRALCEL OJ-H (250 mm×30 mm, 5 μm); A: $CO_2$ B=EtOH 0.1% $NH_3·H_2O$, 15% B; 60 mL/min; to give the product (124.0 mg, 0.29 mmol) as a solid. $^1$H NMR (400 MHz, $CDCl_3$) $\delta_H$=9.40 (d, 1H), 8.65 (d, 1H), 8.44 (d, 1H), 8.02 (dd, 1H), 5.31 (q, 1H), 3.66-3.53 (m, 1H), 3.41 (qd, 1H), 2.99-2.84 (m, 2H), 2.81-2.69 (m, 2H), 2.12-1.92 (m, 2H), 1.76 (d, 3H), 1.24 (t, 3H). LCMS $R_t$=1.30 min in 2.0 min chromatography, 10-80AB, MS ESI calcd. for $C_{19}H_{20}F_4N_5O_2$ [M+H]$^+$ 426.1, found 426.1.

Example I-11. Syntheses of Compounds I-15, I-16, I-17 & I-18: 6-(6-((R)-1-cyclopropyl-2,2,2-trifluoroethoxy)-5-fluoropyridin-3-yl)-3-((R)-1-methoxyethyl)-[1,2,4]triazolo[4,3-a]pyrazine & 6-(6-((R)-1-cyclopropyl-2,2,2-trifluoroethoxy)-5-fluoropyridin-3-yl)-3-((S)-1-methoxyethyl)-[1,2,4]triazolo[4,3-a]pyrazine & 6-(6-((S)-1-cyclopropyl-2,2,2-trifluoroethoxy)-5-fluoropyridin-3-yl)-3-((R)-1-methoxyethyl)-[1,2,4]triazolo[4,3-a]pyrazine & 6-(6-((S)-1-cyclopropyl-2,2,2-trifluoroethoxy)-5-fluoropyridin-3-yl)-3-((S)-1-methoxyethyl)-[1,2,4]triazolo[4,3-a]pyrazine Note stereochemistry is randomly assigned

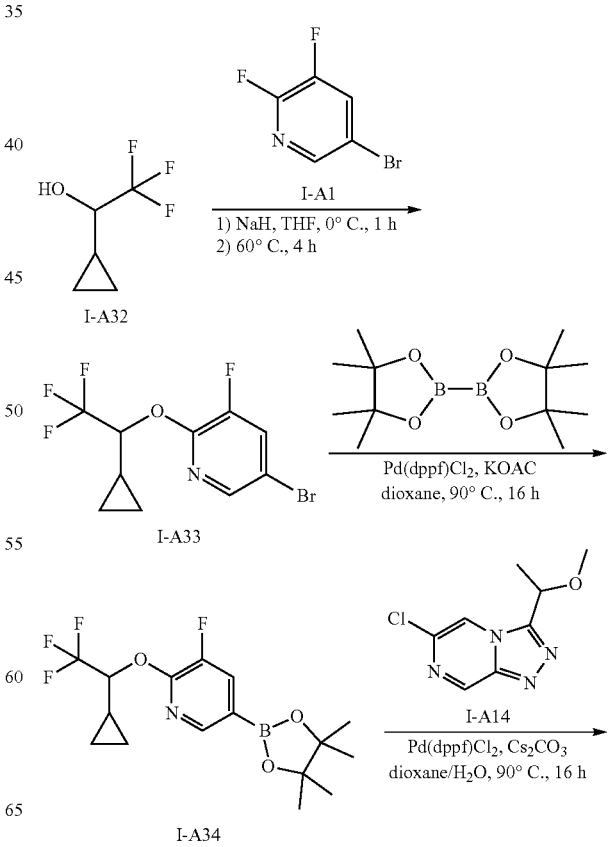

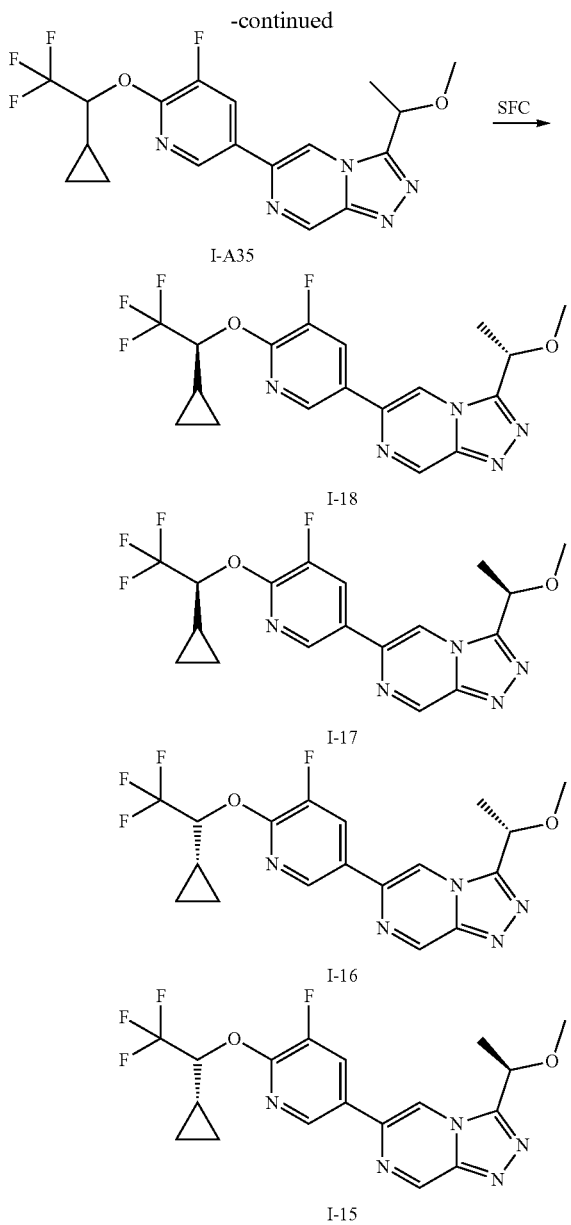

I-A33: 5-bromo-2-(1-cyclopropyl-2, 2, 2-trifluoro-ethoxy)-3-fluoropyridine

To a solution of NaH (342.6 mg, 8.57 mmol) in THF (10 mL) was added 1-cyclopropyl-2, 2, 2-trifluoro-ethanol (1.20 g, 8.57 mmol) in portions at 0° C. After stirring at 0° C. for 1 hour, 5-bromo-2, 3-difluoro-pyridine (1.66 g, 8.57 mmol) was added. The mixture was stirred at 25° C. for 16 hours. The mixture was quenched with $H_2O$ (10 mL) and extracted with EtOAc (10 mL×3). The combined organic layers were washed with brine (50 mL), dried over anhydrous $Na_2SO_4$, filtered, and concentrated. The residue was purified by flash column chromatography (0% of EtOAc in PE) to give the product (2.10 g, 6.02 mmol, 70% yield) as an oil. $^1$H NMR (400 MHz, CDCl$_3$) $\delta_H$=7.93 (d, 1H), 7.55 (dd, 8.8 Hz, 1H), 5.32-5.13 (m, 1H), 1.37-1.29 (m, 1H), 0.86 (br d, 1H), 0.80-0.73 (m, 1H), 0.62-0.55 (m, 2H).

I-A34: 2-(1-cyclopropyl-2, 2, 2-trifluoroethoxy)-3-fluoro-5-(4, 4, 5, 5-tetramethyl-1, 3, 2-dioxaborolan-2-yl) pyridine A mixture of 5-bromo-2-(1-cyclopropyl-2,2,2-trifluoro-ethoxy)-3-fluoro-pyridine (2.5 g, 7.96 mmol), 4,4,5,5-tetramethyl-2-(4,4,5,5-tetramethyl-1,3,2-dioxaborolan-2-yl)-1,3,2-dioxaborolane (3.03 g, 11.94 mmol), Pd(dppf)Cl$_2$ (582.4 mg, 0.80 mmol) and KOAc (1.56 g, 15.9 mmol) in 1,4-dioxane (15 mL) was stirred at 90° C. for 16 hours under $N_2$. The mixture was cooled to room temperature, filtered, and concentrated. The residue was purified by flash column chromatography (0 to 5% of EtOAc in PE) to give the product (3.70 g, 7.17 mmol, 90% yield) as an oil. $^1$H NMR (400 MHz, CDCl$_3$) $\delta_H$=8.20 (d, 1H), 7.69 (dd, 10.4 Hz, 1H), 5.47-5.33 (m, 1H), 1.33 (s, 12H), 1.26 (s, 2H), 0.78-0.71 (m, 1H), 0.64-0.59 (m, 2H).

I-A35: 6-(6-(1-cyclopropyl-2, 2, 2-trifluoroethoxy)-5-fluoropyridin-3-yl)-3-(1-methoxyethyl)-[1, 2, 4] triazolo [4, 3-a] pyrazine To a mixture of 2-(1-cyclopropyl-2,2,2-trifluoro-ethoxy)-3-fluoro-5-(4,4,5,5-tetramethyl-1,3,2-dioxaborolan-2-yl) pyridine (800 mg, 2.22 mmol) and 6-chloro-3-(1-methoxy-ethyl)-[1,2,4]triazolo[4,3-a]pyrazine (565.2 mg, 2.66 mmol) and Cs$_2$CO$_3$ (1443.4 mg, 4.43 mmol) in 1,4-dioxane (5 mL) and water (0.50 mL) was added Pd(dppf)Cl$_2$ (162.1 mg, 0.22 mmol) under $N_2$. The mixture was stirred at 90° C. for 16 hours. The mixture was filtered, and the filtrate was concentrated to remove dioxane. The aqueous layer was extracted with EtOAc (10 mL×3). The combined organic layers were washed with brine (30 mL), dried over anhydrous Na$_2$SO$_4$, filtered, and concentrated. The residue was purified by flash column chromatography (50 to 70% of EtOAc in PE) to give 500 mg of impure product, which was further purified by pre-HPLC (Phenomenex Gemini-NX (80×30 mm, 3 μm; A=water (10 mM NH$_4$HCO$_3$), B=acetonitrile; Gradient: from 49% to 79% of B) to give 6-[6-(1-cyclopropyl-2,2,2-trifluoro-ethoxy)-5-fluoro-3-pyridyl]-3-(1-methoxyethyl)-[1,2,4]triazolo[4,3-a]pyrazine (400 mg, 0.68 mmol, 80% yield) as an oil. $^1$H NMR (400 MHz, CDCl$_3$) $\delta_H$=9.41 (d, 1H), 8.57 (d, 1H), 8.49-8.38 (m, 1H), 8.12-7.95 (m, 1H), 5.42-5.32 (m, 1H), 5.26-5.17 (m, 1H), 3.56 (s, 1H), 3.36 (s, 3H), 1.78 (d, 3H), 1.43-1.33 (m, 1H), 0.83-0.74 (m, 1H), 0.64-0.55 (m, 2H).

Compounds I-15, I-16, I-17 & I-18: 6-(6-((R)-1-cyclopropyl-2,2,2-trifluoroethoxy)-5-fluoropyridin-3-yl)-3-((R)-1-methoxyethyl)-[1,2,4]triazolo[4,3-a]pyrazine & 6-(6-((R)-1-cyclopropyl-2,2,2-trifluoroethoxy)-5-fluoropyridin-3-yl)-3-((S)-1-methoxyethyl)-[1,2,4]triazolo[4,3-a]pyrazine & 6-(6-((S)-1-cyclopropyl-2,2,2-trifluoroethoxy)-5-fluoropyridin-3-yl)-3-((R)-1-methoxyethyl)-[1,2,4]triazolo[4,3-a]pyrazine & 6-(6-((S)-1-cyclopropyl-2,2,2-trifluoroethoxy)-5-fluoropyridin-3-yl)-3-((S)-1-methoxyethyl)-[1,2,4]triazolo[4,3-a]pyrazine 6-[6-(1-cyclopropyl-2,2,2-trifluoro-ethoxy)-5-fluoro-3-pyridyl]-3-(1-methoxyethyl)-[1,2,4]triazolo[4,3-a]pyrazine (400 mg, 0.97 mmol) was purified by SFC (DAICALPAK AD (250 mm×30 mm, 10 μm); A: CO$_2$ and B=EtOH 0.1% NH$_3$·H$_2$O; 15% B) to give 6-(6-((S)-1-cyclopropyl-2,2,2-trifluoroethoxy)-5-fluoropyridin-3-yl)-3-((S)-1-methoxyethyl)-[1,2,4]triazolo[4,3-a]pyrazine (Rt of Peak 4=2.737 min) (80 mg) and a mixture of Peak 1, Peak 2 and Peak 3 (270 mg) both as an oil.

A mixture of Peak 1, Peak 2 and Peak 3 (270 mg, 0.66 mmol) was purified by SFC (DAICALPAK AD (250 mm×10 mm, 10 μm); A: CO₂ and B=MeOH 0.1% NH₃·H₂O; 20% B); to give 6-(6-((R)-1-cyclopropyl-2,2,2-trifluoroethoxy)-5-fluoropyridin-3-yl)-3-((R)-1-methoxyethyl)-[1,2,4] triazolo[4,3-a]pyrazine (Rt of Peak 1=2.551 min) (30 mg, 0.07 mmol, 10% yield) and a mixture of Peak 2 and Peak 3 (120 mg, 0.29 mmol) both as an oil.

A mixture of Peak 2 and Peak 3 (120 mg, 0.29 mmol) was purified by SFC (DAICALPAK AD (250 mm×30 mm, 10 μm); A: CO₂ and B=EtOH 0.1% NH₃·H₂O; 15% B); to give 6-(6-((R)-1-cyclopropyl-2,2,2-trifluoroethoxy)-5-fluoropyridin-3-yl)-3-((S)-1-methoxyethyl)-[1,2,4]triazolo[4,3-a] pyrazine (Rt of Peak 2=2.072 min) (50.0 mg, 0.12 mmol, 41.7% yield) and 6-(6-((S)-1-cyclopropyl-2,2,2-trifluoroethoxy)-5-fluoropyridin-3-yl)-3-((R)-1-methoxyethyl)-[1,2,4]triazolo[4,3-a]pyrazine (Rt of Peak 3=2.201 min) (50.0 mg, 0.12 mmol, 41.7% yield) both as an oil.

The above Peak 1 (30.0 mg, 0.07 mmol) was purified by prep-TLC (PE:EA=1:2) to give 6-(6-((R)-1-cyclopropyl-2, 2,2-trifluoroethoxy)-5-fluoropyridin-3-yl)-3-((R)-1-methoxyethyl)-[1,2,4]triazolo[4,3-a]pyrazine (Peak 1, Rt=2.551 min, 3.16 mg) as an oil.

The above Peak 2 (40.0 mg, 0.10 mmol) was purified by prep-TLC (PE:EA=1:2) to give 6-(6-((R)-1-cyclopropyl-2, 2,2-trifluoroethoxy)-5-fluoropyridin-3-yl)-3-((S)-1-methoxyethyl)-[1,2,4]triazolo[4,3-a]pyrazine (Peak 2, Rt=2.072 min, 15.1 mg) as an oil.

The above Peak 3 (40 mg, 0.10 mmol) was purified by prep-TLC (PE:EA=1:2) to give 6-(6-((S)-1-cyclopropyl-2, 2,2-trifluoroethoxy)-5-fluoropyridin-3-yl)-3-((R)-1-methoxyethyl)-[1,2,4]triazolo[4,3-a]pyrazine (Peak 3, Rt=2.201 min, 26.82 mg) as an oil.

The above Peak 4 (40.0 mg, 0.10 mmol) was purified by prep-TLC (PE:EA=1:2) to give 6-(6-((S)-1-cyclopropyl-2, 2,2-trifluoroethoxy)-5-fluoropyridin-3-yl)-3-((S)-1-methoxyethyl)-[1,2,4]triazolo[4,3-a]pyrazine (peak 4, Rt=2.737 min, 6.28 mg) as an oil.

Compound I-15: ¹H NMR (400 MHz, CDCl₃) $\delta_H$=9.40 (d, 1H), 8.57 (d, 1H), 8.43 (d, 1H), 8.07-7.96 (m, 1H), 5.43-5.29 (m, 1H), 5.25-5.15 (m, 1H), 3.36 (s, 3H), 1.77 (d, 3H), 1.40-1.32 (m, 1H), 0.83-0.75 (m, 1H), 0.68-0.59 (m, 3H). MS ESI calcd. for $C_{18}H_{18}F_4N_5O_2[M+H]^+$ 412.1

Compound I-16: ¹H NMR (400 MHz, CDCl₃) $\delta_H$=9.41 (d, 1H), 8.57 (d, 1H), 8.43 (d, 1H), 8.05-7.98 (m, 1H), 5.42-5.34 (m, 1H), 5.25-5.19 (m, 1H), 3.36 (s, 3H), 1.78 (d, 3H), 1.42-1.34 (m, 1H), 0.83-0.76 (m, 1H), 0.68-0.61 (m, 3H). MS ESI calcd. for $C_{18}H_{18}F_4N_5O_2[M+H]^+$ 412.1

Compound I-17: ¹H NMR (400 MHz, CDCl₃) $\delta_H$=9.41 (d, 1H), 8.57 (d, 1H), 8.43 (d, 1H), 8.07-6.98 (m, 1H), 5.43-5.33 (m, 1H), 5.25-5.17 (m, 1H), 3.36 (s, 3H), 1.77 (d, 3H), 1.41-1.32 (m, 1H), 0.83-0.75 (m, 1H), 0.69-0.61 (m, 3H). 0 MS ESI calcd. for $C_{18}H_{18}F_4N_5O_2[M+H]^+$ 412.1

Compound I-18: 1H NMR (400 MHz, CDCl₃) $\delta_H$=9.41 (s, 1H), 8.57 (s, 1H), 8.43 (br s, 1H), 8.02 (br d, 1H), 5.41-5.34 (m, 1H), 5.25-5.18 (m, 1H), 3.36 (s, 3H), 1.77 (br d, 3H), 1.42-1.32 (m, 1H), 0.83-0.75 (m, 1H), 0.68-0.58 (m, 3H). MS ESI calcd. for $C_{18}H_{18}F_4N_5O_2[M+H]^+$ 412.1, found 412.1

Example I-12. Synthesis of Compound I-19: (R)-3-(1-ethoxyethyl)-6-(6-((1,1,1-trifluoro-2-methylpropan-2-yl)oxy)pyridin-3-yl)-[1,2,4]triazolo[4,3-a] pyrazine

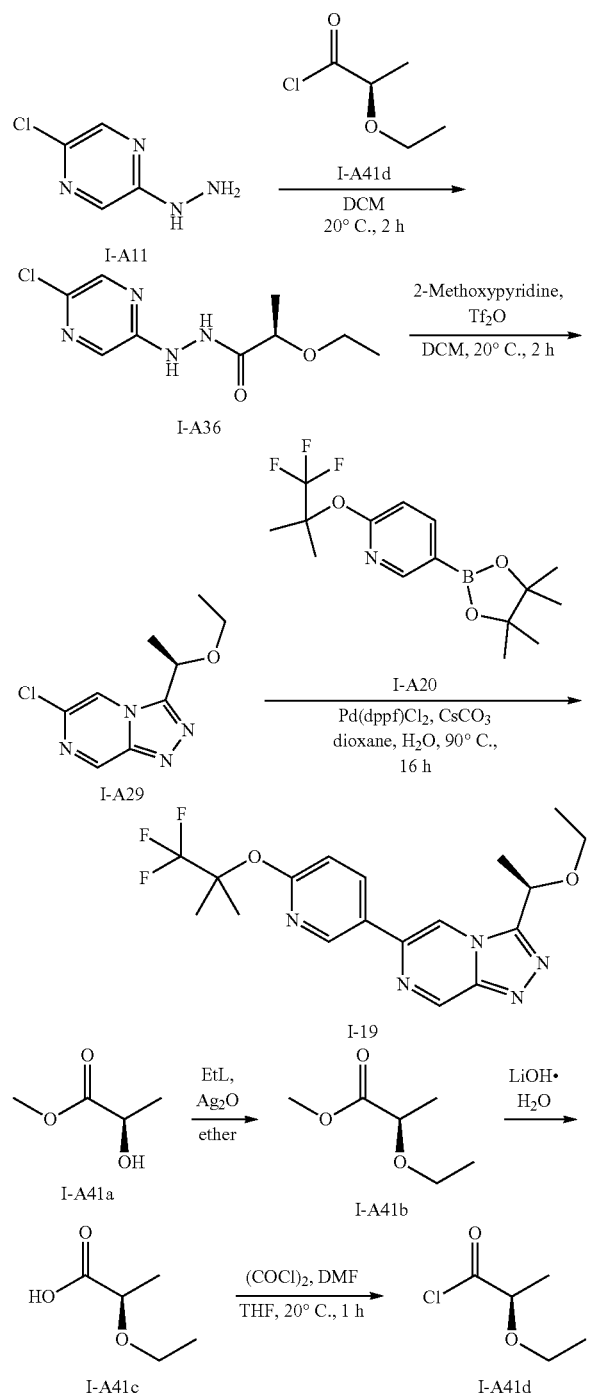

I-A41b: (R)-2-ethoxypropanoate

To a solution of Ag₂O (178.1 g, 768.5 mmol), methyl (2R)-2-hydroxypropanoate (40 g, 384.3 mmol) in ether (600 mL) under N₂, shielded from the light, was added iodoethane (62.1 mL, 768.5 mmol). After stirring at 20° C. for 12 hours under $N_2$, the reaction mixture was filtered, and the filter cake was washed with DCM (50 mL). The filtrate was concentrated to give methyl (R)-2-ethoxypropanoate (70 g, 524.4 mmol, crude) as an oil. 1H NMR (400 MHz, CDCl$_3$) $\delta_H$=4.40-4.24 (m, 3H), 3.86-3.71 (m, 3H), 3.66-3.39 (m, 1H), 1.45-1.41 (m, 5H).

I-A41c: (R)-2-ethoxypropanoic acid

To a solution of methyl (2R)-2-ethoxypropanoate (70.0 g, 529.7 mmol), in THF/MeOH/H$_2$O (700 mL), was added LiOH·H$_2$O (105.9 g, 2648.3 mmol). After stirring at 20° C. for 4 hours, HCl (2 M) (800 mL) was added, and the aqueous phase was extracted with DCM (2×400 mL). The combined organic phase was concentrated to give (R)-2-ethoxypropanoic acid (28.0 g, 234.7 mmol, 44.3% yield) as an oil. $^1$H NMR (400 MHz, CDCl$_3$) $\delta_H$=4.01-3.94 (m, 1H), 3.75 (s, 3H), 3.52-3.35 (m, 1H), 1.43-1.39 (m, 4H), 1.25-1.18 (m, 3H).

I-A41d: (R)-2-ethoxypropanoyl chloride

To a solution of (R)-2-ethoxypropanoic acid (4.0 g, 33.9 mmol) in THF (150 mL) was added oxalyl chloride (5.16 g, 40.6 mmol) and DMF (1.0 mL, 33.9 mmol). The mixture was stirred at 25° C. for 1 hour. The solution was used for the next step directly without further purification.

I-A36: (R)—N'-(5-chloropyrazin-2-yl)-2-ethoxypropanehydrazide

To a solution of (2R)-2-ethoxypropanoyl chloride (4.82 g, 35.3 mmol) in THF (80 mL) was added (5-chloropyrazin-2-yl)hydrazine (3.0 g, 20.8 mmol) at 0° C. After stirring at 25° C. for 1 hour, water (100 mL) was added to the mixture, and the aqueous phase was extracted with DCM (100 mL×2). The combined organic phase was washed with brine (200 mL), dried over anhydrous Na$_2$SO$_4$, filtered, and concentrated to give crude product as a solid. The crude product was triturated from (PE:EtOAc=6:1, 60 ml) at 25° C. to give the product (3.3 g, 13.5 mmol, 65% yield) as a solid. $^1$H NMR (400 MHz, CDCl$_3$) $\delta_H$=8.50 (s, 1H), 8.25-8.06 (m, 1H), 7.90 (s, 1H), 4.15-3.99 (m, 1H), 3.80-3.66 (m, 1H), 3.65-3.46 (m, 1H), 1.53-1.41 (m, 3H), 1.36-1.22 (m, 3H).

I-A29: (R)-6-chloro-3-(1-ethoxyethyl)-[1,2,4]triazolo[4,3-a]pyrazine

To a mixture of (R)—N'-(5-chloropyrazin-2-yl)-2-ethoxypropanehydrazide (3.3 g, 13.5 mmol) in DCM (30 mL) was added 2-methoxypyridine (5.89 g, 54.0 mmol) and Tf$_2$O (7.61 g, 27.0 mmol). After stirring at 20° C. for 2 hours, water (60 mL) was added to the mixture, and the aqueous phase was extracted with DCM (30 mL×2). The combined organic phase was washed with saturated NaHCO$_3$ aqueous solution (60 mL), brine (60 mL), dried over anhydrous Na$_2$SO$_4$, filtered, and concentrated. The residue was purified by flash column chromatography (0 to 40% of EtOAc in PE) to give (R)-6-chloro-3-(1-ethoxyethyl)-[1,2,4]triazolo[4,3-a]pyrazine (1.2 g, 5.02 mmol, 37% yield) as a solid. $^1$H NMR (400 MHz, CDCl$_3$) $\delta_H$=9.27-9.06 (m, 1H), 8.63-8.30 (m, 1H), 5.39-5.14 (m, 1H), 4.25-4.02 (m, 1H), 3.71-3.49 (m, 1H), 3.45-3.22 (m, 1H), 2.04 (s, 1H), 1.72 (br d, 3H), 1.29-1.18 (m, 4H).

Compound I-19: (R)-3-(1-ethoxyethyl)-6-(6-((1,1,1-trifluoro-2-methylpropan-2-yl)oxy)pyridin-3-yl)-[1,2,4]triazolo[4,3-a]pyrazine To a mixture of (R)-6-chloro-3-(1-ethoxyethyl)-[1,2,4]triazolo[4,3-a]pyrazine (200 mg, 0.88 mmol) and 5-(4,4,5,5-tetramethyl-1,3,2-dioxaborolan-2-yl)-2-(2,2,2-trifluoro-1,1-dimethyl-ethoxy)pyridine (321.4 mg, 0.97 mmol) and Cs$_2$CO$_3$ (575.0 mg, 1.76 mmol) in 1,4-dioxane (5 mL) and water (0.50 mL) was added Pd(dppf)Cl$_2$ (64.6 mg, 0.09 mmol) under N$_2$. After stirring at 90° C. for 2 hours, the mixture was filtered and poured into water (20 mL). The aqueous layer was extracted with EtOAc (20 mL×2). The combined organic layers were washed with brine (30 mL), dried over anhydrous Na$_2$SO$_4$, filtered, and concentrated. The residue was purified by flash column chromatography (0 to 70% of EtOAc in PE) to give 260 mg of impure product as a solid, which was further purified by prep-HPLC (Phenomenex Gemini-NX (80×30 mm, 3 μm); A: water 10 mM NH$_4$HCO$_3$ B: CH$_3$CN; Gradient: from 48% to 78% of B and hole 78% for 9 min then hold 100% of B for 1.5 min; 30 mL/min; 5 injections) to give the product (128.2 mg, 0.32 mmol, 49% yield) as a solid. $^1$H NMR (400 MHz, CDCl$_3$) $\delta_H$=9.41 (d, 1H), 8.68 (d, 1H), 8.61 (d, 1H), 8.18-8.10 (m, 1H), 6.91 (d, 1H), 5.34-5.25 (m, 1H), 3.69-3.52 (m, 1H), 3.48-3.31 (m, 1H), 1.86 (s, 6H), 1.76 (d, 3H), 1.24 (t, 3H). LCMS R$_t$=1.024 min in 1.5 min chromatography, 5-95AB, MS ESI calcd. for C$_{18}$H$_{21}$F$_3$N$_5$O$_2$[M+H]$^+$ 396.5, found 396.5.

Example I-13. Synthesis of Compound I-20: (R)-3-(1-ethoxyethyl)-6-(6-(1-(trifluoromethyl)cyclobutoxy)pyridin-3-yl)-[1,2,4]triazolo[4,3-a]pyrazine

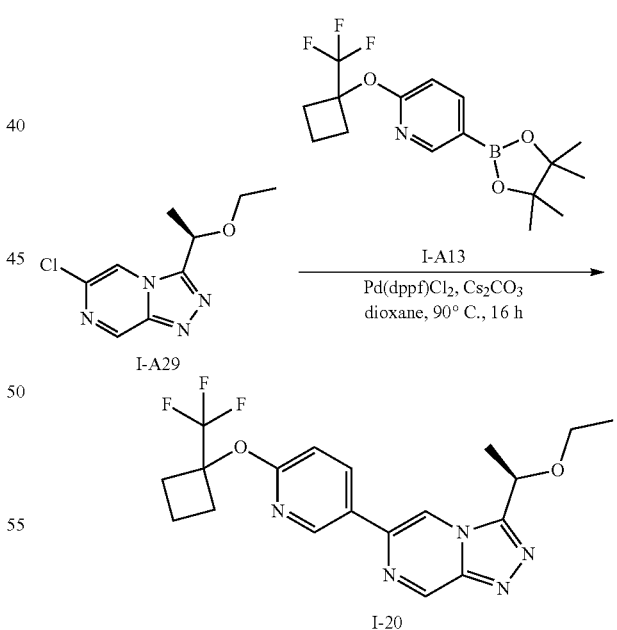

Compound I-20: (R)-3-(1-ethoxyethyl)-6-(6-(1-(trifluoromethyl)cyclobutoxy)pyridin-3-yl)-[1,2,4]triazolo[4,3-a]pyrazine To a mixture of (R)-6-chloro-3-(1-ethoxyethyl)-[1,2,4]triazolo[4,3-a]pyrazine (200 mg, 0.88 mmol) and 5-(4,4,5, 5-tetramethyl-1,3,2-dioxaborolan-2-yl)-2-[1-(trifluorom-ethyl) cyclobutoxy]pyridine (393.6 mg, 1.15 mmol) and Cs$_2$CO$_3$ (575.0 mg, 1.76 mmol) in 1,4-dioxane (10 mL) and water (1 mL) was added Pd(dppf)Cl$_2$ (64.6 mg, 0.09 mmol) under N$_2$. The mixture was stirred at 90° C. for 2 hours. The mixture was filtered and the filtrate was concentrated to remove dioxane. The aqueous layer was extracted with EtOAc (30 mL×3). The combined organic layers were washed with brine (30 mL), dried over anhydrous Na$_2$SO$_4$, filtered, and concentrated. The crude of was purified by SFC (DAICEL CHIRALCEL OD (250 mm×30 mm, 10 μm); A: CO$_2$ and B=EtOH 0.1% NH$_3$H$_2$O; 20% B); to give the product (190.5 mg, 0.46 mmol, 62% yield) as a solid. $^1$H NMR (400 MHz, CDCl$_3$) δ$_H$=9.49-9.33 (m, 1H), 8.74-8.57 (m, 2H), 8.27-8.15 (m, 1H), 6.99-6.87 (m, 1H), 5.37-5.24 (m, 1H), 3.59 (s, 1H), 3.47-3.33 (m, 1H), 3.01-2.84 (m, 2H), 2.78-2.63 (m, 2H), 2.10-1.87 (m, 2H), 1.76 (d, 3H), 1.24 (t, 3H) LCMS R$_t$=1.449 min in 4.0 min chromatography, 50-100AB 4 min, MS ESI calcd. for C$_{19}$H$_{21}$F$_3$N$_5$O$_2$[M+H]$^+$ 408.2, found 408.2.

Example I-14. Syntheses of Compounds I-21, I-22, I-23, I-24: 6-(6-((S)-1-cyclopropyl-2,2,2-trifluoro-ethoxy)pyridin-3-yl)-3-((S)-1-methoxyethyl)-[1,2,4]triazolo[4,3-a]pyrazine & 6-(6-((S)-1-cyclopropyl-2,2,2-trifluoroethoxy)pyridin-3-yl)-3-((R)-1-methoxyethyl)-[1,2,4]triazolo[4,3-a]pyrazine & 6-(6-((R)-1-cyclopropyl-2,2,2-trifluoroethoxy)pyridin-3-yl)-3-((S)-1-methoxyethyl)-[1,2,4]triazolo[4,3-a]pyrazine & 6-(6-((R)-1-cyclopropyl-2,2,2-trifluoroethoxy)pyridin-3-yl)-3-((R)-1-methoxyethyl)-[1,2,4]triazolo[4,3-a]pyrazine Note that stereochemistry is randomly assigned

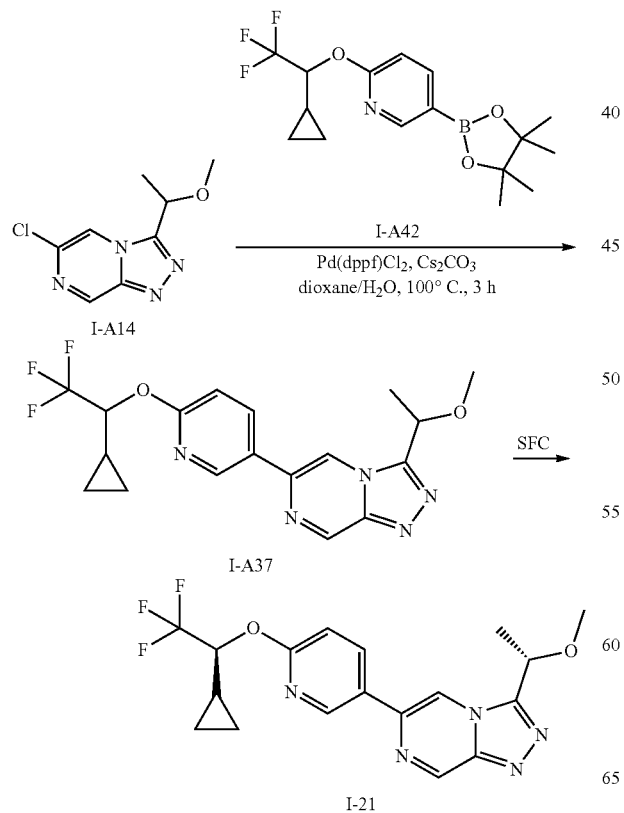

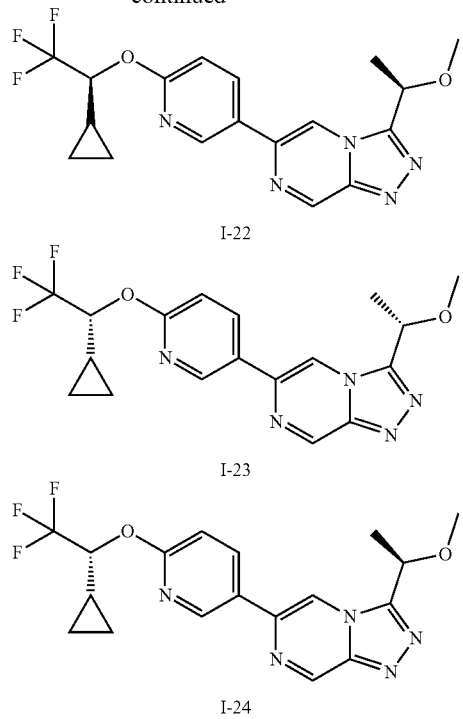

I-A37: 6-(6-(1-cyclopropyl-2,2,2-trifluoroethoxy)pyridin-3-yl)-3-(1-methoxyethyl)-[1,2,4]triazolo[4,3-a]pyrazine To a mixture of 6-chloro-3-(1-methoxyethyl)-[1,2,4]triazolo[4,3-a] (92.9 mg, 0.44 mmol) and 2-(1-cyclopropyl-2,2,2-trifluoro-ethoxy)-5-(4,4,5,5-tetramethyl-1,3,2-dioxaborolan-2-yl) pyridine (100 mg, 0.29 mmol) and Cs$_2$CO$_3$ (189.9 mg, 0.58 mmol) in 1,4-dioxane (5 mL) and water (0.50 mL) was added Pd(dppf)Cl$_2$ (32.0 mg, 0.04 mmol) under N$_2$. The mixture was stirred at 100° C. for 3 hours. The mixture was filtered, and the filtrate was concentrated to remove dioxane. The aqueous layer was extracted with EtOAc (5 mL×3). The combined organic layers were washed with brine (10 mL), dried over anhydrous Na$_2$SO$_4$, filtered, and concentrated. The residue was purified by prep-TLC (PE/EtOAc=1:1) to afford 6-(6-(1-cyclopropyl-2,2,2-trifluoroethoxy)pyridin-3-yl)-3-(1-methoxyethyl)-[1,2,4]triazolo[4,3-a]pyrazine (50 mg, 0.13 mmol, 43.6% yield) as a solid. LCMS R$_t$=0.907 min in 1.5 min chromatography, 5-95AB, MS ESI calcd. for C$_{18}$H$_{19}$F$_3$N$_5$O$_2$[M+H]$^+$ 394.0, found 394.0.

Compounds I-21, I-22, I-23 & I-24: 6-(6-((S)-1-cyclopropyl-2,2,2-trifluoroethoxy)pyridin-3-yl)-3-((S)-1-methoxyethyl)-[1,2,4]triazolo[4,3-a]pyrazine and 6-(6-((S)-1-cyclopropyl-2,2,2-trifluoroethoxy)pyridin-3-yl)-3-((R)-1-methoxyethyl)-[1,2,4]triazolo[4,3-a]pyrazine and 6-(6-((R)-1-cyclopropyl-2,2,2-trifluoroethoxy)pyridin-3-yl)-3-((S)-1-methoxyethyl)-[1,2,4]triazolo[4,3-a]pyrazine and 6-(6-((R)-1-cyclopropyl-2,2,2-trifluoroethoxy)pyridin-3-yl)-3-((R)-1-methoxyethyl)-[1,2,4]triazolo[4,3-a]pyrazine The residue was purified by SFC (DAICEL CHIRALPAK AY-H (250 mm×30 mm, 5 μm), EtOH 0.1% NH$_3$·H$_2$O; 15%

B; 60 mL/min); to afford 6-(6-(1-cyclopropyl-2,2,2-trifluoroethoxy)pyridin-3-yl)-3-(1-methoxyethyl)-[1,2,4]triazolo[4,3-a]pyrazine (Fraction 1, 30 mg, 0.08 mmol) as a solid and 6-(6-(1-cyclopropyl-2,2,2-trifluoroethoxy)pyridin-3-yl)-3-(1-methoxyethyl)-[1,2,4]triazolo[4,3-a]pyrazine (Fraction 2, 50 mg, 0.13 mmol) as a solid. LCMS $R_t$=0.903 min in 1.5 min chromatography, 5-95AB, MS ESI calcd for $C_{18}H_{19}F_3N_5O_2$[M+H]$^+$ 394.0, found 394.0. LCMS $R_t$=0.910 min in 1.5 min chromatography, 5-95AB, MS ESI calcd for $C_{18}H_{19}F_3N_5O_2$[M+H]$^+$ 394.0, found 394.0.

The material of the above Fraction 1 (30 mg, 0.08 mmol) was purified by SFC (DAICEL CHIRALPAK AS (250 mm×30 mm, 10 μm), A: $CO_2$ B=hexane-IPA (0.1% NH$_3$), 20% B; 60 min; 25 mL/min); to afford 6-(6-((S)-1-cyclopropyl-2,2,2-trifluoroethoxy)pyridine-3-yl)-3-((S)-1-methoxyethyl)-[1,2,4]triazolo[4,3-a]pyrazine (6.60 mg, 0.02 mmol) as a solid and 6-(6-((S)-1-cyclopropyl-2,2,2-trifluoroethoxy)pyridine-3-yl)-3-((R)-1-methoxyethyl)-[1,2,4]triazolo[4,3-a]pyrazine (7.41 mg, 0.02 mmol) as a solid.

The material of Fraction 2 (50 mg, 0.13 mmol) was purified by SFC (DAICEL CHIRALPAK AS (250 mm×30 mm, 10 μm); A: $CO_2$ B=IPA 0.1% NH$_3$·H$_2$O; 15% B; 60 mL/min); to afford 6-(6-((R)-1-cyclopropyl-2,2,2-trifluoroethoxy)pyridine-3-yl)-3-((S)-1-methoxyethyl)-[1,2,4]triazolo[4,3-a]pyrazine (10.4 mg, 0.03 mmol) as a solid and 6-(6-((R)-1-cyclopropyl-2,2,2-trifluoroethoxy)pyridine-3-yl)-3-((R)-1-methoxyethyl)-[1,2,4]triazolo [4,3-a]pyrazine (4.91 mg, 0.01 mmol) as a solid. All chiral centers are randomly assigned.

Compound I-21: $^1$H NMR (400 MHz, CDCl$_3$) $\delta_H$=9.42 (d, 1H), 8.66 (d, 1H), 8.54 (d, 1H), 8.25-8.15 (m, 1H), 6.98 (d, 1H), 5.49-5.36 (m, 1H), 5.21 (q, 1H), 3.36 (s, 3H), 1.78 (d, 3H), 1.29-1.28 (m, 1H), 0.79-0.71 (m, 1H), 0.67-0.57 (m, 3H). LCMS $R_t$=1.229 min in 2.0 min chromatography, 10-80AB, MS ESI calcd for $C_{18}H_{19}F_3N_5O_2$[M+H]$^+$ 394.2, found 394.2.

Compound I-22: $^1$H NMR (400 MHz, CDCl$_3$) $\delta_H$=9.42 (d, 1H), 8.66 (d, 1H), 8.54 (d, 1H), 8.24-8.16 (m, 1H), 6.98 (d, 1H), 5.46-5.37 (m, 1H), 5.21 (q, 1H), 3.36 (s, 3H), 1.77 (d 3H), 1.28 (s, 1H), 0.79-0.72 (m, 1H), 0.67-0.57 (m, 3H). LCMS $R_t$=1.217 min in 2.0 min chromatography, 10-80AB, MS ESI calcd for $C_{18}H_{20}F_4N_5O_2$ [M+H]$^+$ 394.2, found 394.2.

Compound I-23: $^1$H NMR (400 MHz, CDCl$_3$) $\delta_H$=9.42 (d, 1H), 8.66 (d, 1H), 8.54 (d, 1H), 8.26-8.15 (m, 1H), 7.03-6.94 (m, 1H), 5.47-5.36 (m, 1H), 5.21 (q, 1H), 3.36 (s, 3H), 1.77 (d, 3H), 1.33-1.30 (m, 1H), 0.78-0.72 (m, 1H), 0.66-0.59 (m, 3H). LCMS $R_t$=1.220 min in 2.0 min chromatography, 10-80AB, MS ESI calcd for $C_{18}H_{20}F_4N_5O_2$ [M+H]$^+$ 394.2, found 394.2.

Compound I-24: $^1$H NMR (400 MHz, CDCl$_3$) $\delta_H$=9.41 (d, 1H), 8.65 (d, 1H), 8.54 (d, 1H), 8.24-8.16 (m, 1H), 6.97 (d, 1H), 5.49-5.33 (m, 1H), 5.21 (q, 1H), 3.44-3.26 (m, 3H), 1.77 (d, 3H), 1.35-1.26 (m, 1H), 0.79-0.71 (m, 1H), 0.68-0.56 (m, 3H) LCMS $R_t$=1.218 min in 2.0 min chromatography, 10-80AB, MS ESI calcd for $C_{18}H_{20}F_4N_5O_2$ [M+H]$^+$ 394.2, found 394.2.

Example I-15: Synthesis of Intermediate I-A13

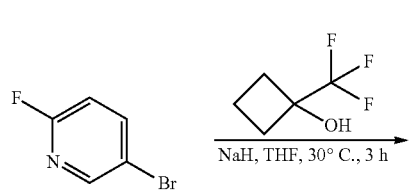

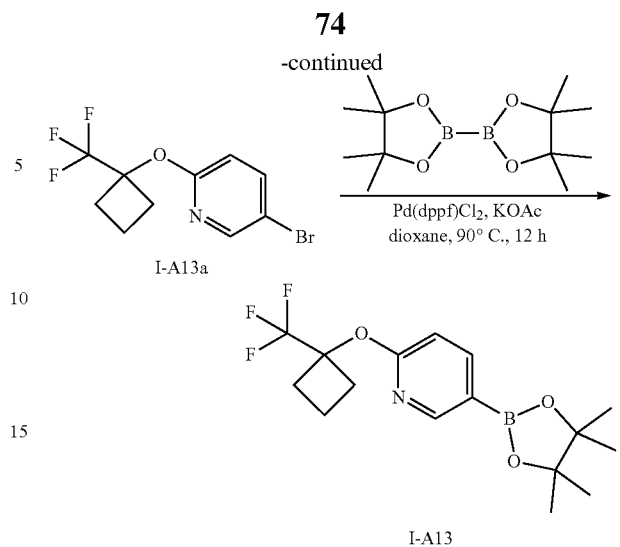

Synthesis of I-A13a

To a solution of 1-(trifluoromethyl)cyclobutanol (5 g, 35.69 mmol) in THF (300 mL) was added NaH (1.86 g, 46.4 mmol) at 0° C. over 20 minutes, and the mixture was stirred at 0° C. for 30 mins. Then to the mixture was added 5-bromo-2-fluoro-pyridine (8.48 g, 48.18 mmol), and the mixture was stirred at 30° C. for 3 hours. The mixture was quenched with sat. NH$_4$Cl (50 mL), then the mixture was extracted with EtOAc (50 mL). The combined organic phase was washed with brine (50 mL×3), dried over Na$_2$SO$_4$, filtered and concentrated to give the crude product (4.8 g, 15.49 mmol, 43% yield) as an oil. LCMS $R_t$=0.99 min in 1.5 min chromatography, 5-95AB, MS ESI calcd. for $C_{10}H_{10}BrF_3NO$ [M+H]$^+$ 295.9, found 296.0.

Synthesis of I-A13

A mixture of 5-bromo-2-[1-(trifluoromethyl)cyclobutoxy]pyridine (2.5 g, 8.44 mmol), 4,4,5,5-tetramethyl-2-(4,4,5,5-tetramethyl-1,3,2-dioxaborolan-2-yl)-1,3,2-dioxaborolane (3.22 g, 12.67 mmol), KOAc (1.66 g, 16.89 mmol) and Pd(dppf)Cl$_2$ (432.48 mg, 0.59 mmol) in 1,4-Dioxane (50 mL) was stirred at 90° C. for 12 hours under N$_2$. After cooling to room temperature, the mixture was concentrated to give the residue. The residue was diluted with H$_2$O (40 mL), and the mixture was extracted with EtOAc (40 mL×2). The combined organic phase was washed with water (40 mL) and brine (40 mL), dried over Na$_2$SO$_4$, filtered and concentrated to give the crude product. The crude product was purified by flash chromatography on silica gel (EtOAc in PE=0% to 1%) to give the crude product (2.65 g, 3.92 mmol, 46% yield) as an oil. $^1$H NMR (CDCl$_3$, 400 MHz) $\delta_H$=8.54 (d, 1H), 7.95 (dd, 1H), 6.74 (d, 1H), 2.99-2.81 (m, 2H), 2.75-2.53 (m, 2H), 2.13-1.78 (m, 2H), 1.34 (s, 12H).

Example I-16. Synthesis of Intermediate I-A42

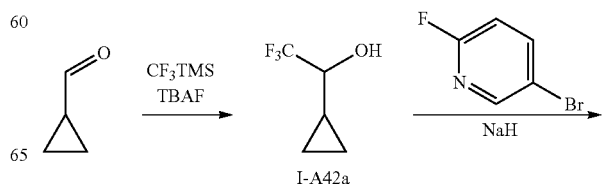

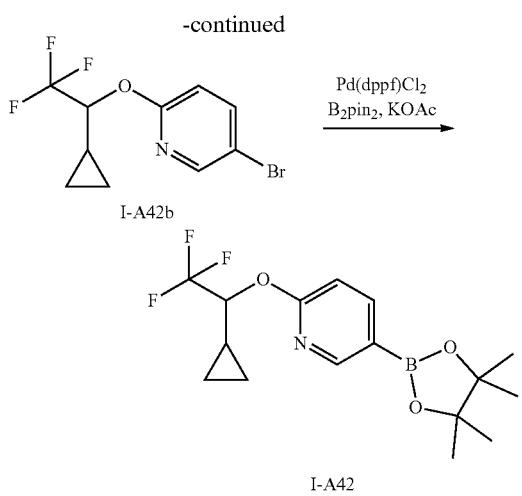

I-A42a: 1-cyclopropyl-2,2,2-trifluoroethan-1-ol

To a stirred solution of cyclopropanecarbaldehyde (5.0 g, 71.34 mmol) in THF (50.0 mL) was added trimethyl(trifluoromethyl)silane (11.16 g, 78.47 mmol) and TBAF (1.0 M in THF, 7.14 mL, 7.1 mmol) at 0° C. The reaction mixture was slowly warmed to room temperature and stirred for 4 hours. To the reaction mixture TBAF (1.0 M in THF, 142.6 mL, 142.6 mmol) was added at room temperature and stirred for 30 min. The reaction mixture was treated with water (50.0 mL) and extracted with diethyl ether (2×100 mL). The organic layer was washed with 10% NaHCO$_3$ solution (50.0 mL) and brine (50 mL). The organic layer was dried over anhydrous Na$_2$SO$_4$ and concentrated at 30° C. to afford 1-cyclopropyl-2,2,2-trifluoroethan-1-ol (3.2 g), which was used for the next step without further purification.

I-A42b: 5-bromo-2-(1-cyclopropyl-2,2,2-trifluoroethoxy)pyridine

To a stirred solution of 1-cyclopropyl-2,2,2-trifluoroethan-1-ol (3.0 g, 21.41 mmol) in THF (30.0 mL) at 0° C. was added NaH (60% in mineral oil, 1.28 g, 32.12 mmol) in small portions. The reaction mixture was stirred for 10 min and 5-bromo-2-fluoro-pyridine (3.77 g, 21.41 mmol) was added. The reaction mixture was slowly warmed to room temperature and stirred for 1 hour. The reaction mixture was cooled to 10° C. and treated with ice water (100 mL). The reaction mixture was extracted with EtOAc (2×100 mL). The organic layer was washed with brine (80 mL), dried over anhydrous Na$_2$SO$_4$ and concentrated to give a crude product. The crude product was purified by column chromatography on silica gel with PE to afford 5-bromo-2-(1-cyclopropyl-2,2,2-trifluoroethoxy)pyridine (3.1 g, 10.47 mmol, 48% yield). LCMS: 296.0 (M+H)$^+$ and 298.0 (M+2+H)$^+$, Rt 2.90 min; Column: ZORBAX XDB C-18 (50×4.6 mm), 3.5 μm; Mobile Phase: A: 0.1% HCOOH in water: ACN (95:5), B: ACN; Flow Rate: 1.5 mL/min.

I-A42: 2-(1-cyclopropyl-2,2,2-trifluoroethoxy)-5-(4,4,5,5-tetramethyl-1,3,2-dioxaborolan-2-yl)pyridine To a stirred solution of 5-bromo-2-(1-cyclopropyl-2,2,2-trifluoroethoxy)pyridine (3.1 g, 10.47 mmol) and bis(pinacolato)diboron (3.46 g, 13.61 mmol) in 1,4-dioxane (30 mL) was added potassium acetate (1.72 g, 20.94 mmol). Pd(dppf)Cl$_2$·DCM (0.86 g, 1.05 mmol) was added to the reaction mixture under nitrogen atmosphere and heated at 90° C. for 3 hours. The reaction mixture was cooled to room temperature and filtered through celite. The reaction mixture was treated with ice water (50 mL) and extracted with EtOAc (2×50 mL). The organic layer was washed with brine (30 mL), dried over anhydrous Na$_2$SO$_4$ and concentrated to give a crude product. The crude product was purified by column chromatography on silica gel with 4% EtOAc/PE to afford 2-(1-cyclopropyl-2,2,2-trifluoroethoxy)-5-(4,4,5,5-tetramethyl-1,3,2-dioxaborolan-2-yl)pyridine (3.2 g, 9.3 mmol, 89% yield). LCMS: 344.1 (M+H)$^+$, Rt 3.18 min; Column: ZORBAX XDB C-18 (50×4.6 mm), 3.5 μm; Mobile Phase: A: 0.1% HCOOH in water: ACN (95:5), B: ACN; Flow Rate: 1.5 mL/min.

Example II-1. Synthesis of Compound II-1: 6-(5-fluoro-6-(2,2,2-trifluoroethoxy)pyridin-3-yl)-3-(1-methoxycyclopropyl)-[1,2,4]triazolo[4,3-a]pyrazine

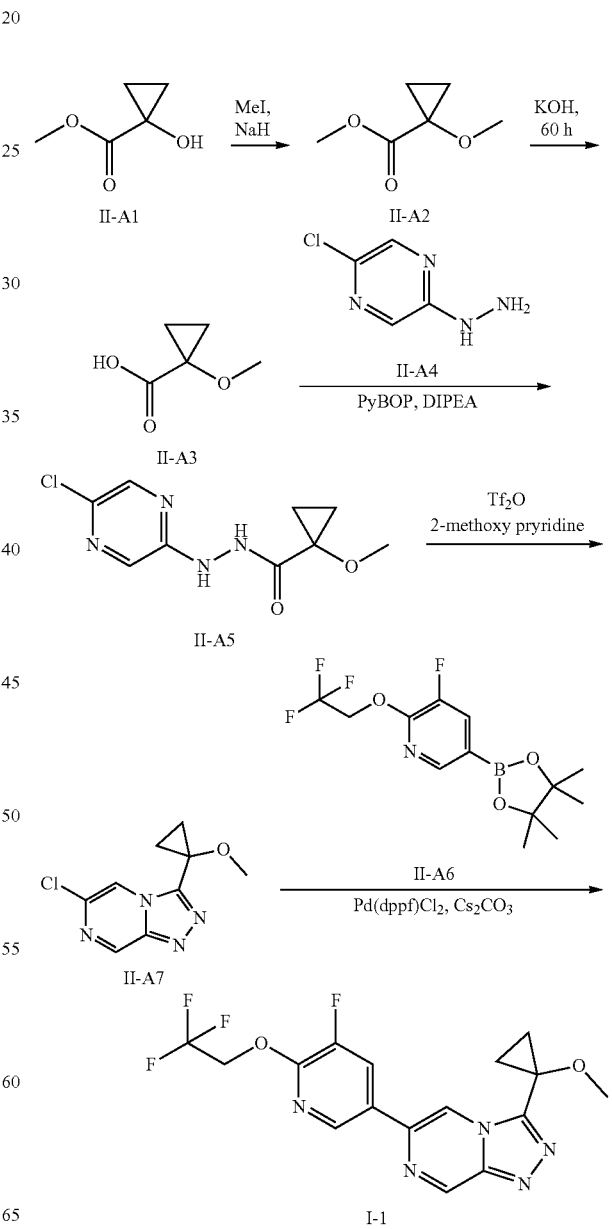

II-A2: Methyl 1-methoxycyclopropane-1-carboxylate

To a stirred solution of methyl 1-hydroxycyclopropane-1-carboxylate (3.0 g, 25.84 mmol) in THF (10.0 mL) was added NaH (60% in mineral oil, 1.13 g, 28.42 mmol) at 0° C. and stirred for 30 mins. To the reaction mixture iodomethane (3.67 g, 25.84 mmol) was added dropwise. The reaction mixture was slowly warmed to room temperature and stirred for 2 hours. The reaction mixture was cooled to 10° C. and treated with ice cold water (50 mL). The reaction mixture was extracted with ethyl acetate (2×50 mL). The organic layer was washed with brine (40 mL), dried over anhydrous $Na_2SO_4$ and concentrated to afford methyl 1-methoxycyclopropane-1-carboxylate (2.0 g), which was used for the next step without further purification.

II-A3: 1-methoxycyclopropane-1-carboxylic acid

To a stirred solution of methyl 1-methoxycyclopropane-1-carboxylate (1.0 g, 7.68 mmol) in THF (6.0 mL) and methanol (6.0 mL) was added 2.0 M KOH (10.0 mL). The reaction mixture was stirred at room temperature for 60 hours. The reaction mixture was concentrated, treated with water (20 mL) and extracted with ethyl acetate (30 mL). The aqueous layer treated with 6.0 N HCl (5.0 mL) and extracted with diethyl ether (2×50 mL). The organic layer was washed with brine (40 mL), dried over anhydrous $Na_2SO_4$ and concentrated to afford 1-methoxycyclopropane-1-carboxylic acid (650 mg), which was used for the next step without further purification.

II-A5: N'-(5-chloropyrazin-2-yl)-1-methoxycyclopropane-1-carbohydrazide

To a stirred solution of 1-methoxycyclopropane-1-carboxylic acid (275 mg, 2.37 mmol) in DCM (6.0 mL) was added DIPEA (1.23 mL, 7.11 mmol) followed by PyBOP (1.85 g, 3.55 mmol) and 2-chloro-5-hydrazinylpyrazine (340.0 mg, 2.37 mmol). The reaction mixture was stirred at room temperature for 16 hours. The reaction mixture was treated with water (30 mL) and extracted with ethyl acetate (2×30 mL). The organic layer was washed with brine (40 mL), dried over anhydrous $Na_2SO_4$ and concentrated to give a crude product. The crude product was purified by column chromatography on silica gel with 20% ethyl acetate/PE to afford N'-(5-chloropyrazin-2-yl)-1-methoxycyclopropane-1-carbohydrazide (220 mg, 0.90 mmol, 37% yield). LCMS: 243.1 (M+H), Rt 1.55 min; Column: Atlantis dC-18 (50×4.6 mm), 5 μm; Mobile Phase: A: 0.1% HCOOH in water: $CH_3CN$ (95:5), B: $CH_3CN$; Flow Rate: 1.5 mL/min.

II-A7: 6-chloro-3-(1-methoxycyclopropyl)-[1,2,4]triazolo[4,3-a]pyrazine

To a stirred solution of N'-(5-chloropyrazin-2-yl)-1-methoxycyclopropane-1-carbohydrazide (520 mg, 2.1 mmol) in DCM (6.0 mL) was added 2-methoxypyridine (461 mg, 4.23 mmol) and trifluoromethanesulfonic anhydride (0.43 mL, 2.54 mmol) at 0° C. The reaction mixture was slowly warmed to room temperature and stirred for 16 hours. The reaction mixture was treated with 10% sodium bicarbonate solution (10 mL) and extracted with ethyl acetate (2×25 mL). The organic layer was washed with brine (20 mL), dried over $Na_2SO_4$ and concentrated to give a crude product. The crude product was purified by column chromatography on silica gel with 20% EtOAc/PE to afford 6-chloro-3-(1-methoxycyclopropyl)-[1,2,4]triazolo[4,3-a]pyrazine (80 mg, 0.35 mmol, 16% yield). LCMS: 225.1 (M+H), Rt 1.61 min; Column: Atlantis dC-18 (50×4.6 mm), 5 μm; Mobile Phase: A: 0.1% HCOOH in water:ACN (95:5), B: ACN; Flow Rate: 1.5 mL/min.

Compound II-1: 6-(5-fluoro-6-(2,2,2-trifluoroethoxy)pyridin-3-yl)-3-(1-methoxycyclopropyl)-[1,2,4]triazolo[4,3-a]pyrazine To a stirred solution of 3-fluoro-5-(4,4,5,5-tetramethyl-1,3,2-dioxaborolan-2-yl)-2-(2,2,2-trifluoroethoxy)pyridine (120 mg, 0.37 mmol) and 6-chloro-3-(1-methoxycyclopropyl)-[1,2,4]triazolo[4,3-a]pyrazine (80 mg, 0.35 mmol) in 1,4-dioxane (3.0 mL) was added water (0.5 mL) and $Cs_2CO_3$ (243 mg, 0.75 mmol). Pd(dppf)$Cl_2$·DCM (29 mg, 0.04 mmol) was added to the reaction mixture under nitrogen atmosphere and heated at 80° C. for 16 hours. The reaction mixture was cooled to room temperature, filtered through Celite and concentrated under reduced pressure to give a crude product. The crude product was purified by preparative HPLC to afford the product (34 mg, 0.08 mmol, 25% yield) as a solid. Prep-HPLC method: Rt 18.1; Column: X-Bridge (150×19 mm), 5.0 μm; 0.1% TFA in water/acetonitrile; Flow Rate: 15.0 mL/min. HPLC: Rt 4.45 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 384.2 (M+H), Rt 2.13 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. 1H NMR (400 MHz, DMSO-$d_6$): $\delta_H$=9.57 (d, 1H), 9.00 (d, 1H), 8.78 (d, 1H), 8.57 (dd, 1H), 5.18 (q, 2H), 3.19 (s, 3H), 1.44-1.40 (m, 2H), 1.31-1.27 (m, 2H).

Example II-2. Synthesis of Compound II-2: (R)-6-(5-fluoro-6-((1,1,1-trifluoropropan-2-yl)oxy)pyridin-3-yl)-3-(1-methoxycyclopropyl)-[1,2,4]triazolo[4,3-a]pyrazine

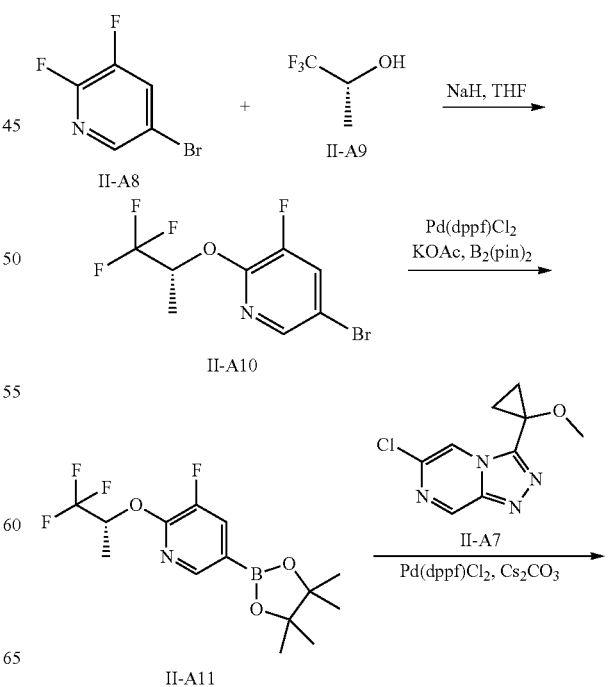

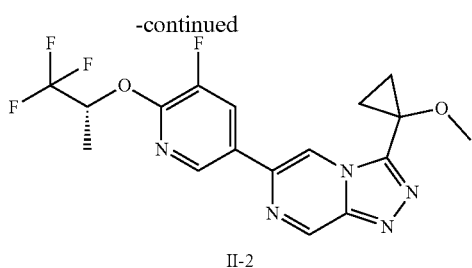

II-2

II-A10: (R)-5-bromo-3-fluoro-2-((1,1,1-trifluoropropan-2-yl)oxy)pyridine

To a solution of (R)-1,1,1-trifluoropropan-2-ol (9.64 mmol) in THF was added NaH (578 mg, 14.46 mmol) portion wise at 0° C. and stirred for 30 min. 5-bromo-2,3-difluoro-pyridine (1.36 g, 7.0 mmol) was added to the reaction mixture slowly at 0° C. The reaction mixture was slowly warmed to room temperature and stirred for 3 hours. The reaction mixture was cooled to 10° C., treated with ice water (10 mL) and extracted with ethyl acetate (2×30 mL). The organic layer was washed with brine (30 mL), dried over $Na_2SO_4$ and concentrated to give a crude product. The crude product was purified by column chromatography on silica gel with 20% EtOAc/PE to afford (R)-5-bromo-3-fluoro-2-((1,1,1-trifluoropropan-2-yl)oxy)pyridine (1.6 g) as a liquid. It was used for the next step without further purification.

II-A11: (R)-3-fluoro-5-(4,4,5,5-tetramethyl-1,3,2-dioxaborolan-2-yl)-2-((1,1,1-trifluoropropan-2-yl)oxy)pyridine To a stirred solution of (R)-5-bromo-3-fluoro-2-((1,1,1-trifluoropropan-2-yl)oxy)pyridine (1.6 g, 5.55 mmol) and bis(pinacolato)diboron (1.83 g, 7.22 mmol) in 1,4-dioxane (20.0 mL) was added potassium acetate (1.09 g, 11.11 mmol). Pd(dppf)Cl₂·DCM (0.68 g, 0.83 mmol) was added to the reaction mixture under nitrogen atmosphere and heated at 85° C. for 16 hours. The reaction mixture was cooled to room temperature, filtered through Celite and concentrated under reduced pressure to give a crude product. The crude product was purified by column chromatography on silica gel with 6% ethyl acetate/PE to afford the product (300 mg, 0.89 mmol, 16% yield) as a solid. LCMS: 336.1 (M+H), Rt 2.93 min; Column: Atlantis dC18 (50×4.6 mm), 5.0 µm; Mobile Phase: A: 0.1% HCOOH in water:ACN (95:5), B: ACN; Flow Rate: 1.5 mL/min.

Compound II-2: (R)-6-(5-fluoro-6-((1,1,1-trifluoropropan-2-yl)oxy)pyridin-3-yl)-3-(1-methoxycyclopropyl)-[1,2,4]triazolo[4,3-a]pyrazine To a stirred solution of (R)-3-fluoro-5-(4,4,5,5-tetramethyl-1,3,2-dioxaborolan-2-yl)-2-((1,1,1-trifluoropropan-2-yl)oxy)pyridine (123 mg, 0.37 mmol) and 6-chloro-3-(1-methoxycyclopropyl)-[1,2,4]triazolo[4,3-a]pyrazine (75.0 mg, 0.33 mmol) in 1,4-dioxane (10.0 mL) was added water (1.0 mL) and cesium carbonate (217 mg, 0.67 mmol). Pd(dppf)Cl₂·DCM (27 mg, 0.03 mmol) was added to the reaction mixture under nitrogen atmosphere and heated at 80° C. for 16 hours. The reaction mixture was cooled to room temperature, filtered through Celite and concentrated under reduced pressure to give a crude product. The crude product was purified by preparative HPLC to afford the product (30 mg, 0.075 mmol, 22% yield). Prep-HPLC method: Rt 8.37; Column: X-Bridge C-18 (150×19 mm), 5.0 µm; 0.1% TFA in water/acetonitrile; Flow Rate: 15.0 mL/min. HPLC: Rt 4.76 min; Column: X-Bridge C8 (50× 4.6) mm, 3.5 µm; Mobile phase: A: 0.1% TFA in water, B: 0.1% TFA in ACN; Flow Rate: 2.0 mL/min. LCMS: 398.1 (M+H), Rt 2.33 min; Column: ZORBAX XDB C-18 (50× 4.6 mm), 3.5 µm; Mobile Phase: A: 0.1% HCOOH in water:ACN (95:5), B: ACN; Flow Rate: 1.5 mL/min. ¹H NMR (400 MHz, DMSO-d₆): $δ_H$=9.57 (d, 1H), 9.00 (d, 1H), 8.77 (d, 1H), 8.56 (dd, 1H), 6.05-6.01 (m, 1H), 3.20 (s, 3H), 1.55 (d, 3H), 1.43-1.41 (m, 2H), 1.31-1.29 (m, 2H).

Example II-3. Synthesis of Compound II-3: (S)-6-(5-fluoro-6-((1,1,1-trifluoropropan-2-yl)oxy)pyridin-3-yl)-3-(1-methoxycyclopropyl)-[1,2,4]triazolo[4,3-a]pyrazine

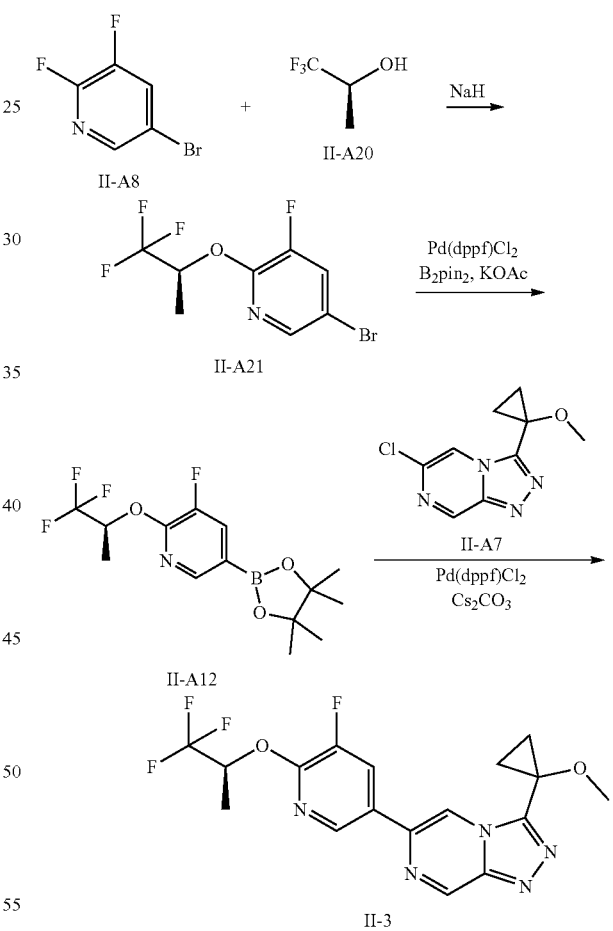

II-A21: (S)-5-bromo-3-fluoro-2-((1,1,1-trifluoropropan-2-yl)oxy)pyridine

To a solution of 2(S)-1,1,1-trifluoropropan-2-ol (35.07 mmol) in THF (30.0 mL) was added NaH (1.54 g, 38.57 mmol) portion wise at 0° C. and stirred for 30 min. 5-bromo-2,3-difluoro-pyridine (6.8 g, 35.07 mmol) was added to the reaction mixture slowly at 0° C. The reaction mixture was slowly warmed to room temperature and stirred for 3 hours.

The reaction mixture was cooled to 10° C., treated with ice water (30 mL) and extracted with ethyl acetate (2×50 mL). The organic layer was washed with brine (40 mL), dried over Na₂SO₄ and concentrated to give a crude product. The crude product was purified by column chromatography on silica gel with 20% EtOAc/PE to afford the product (4 g, 13.9 mmol, 39% yield). LCMS: 288.0 (M+H) and 290.0 (M+2+H), Rt 2.77 min; Column: ZORBAX XDB C-18 (50×4.6 mm), 3.5 µm; Mobile Phase: A: 0.1% HCOOH in water:ACN (95:5), B: ACN; Flow Rate: 1.5 mL/min.

II-A12: (S)-3-fluoro-5-(4,4,5,5-tetramethyl-1,3,2-dioxaborolan-2-yl)-2-((1,1,1-trifluoropropan-2-yl)oxy)pyridine To a stirred solution of (S)-5-bromo-3-fluoro-2-((1,1,1-trifluoropropan-2-yl)oxy)pyridine (2.0 g, 6.94 mmol) and bis(pinacolato)diboron (1.94 g, 7.64 mmol) in 1,4-dioxane (25.0 mL) was added potassium acetate (1.36 g, 13.89 mmol). Pd(dppf)Cl₂·DCM (0.57 g, 0.69 mmol) was added to the reaction mixture under nitrogen atmosphere and heated at 80° C. for 12 hours. The reaction mixture was cooled to room temperature, filtered through Celite and concentrated under reduced pressure to give a crude product. The crude product was purified by column chromatography on silica gel with 10% ethyl acetate/PE to afford the product (1.06 g, 3.17 mmol, 45% yield). LCMS: 336.2 (M+H), Rt 3.09 min; Column: ZORBAX XDB C-18 (50×4.6 mm), 3.5 µm; Mobile Phase: A: 0.1% HCOOH in water:ACN (95:5), B: ACN; Flow Rate: 1.5 mL/min.

Compound II-3: (S)-6-(5-fluoro-6-((1,1,1-trifluoropropan-2-yl)oxy)pyridin-3-yl)-3-(1-methoxycyclopropyl)-[1,2,4]triazolo[4,3-a]pyrazine To a stirred solution of (S)-3-fluoro-5-(4,4,5,5-tetramethyl-1,3,2-dioxaborolan-2-yl)-2-((1,1,1-trifluoropropan-2-yl)oxy)pyridine (98 mg, 0.29 mmol) and 6-chloro-3-(1-methoxycyclopropyl)-[1,2,4]triazolo[4,3-a]pyrazine (60 mg, 0.27 mmol) in 1,4-dioxane (2.7 mL) was added water (0.30 mL) and Cs₂CO₃ (174 mg, 0.53 mmol). Pd(dppf)Cl₂·DCM (22 mg, 0.03 mmol) was added to the reaction mixture under nitrogen atmosphere and heated at 90° C. for 3 hours. The reaction mixture was cooled to room temperature and filtered through Celite. The reaction mixture was treated with water (30 mL) and extracted with ethyl acetate (2×30 mL). The organic layer was washed with brine (30 mL), dried over anhydrous Na₂SO₄ and concentrated to give a crude product. The crude product was purified by preparative HPLC to afford the product (10 mg, 0.025 mmol, 9% yield) as a solid. Prep. HPLC method: Rt 13.06; Column: Sunfire C18 (150×19 mm), 5.0 µm; Mobile phase: 0.1% TFA in water/acetonitrile; Flow Rate: 15.0 mL/min. HPLC: Rt 4.77 min; Column: X-Bridge C8 (50×4.6) mm, 3.5 µm; Mobile phase: A: 0.1% TFA in water, B: 0.1% TFA in ACN; Flow Rate: 2.0 mL/min. LCMS: 398.1 (M+H), Rt 2.34 min; Column: ZORBAX XDB C-18 (50×4.6 mm), 3.5 µm; Mobile Phase: A: 0.1% HCOOH in water:ACN (95:5), B: ACN; Flow Rate: 1.5 mL/min. ¹H NMR (400 MHz, DMSO-d₆): δ$_H$=9.57 (d, 1H), 8.99 (d, 1H), 8.77 (d, 1H), 8.56 (dd, 1H), 6.06-5.99 (m, 1H), 3.20 (s, 3H), 1.55 (d, 3H), 1.44-1.41 (m, 2H), 1.31-1.28 (m, 2H).

Example II-4. Synthesis of Compound II-4: 6-(5-fluoro-6-(2,2,2-trifluoroethoxy)pyridin-3-yl)-3-(2-methoxypropan-2-yl)-[1,2,4]triazolo[4,3-a]pyrazine

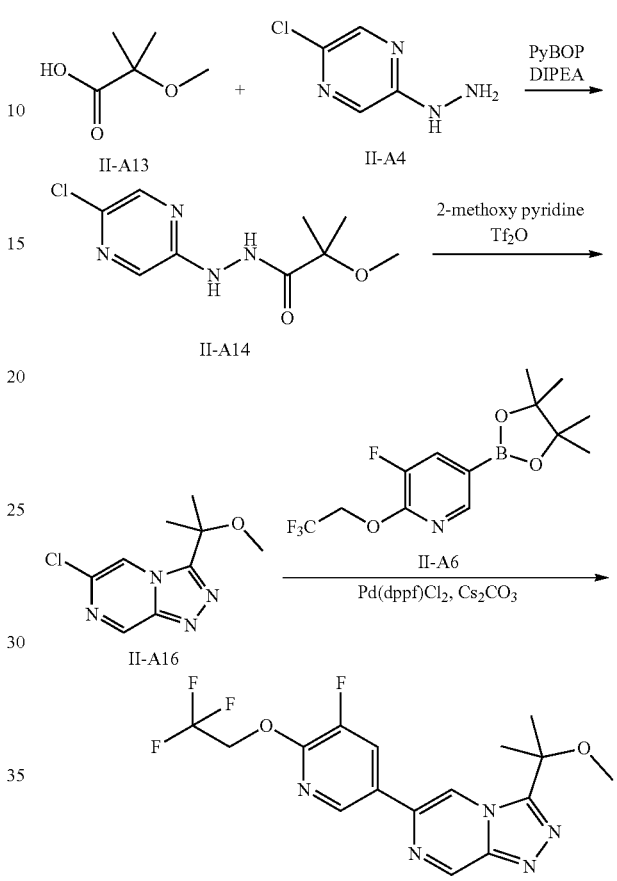

II-A14: N'-(5-chloropyrazin-2-yl)-2-methoxy-2-methylpropanehydrazide

To a stirred solution of 2-chloro-5-hydrazinylpyrazine (5.0 g, 34.59 mmol) in DCM (100 mL) was added 2-methoxy-2-methylpropanoic acid (4.49 g, 38.05 mmol) followed by PyBOP (27.0 g, 51.88 mmol) and DIPEA (12.05 mL, 69.18 mmol). The reaction mixture was stirred at room temperature for 16 hours. The reaction mixture was treated with water (60 mL) and extracted with DCM (2×100 mL). The organic layer was washed with brine (50 mL), dried over anhydrous Na₂SO₄ and concentrated to give a crude product. The crude product was purified by column chromatography on silica gel with 18% EtOAc/PE to afford the product (4.77 g, 19.56 mmol, 56% yield). LCMS: 245.1 (M+H), Rt 1.24 min; Column: ZORBAX XDB C-18 (50× 4.6 mm), 3.5 µm; Mobile Phase: A: 0.1% HCOOH in water:ACN (95:5), B: ACN; Flow Rate: 1.5 mL/min.

II-A16: 6-chloro-3-(2-methoxypropan-2-yl)-[1,2,4]triazolo[4,3-a]pyrazine

To a stirred solution of N'-(5-chloropyrazin-2-yl)-2-methoxy-2-methylpropanehydrazide (2.29 g, 9.39 mmol) in DCM (24.0 mL) was added 2-methoxypyridine (1.97 mL, 18.78 mmol) and trifluoromethanesulfonic anhydride (1.9 mL, 11.27 mmol) at 0° C. The reaction mixture was slowly warmed to room temperature and stirred for 1 hour. To the reaction mixture 2-methoxypyridine (1.97 mL, 18.78 mmol) and trifluoromethanesulfonic anhydride (1.9 mL, 11.27 mmol) were added and stirred for 16 h at room temperature. The reaction mixture was treated with water (50 mL) and extracted with DCM (2×60 mL). The organic layer was washed with brine (30 mL), dried over Na$_2$SO$_4$ and concentrated to give a crude product. The crude product was purified by column chromatography on silica gel with 55% EtOAc/PE to afford the product (180 mg, 0.80 mmol, 8% yield). LCMS: 227.1 (M+H), Rt 1.36 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Compound II-4: 6-(5-fluoro-6-(2,2,2-trifluoroethoxy)pyridin-3-yl)-3-(2-methoxypropan-2-yl)-[1,2,4]triazolo[4,3-a]pyrazine To a stirred solution of 6-chloro-3-(2-methoxypropan-2-yl)-[1,2,4]triazolo[4,3-a]pyrazine (60 mg, 0.27 mmol) and 3-fluoro-5-(4,4,5,5-tetramethyl-1,3,2-dioxaborolan-2-yl)-2-(2,2,2-trifluoroethoxy)pyridine (171 mg, 0.54 mmol) in 1,4-dioxane (1.8 mL) was added water (0.2 mL) and Cs$_2$CO$_3$ (174 mg, 0.54 mmol). Pd(dppf)Cl$_2$·DCM (22 mg, 0.027 mmol) was added to the reaction mixture under nitrogen atmosphere and heated at 90° C. for 3 hours. The reaction mixture was cooled to room temperature, filtered through Celite and concentrated under reduced pressure to give a crude product. The crude product was purified by preparative HPLC to afford the product (57 mg, 0.14 mmol, 54% yield) as a solid. Prep-HPLC method: Rt 13.7; Column: X-Bridge C-18 (150×19 mm), 5.0 μm; 0.1% TFA in water/acetonitrile; Flow Rate: 15.0 mL/min. LCMS: 386.1 (M+H), Rt 2.24 min, 97.6%; Column: ZORBAX XDB C-18 (50×4.6 mm), 3.5 μm; Mobile Phase: A: 0.1% HCOOH in water: ACN (95:5), B: ACN; Flow Rate: 1.5 mL/min. $^1$H NMR (400 MHz, CD$_3$OD): δ$_H$=9.44 (d, 1H), 8.93 (d, 1H), 8.68 (d, 1H), 8.30 (dd, 1H), 5.06 (q, 2H), 3.18 (s, 3H), 1.85 (s, 6H).

Example II-5. Synthesis of Compound II-5: 3-(2-methoxypropan-2-yl)-6-(6-(2,2,2-trifluoroethoxy)pyridin-3-yl)-[1,2,4]triazolo[4,3-a]pyrazine

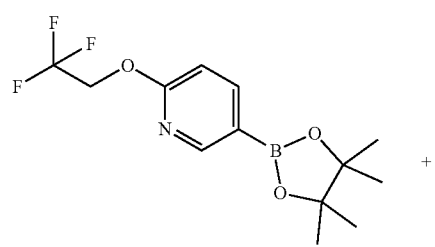

II-A17

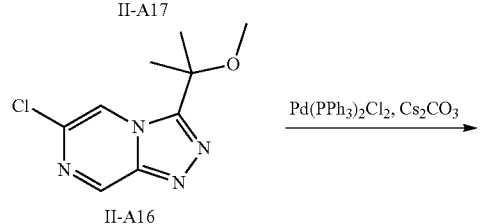

II-A16

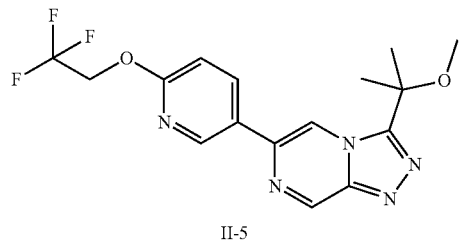

II-5

To a stirred solution of 5-(4,4,5,5-tetramethyl-1,3,2-dioxaborolan-2-yl)-2-(2,2,2-trifluoroethoxy)pyridine (110 mg, 0.36 mmol) and 6-chloro-3-(2-methoxypropan-2-yl)-[1,2,4]triazolo[4,3-a]pyrazine (82 mg, 0.36 mmol) in 1,4-dioxane (2.7 mL) was added water (0.3 mL) and Cs$_2$CO$_3$ (214 mg, 0.66 mmol). Pd(PPh$_3$)$_2$Cl$_2$·DCM (0.27 mg, 0.033 mmol) was added to the reaction mixture under nitrogen atmosphere and heated at 90° C. for 3 hours. The reaction mixture was cooled to room temperature and filtered through Celite. The reaction mixture was treated with water (30 mL) and extracted with ethyl acetate (2×30 mL). The organic layer was washed with brine (30 mL), dried over anhydrous Na$_2$SO$_4$ and concentrated to give a crude product. The crude product was purified by column chromatography on silica gel with 18% ethyl acetate/PE to afford the product (45 mg, 0.12 mmol, 33% yield) as a solid. LCMS: 368.1 (M+H), Rt 2.11 min, 97.5%; Column: ZORBAX XDB C-18 (50×4.6 mm), 5.0 μm; Mobile Phase: A: 0.1% HCOOH in water: ACN (95:5), B: ACN; Flow Rate: 1.5 mL/min. $^1$H NMR (400 MHz, DMSO-d$_6$): δ$_H$=9.57 (d, 1H), 8.87 (d, 1H), 8.81 (d, 1H), 8.45 (dd, 1H), 7.17 (d, 1H), 5.09 (q, 2H), 3.06 (s, 3H), 1.77 (s, 6H).

Example II-6. Synthesis of Compound II-6: 3-(1-methoxy-1-methyl-ethyl)-6-[6-[rac-(1R)-2,2,2-trifluoro-1-methyl-ethoxy]-3-pyridyl]-[1,2,4]triazolo[4,3-a]pyrazine

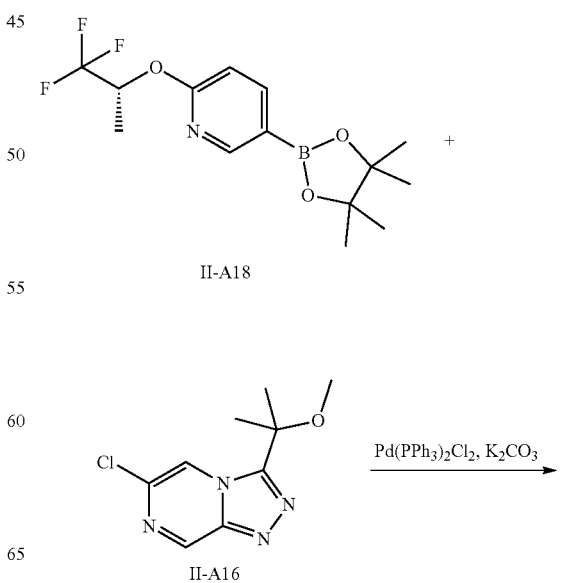

II-A18

II-A16

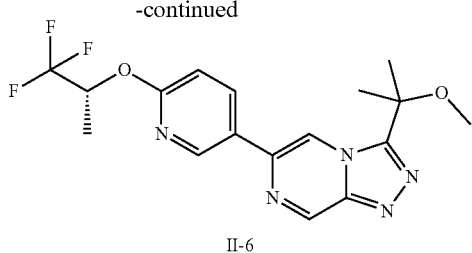

II-6

To a stirred solution of 6-chloro-3-(2-methoxypropan-2-yl)-[1,2,4]triazolo[4,3-a]pyrazine (100 mg, 0.44 mmol) and (R)-5-(4,4,5,5-tetramethyl-1,3,2-dioxaborolan-2-yl)-2-((1,1,1-trifluoropropan-2-yl)oxy)pyridine (154 mg, 0.49 mmol) in 1,4-dioxane (10 mL) was added water (1.0 mL) and K$_2$CO$_3$ (744 mg, 2.29 mmol). Pd(PPh$_3$)Cl$_2$ (0.3 g, 0.044 mmol) was added to the reaction mixture under nitrogen atmosphere and heated at 80° C. for 16 hours. The reaction mixture was cooled to room temperature, filtered through Celite and concentrated under reduced pressure to give a crude product. The crude product was purified by preparative HPLC to afford the product (45 mg, 0.11 mmol, 26% yield) as a solid. Prep-HPLC method: Rt 12.1; Column: X-Bridge C-18 (150×19 mm), 5.0 µm; 0.1% TFA in water/acetonitrile; Flow Rate: 15.0 mL/min. LCMS: 381.9 (M+H), Rt 2.32 min, 99.8%; Column: ZORBAX XDB C-18 (50×4.6 mm), 3.5 µm; Mobile Phase: A: 0.1% HCOOH in water: ACN (95:5), B: ACN; Flow Rate: 1.5 mL/min. $^1$H NMR (400 MHz, CDCl$_3$): δ$_H$=9.45 (d, 1H), 8.73-8.70 (m, 2H), 8.23 (dd, 1H), 6.99 (dd, 1H), 5.91-5.87 (m, 1H), 3.16 (s, 3H), 1.87 (s, 6H), 1.56 (d, 3H).

Example II-7. Synthesis of Compound II-7: (S)-3-(chlorodifluoromethyl)-6-(6-((1,1,1-trifluoropropan-2-yl)oxy)pyridin-3-yl)-[1,2,4]triazolo[4,3-a]pyrazine To a stirred solution of (S)-5-(4,4,5,5-tetramethyl-1,3,2-dioxaborolan-2-yl)-2-((1,1,1-

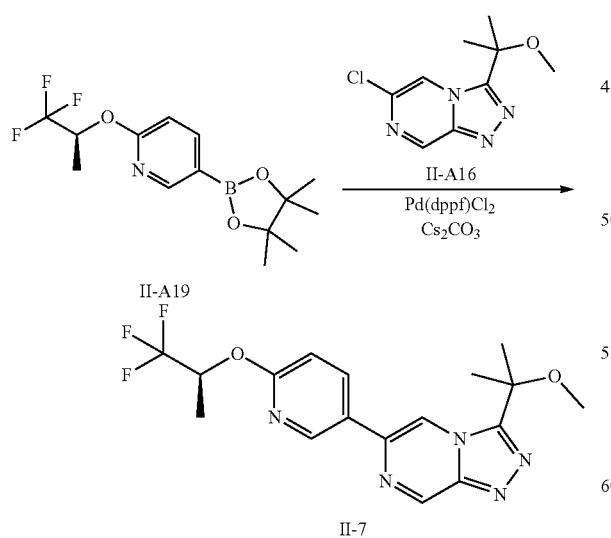

II-7 trifluoropropan-2-yl)oxy)pyridine (154 mg, 0.48 mmol) and 6-chloro-3-(2-methoxypropan-2-yl)-[1,2,4]triazolo[4,3-a]pyrazine (100 mg, 0.44 mmol) in 1,4-dioxane (2.7 mL) was added water (0.30 mL) and Cs$_2$CO$_3$ (288 mg, 0.88 mmol).

Pd(dppf)Cl$_2$·DCM (36 mg, 0.04 mmol) was added to the reaction mixture under nitrogen atmosphere and heated at 90° C. for 3 hours. The reaction mixture was cooled to room temperature, filtered through Celite and concentrated under reduced pressure to give a crude product. The reaction mixture was treated with water (20 mL) and extracted with EtOAc (2×30 mL). The organic layer was washed with brine (20 mL), dried over Na$_2$SO$_4$ and concentrated to give a crude product. The crude product was purified by column chromatography on silica gel with 40% EtOAc/PE to afford the product (18 mg, 0.046 mmol, 10% yield) as a solid. LCMS: 382.1 (M+H), Rt 2.34 min, 98.0%; Column: ZORBAX XDB C-18 (50×4.6 mm), 3.5 µm; Mobile Phase: A: 0.1% HCOOH in water:ACN (95:5), B: ACN; Flow Rate: 1.5 mL/min. $^1$H NMR (400 MHz, DMSO-d$_6$): δ$_H$=9.57 (d, 1H), 8.86 (d, 1H), 8.80 (d, 1H), 8.43 (dd, 1H), 7.12 (d, 1H), 6.00-5.96 (m, 1H), 3.06 (s, 3H), 1.77 (s, 6H), 1.51 (d, 3H).

Example II-8. Synthesis of Compound II-8: (R)-6-(5-fluoro-6-((1,1,1-trifluoropropan-2-yl)oxy)pyridin-3-yl)-3-(2-methoxypropan-2-yl)-[1,2,4]triazolo[4,3-a]pyrazine

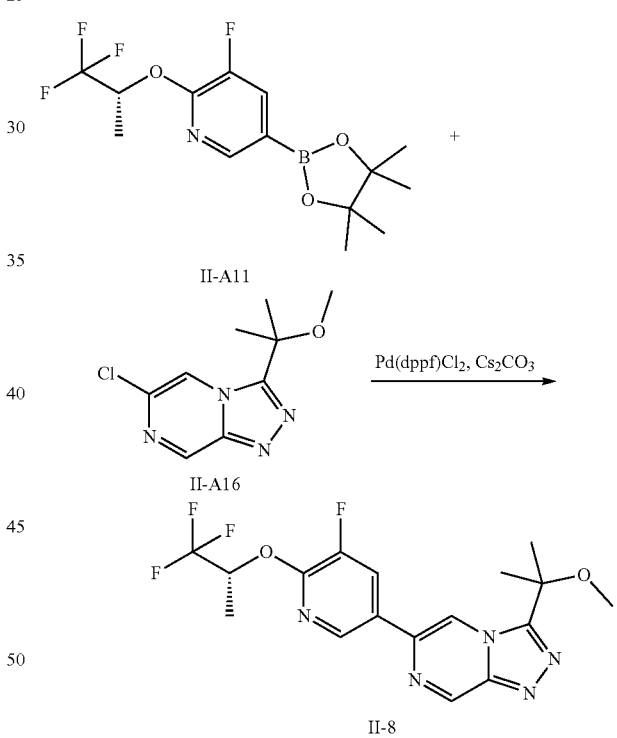

II-8

To a stirred solution of (R)-3-fluoro-5-(4,4,5,5-tetramethyl-1,3,2-dioxaborolan-2-yl)-2-((1,1,1-trifluoropropan-2-yl)oxy)pyridine (100 mg, 0.29 mmol) and 6-chloro-3-(2-methoxypropan-2-yl)-[1,2,4]triazolo[4,3-a]pyrazine (128 mg, 0.57 mmol) in 1,4-dioxane (1.8 mL) was added water (0.2 mL) and Cs$_2$CO$_3$ (186 mg, 0.57 mmol). Pd(dppf)Cl$_2$·DCM (24 mg, 0.03 mmol) was added to the reaction mixture under nitrogen atmosphere and heated at 90° C. for 3 hours. The reaction mixture was cooled to room temperature, filtered through Celite and concentrated under reduced pressure. The reaction mixture was treated with water (20 mL) and extracted with ethyl acetate (2×25 mL). The organic layer was washed with brine (20 mL), dried over Na$_2$SO$_4$ and concentrated to give a crude product. The crude product was purified by preparative HPLC to afford the product (57 mg, 0.14 mmol, 48% yield) as a solid. Prep-HPLC method: Rt 10.15; Column: YMC C-18 (150×19 mm), 5.0 µm; 0.1% TFA in water/acetonitrile; Flow Rate: 15.0 mL/min. LCMS: 400.0 (M+H), Rt 2.39 min, 98.0%; Column: ZORBAX XDB C-18 (50×4.6 mm), 3.5 µm; Mobile Phase: A: 0.1% HCOOH in water:ACN (95:5), B: ACN; Flow Rate: 1.5 mL/min. $^1$H NMR (400 MHz, CD$_3$OD): $\delta_H$=9.44 (d, 1H), 8.93 (d, 1H), 8.67 (d, 1H), 8.28 (dd, 1H), 6.05-5.98 (m, 1H), 3.18 (s, 3H), 1.85 (s, 6H), 1.59 (d, 3H).

Example II-9. Synthesis of Compound II-9: (S)-6-(5-fluoro-6-((1,1,1-trifluoropropan-2-yl)oxy)pyridin-3-yl)-3-(2-methoxypropan-2-yl)-[1,2,4]triazolo[4,3-a]pyrazine

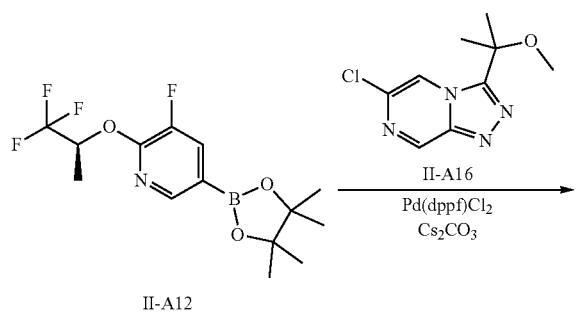

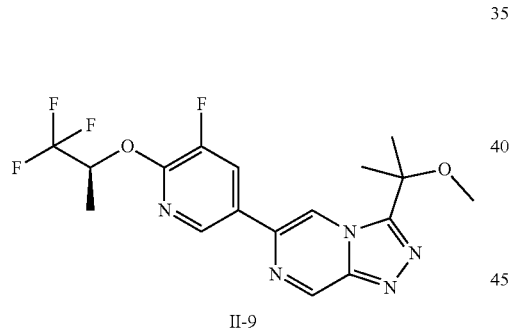

To a stirred solution of (S)-3-fluoro-5-(4,4,5,5-tetramethyl-1,3,2-dioxaborolan-2-yl)-2-((1,1,1-trifluoropropan-2-yl)oxy)pyridine (163 mg, 0.49 mmol) and 6-chloro-3-(2-methoxypropan-2-yl)-[1,2,4]triazolo[4,3-a]pyrazine (100 mg, 0.44 mmol) in 1,4-dioxane (2.7 mL) was added water (0.30 mL) and Cs$_2$CO$_3$ (287 mg, 0.88 mmol). Pd(dppf)Cl$_2$·DCM (36 mg, 0.044 mmol) was added to the reaction mixture under nitrogen atmosphere and heated at 90° C. for 3 hours. The reaction mixture was cooled to room temperature and filtered through Celite. The reaction mixture was treated with water (30 mL) and extracted with ethyl acetate (2×30 mL). The organic layer was washed with brine (30 mL), dried over anhydrous Na$_2$SO$_4$ and concentrated to give a crude product. The crude product was purified by preparative HPLC to afford the product (82 mg, 0.20 mmol, 45% yield) as a solid. Prep. HPLC method: Rt 10.35; Column: X-Bridge C18 (150×19 mm), 5.0 µm; Mobile phase: 0.1% TFA in water/acetonitrile; Flow Rate: 15.0 mL/min. LCMS: 400.1 (M+H), Rt 2.37 min, 98.0%; Column: ZORBAX XDB C-18 (50×4.6 mm), 3.5 µm; Mobile Phase: A: 0.1% HCOOH in water:ACN (95:5), B: ACN; Flow Rate: 1.5 mL/min. $^1$H NMR (400 MHz, DMSO-d$_6$): $\delta_H$=9.57 (d, 1H), 8.87 (d, 1H), 8.72 (d, 1H), 8.50 (dd, 1H), 6.06-5.99 (m, 1H), 3.05 (s, 3H), 1.78 (s, 6H), 1.55 (d, 3H).

Example II-10. Synthesis of Compound II-10: 6-[5-fluoro-6-(2,2,2-trifluoro-1,1-dimethyl-ethoxy)-3-pyridyl]-3-(1-methoxy-1-methyl-ethyl)-[1,2,4]triazolo[4,3-a]pyrazine

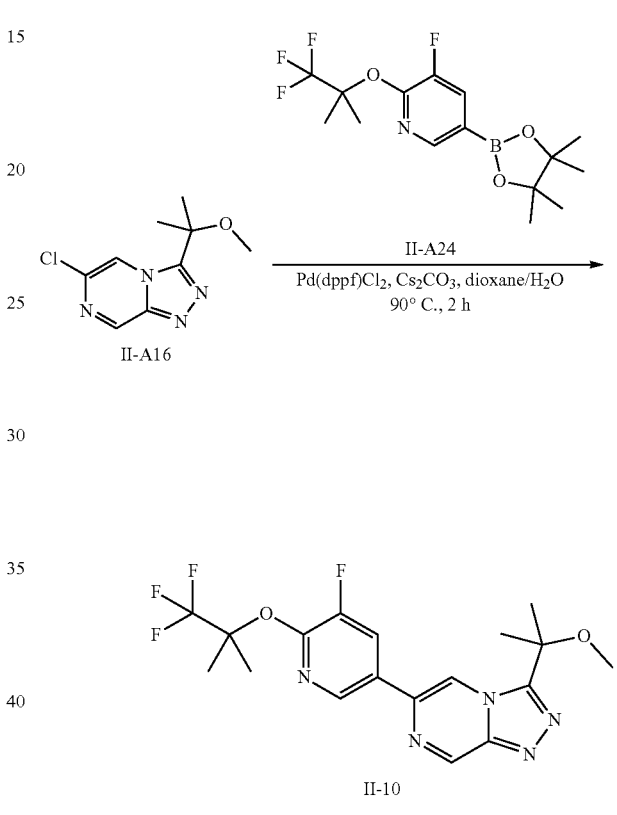

To a mixture of 6-chloro-3-(1-methoxy-1-methyl-ethyl)-[1,2,4]triazolo[4,3-a]pyrazine (220 mg, 0.97 mmol) and 3-fluoro-5-(4,4,5,5-tetramethyl-1,3,2-dioxaborolan-2-yl)-2-(2,2,2-trifluoro-1,1-dimethyl-ethoxy)pyridine (339 mg, 0.97 mmol) and Cs$_2$CO$_3$ (632 mg, 1.94 mmol) in 1,4-dioxane (5 mL) and water (0.5 mL) was added Pd(dppf)Cl$_2$ (71 mg, 0.10 mmol) under N$_2$. The mixture was stirred at 90° C. for 2 hours. The mixture was filtered and the filtrated was concentrated to remove dioxane. The aqueous layer was extracted with EtOAc (30 mL×3). The combined organic layers were washed with brine (30 mL), dried over anhydrous Na$_2$SO$_4$, filtered, and concentrated to give a crude product. The crude product was purified by prep-HPLC (Phenomenex Gemini-NX 80×30 mm, 3 µm) A=H$_2$O (10 mM NH$_4$HCO$_3$) and B=CH$_3$CN; 42-72% B over 9.5 minutes) to afford the product (158.4 mg, 0.38 mmol, 39% yield) as a solid. $^1$H NMR (400 MHz, CDCl$_3$) $\delta_H$=9.43 (s, 1H), 8.71 (s, 1H), 8.49 (s, 1H), 8.01 (d, 1H), 3.16 (s, 3H), 1.88 (s, 6H), 1.85 (s, 6H). LCMS R$_t$=1.21 min in 2.0 min chromatography, 10-80AB, MS ESI calcd. for C$_{18}$H$_{20}$F$_4$N$_5$O$_2$ [M+H]$^+$ 414.2, found 414.1.

Example II-11: Synthesis of Intermediates

Synthesis of II-A6: 3-[cyclopropylmethoxy(difluoro)methyl]-6-[5-fluoro-6-(2,2,2-trifluoroethoxy)-3-pyridyl]-[1,2,4]triazolo[4,3-a]pyridine

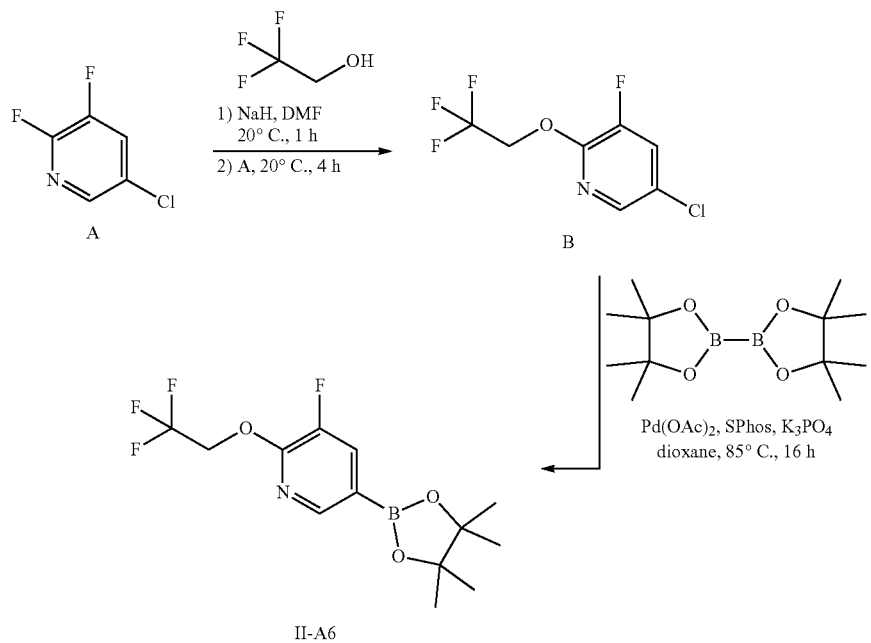

II-A6

B: To a suspension of NaH (2.94 g, 73.56 mmol) in THF (50 mL) was added 2,2,2-trifluoroethanol (7.36 g, 73.56 mmol) slowly at 20° C., and the mixture was stirred for 1 hour. 5-chloro-2,3-difluoro-pyridine (10 g, 66.88 mmol) was then added, and the mixture was stirred at 20° C. for another 4 hours. The mixture was quenched with saturated aqueous NH$_4$Cl (50 mL) and extracted with EtOAc (100 mL×2). The combined organic phase was washed with brine (50 mL), dried over Na$_2$SO$_4$, filtered, and concentrated to afford B (15000 mg, 65.34 mmol) as an oil. $^1$H NMR (400 MHz, CDCl$_3$) $\delta_H$=7.83 (d, 1H), 7.38 (dd, 1H), 4.73 (q, 2H).

II-A6: A mixture of B (8 g, 34.85 mmol), 4,4,5,5-tetramethyl-2-(4,4,5,5-tetramethyl-1,3,2-dioxaborolan-2-yl)-1,3,2-dioxaborolane (26.55 g, 104.55 mmol), K$_3$PO$_4$ (14.79 g, 69.7 mmol), SPhos (4.29 g, 10.45 mmol) and Pd(OAc)$_2$ (782.4 mg, 3.48 mmol) in 1,4-dioxane (250 mL) was stirred at 85° C. for 16 hours. After cooling to room temperature, the mixture was filtered through Celite and eluted with EtOAc (50 mL×2). The filtrate was concentrated and diluted with EtOAc (200 mL), washed with water (100 mL×2) and brine (100 mL), dried over Na$_2$SO$_4$, filtered, and concentrated to give the crude product, which was purified by flash chromatography on silica gel (EtOAc in PE=0 to 10% to 40%) to afford the product (3 g, 4.6021 mmol) as an oil. $^1$H NMR (400 MHz, CDCl$_3$) $\delta_H$=8.26 (d, 1H), 7.72 (dd, 1H), 4.87 (q, 2H), 1.35 (s, 12H). LCMS R$_t$=0.94 min using Method B, MS ESI calcd. for C$_{13}$H$_{17}$BF$_4$NO$_3$ [M+H]$^+$ 322.1, found 322.3.

Synthesis of II-A17: (5-(4,4,5,5-tetramethyl-1,3,2-dioxaborolan-2-yl)-2-(2,2,2-trifluoroethoxy)pyridine)

A mixture of 5-bromo-2-(2,2,2-trifluoroethoxy)pyridine (7 g, 27.34 mmol), 4,4,5,5-tetramethyl-2-(4,4,5,5-tetramethyl-1,3,2-dioxaborolan-2-yl)-1,3,2-dioxaborolane (7.64 g, 30.08 mmol), KOAc (5.37 g, 54.68 mmol) and Pd(dppf)Cl$_2$ (1 g, 1.37 mmol) in 1,4-dioxane (80 mL) was stirred at 85° C. for 12 hours under N$_2$. After cooling to room temperature, the mixture was filtered through Celite and then the filtrate was concentrated to give a crude product. The crude product was purified by flash chromatography on silica gel (EtOAc in PE=0% to 5%) to give the product (8 g, 26.4 mmol, 96% yield) as an oil. $^1$H NMR (400 MHz, CDCl$_3$) $\delta_H$=8.53 (s, 1H), 8.00 (dd, 1H), 6.84 (d, 1H), 4.80 (q, 2H), 1.35 (s, 12H).

Synthesis of II-A18: ((R)-5-(4,4,5,5-tetramethyl-1,3,2-dioxaborolan-2-yl)-2-((1,1,1-trifluoropropan-2-yl)oxy)pyridine)

To a stirred solution of (R)-5-bromo-2-((1,1,1-trifluoropropan-2-yl)oxy)pyridine (3.1 g, 11.5 mmol) and bis(pinacolato)diboron (3.79 g, 14.92 mmol) in 1,4-dioxane (35.0 mL) was added potassium acetate (2.25 g, 22.96 mmol). Pd(dppf)Cl$_2$·DCM (1.41 g, 1.72 mmol) was added to the reaction mixture under nitrogen atmosphere and heated at 90° C. for 12 hours. The reaction mixture was cooled to room temperature, filtered through Celite and concentrated under reduced pressure to give a crude product. The crude product was purified by column chromatography on silica gel with 6% ethyl acetate/PE to afford (R)-5-(4,4,5,5-tetramethyl-1,3,2-dioxaborolan-2-yl)-2-((1,1,1-trifluoropropan-2-yl)oxy)pyridine (2.8 g, 8.83 mmol, 76% yield) as a solid. LCMS: 318.0 (M+H), Rt 4.04 min; Column: ZORBAX Extend (50×4.6 mm), 5 µm; Mobile Phase: A: 10 mM Ammonium acetate in water, B: ACN; Flow Rate: 1.2 mL/min.

Synthesis of II-A19: ((S)-5-(4,4,5,5-tetramethyl-1,3,2-dioxaborolan-2-yl)-2-((1,1,1-trifluoropropan-2-yl)oxy)pyridine)

To a stirred solution of (S)-5-bromo-2-((1,1,1-trifluoropropan-2-yl)oxy)pyridine (0.5 g, 1.85 mmol) and bis(pinacolato)diboron (0.52 g, 2.04 mmol) in 1,4-dioxane (5.0 mL) was added potassium acetate (0.36 g, 3.7 mmol). Pd(dppf)Cl$_2$·DCM (0.15 g, 0.19 mmol) was added to the reaction mixture under nitrogen atmosphere and heated at 80° C. for 12 hours. The reaction mixture was cooled to room temperature, filtered through Celite and concentrated under reduced pressure to give a crude product. The crude product was purified by column chromatography on silica gel with 10% ethyl acetate/PE to afford (S)-5-(4,4,5,5-tetramethyl-1,3,2-dioxaborolan-2-yl)-2-((1,1,1-trifluoropropan-2-yl)oxy)pyridine (302 mg, 0.95 mmol, 51% yield). LCMS: 318.1 (M+H), Rt 3.04 min; Column: ZORBAX XDB C-18 (50× 4.6 mm), 3.5 μm; Mobile Phase: A: 0.1% HCOOH in water:ACN (95:5), B: ACN; Flow Rate: 1.5 mL/min.

Synthesis of II-A24: (3-fluoro-5-(4,4,5,5-tetramethyl-1,3,2-dioxaborolan-2-yl)-2-(2,2,2-trifluoro-1,1-dimethyl-ethoxy)pyridine)

A mixture of 5-bromo-3-fluoro-2-(2,2,2-trifluoro-1,1-dimethyl-ethoxy)pyridine (6.3 g, 20.86 mmol), 4,4,5,5-tetramethyl-2-(4,4,5,5-tetramethyl-1,3,2-dioxaborolan-2-yl)-1,3,2-dioxaborolane (5.83 g, 22.94 mmol), Pd(dppf)Cl$_2$ (1.53 g, 2.09 mmol) and KOAc (4.09 g, 41.71 mmol) in 1,4-dioxane (100 mL) was stirred at 90° C. for 2.5 hours. After cooling to 25° C., the suspension was diluted with EtOAc (50 mL), filtered through silica gel and eluted with EtOAc (50 mL). The combined filtrates were concentrated to give a crude product. The crude product was purified by flash chromatography on silica gel (EtOAc in PE=0% to 10%) to give the product (5.7 g, 16.33 mmol, 78% yield) as an oil. $^1$H NMR (400 MHz, CDCl$_3$) $\delta_H$=8.26 (s, 1H), 7.67 (d, 1H), 1.83 (s, 6H), 1.34 (s, 12H). LCMS R$_t$=1.06 min in 1.5 min chromatography, 5-95AB, MS ESI calcd. for C$_{15}$H$_{21}$BF$_4$NO$_3$ [M+H]$^+$ 350.1, found 350.0.

Example II-12. Synthesis of Compound II-11: 3-(2-ethoxypropan-2-yl)-6-(5-fluoro-6-((1,1,1-trifluoro-2-methylpropan-2-yl)oxy)pyridin-3-yl)-[1,2,4]triazolo[4,3-a]pyrazine

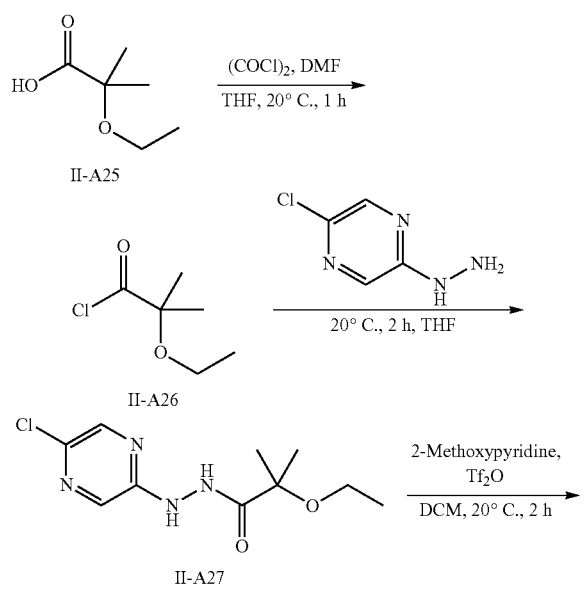

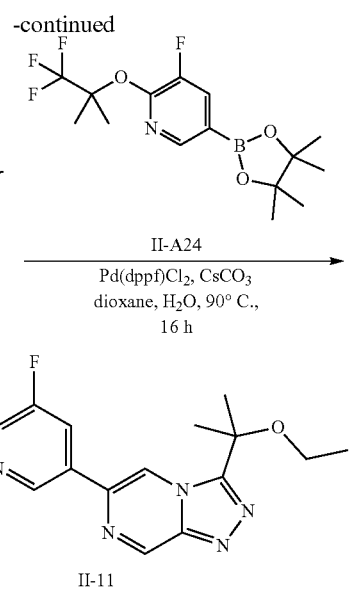

II-A26: 2-ethoxy-2-methylpropanoyl chloride

To a solution of 2-ethoxy-2-methyl-propanoic acid (2 g, 15.13 mmol) in THF (20 mL) was added (COCl)$_2$ (1.56 mL, 18.2 mmol) and DMF (0.20 mL) at 0° C. under N$_2$. The mixture was stirred at 25° C. under N$_2$ for 1 hour. The solution was used in the next step directly.

II-A27: N'-(5-chloropyrazin-2-yl)-2-ethoxy-2-methylpropanehydrazide

To the above solution was added 2-ethoxy-2-methylpropanoyl chloride (2.28 g, 15.1 mmol) in THF (20 mL) at 0° C. under N$_2$. After stirring at 25° C. under N$_2$ for 2 hours, the mixture was poured into H$_2$O (50 mL) and extracted with EtOAc (30×2 mL). The combined organic phases were washed with NaHCO$_3$ (50 mL), brine (50 mL), dried over Na$_2$SO$_4$, filtered, and concentrated to give N'-(5-chloropyrazin-2-yl)-2-ethoxy-2-methyl-propanehydrazide (3 g, 9.28 mmol, 61.3% yield) as a solid. LCMS R$_t$=0.816 min in 1.5 min chromatography, 5-95AB, MS ESI calcd. for C$_{10}$H$_{16}$ClN$_4$O$_2$[M+H]$^+$ 258.9, found 258.9.

II-A28: 6-chloro-3-(2-ethoxypropan-2-yl)-[1,2,4]triazolo[4,3-a] pyrazine

To a solution of N'-(5-chloropyrazin-2-yl)-2-ethoxy-2-methyl-propanehydrazide (3 g, 11.6 mmol) in DCM (10 mL) was added 2-methoxypyridine (5.06 g, 46.4 mmol) and Tf$_2$O (3.92 mL, 23.2 mmol) under N$_2$. After stirring at 20° C. for 2 hours. The reaction was poured into water (50 mL) and extracted with DCM (30 mL×2). The combined organic layer was washed with brine (50 mL), dried over Na$_2$SO$_4$, filtered, and concentrated. The residue was purified by flash column chromatography (15 to 25% of EtOAc in PE) to give 6-chloro-3-(1-ethoxy-1-methyl-ethyl)-[1,2,4]triazolo[4,3-a]pyrazine (600 mg, 1.50 mmol, 13% yield) as an oil. LCMS R$_t$=0.818 min in 1.5 min chromatography, 5-95AB, MS ESI calcd. for C$_{10}$H$_{14}$ClN$_4$O$_1$[M+H]$^+$ 240.9, found 240.9.

Compound II-A11: 3-(2-ethoxypropan-2-yl)-6-(5-fluoro-6-((1,1,1-trifluoro-2-methylpropan-2-yl)oxy)pyridin-3-yl)-[1,2,4]triazolo[4,3-a]pyrazine To a solution of 6-chloro-3-(1-ethoxy-1-methyl-ethyl)-[1,2,4]triazolo[4,3-a]pyrazine (600 mg, 2.49 mmol) in 1,4- dioxane (5 mL) and water (0.50 mL) was added 3-fluoro-5-(4,4,5,5-tetramethyl-1,3,2-dioxaborolan-2-yl)-2-(2,2,2-trifluoro-1,1-dimethyl-ethoxy)pyridine (957.4 mg, 2.74 mmol), Cs$_2$CO$_3$ (1.62 g, 4.99 mmol) and Pd(dppf)Cl$_2$ (182.4 mg, 0.25 mmol) under N$_2$. After stirring at 90° C. for 16 hours, the mixture was filtered, and the filtrate was concentrated to remove dioxane. The aqueous layer was extracted with EtOAc (10 mL×3). The combined organic layers were washed with brine (10 mL), dried over anhydrous Na$_2$SO$_4$, filtered, and concentrated. The residue was purified by flash column chromatography (20% to 30% of EtOAc in PE) to give the product (300 mg, 0.63 mmol, 25% yield) as an oil, which was purified by prep-HPLC (Phenommenex Genmini-NX 80 mm×30 mm, 3 um; Condition: A=water (10 mM NH$_4$HCO$_3$) B=ACN; 51-81% B) to give 3-(1-ethoxy-1-methyl-ethyl)-6-[5-fluoro-6-(2,2,2-trifluoro-1,1-dimethyl-ethoxy)-3-pyridyl]-[1,2,4]triazolo[4,3-a]pyrazine (173.54 mg, 0.41 mmol, 58% yield) as a solid. $^1$H NMR (400 MHz, CDCl$_3$) $\delta_H$=9.41 (d, 1H), 8.79 (d, 1H), 8.45 (d, 1H), 8.01-7.96 (m, 1H), 3.32-3.23 (m, 2H), 1.86 (s, 6H), 1.84 (s, 6H), 1.23-1.17 (m, 3H). $^{19}$F NMR (376.5 MHz, CDCl$_3$) $\delta_F$=−83.963, −135.024. LCMS R$_t$=1.091 min in 2.0 min chromatography, 30-90AB, MS ESI calcd. for C$_{19}$H$_{22}$F$_4$N$_5$O$_2$[M+H]$^+$ 428.1, found 428.1.

Example II-13. Synthesis of Compound II-12: 6-(5-fluoro-6-(1-(trifluoromethyl)cyclobutoxy)pyridin-3-yl)-3-(2-methoxypropan-2-yl)-[1,2,4]triazolo[4,3-a] pyrazine (10 mL) and water (1 mL) was added Pd(dppf)Cl$_2$ (48.4 mg, 0.07 mmol) under N$_2$. After stirring at 90° C. for 16 hours, the mixture was filtered, and the filtrate was concentrated to remove dioxane. The aqueous layer was extracted with EtOAc (30 mL×3). The combined organic layers were washed with brine (30 mL), dried over anhydrous Na$_2$SO$_4$, filtered, and concentrated. The crude mixture was purified by prep-HPLC (Phenomenex Gemini-NX 80×30 mm, 3 μm, A=water (10 mM NH$_4$HCO$_3$) B=ACN), 47-77% B over 9 min., 100% for 2.5 min.) to give 6the product (13.59 mg, 0.03 mmol, 5% yield) as a solid. $^1$H NMR (400 MHz, CDCl$_3$) $\delta_H$=9.41 (d, 1H), 8.71 (d, 1H), 8.46 (d, 1H), 8.03 (dd, 1H), 3.14 (s, 3H), 2.99-2.85 (m, 2H), 2.81-2.66 (m, 2H), 2.09-1.91 (m, 2H), 1.84 (s, 6H). LCMS R$_t$=1.28 min in 2.0 min chromatography, 10-80AB, MS ESI calcd. for C$_{19}$H$_{20}$F$_4$N$_5$O$_2$ [M+H]$^+$ 426.1, found 426.2

Example II-14. Synthesis of Compound II-13: 3-(1-methoxy-1-methyl-ethyl)-6-[6-[1-(trifluoromethyl)cyclobutoxy]-3-pyridyl]-[1,2,4]triazolo[4,3-a]pyrazine

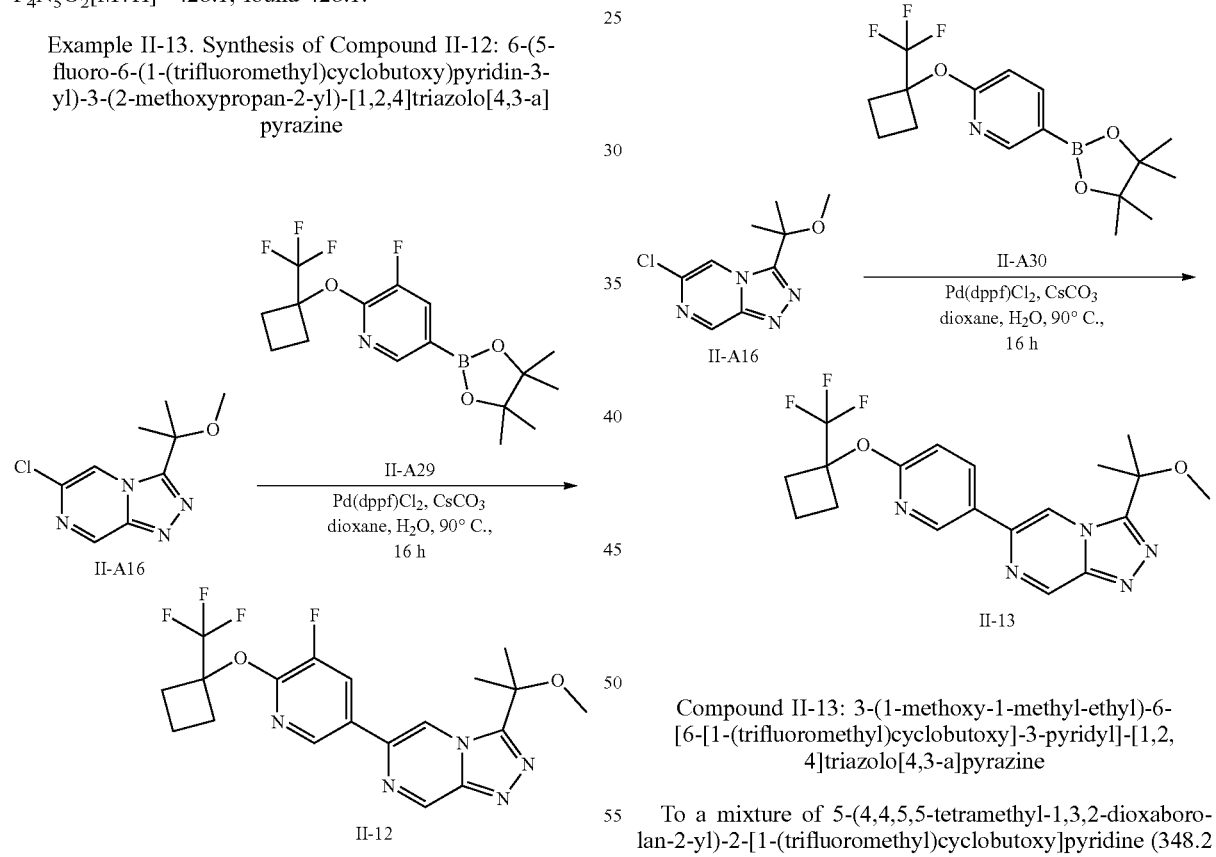

Compound II-13: 3-(1-methoxy-1-methyl-ethyl)-6-[6-[1-(trifluoromethyl)cyclobutoxy]-3-pyridyl]-[1,2,4]triazolo[4,3-a]pyrazine Compound I-12: 6-(5-fluoro-6-(1-(trifluoromethyl)cyclobutoxy)pyridin-3-yl)-3-(2-methoxypropan-2-yl)-[1,2,4]triazolo[4,3-a]pyrazine To a mixture of 3-fluoro-5-(4,4,5,5-tetramethyl-1,3,2-dioxaborolan-2-yl)-2-[1-(trifluoromethyl)cyclobutoxy]pyridine (262.9 mg, 0.73 mmol) and 6-chloro-3-(1-methoxy-1-methyl-ethyl)-[1,2,4]triazolo[4,3-a]pyrazine (150 mg, 0.66 mmol) and Cs$_2$CO$_3$ (431.2 mg, 1.32 mmol) in 1,4-dioxane To a mixture of 5-(4,4,5,5-tetramethyl-1,3,2-dioxaborolan-2-yl)-2-[1-(trifluoromethyl)cyclobutoxy]pyridine (348.2 mg, 1.01 mmol) and 6-chloro-3-(1-methoxy-1-methyl-ethyl)-[1,2,4]triazolo[4,3-a]pyrazine (200 mg, 0.88 mmol) and Cs$_2$CO$_3$ (574.9 mg, 1.76 mmol) in 1,4-dioxane (10 mL) and water (1 mL) was added Pd(dppf)Cl$_2$ (64.6 mg, 0.09 mmol) under N$_2$. After stirring at 90° C. for 3 hours, the mixture was filtered, poured into water (30 ml), and extracted with EtOAc (20 mL×2). The combined organic layers were washed with brine (30 mL), dried over anhydrous Na$_2$SO$_4$, filtered, and concentrated. The crude mixture was purified by flash column chromatography (0 to 50% of EtOAc in PE) to give the product (230 mg, 0.56 mmol, 64% yield) as an oil. The 3-(1-methoxy-1-methyl-ethyl)-6-[6-[1-(trifluoromethyl)cyclobutoxy]-3-pyridyl]-[1,2,4]triazolo[4,3-a]pyrazine (230 mg, 0.56 mmol) was purified by HPLC (Phenomenex Gemini-NX 80×30 mm, 3 μm A=water (10 mM NH$_4$HCO$_3$) B=ACN, 47-77% B over 9 min., 100% B for 1.5 min., 30 mL/min, 5 injections) to give 3-(1-methoxy-1-methyl-ethyl)-6-[6-[1-(trifluoromethyl)cyclobutoxy]-3-pyridyl]-[1,2,4]triazolo[4,3-a]pyrazine (10.6 mg, 0.03 mmol) as a solid. $^1$H NMR (400 MHz, CDCl$_3$) $\delta_H$=9.43 (d, 1H), 8.69 (d, 2H), 8.26-8.16 (m, 1H), 6.96-6.87 (m, 1H), 3.14 (s, 3H), 2.99-2.85 (m, 2H), 2.77-2.64 (m, 2H), 2.09-1.90 (m, 2H), 1.84 (s, 6H). $^{19}$F NMR (400 MHz, CDCl$_3$) $\delta_F$=−81.188. LCMS R$_t$=1.039 min in 1.5 min chromatography, 5-95AB, MS ESI calcd. for C$_{19}$H$_{21}$F$_3$N$_5$O$_2$[M+H]$^+$ 408.1, found 408.1.

Example II-15. Synthesis of Compound II-14: 3-(1-methoxy-1-methyl-ethyl)-6-[6-(2,2,2-trifluoro-1,1-dimethyl-ethoxy)-3-pyridyl]-[1,2,4]triazolo[4,3-a]pyrazine

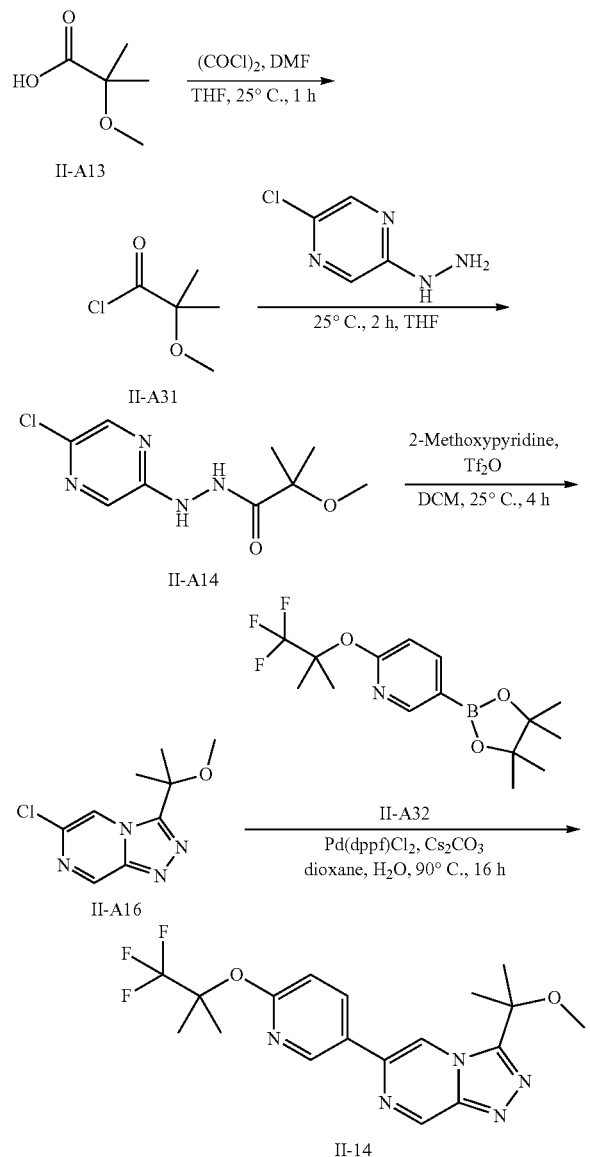

II-A31: 2-methoxy-2-methyl-propanoyl chloride

To a solution of 2-methoxy-2-methyl-propanoic acid (3.00 g, 25.0 mmol) in THF (30 mL) was added DMF (0.1 mL, 25 mmol) and (COCl)$_2$ (2.4 mL, 28 mmol) at 0° C. under N$_2$. The mixture was stirred at 25° C. under N$_2$ for 1 hour. The solution was used directly for the next step without characterization.

II-A14: N'-(5-chloropyrazin-2-yl)-2-methoxy-2-methyl-propanehydrazide

To a solution of (5-chloropyrazin-2-yl)hydrazine (3.00 g, 21.0 mmol) in THF (30 mL) was added 2-methoxy-2-methyl-propanoyl chloride (3.40 g, 25.0 mmol) at 25° C. The reaction was stirred at 25° C. for 2 hours. The reaction was quenched with water (50 mL) and extracted with EtOAc (3×50 mL). The combined organic layer was washed with brine (50 mL), dried over Na$_2$SO$_4$, filtered, and concentrated in vacuum to give N'-(5-chloropyrazin-2-yl)-2-methoxy-2-methyl-propanehydrazide (4.00 g, 79.0% yield), which was used directly in the next step. LCMS R$_t$=0.778 min in 1.5 min chromatography, 5-95AB, MS ESI calcd. for C$_9$H$_{14}$ClN$_4$O$_2$ [M+H]$^+$ 244.9, found 244.9.

II-A16: 6-chloro-3-(1-methoxy-1-methyl-ethyl)-[1,2,4]triazolo[4,3-a]pyrazine

To a solution of N'-(5-chloropyrazin-2-yl)-2-methoxy-2-methyl-propanehydrazide (4.00 g, 16.0 mmol) in DCM (40 mL) was added 2-methoxypyridine (11.2 g, 103.0 mmol) and Tf$_2$O (8.30 mL, 49.0 mmol) at 0° C. After stirring at 25° C. for 4 hours, the reaction was quenched with water (50 mL) and extracted with DCM (2×50 mL). The combined organic layer was washed with brine (50 mL), dried over Na$_2$SO$_4$, filtered, and concentrated in vacuum. The crude mixture was purified by column chromatography (EtOAc in PE, 0% to 30%) to give 6-chloro-3-(1-methoxy-1-methyl-ethyl)-[1,2,4]triazolo[4,3-a]pyrazine (900 mg, 24.0% yield) as an oil, which was used directly in the next step. LCMS R$_t$=0.779 min in 1.5 min chromatography, 5-95AB, MS ESI calcd. for C$_9$H$_{12}$ClN$_4$O [M+H]$^+$ 226.9, found 226.9.

II-14: 3-(1-methoxy-1-methyl-ethyl)-6-[6-(2,2,2-trifluoro-1,1-dimethyl-ethoxy)-3-pyridyl]-[1,2,4]triazolo[4,3-a]pyrazine To a solution of 6-chloro-3-(1-methoxy-1-methyl-ethyl)-[1,2,4]triazolo[4,3-a]pyrazine (200 mg, 0.88 mmol) in 1,4-dioxane (5 mL) and water (0.5 mL) was added 5-(4,4,5,5-tetramethyl-1,3,2-dioxaborolan-2-yl)-2-(2,2,2-trifluoro-1,1-dimethyl-ethoxy)pyridine (350.0 mg, 1.10 mmol), Cs$_2$CO$_3$ (575.0 mg, 1.80 mmol) and Pd(dppf)Cl$_2$ (32.0 mg, 0.040 mmol) under N$_2$. After stirring at 90° C. for 16 hours, the mixture was filtered, and the filtrate was concentrated in vacuum. The residue was purified by prep-HPLC (Phenommenex Gemini-NX 80×40 mm, 3 m; A=water (0.05% NH$_3$·H$_2$O) B=ACN; 37-69% B) to give 3-(1-methoxy-1-methyl-ethyl)-6-[6-(2,2,2-trifluoro-1,1-dimethyl-ethoxy)-3-pyridyl]-[1,2,4]triazolo[4,3-a]pyrazine (24.88 mg, 7.10% yield) as a solid. $^1$H NMR (400 MHz, CDCl$_3$) $\delta_H$=9.43 (d, 1H), 8.70-8.65 (m, 2H), 8.20-8.13 (m, 1H), 6.92 (d, 1H), 3.14 (s, 3H), 1.86 (s, 6H), 1.84 (s, 6H). $^{19}$F NMR (376.5 MHz CDCl$_3$) $\delta_F$=83.846. LCMS R$_t$=2.351 min in 3 min chromatography, 30-90AB, MS ESI calcd. for C$_{18}$H$_{21}$F$_3$N$_5$O$_2$[M+H]$^+$ 396.2, found 396.2.

Example II-16. Synthesis of Compound II-15: 3-(2-ethoxypropan-2-yl)-6-(6-((1,1,1-trifluoro-2-methylpropan-2-yl)oxy)pyridin-3-yl)-[1,2,4]triazolo[4,3-a]pyrazine

Example II-17. Synthesis of Compound II-16: 6-(5-fluoro-6-((1,1,1-trifluoro-2-methylpropan-2-yl)oxy)pyridin-3-yl)-3-(1-methoxycyclopropyl)-[1,2,4]triazolo[4,3-a]pyrazine

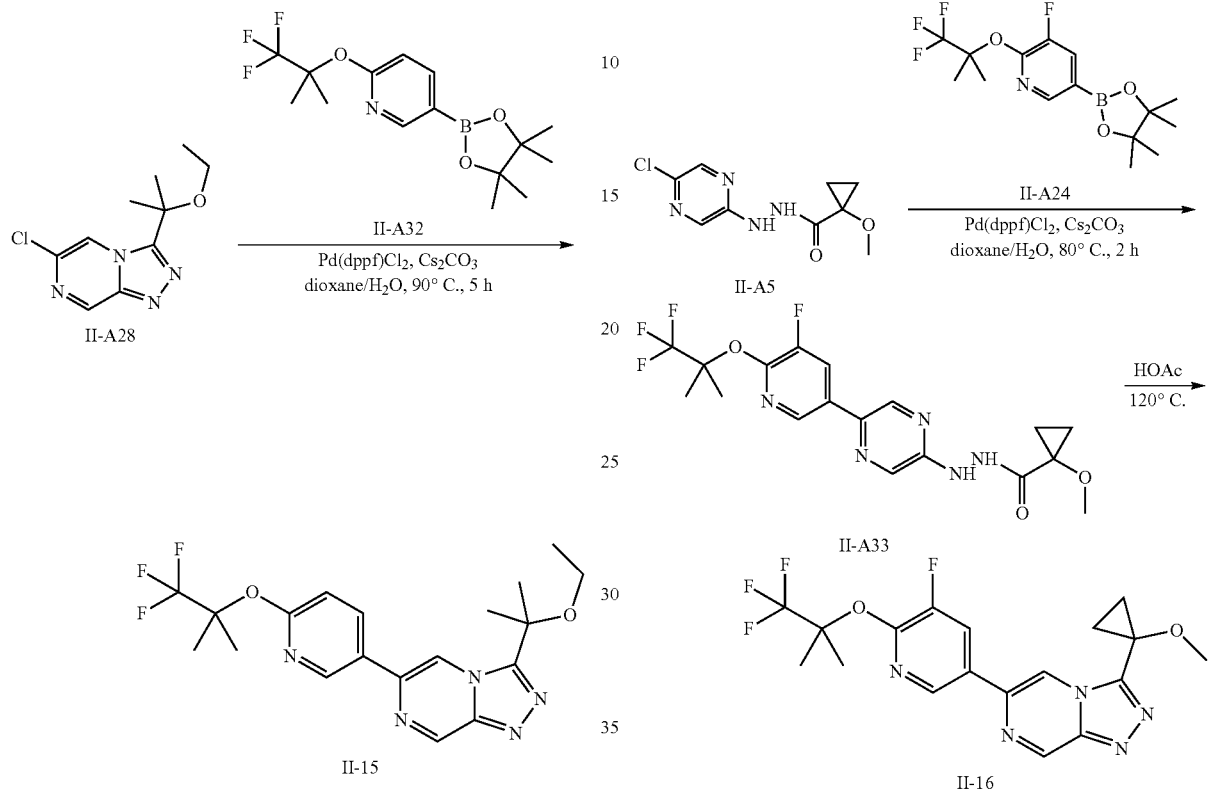

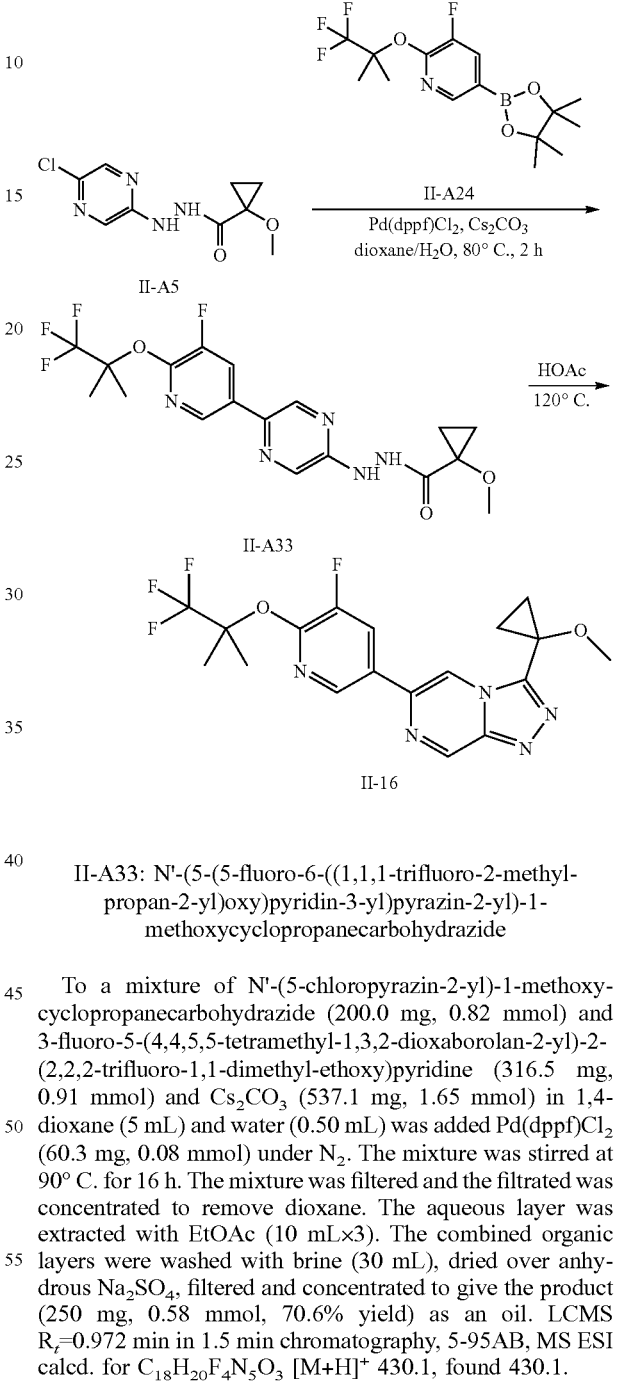

Compound II-15: 3-(2-ethoxypropan-2-yl)-6-(6-((1,1,1-trifluoro-2-methylpropan-2-yl)oxy)pyridin-3-yl)-[1,2,4]triazolo[4,3-a]pyrazine To a mixture of 6-chloro-3-(1-ethoxy-1-methyl-ethyl)-[1,2,4]triazolo[4,3-a]pyrazine (70.0 mg, 0.29 mmol) and 5-(4,4,5,5-tetramethyl-1,3,2-dioxaborolan-2-yl)-2-(2,2,2-trifluoro-1,1-dimethyl-ethoxy)pyridine (111.7 mg, 0.34 mmol) and $Cs_2CO_3$ (189.5 mg, 0.58 mmol) in 1,4-dioxane (5 mL) and water (0.50 mL) was added Pd(dppf)Cl$_2$ (21.3 mg, 0.03 mmol) under $N_2$. The mixture was stirred at 90° C. for 16 hours. The mixture was filtered, and the filtrate was concentrated to remove dioxane. The aqueous layer was extracted with EtOAc (20 mL×3). The combined organic layers were washed with brine (30 mL), dried over anhydrous $Na_2SO_4$, filtered, and concentrated. The crude mixture was purified by prep-HPLC [Phenomenex Gemini-NX 80×30 mm, 3 μm, water (10 mM $NH_4HCO_3$)) and B=$CH_3CN$; 53-83% B over 9.0 minutes)] to give the product ((8.0 mg, 0.02 mmol, 16% yield) as a solid. $^1H$ NMR (400 MHz, CDCl$_3$) $\delta_H$=9.51-9.40 (m, 1H), 8.76 (s, 1H), 8.68 (s, 1H), 8.16 (br d, 1H), 6.92 (d, 1H), 3.27 (d, 2H), 1.85 (br s, 12H), 1.23-1.15 (m, 3H) $^{19}F$ NMR (376.5 MHz, CDCl3) $\delta_F$=−83.839. LCMS R$_t$=2.581 min in 4.0 min chromatography, 30-90AB, MS ESI calcd. for $C_{19}H_{23}F_3N_5O_2$ [M+H]$^+$ 410.2, found 410.2.

II-A33: N'-(5-(5-fluoro-6-((1,1,1-trifluoro-2-methylpropan-2-yl)oxy)pyridin-3-yl)pyrazin-2-yl)-1-methoxycyclopropanecarbohydrazide To a mixture of N'-(5-chloropyrazin-2-yl)-1-methoxycyclopropanecarbohydrazide (200.0 mg, 0.82 mmol) and 3-fluoro-5-(4,4,5,5-tetramethyl-1,3,2-dioxaborolan-2-yl)-2-(2,2,2-trifluoro-1,1-dimethyl-ethoxy)pyridine (316.5 mg, 0.91 mmol) and $Cs_2CO_3$ (537.1 mg, 1.65 mmol) in 1,4-dioxane (5 mL) and water (0.50 mL) was added Pd(dppf)Cl$_2$ (60.3 mg, 0.08 mmol) under $N_2$. The mixture was stirred at 90° C. for 16 h. The mixture was filtered and the filtrated was concentrated to remove dioxane. The aqueous layer was extracted with EtOAc (10 mL×3). The combined organic layers were washed with brine (30 mL), dried over anhydrous $Na_2SO_4$, filtered and concentrated to give the product (250 mg, 0.58 mmol, 70.6% yield) as an oil. LCMS R$_t$=0.972 min in 1.5 min chromatography, 5-95AB, MS ESI calcd. for $C_{18}H_{20}F_4N_5O_3$ [M+H]$^+$ 430.1, found 430.1.

Compound II-16: 6-(5-fluoro-6-((1,1,1-trifluoro-2-methylpropan-2-yl)oxy)pyridin-3-yl)-3-(1-methoxycyclopropyl)-[1,2,4]triazolo[4,3-a]pyrazine To a mixture of N'-[5-[5-fluoro-6-(2,2,2-trifluoro-1,1-dimethyl-ethoxy)-3-pyridyl]pyrazin-2-yl]-1-methoxy-cyclopropanecarbohydrazide (0.15 g, 0.35 mmol) in acetic acid (5 mL) was stirred at 120° C. for 16 h to give a solution. Water (10 mL) was added to the solution and the mixture was extracted with EtOAc (15 mL×2). The combined organic phase was washed with saturated NaHCO₃ aqueous (10 mL), brine (30 mL), dried over anhydrous Na₂SO₄, filtered and concentrated to give the crude product, which was purified by pre-HPLC (Column: Phenomenex Gemini-NX 80×40 mm×3 um; Condition: Water (0.05% NH₃H₂O)-ACN; Begin B: 40, End B: 70) to give the product (10 mg, 0.03 mmol, 6.2% yield) as an oil. $^{1}$H NMR (CDCl₃, 400 MHz) $\delta_H$=9.44 (s, 1H), 8.68 (s, 1H), 8.54 (s, 1H), 8.03 (br d, H), 3.29 (s, 3H), 1.87 (s, 6H), 1.45 (s, 4H). $^{19}$F NMR (376.5 MHz, CDCl3) $\delta_F$ −83.675, −135.098. LCMS R$_t$=2.239 min in 3 min chromatography, 10-80AB, MS ESI calcd. for C₁₈H₁₈F₄N₅O₂ [M+H]⁺ 412.2, found 412.2.

Example III-1. Syntheses of Compound III-1: 6-[2-cyclopropyl-4-(trifluoromethoxy)phenyl]-3-(trifluoromethyl)-[1,2,4]triazolo[4,3-a]pyrazine & Compound III-2: 6-[2-cyclopropyl-4-(trifluoromethoxy)phenyl]-3-[ethoxy(difluoro)methyl]-[1,2,4]triazolo[4,3-a]pyrazine

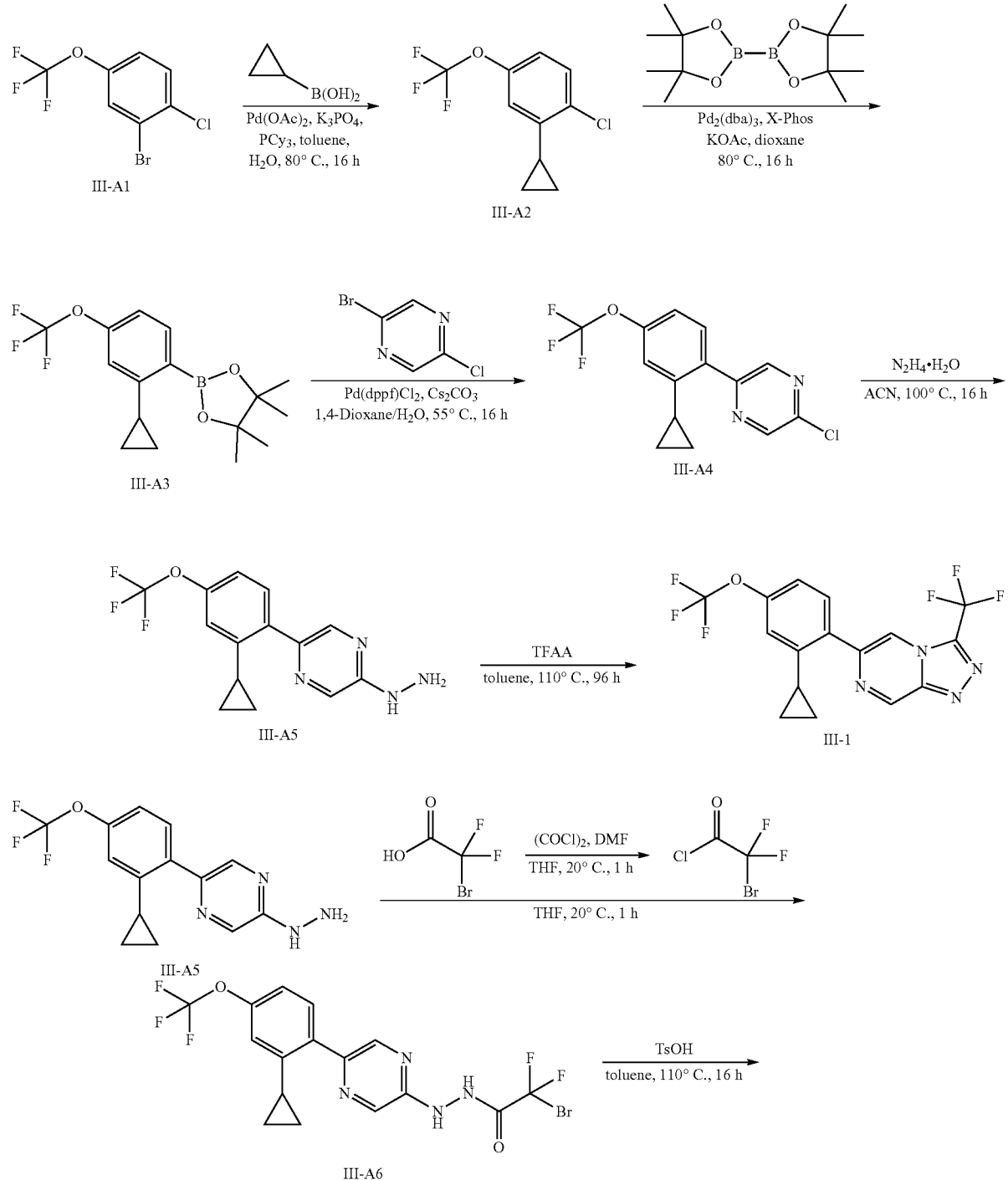

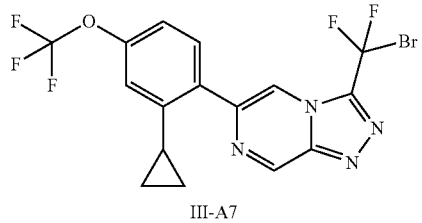
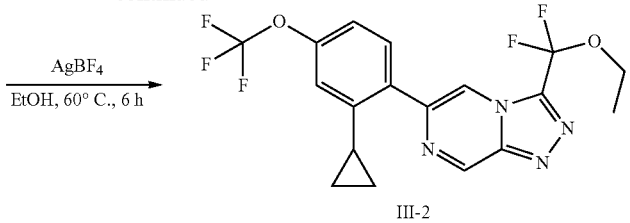

III-A2: 1-chloro-2-cyclopropyl-4-(trifluoromethoxy)benzene

A mixture of 2-bromo-1-chloro-4-(trifluoromethoxy)benzene (3 g, 10.89 mmol), cyclopropylboronic acid (982.34 mg, 11.44 mmol), $K_3PO_4$ (8.09 g, 38.12 mmol), $PCy_3$ (610.85 mg, 2.18 mmol) and $Pd(OAc)_2$ (244.52 mg, 1.09 mmol) in toluene (50 mL) and water (5 mL) was stirred at 80° C. under $N_2$ for 16 hours. After cooling to room temperature, water (50 mL) was added, and the mixture was filtered through Celite. The filtrate was extracted with EtOAc (50 mL×2). The combined organic phase was washed with brine (50 mL), dried over anhydrous $Na_2SO_4$, filtered, and concentrated. The crude product was purified by flash column chromatography (EtOAc in PE=0% to 2%) to give the product (2.57 g, 10.86 mmol, 99% yield) as an oil. $^1H$ NMR (400 MHz, $CDCl_3$) $\delta_H$=7.36 (d, 1H), 7.01-6.95 (m, 1H), 6.78 (d, 1H), 2.21 (tt, 1H), 1.13-1.04 (m, 2H), 0.73-0.67 (m, 2H).

III-A3: 2-[2-cyclopropyl-4-(trifluoromethoxy)phenyl]-4,4,5,5-tetramethyl-1,3,2-dioxaborolane A mixture of 1-chloro-2-cyclopropyl-4-(trifluoromethoxy)benzene (2.57 g, 10.86 mmol), 4,4,5,5-tetramethyl-2-(4,4,5,5-tetramethyl-1,3,2-dioxaborolan-2-yl)-1,3,2-dioxaborolane (3.31 g, 13.03 mmol), KOAc (2.13 g, 21.72 mmol), X-phos (1.04 g, 2.17 mmol) and $Pd_2(dba)_3$ (0.99 g, 1.09 mmol) in 1,4-dioxane (50 mL) was stirred at 80° C. under $N_2$ for 16 hours. After cooling to room temperature, water (50 mL) was added, and the mixture was filtered through Celite. The filtrate was extracted with EtOAc (80 mL×2). The combined organic phase was washed with brine (50 mL), dried over anhydrous $Na_2SO_4$, filtered, and concentrated. The crude product was purified by flash column chromatography on silica gel (EtOAc in PE=0% to 2%) to give the product (2.5 g, 7.62 mmol, 70% yield) as an oil. $^1H$ NMR (400 MHz, $CDCl_3$) $\delta_H$=7.77 (d, 1H), 6.98-6.96 (m, 1H), 6.64 (s, 1H), 2.75-2.68 (m, 1H), 1.36 (s, 12H), 1.04-1.00 (m, 2H), 0.70-0.66 (m, 2H).

III-A4: 2-chloro-5-[2-cyclopropyl-4-(trifluoromethoxy)phenyl]pyrazine

A mixture of 2-bromo-5-chloro-pyrazine (1.35 g, 6.98 mmol), 2-[2-cyclopropyl-4-(trifluoromethoxy)phenyl]-4,4,5,5-tetramethyl-1,3,2-dioxaborolane (2.5 g, 7.62 mmol), $Cs_2CO_3$ (4.55 g, 13.96 mmol) and $Pd(dppf)Cl_2$ (766.01 mg, 1.05 mmol) in 1,4-dioxane (20 mL) and water (1.5 mL) was stirred at 55° C. under $N_2$ for 16 hours. After cooling to room temperature, water (20 mL) was added, and the mixture was filtered through Celite. The filtrate was extracted with EtOAc (50 mL×2). The combined organic phase was washed with brine (50 mL), dried over anhydrous $Na_2SO_4$, filtered, and concentrated. The crude product was purified by flash column chromatography on silica gel (EtOAc in PE=0% to 2% to 5%) to give the product (1.9 g, 4.64 mmol, 66% yield) as an oil. $^1H$ NMR (400 MHz, $CDCl_3$) $\delta_H$=8.70 (d, 1H), 8.65 (d, 1H), 7.48 (d, 1H), 7.17-7.14 (m, 1H), 6.94-6.90 (m, 1H), 2.05-2.00 (m, 1H), 0.99-0.93 (m, 2H), 0.72-0.67 (m, 2H).

III-A5: [5-[2-cyclopropyl-4-(trifluoromethoxy)phenyl]pyrazin-2-yl]hydrazine

A solution of 2-chloro-5-[2-cyclopropyl-4-(trifluoromethoxy)phenyl]pyrazine (1.9 g, 4.64 mmol) and hydrazine hydrate (2.33 g, 46.45 mmol) in MeCN (20 mL) was stirred at 100° C. for 16 hours. After cooling to room temperature, water (50 mL) was added, and the mixture was extracted with EtOAc (50 mL×2). The combined organic phase was washed with brine (50 mL), dried over anhydrous $Na_2SO_4$, filtered, and concentrated. The crude product was purified by flash column chromatography on silica gel (EtOAc in PE=30% to 50% to 80%) to give the product (1.44 g, 4.64 mmol, 99% yield) as an oil. $^1H$ NMR (400 MHz, DMSO-$d_6$) $\delta_H$=8.23-8.18 (m, 2H), 8.11 (s, 1H), 7.47 (d, 1H), 7.21 (d, 1H), 6.93 (s, 1H), 4.33 (brs, 2H), 2.17-2.06 (m, 1H), 0.92-0.85 (m, 2H), 0.70-0.63 (m, 2H).

Compound III-1: 6-[2-cyclopropyl-4-(trifluoromethoxy)phenyl]-3-(trifluoromethyl)-[1,2,4]triazolo[4,3-a]pyrazine A mixture of [5-[4-(trifluoromethoxy)phenyl]pyrazin-2-yl]hydrazine (200 mg, 0.74 mmol) and (2,2,2-trifluoroacetyl) 2,2,2-trifluoroacetate (171 mg, 0.81 mmol) in toluene (5 mL) was stirred at 110° C. for 96 hours. After cooling to room temperature, the reaction mixture was diluted with water (20 mL). The mixture was extracted with EtOAc (20 mL×2). The combined organic phases were washed with brine (20 mL), dried over anhydrous $Na_2SO_4$, filtered, and concentrated. The residue was purified by pre-HPLC [Welch Xtimate C18 (150 mm×25 mm, 5 mm) A=$H_2O$ (10 mM $NH_4HCO_3$) and B=$CH_3CN$; 50-80% B over 8 minutes)] to give the product (30.35 mg, 0.078 mmol, 11% yield) as a solid. $^1H$ NMR (400 MHz, $CDCl_3$) $\delta_H$=9.61 (d, 1H), 8.41 (s, 1H), 7.58 (d, 1H), 7.25-7.18 (m, 1H), 6.97 (s, 1H), 2.10-2.00 (m, 1H), 1.05-0.95 (m, 2H), 0.82-0.72 (m, 2H). LCMS $R_t$=1.01 min in 1.5 min chromatography, 5-95AB

III-A6: 2-bromo-N'-[5-[2-cyclopropyl-4-(trifluoromethoxy)phenyl]pyrazin-2-yl]-2,2-difluoro-acetohydrazide To a solution of 2-bromo-2,2-difluoro-acetic acid (0.51 g, 2.9 mmol) in THF (5 mL) was added one drop of DMF and $(COCl)_2$ (0.29 mL, 3.48 mmol). The resulting mixture was stirred at 20° C. for 1 hour. Then a solution of [5-[2-cyclopropyl-4-(trifluoromethoxy)phenyl]pyrazin-2-yl]hydrazine (600 mg, 1.93 mmol) in THF (5 mL) was added to the above mixture. The resulting mixture was stirred at 20° C. for 1 hour. Water (20 mL) was added and the aqueous layer was extracted with EtOAc (20 mL×2). The combined organic phase was washed with brine (20 mL), dried over anhydrous $Na_2SO_4$, filtered, and concentrated to give the crude product (0.9 g, 1.93 mmol) as an oil, which was used directly for the next step without further purification. LCMS $R_t$=0.96 min in 1.5 min chromatography, 5-95AB, MS ESI calcd. for $C_{16}H_{13}BrF_5N_4O_2$ [M+H]$^+$ 466.9, found 466.9.

III-A7: 3-[bromo(difluoro)methyl]-6-[2-cyclopropyl-4-(trifluoromethoxy)phenyl]-[1,2,4]triazolo[4,3-a]pyrazine A mixture of 2-bromo-N'-[5-[2-cyclopropyl-4-(trifluoromethoxy)phenyl]pyrazin-2-yl]-2,2-difluoro-acetohydrazide (0.9 g, 1.93 mmol) and TsOH (99.52 mg, 0.58 mmol) in toluene (10 mL) was stirred at 110° C. for 16 hours. After cooling to room temperature, water (20 mL) was added, and the aqueous layer was extracted with EtOAc (20 mL×3). The combined organic phase was washed with brine (20 mL), dried over anhydrous $Na_2SO_4$, filtered, and concentrated. The crude product was purified by flash column chromatography on silica gel (EtOAc in PE=0% to 20%) to give the product (140 mg, 0.31 mmol, 16% yield) as an oil. $^1$H NMR (400 MHz, CDCl$_3$) $\delta_H$=9.61 (s, 1H), 8.58 (d, 1H), 7.59 (d, 1H), 7.20-7.15 (m, 1H), 6.92 (s, 1H), 2.10-2.00 (m, 1H), 1.05-0.92 (m, 2H), 0.82-0.70 (m, 2H). LCMS $R_t$=1.01 min in 1.5 min chromatography, 5-95AB, MS ESI calcd. for $C_{16}H_{11}BrF_5N_4O$ [M+H]$^+$ 448.9, found 448.9.

Compound I-2: 6-[2-cyclopropyl-4-(trifluoromethoxy)phenyl]-3-[ethoxy(difluoro)methyl]-[1,2,4]triazolo[4,3-a]pyrazine To a solution of 3-[bromo(difluoro)methyl]-6-[2-cyclopropyl-4-(trifluoromethoxy)phenyl]-[1,2,4]triazolo[4,3-a]pyrazine (140 mg, 0.31 mmol) in ethanol (5 mL) was added AgBF$_4$ (120.93 mg, 0.62 mmol). The mixture was stirred at 60° C. for 6 hours. Brine (20 mL) was added, and the mixture was filtered through Celite. The filtrate was separated, and the aqueous phase was extracted with EtOAc (20 mL×2). The combined organic phase was washed with brine (20 mL), dried over anhydrous $Na_2SO_4$, filtered, and concentrated. The crude product was purified by prep-HPLC [Welch Xtimate C18 (150 mm×25 mm, 5 mm) A=$H_2O$ (10 mM $NH_4HCO_3$) and B=$CH_3CN$; 60-80% B over 8 minutes)] to afford the product (32.74 mg, 0.079 mmol, 25% yield) as an oil. $^1$H NMR (400 MHz, CDCl$_3$) $\delta_H$=9.52 (d, 1H), 8.45 (s, 1H), 7.57 (d, 1H), 7.22-7.15 (m, 1H), 6.95 (s, 1H), 4.33 (q, 2H), 2.12-1.98 (m, 1H), 1.46 (t, 3H), 1.05-0.95 (m, 2H), 0.82-0.72 (m, 2H). LCMS $R_t$=1.46 min in 2.0 min chromatography, 10-80AB, MS ESI calcd. for $C_{18}H_{16}F_5N_4O_2$[M+H]$^+$ 414.9, found 415.2.

Example III-2. Syntheses of Compound III-3: 3-[difluoro(methoxy)methyl]-6-[4-[(1S)-2,2-difluorocyclopropyl]phenyl]-[1,2,4]triazolo[4,3-a]pyrazine & Compound III-4: 3-[difluoro(methoxy)methyl]-6-[4-[(1R)-2,2-difluorocyclopropyl]phenyl]-[1,2,4]triazolo[4,3-a]pyrazine Note stereochemistry is randomly assigned.

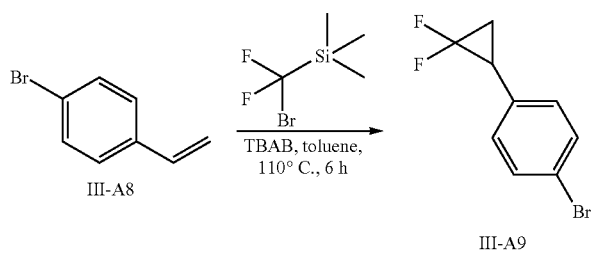
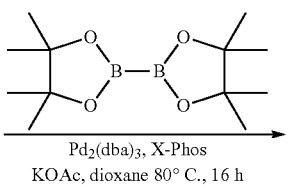
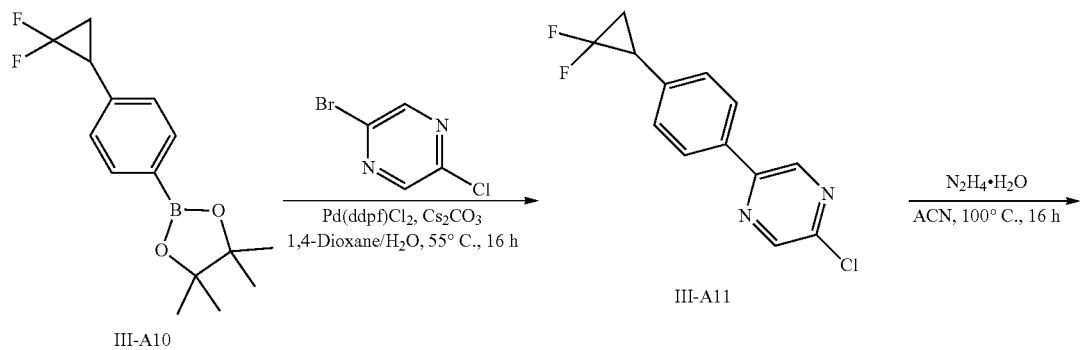

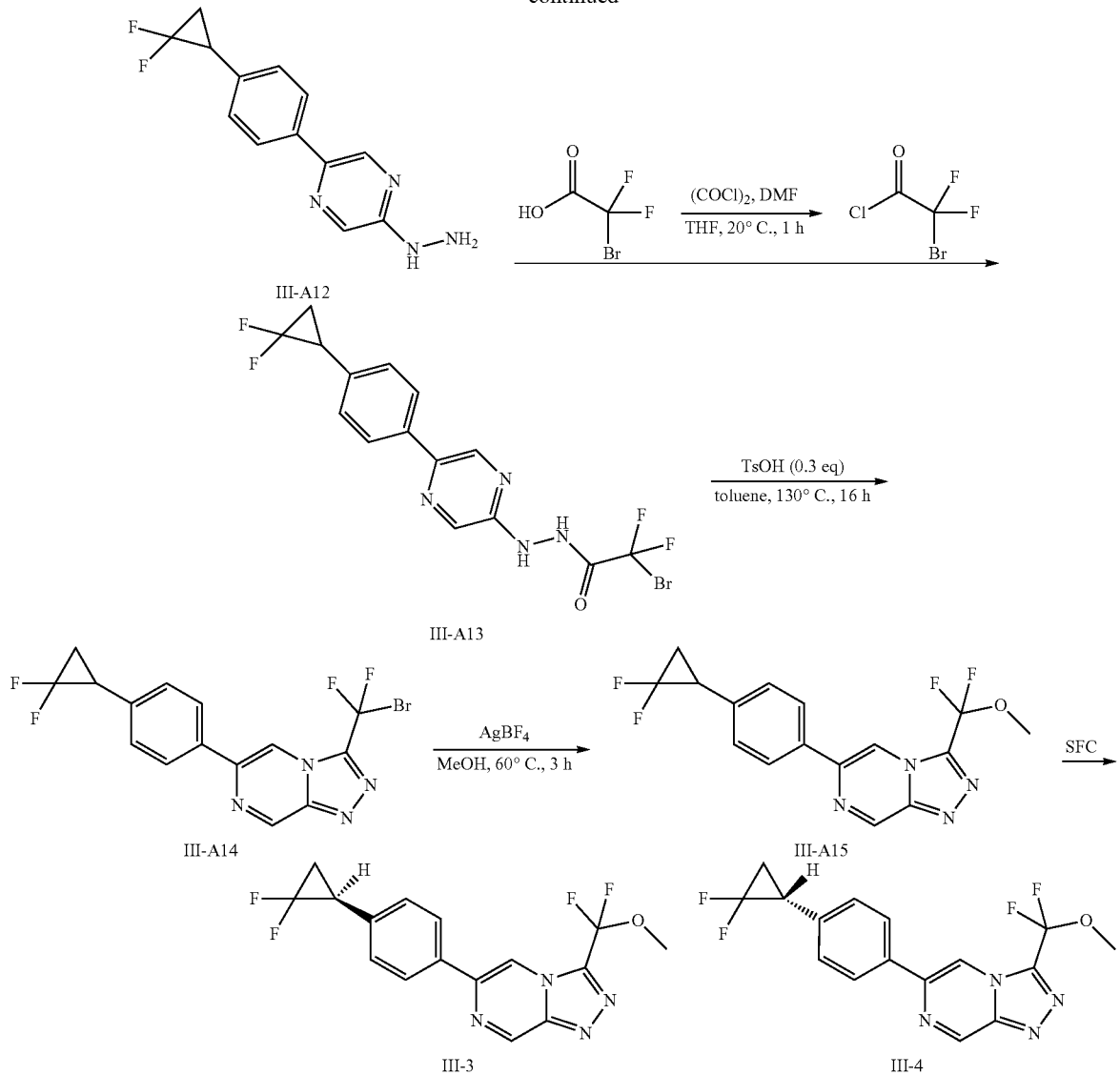

III-A9: bromo-4-(2,2-difluorocyclopropyl)benzene

A mixture of 1-bromo-4-vinyl-benzene (4.5 g, 24.58 mmol), [bromo(difluoro)methyl]-trimethyl-silane (6.0 g, 29.50 mmol) and TBAB (237.7 mg, 0.74 mmol) in toluene (20 mL) was stirred at 110° C. for 6 hours. After cooling to room temperature, the mixture was diluted with H$_2$O (30 mL), and the aqueous layer was extracted with EtOAc (30 mL×2). The combined organic phase was washed with brine (30 mL), dried over anhydrous Na$_2$SO$_4$, filtered, and concentrated. The crude product was purified by flash chromatography on silica gel (PE) to give the product (4.6 g, 19.74 mmol, 80% yield) as an oil. $^1$H NMR (400 MHz, CDCl$_3$) $\delta_H$=7.46 (dd, 2H), 7.10 (d, 2H), 2.75-2.65 (m, 1H), 1.92-1.78 (m, 1H), 1.65-1.55 (m, 1H).

III-A10: 2-[4-(2,2-difluorocyclopropyl)phenyl]-4,4,5,5-tetramethyl-1,3,2-dioxaborolane To a mixture of 1-bromo-4-(2,2-difluorocyclopropyl)benzene (2.0 g, 8.58 mmol), 4,4,5,5-tetramethyl-2-(4,4,5,5-tetramethyl-1,3,2-dioxaborolan-2-yl)-1,3,2-dioxaborolane (2.4 g, 9.44 mmol), KOAc (1.7 g, 17.16 mmol) in 1,4-dioxane (20 mL) was added Pd(dppf)Cl$_2$ (628 mg, 0.86 mmol). The mixture was stirred at 100° C. for 15 hours. Water (20 mL) was added, and the mixture was filtered. The filtrate was concentrated under reduced pressure to remove dioxane. The aqueous layer was extracted with EtOAc (20 mL×3). The combined organic layers were washed with brine (20 mL), dried over anhydrous Na$_2$SO$_4$, filtered, and concentrated. The crude product was purified by flash chromatography on silica gel (PE) to afford the product (1.8 g, 6.43 mmol, 75% yield) as an oil. $^1$H NMR (400 MHz, CDCl$_3$) $\delta_H$=7.85-7.75 (m, 2H), 7.28-7.20 (m, 2H), 2.82-2.72 (m, 1H), 1.86-1.78 (m, 1H), 1.72-1.60 (m, 1H), 1.35 (s, 12H).

III-A11: 2-chloro-5-[4-(2,2-difluorocyclopropyl)phenyl]pyrazine

To a mixture of 2-bromo-5-chloro-pyrazine (1.37 g, 7.07 mmol), 2-[4-(2,2-difluorocyclopropyl)phenyl]-4,4,5,5-tetramethyl-1,3,2-dioxaborolane (1.8 g, 6.43 mmol) and $Cs_2CO_3$ (4.2 g, 12.85 mmol) in 1,4-dioxane (20 mL) and water (2 mL) was added $Pd(dppf)Cl_2$ (470 mg, 0.64 mmol). The mixture was stirred at 80° C. for 12 hours. The mixture was filtered, and the filtrate was concentrated under reduced pressure to remove dioxane. Water (20 mL) was added, and the aqueous layer was extracted with EtOAc (20 mL×3). The combined organic layer was washed with brine (20 mL), dried over anhydrous $Na_2SO_4$, filtered, and concentrated under reduced pressure. The crude product was purified by flash chromatography on silica gel (EtOAc in PE 0 to ~5%) to afford the product (840 mg, 3.15 mmol, 49% yield) as a solid. $^1$H NMR (400 MHz, $CDCl_3$) $\delta_H$=8.78 (s, 1H), 8.63 (s, 1H), 7.96 (d, 2H), 7.37 (d, 2H), 2.87-2.78 (m, 1H), 1.96-1.80 (m, 1H), 1.75-1.65 (m, 1H).

III-A12: [5-[4-(2,2-difluorocyclopropyl)phenyl] pyrazin-2-yl]hydrazine

To a solution of 2-chloro-5-[4-(2,2-difluorocyclopropyl) phenyl]pyrazine (840 mg, 3.15 mmol) in MeCN (10 mL) was added $NH_2NH_2 \cdot H_2O$ (1.57 mL, 31.5 mmol). The mixture was stirred at 80° C. for 10 hours. Water (30 mL) was added and the aqueous layer was extracted with EtOAc (30 mL×3). The combined organic layers were washed with brine (30 mL), dried over anhydrous $Na_2SO_4$, filtered, and concentrated. The crude product was triturated with PE/EtOAc (20 mL/2 mL) to afford the product (690 mg, 2.63 mmol, 84% yield) as a solid. $^1$H NMR (400 MHz, DMSO-$d_6$) $\delta_H$=8.56 (d, 1H), 8.18 (d, 1H), 8.10 (brs, 1H), 7.90 (d, 2H), 7.32 (d, 2H), 4.33 (brs, 2H), 3.10-2.97 (m, 1H), 2.05-1.92 (m, 2H).

III-A13: 2-bromo-N'-[5-[4-(2,2-difluorocyclopropyl) phenyl]pyrazin-2-yl]-2,2-difluoro-acetohydrazide To a solution of 2-bromo-2,2-difluoro-acetic acid (0.49 g, 2.8 mmol) in THF (5 mL) was added DMF (10 mg, 0.14 mmol) and $(COCl)_2$ (0.28 mL, 3.36 mmol). The resulting mixture was stirred at 25° C. for 1 hour. A solution of [5-[4-(2,2-difluorocyclopropyl)phenyl]pyrazin-2-yl]hydrazine (490 mg, 1.87 mmol) in THF (2 mL) was added to the above mixture. The mixture was stirred at 25° C. for 2 hours. Water (30 mL) was added, and the aqueous layer was extracted with EtOAc (30 mL×3). The combined organic layers were washed with brine (30 mL), dried over anhydrous $Na_2SO_4$, filtered, and concentrated to afford the product (780 mg, 1.86 mmol) as an oil. LCMS $R_t$=0.85 min in 1.5 min chromatography, 5-95AB, MS ESI calcd. for $C_{15}H_{12}BrF_4N_4O$ [M+H]$^+$ 418.9, found 418.9.

III-A14: 3-[bromo(difluoro)methyl]-6-[4-(2,2-difluorocyclopropyl)phenyl]-[1,2,4]triazolo[4,3-a]pyrazine To a solution of 2-bromo-N'-[5-[4-(2,2-difluorocyclopropyl)phenyl]pyrazin-2-yl]-2,2-difluoro-acetohydrazide (780 mg, 1.86 mmol) in toluene (10 mL) was added TsOH (96 mg, 0.56 mmol). The mixture was stirred at 110° C. for 48 hours. Water (30 mL) was added, and the aqueous layer was extracted with EtOAc (30 mL×2). The combined organic layers were washed with brine (30 mL), dried over anhydrous $Na_2SO_4$, filtered, and concentrated. The crude product was purified by flash chromatography on silica gel (EtOAc in PE 0 to 20%) to afford the product (300 mg, 0.75 mmol, 40% yield) as a solid. $^1$H NMR (400 MHz, $CDCl_3$) $\delta_H$=9.60 (s, 1H), 8.45 (s, 1H), 7.96 (d, 2H), 7.42 (d, 2H), 2.90-2.80 (m, 1H), 2.00-1.85 (m, 1H), 1.80-1.68 (m, 1H).

III-A15: 6-[4-(2,2-difluorocyclopropyl)phenyl]-3-[difluoro(methoxy)methyl]-[1,2,4]triazolo[4,3-a] pyrazine To a solution of 3-[bromo(difluoro)methyl]-6-[4-(2,2-difluorocyclopropyl)phenyl]-[1,2,4]triazolo[4,3-a]pyrazine (150 mg, 0.37 mmol) in methanol (3 mL) was added $AgBF_4$ (145 mg, 0.75 mmol). The mixture was stirred at 60° C. for 2 hours. Brine (20 mL) was added and the suspension was filtered. The filter cake was washed with EtOAc (20 mL×2). The aqueous layer was extracted with EtOAc (20 mL×2). The combined organic layers were washed with brine (20 mL), dried over anhydrous $Na_2SO_4$, filtered, and concentrated. The crude product was purified by flash chromatography on silica gel (EtOAc in PE 0-30%) to afford the product (120 mg, 0.34 mmol, 91% yield) as a solid. LCMS $R_t$=0.91 min in 1.5 min chromatography, 5-95AB, MS ESI calcd. for $C_{16}H_{13}F_4N_4O$ [M+H]$^+$ 353.1, found 353.0.

Compounds III-3 & III-4: 3-[difluoro(methoxy) methyl]-6-[4-[(1R)-2,2-difluorocyclopropyl]phenyl]- [1,2,4]triazolo[4,3-a]pyrazine & 3-[difluoro (methoxy)methyl]-6-[4-[(1S)-2,2-difluorocyclopropyl]phenyl]-[1,2,4]triazolo[4,3-a] pyrazine Analytical SFC: (Chiralcel AD-3 150 mm×4.6 mm I.D., 3 µm, Mobile phase: A: $CO_2$, B: ethanol (0.05% DEA), Gradient: from 5% to 40% of B in 2 min and hold 40% of B for 1.2 min, then 5% of B for 0.8 min. Flow rate: 4 mL/min, Column temperature: 35° C.) showed two peaks at 1.01 min (49.8%) and 1.10 min (50.2%).

6-[4-(2,2-difluorocyclopropyl)phenyl]-3-[difluoro (methoxy)methyl]-[1,2,4]triazolo[4,3-a]pyrazine (120 mg, 0.34 mmol) was purified by SFC (DAICEL CHIRALCEL AD-H (250 mm×30 mm, 5 mm); A=$CO_2$ and B=EtOH (0.1% $NH_3 \cdot H_2O$); 35° C.; 60 mL/min; 20% B; 8 min run; 70 injections) to give enantiomer 1, randomly assigned as 3-[difluoro(methoxy)methyl]-6-[4-[(1R)-2,2-difluorocyclopropyl]phenyl]-[1,2,4]triazolo[4,3-a]pyrazine (30.23 mg, 0.086 mmol, 25% yield) (Rt of Peak 1=1.01 min) as a solid and the enantiomer 2, randomly assigned as 3-[difluoro (methoxy)methyl]-6-[4-[(1S)-2,2-difluorocyclopropyl]phenyl]-[1,2,4]triazolo[4,3-a]pyrazine (31.16 mg, 0.088 mmol, 26% yield) (Rt of peak 2=1.10 min) as a solid. The stereochemistry of the compounds were randomly assigned.

Compound III-3: $^1$H NMR (400 MHz, $CDCl_3$) $\delta_H$=9.52 (d, 1H), 8.46 (d, 1H), 7.93 (d, 2H), 7.40 (d, 2H), 3.97 (s, 3H), 2.90-2.77 (m, 1H), 1.97-1.82 (m, 1H), 1.77-1.67 (m, 1H). LCMS $R_t$=1.35 min in 2.0 min chromatography, 10-80AB, MS ESI calcd. for $C_{16}H_{13}F_4N_4O$ [M+H]$^+$ 353.1, found 353.2.

Compound III-4: $^1$H NMR (400 MHz, $CDCl_3$) $\delta_H$=9.52 (d, 1H), 8.46 (s, 1H), 7.93 (d, 2H), 7.40 (d, 2H), 3.97 (s, 3H), 2.90-2.77 (m, 1H), 1.97-1.82 (m, 1H), 1.77-1.67 (m, 1H). LCMS $R_t$=1.35 min in 2.0 min chromatography, 10-80AB, MS ESI calcd. for $C_{16}H_{13}F_4N_4O$ [M+H]$^+$ 353.1, found 353.2.

Example III-3. Synthesis of Compound III-5: 3-[ethoxy(difluoro)methyl]-6-[2-methyl-4-(2,2,2-trifluoroethoxymethyl)phenyl]-[1,2,4]triazolo[4,3-a]pyrazine

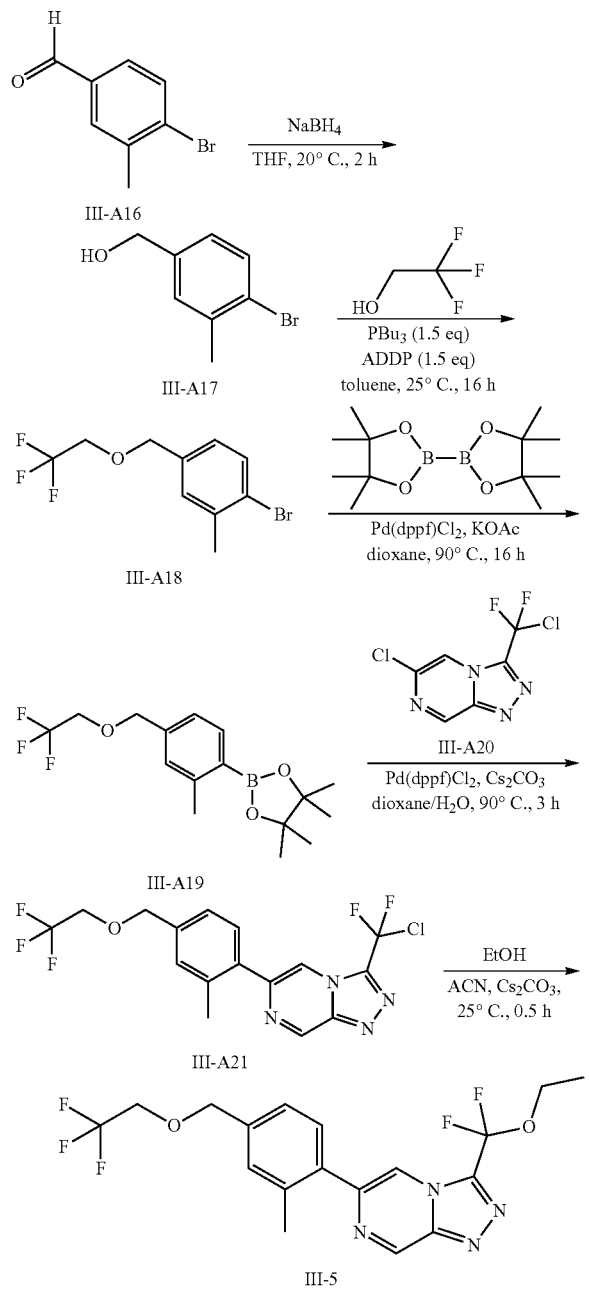

III-A17: 4-bromo-3-methyl-benzaldehyde

To a solution of 4-bromo-3-methyl-benzaldehyde (10 g, 50.24 mmol) in THF (150 mL) was added NaBH$_4$ (4.77 g, 125.6 mmol) in portions. The mixture was stirred at 20° C. for 2 hours. 0.5 N HCl aqueous (300 mL) was added to the mixture slowly, and the mixture was extracted with EtOAc (500 mL×2). The combined organic phase was washed with brine (500 mL), dried over anhydrous Na$_2$SO$_4$, filtered, and concentrated to give the crude product (10 g, 50.24 mmol) as an oil. $^1$H NMR (400 MHz, CDCl$_3$) δ$_H$=7.50 (d, 1H), 7.22 (s, 1H), 7.03 (dd, 1H), 4.60 (s, 2H), 2.40 (s, 3H).

III-A18: 1-bromo-2-methyl-4-(2,2,2-trifluoroethoxymethyl)benzene

To a solution of (4-bromo-3-methyl-phenyl)methanol (5 g, 24.87 mmol) in toluene (200 mL) were added 1,1-(azodicarbonyl)dipiperidine (9.41 g, 37.3 mmol) and tributylphosphine (7.55 g, 37.3 mmol) under N$_2$. The mixture was stirred at 25° C. for 15 minutes. Then 2,2,2-trifluoroethanol (4.98 g, 49.74 mmol) was added to the mixture, and the mixture was stirred at 25° C. for 16 hours. The mixture was filtered through Celite. The filtrate was concentrated to give the crude product. The crude product was purified by flash chromatography on silica gel (DCM in PE=0% to 5% to 10%, UV=220 nm) to give the product (2.66 g, 9.39 mmol, 37% yield) as an oil. $^1$H NMR (400 MHz, CDCl$_3$) δ$_H$=7.54 (d, 1H), 7.23 (d, 1H), 7.04 (dd, 1H), 4.61 (s, 2H), 3.83 (q, 2H), 2.42 (s, 3H).

III-A19: 4,4,5,5-tetramethyl-2-[2-methyl-4-(2,2,2-trifluoroethoxymethyl)phenyl]-1,3,2-dioxaborolane A mixture of 1-bromo-2-methyl-4-(2,2,2-trifluoroethoxymethyl)benzene (3.85 g, 13.6 mmol), 4,4,5,5-tetramethyl-2-(4,4,5,5-tetramethyl-1,3,2-dioxaborolan-2-yl)-1,3,2-dioxaborolane (4.14 g, 16.32 mmol), KOAc (2.67 g, 27.2 mmol) and Pd(dppf)Cl$_2$ (1.49 g, 2.04 mmol) in 1,4-dioxane (50 mL) was stirred at 90° C. under N$_2$ for 16 hours. After cooling to room temperature, the mixture was filtered through Celite, and the filtrate was concentrated. The crude product was purified by flash chromatography on silica gel (DCM in PE=0% to 5% to 10%) to give the product (3.87 g, 11.72 mmol, 86% yield) as a solid. $^1$H NMR (400 MHz, CDCl$_3$) δ$_H$=7.78 (d, 1H), 7.17-7.11 (m, 2H), 4.66 (s, 2H), 3.85-3.73 (m, 2H), 2.56 (s, 3H), 1.36 (s, 12H).

III-A21: 3-[chloro(difluoro)methyl]-6-[2-methyl-4-(2,2,2-trifluoroethoxymethyl)phenyl]-[1,2,4]triazolo[4,3-a]pyrazine A mixture of 6-chloro-3-[chloro(difluoro)methyl]-[1,2,4]triazolo[4,3-a]pyrazine (200 mg, 0.84 mmol), 4,4,5,5-tetramethyl-2-[2-methyl-4-(2,2,2-trifluoroethoxymethyl)phenyl]-1,3,2-dioxaborolane (304 mg, 0.92 mmol), Cs$_2$CO$_3$ (545 mg, 1.67 mmol) and then Pd(dppf)Cl$_2$ (92 mg, 0.13 mmol) in 1,4-dioxane (10 mL) and water (1 mL) was stirred at 90° C. for 3 hours. After cooling to room temperature, water (30 mL) and EtOAc (30 mL) were added to the mixture, and the mixture was filtered through Celite. After separation, the organic phase was washed with brine (50 mL), dried over anhydrous Na$_2$SO$_4$, filtered, and concentrated. The crude product was purified by flash chromatography on silica gel (EtOAc in PE=0% to 15% to 30%) to give the product (160 mg, 393.4 μmol, 47% yield) as an oil. $^1$H NMR (400 MHz, CDCl$_3$) δ$_H$=9.58 (s, 1H), 8.21 (s, 1H), 7.47 (d, 1H), 7.38-7.31 (m, 2H), 4.74 (s, 2H), 3.89 (q, 2H), 2.45 (s, 3H). LCMS R$_t$=0.89 min in 1.5 min chromatography, 5-95AB, MS ESI calcd. for C$_{16}$H$_{13}$ClF$_5$N$_4$O [M+H]$^+$ 407.1, found 406.9.

Compound I-5: 3-[ethoxy(difluoro)methyl]-6-[2-methyl-4-(2,2,2-trifluoroethoxymethyl)phenyl]-[1,2,4]triazolo[4,3-a]pyrazine To a solution of 3-[chloro(difluoro)methyl]-6-[2-methyl-4-(2,2,2-trifluoroethoxymethyl)phenyl]-[1,2,4]triazolo[4,3- a]pyrazine (160 mg, 0.39 mmol) in MeCN (5 mL) were added Cs$_2$CO$_3$ (769 mg, 2.36 mmol) and EtOH (181 mg, 3.93 mmol). The mixture was stirred at 25° C. for 0.5 hours. Water (50 mL) was added to the mixture, and the mixture was extracted with EtOAc (50 mL×2). The combined organic phase was washed with brine (50 mL), dried over anhydrous Na$_2$SO$_4$, filtered, and concentrated. The crude product was purified by flash chromatography on silica gel (EtOAc in PE=0% to 30% to 50%) to give the product (53.22 mg, 123.6 µmol, 31% yield) as a solid. $^1$H NMR (400 MHz, CDCl$_3$) δ$_H$=9.52 (s, 1H), 8.24 (s, 1H), 7.47 (d, 1H), 7.36-7.31 (m, 2H), 4.74 (s, 2H), 4.33 (q, 2H), 3.89 (q, 2H), 2.44 (s, 3H), 1.47 (t, 3H). LCMS R$_t$=1.39 min in 2.0 min chromatography, 10-80AB, MS ESI calcd. for C$_{18}$H$_{18}$F$_5$N$_4$O$_2$[M+H]$^+$ 417.1, found 417.3.

Example III-4. Synthesis of Compound III-6: 3-[difluoro(methoxy)methyl]-6-[2-methyl-4-(2,2,2-trifluoroethoxymethyl)phenyl]-[1,2,4]triazolo[4,3-a]pyrazine

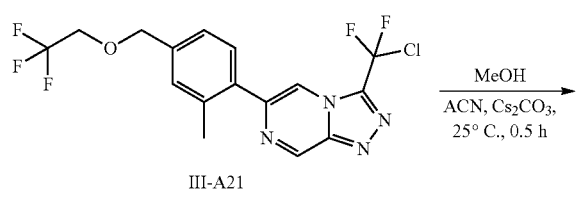

III-A21

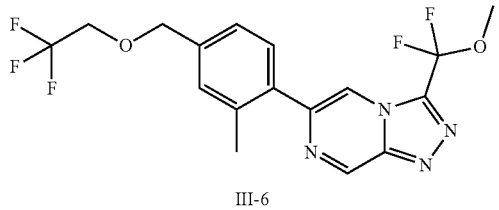

III-6

To a solution of 3-[chloro(difluoro)methyl]-6-[2-methyl-4-(2,2,2-trifluoroethoxymethyl)phenyl]-[1,2,4]triazolo[4,3-a]pyrazine (80 mg, 0.20 mmol) in MeCN (3 mL) were added Cs$_2$CO$_3$ (384.48 mg, 1.18 mmol) and MeOH (90.67 mg, 1.97 mmol). The mixture was stirred at 25° C. for 0.5 hour. Water (50 mL) was added, and the mixture was extracted with EtOAc (50 mL×2). The combined organic phase was washed with brine (50 mL), dried over anhydrous Na$_2$SO$_4$, filtered, and concentrated. The crude product was purified by flash chromatography on silica gel (EtOAc in PE=0% to 30% to 50%) to give the product (37.69 mg, 91.7 µmol, 46% yield) as an oil. $^1$H NMR (400 MHz, CDCl$_3$) δ$_H$=9.51 (s, 1H), 8.22 (s, 1H), 7.46 (d, 1H), 7.38-7.30 (m, 2H), 4.74 (s, 2H), 3.96-3.85 (m, 5H), 2.43 (s, 3H). LCMS R$_t$=1.15 min in 2.0 min chromatography, 10-80AB, MS ESI calcd. for C$_{17}$H$_{16}$F$_5$N$_4$O$_2$[M+H]$^+$ 403.1, found 403.1.

Example III-5. Syntheses of Compound III-7: 6-[4-[(1R)-2,2-difluorocyclopropyl]-2-methyl-phenyl]-3-[difluoro(methoxy)methyl]-[1,2,4]triazolo[4,3-a]pyrazine & Compound III-8: 6-[4-[(1S)-2,2-difluorocyclopropyl]-2-methyl-phenyl]-3-[difluoro(methoxy)methyl]-[1,2,4]triazolo[4,3-a]pyrazine Note stereochemistry is randomly assigned.

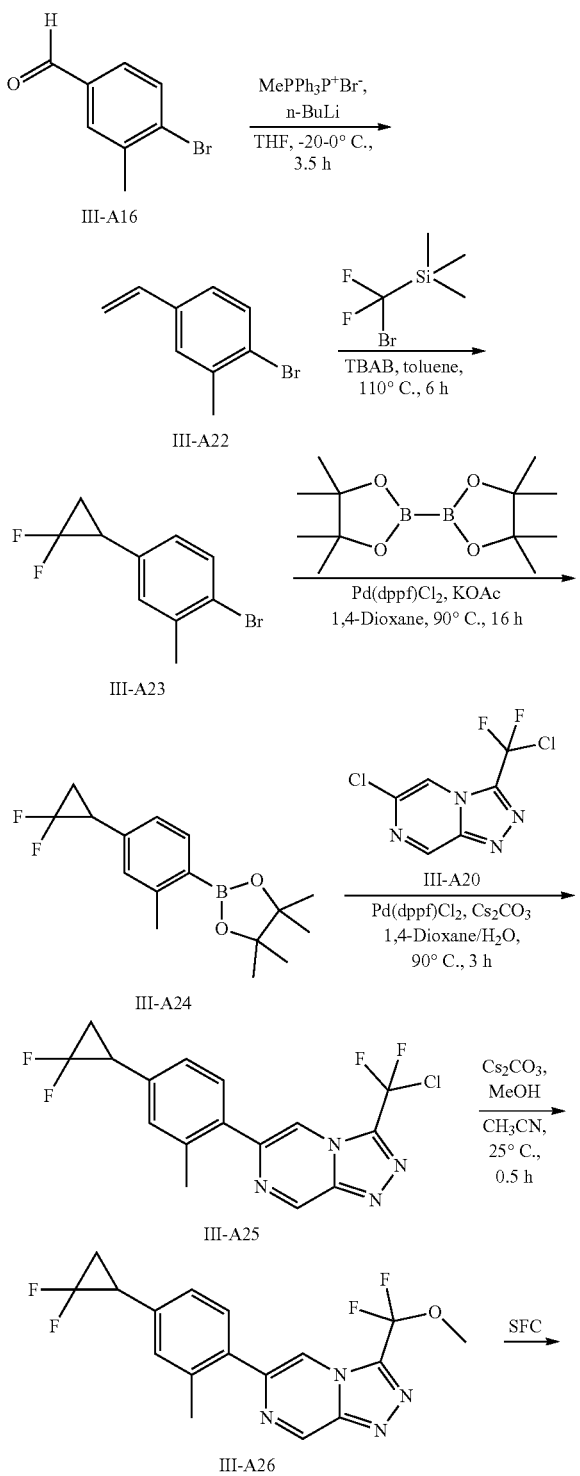

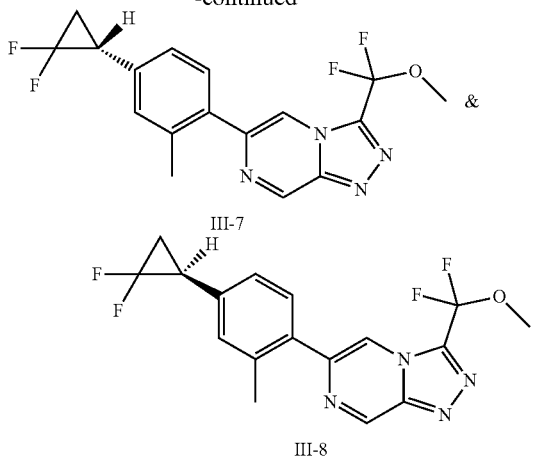

III-A22: 1-bromo-2-methyl-4-vinyl-benzene

To a suspension of methyl(triphenyl)phosphonium bromide (14.36 g, 40.19 mmol) in THF (150 mL) was added n-BuLi (16.08 mL, 40.19 mmol, 2.5 M in hexane) dropwise under $N_2$ at 0° C. The mixture was stirred at 0° C. for 1.5 hours. Then 4-bromo-3-methyl-benzaldehyde (5 g, 25.12 mmol) in THF (10 mL) was added to the above mixture dropwise at −20° C. and stirred at 0° C. for 2 hours. The mixture was poured into water (300 mL) and the aqueous layer was extracted with EtOAc (300 mL×2). The combined organic phase was washed with brine (300 mL), dried over anhydrous $Na_2SO_4$, filtered, and concentrated. The crude product was purified by flash chromatography on silica gel (EtOAc in PE=0% to 5% to 10%) to give the product (2 g, 10.15 mmol, 40% yield) as an oil. $^1$H NMR (400 MHz, $CDCl_3$) $\delta_H$=7.48 (d, 1H), 7.27 (s, 1H), 7.11 (dd, 1H), 6.64 (dd, 1H), 5.75 (d, 1H), 5.27 (d, 1H), 2.41 (s, 3H).

III-A23: 1-bromo-4-(2,2-difluorocyclopropyl)-2-methyl-benzene

A mixture of 1-bromo-2-methyl-4-vinyl-benzene (2 g, 10.15 mmol), [bromo(difluoro)methyl]-trimethyl-silane (2.47 g, 12.18 mmol) and TBAB (98.15 mg, 0.30 mmol) in toluene (20 mL) was stirred at 110° C. for 6 hours. After cooling to room temperature, the mixture was diluted with $H_2O$ (50 mL) and extracted with EtOAc (50 mL×2). The combined organic phase was washed with brine (50 mL), dried over anhydrous $Na_2SO_4$, filtered, and concentrated. The crude product was purified by flash chromatography on silica gel (PE) to give the product (2.4 g, 9.71 mmol, 95% yield) as an oil. $^1$H NMR (400 MHz, $CDCl_3$) $\delta_H$=7.49 (d, 1H), 7.11 (d, 1H), 6.92 (dd, 1H), 2.72-2.64 (m, 1H), 2.40 (s, 3H), 1.87-1.78 (m, 1H), 1.65-1.58 (m, 1H).

III-A24: 2-[4-(2,2-difluorocyclopropyl)-2-methyl-phenyl]-4,4,5,5-tetramethyl-1,3,2-dioxaborolane A mixture of 1-bromo-4-(2,2-difluorocyclopropyl)-2-methyl-benzene (1.91 g, 7.73 mmol), 4,4,5,5-tetramethyl-2-(4,4,5,5-tetramethyl-1,3,2-dioxaborolan-2-yl)-1,3,2-dioxaborolane (2.35 g, 9.28 mmol), KOAc (1.52 g, 15.46 mmol) and $Pd(dppf)Cl_2$ (848.44 mg, 1.16 mmol) in 1,4-dioxane (30 mL) was stirred at 90° C. under $N_2$ for 16 hours. After cooling to room temperature, the mixture was filtered through Celite, and the filtrate was concentrated. The crude product was purified by flash chromatography on silica gel (DCM in PE=0% to 50% to 100%) to give the product (1.19 g, 4.05 mmol, 52% yield) as a solid. 1H NMR (400 MHz, $CDCl_3$) $\delta_H$=7.74 (d, 1H), 7.05-7.00 (m, 2H), 2.76-2.68 (m, 1H), 2.54 (s, 3H), 1.85-1.76 (m, 1H), 1.70-1.62 (m, 1H), 1.35 (s, 12H).

III-A25: 3-[chloro(difluoro)methyl]-6-[4-(2,2-difluorocyclopropyl)-2-methyl-phenyl]-[1,2,4]triazolo[4,3-a]pyrazine A mixture of 6-chloro-3-[chloro(difluoro)methyl]-[1,2,4]triazolo[4,3-a]pyrazine (900 mg, 3.77 mmol), 2-[4-(2,2-difluorocyclopropyl)-2-methyl-phenyl]-4,4,5,5-tetramethyl-1,3,2-dioxaborolane (1.19 g, 4.05 mmol), $Cs_2CO_3$ (2.45 g, 7.53 mmol) and then $Pd(dppf)Cl_2$ (413.29 mg, 0.56 mmol) in 1,4-dioxane (50 mL) and water (5 mL) was stirred at 90° C. under $N_2$ for 3 hours. After cooling to room temperature, the mixture was filtered through Celite. The cake was washed with EtOAc (50 mL×2). The combined filtrate was washed with brine (50 mL×2), dried over anhydrous $Na_2SO_4$, filtered, and concentrated. The crude product was purified by flash chromatography on silica gel (EtOAc in PE=0% to 20% to 40%) to give the product (320 mg, 863.2 μmol, 22% yield) as an oil. LCMS $R_t$=1.18 min in 2.0 min chromatography, 10-80AB, MS ESI calcd. for $C_{16}H_{12}ClF_4N_4[M+H]^+$ 371.1, found 371.0.

III-A26: 6-[4-(2,2-difluorocyclopropyl)-2-methyl-phenyl]-3-[difluoro(methoxy)methyl]-[1,2,4]triazolo[4,3-a]pyrazine A mixture of 3-[chloro(difluoro)methyl]-6-[4-(2,2-difluorocyclopropyl)-2-methyl-phenyl]-[1,2,4]triazolo[4,3-a]pyrazine (320 mg, 0.86 mmol), MeOH (397.92 mg, 8.63 mmol), $Cs_2CO_3$ (1.68 g, 5.18 mmol) in MeCN (10 mL) was stirred at 25° C. for 0.5 hour. Water (50 mL) was added, and the mixture was extracted with EtOAc (50 mL×2). The combined organic phase was washed with brine (50 mL), dried over anhydrous $Na_2SO_4$, filtered, and concentrated. The crude product was purified by flash chromatography on silica gel (EtOAc in PE=0% to 30% to 50%) to give the product (140 mg, 382.2 μmol, 44% yield) as an oil. LCMS $R_t$=0.96 min in 1.5 min chromatography, 5-95AB, MS ESI calcd. for $C_{17}H_{15}F_4N_4O$ $[M+H]^+$ 367.1, found 367.0.

Compounds III-7 & III-8: 6-[4-[(1R)-2,2-difluorocyclopropyl]-2-methyl-phenyl]-3-[difluoro(methoxy)methyl]-[1,2,4]triazolo[4,3-a]pyrazine & 6-[4-[(1S)-2,2-difluorocyclopropyl]-2-methyl-phenyl]-3-[difluoro(methoxy)methyl]-[1,2,4]triazolo[4,3-a]pyrazine Analytical SFC: (Chiralpak AD-3 150×4.6 mm I.D, 3 μm. Mobile phase: A: $CO_2$, B: ethanol (0.05% DEA). Gradient: from 5% to 40% of B in 5 min and hold 40% for 2.5 min, then 5% of B for 5.5 min. Flow rate: 2.5 mL/min Column temperature: 35° C. ABPR: 1500 psi) showed two peaks at 2.97 min (49.68%) and 3.45 min (50.32%). 6-[4-(2,2-difluorocyclopropyl)-2-methyl-phenyl]-3-[difluoro(methoxy)methyl]-[1,2,4]triazolo[4,3-a]pyrazine (140 mg, 0.38 mmol) was separated by SFC (DAICEL CHIRALPAK AD-H (250 mm×30 mm, 5 μm); A: $CO_2$, B=0.1% $NH_3H_2O$ EtOH; 38° C.; 60 mL/min; 25% B; 60 injections) to give the enantiomer 1, randomly assigned as 6-[4-[(1R)-2,2-difluorocyclopropyl]-2-methyl-phenyl]-3-[difluoro(methoxy)methyl]-[1,2,4]

triazolo[4,3-a]pyrazine (42.63 mg, 114.3 µmol, 29% yield) (Rt of Peak 1=2.97 min) as a solid and the enantiomer 2, randomly assigned as 6-[4-[(1S)-2,2-difluorocyclopropyl]-2-methyl-phenyl]-3-[difluoro(methoxy)methyl]-[1,2,4]triazolo[4,3-a]pyrazine (44.46 mg, 117.9 µmol, 30% yield) (Rt of Peak 2=3.45 min) as a solid. The stereochemistry of the compounds were randomly assigned.

Compound III-7: $^1$H NMR (400 MHz, CDCl$_3$) $\delta_H$=9.51 (d, 1H), 8.22 (d, 1H), 7.41 (d, 1H), 7.23 (s, 1H), 7.23-7.18 (m, 1H), 3.94 (s, 3H), 2.85-2.76 (m, 1H), 2.41 (s, 3H), 1.93-1.84 (m, 1H), 1.74-1.66 (m, 1H). LCMS R$_t$=1.20 min in 2.0 min chromatography, 10-80AB, MS ESI calcd. for C$_{17}$H$_{15}$F$_4$N$_4$O [M+H]$^+$ 367.1, found 367.2.

Compound III-8: $^1$H NMR (400 MHz, CDCl$_3$) $\delta_H$=9.51 (d, 1H), 8.22 (s, 1H), 7.42 (d, 1H), 7.23 (s, 1H), 7.22-7.18 (m, 1H), 3.93 (s, 3H), 2.85-2.76 (m, 1H), 2.41 (s, 3H), 1.94-1.85 (m, 1H), 1.74-1.66 (m, 1H). LCMS R$_t$=1.14 min in 2.0 min chromatography, 10-80AB, MS ESI calcd. for C$_{17}$H$_{15}$F$_4$N$_4$O [M+H]$^+$ 367.1, found 367.1.

Example III-6. Synthesis of Compound III-9: 3-[ethoxy(difluoro)methyl]-6-[2-methyl-4-[(1R)-1-(2,2,2-trifluoroethoxy)ethyl]phenyl]-[1,2,4]triazolo[4,3-a]pyrazine & Compound III-10: 3-[ethoxy(difluoro)methyl]-6-[2-methyl-4-[(1S)-1-(2,2,2-trifluoroethoxy)ethyl]phenyl]-[1,2,4]triazolo[4,3-a]pyrazine

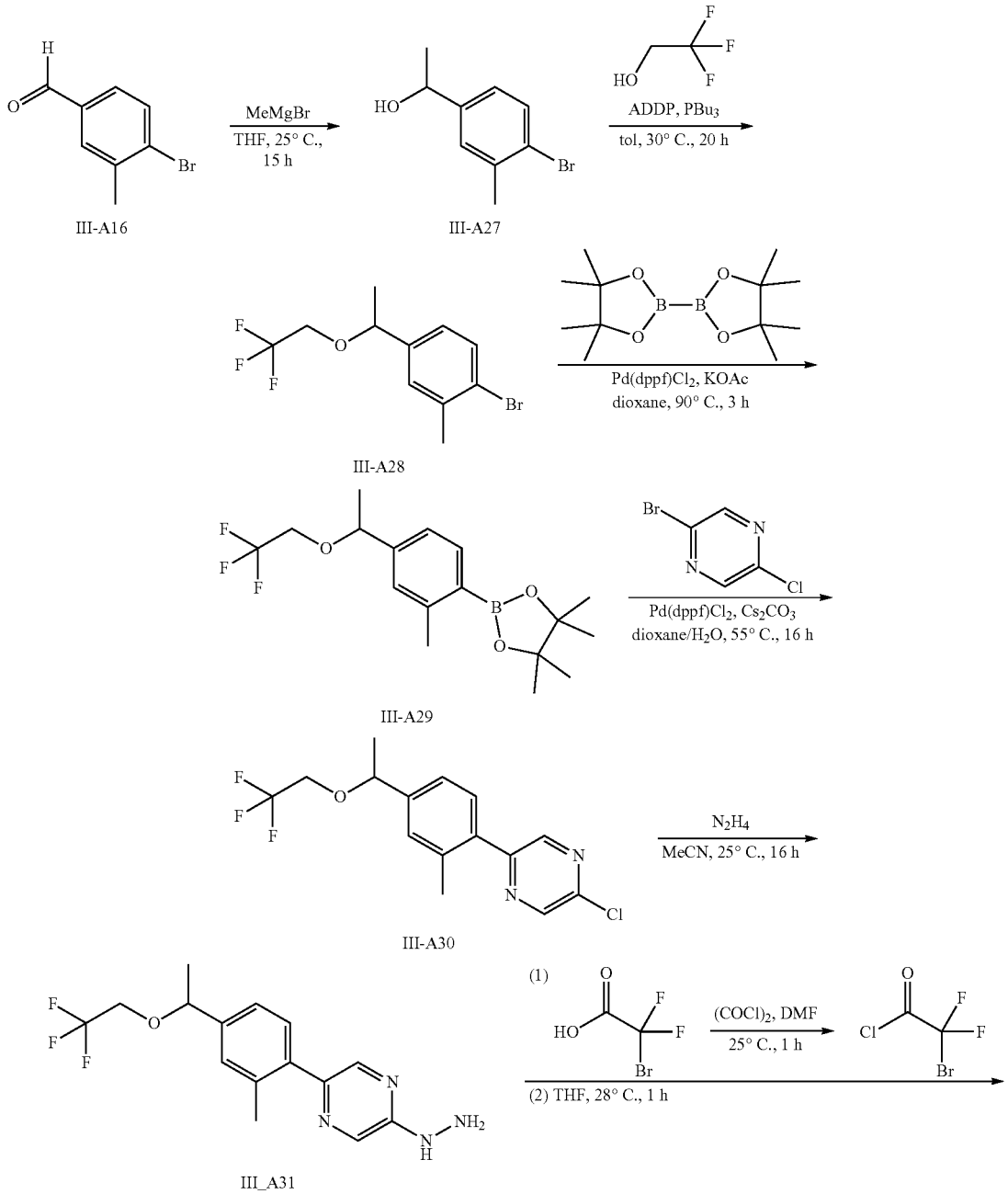

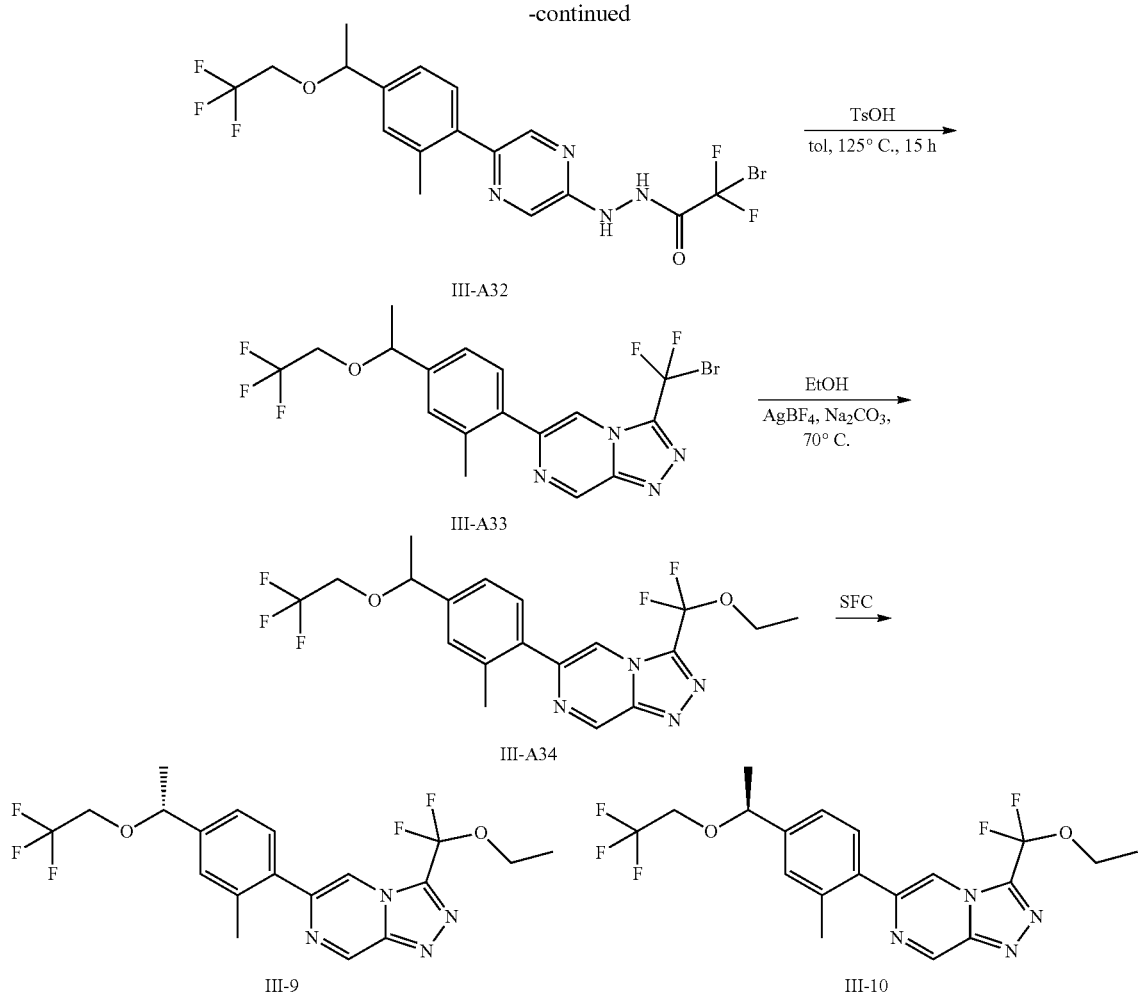

III-A27: 1-(4-bromo-3-methyl-phenyl)ethanol

To a solution of 4-bromo-3-methyl-benzaldehyde (5 g, 25.12 mmol) in THF (100 mL) was added MeMgBr (10.05 mL, 30.14 mmol, 3 M in ethyl ether) dropwise at 0° C. The mixture was stirred at 25° C. for 15 hours. After cooling to room temperature, the mixture was added to the saturated NH$_4$Cl solution (250 mL). The mixture was extracted with EtOAc (150 mL×3). The combined organic phase was washed with brine (250 mL), dried over anhydrous Na$_2$SO$_4$, filtered, and concentrated under reduced pressure to give the product (5.3 g, 24.64 mmol) as a solid. $^1$H NMR (400 MHz, CDCl$_3$) $\delta_H$=7.49 (d, 1H), 7.25 (d, 1H), 7.05 (dd, 1H), 4.84 (q, 1H), 2.41 (s, 3H), 1.47 (d, 3H).

III-A28: 1-bromo-2-methyl-4-[1-(2,2,2-trifluoroethoxy)ethyl]benzene

To a solution of 1-(4-bromo-3-methyl-phenyl) ethanol (5.3 g, 24.64 mmol) in toluene (300 mL) were added tributylphosphine (7.48 g, 36.96 mmol) and 1,1-(azodicarbonyl) dipiperidine (9.33 g, 36.96 mmol) under N$_2$ at 30° C. The mixture was stirred at 30° C. for 15 minutes. 2,2,2-trifluoroethanol (4.93 g, 49.3 mmol) was added to the mixture. The mixture was stirred at 30° C. under N$_2$ for 20 hours. After cooling to room temperature, the mixture was filtered through Celite and concentrated under reduced pressure. The crude product was purified by flash chromatography on silica gel (PE) to give the product (3 g, 10.1 mmol, 41% yield) as an oil. $^1$H NMR (400 MHz, CDCl$_3$) $\delta_H$=7.53 (d, 1H), 7.18 (s, 1H), 7.01 (dd, 1H), 4.51 (q, 1H), 3.71-3.61 (m, 2H), 2.42 (s, 3H), 1.48 (d, 3H).

III-A29: 4,4,5,5-tetramethyl-2-[2-methyl-4-[1-(2,2,2-trifluoroethoxy)ethyl]phenyl]-1,3,2-dioxaborolane To a mixture of 1-bromo-2-methyl-4-[1-(2,2,2-trifluoroethoxy)ethyl]benzene (3 g, 10.1 mmol) in 1,4-dioxane (30 mL) were added 4,4,5,5-tetramethyl-2-(4,4,5,5-tetramethyl-1,3,2-dioxaborolan-2-yl)-1,3,2-dioxaborolane (3.08 g, 12.12 mmol) and KOAc (1.98 g, 20.19 mmol). Pd(dppf)Cl$_2$ (0.74 g, 1.01 mmol) was added, and the mixture was stirred at 90° C. under N$_2$ for 3 hours. After cooling to room temperature, the mixture was filtered through Celite. The filtrate was concentrated, and the crude product was purified by flash chromatography on silica gel (PE) to give the product (3.3 g, 9.6 mmol, 95% yield) as an oil. $^1$H NMR (400 MHz, CDCl$_3$) $\delta_H$=7.83-7.72 (m, 1H), 7.16-7.10 (m, 2H), 4.54 (q, 1H), 3.72-3.57 (m, 2H), 2.56 (s, 3H), 1.49 (d, 3H), 1.35 (s, 12H).

III-A30: 2-chloro-5-[2-methyl-4-[1-(2,2,2-trifluoroethoxy)ethyl]phenyl]pyrazine To a mixture of 4,4,5,5-tetramethyl-2-[2-methyl-4-[1-(2,2,2-trifluoroethoxy)ethyl]phenyl]-1,3,2-dioxaborolane (3.3 g, 9.6 mmol) in 1,4-dioxane (30 mL) and water (3 mL) were added Cs$_2$CO$_3$ (6.25 g, 19.18 mmol) and 2-bromo-5-chloropyrazine (2.23 g, 11.51 mmol). Pd(dppf)Cl$_2$ (0.7 g, 0.96 mmol) was added, and the mixture was stirred at 55° C. under N$_2$ for 16 hours. After cooling to room temperature, the mixture was filtered through Celite, and the filtrate was concentrated. Water (50 mL) was added, and the aqueous layer was extracted with EtOAc (50 mL×2). The combined organic phase was washed with brine (50 mL), dried over anhydrous Na$_2$SO$_4$, filtered, and concentrated. The crude product was purified by flash chromatography on silica gel (EtOAc in PE=0 to 10%) to give the product (1.7 g, 5.14 mmol, 54% yield) as an oil. $^1$H NMR (400 MHz, DMSO-d$^6$) $\delta_H$=8.66 (s, 1H), 8.48 (s, 1H), 7.41 (d, 1H), 7.30-7.25 (m, 2H), 4.59 (q, 1H), 3.75-3.60 (m, 2H), 2.40 (s, 3H), 1.51 (d, 3H). LCMS Rt=0.96 min in 1.5 min chromatography, 5-95AB, MS ESI calcd. for C$_{15}$H$_{15}$ClF$_3$N$_2$O [M+H]$^+$ 331.1, found 330.9.

III-A31: [5-[2-methyl-4-[1-(2,2,2-trifluoroethoxy)ethyl]phenyl]pyrazin-2-yl]hydrazine To a solution of 2-chloro-5-[2-methyl-4-[1-(2,2,2-trifluoroethoxy)ethyl]phenyl]pyrazine (1.7 g, 5.14 mmol) in MeCN (10 mL) was added hydrazine (1.65 g, 51.4 mmol). The mixture was stirred at 25° C. for 16 hours. After cooling to room temperature, water (20 mL) was added to the mixture, and the aqueous layer was extracted with EtOAc (30 mL×2). The combined organic phase was washed with brine (30 mL), dried over anhydrous Na$_2$SO$_4$, filtered, and concentrated to give the crude product. The crude product was purified by flash chromatography on silica gel (EtOAc in PE=50% to 100%) to afford the product (1.1 g, 3.37 mmol, 66% yield) as an oil. $^1$H NMR (400 MHz, CDCl$_3$) $\delta_H$=8.31 (s, 1H), 8.18 (s, 1H), 8.40 (d, 1H), 7.26-7.23 (m, 2H), 6.03 (brs, 1H), 4.59 (q, 1H), 3.77-3.60 (m, 2H), 2.40 (s, 3H), 1.53 (d, 3H). LCMS Rt=1.01 min in 2.0 min chromatography, 10-80AB, MS ESI calcd. for C$_{15}$H$_{18}$F$_3$N$_4$O [M+H]$^+$ 327.1, found 327.2.

III-A32: 2-bromo-2,2-difluoro-N'-[5-[2-methyl-4-[1-(2,2,2-trifluoroethoxy)ethyl]phenyl]pyrazin-2-yl]acetohydrazide To a solution of 2-bromo-2,2-difluoro-acetic acid (435 mg, 2.49 mmol) in THF (4 mL) were added (COCl)$_2$ (0.26 mL, 2.98 mmol) and 1 drop of DMF. The mixture was stirred at 25° C. for 1 hour. A solution of [5-[2-methyl-4-[1-(2,2,2-trifluoroethoxy)ethyl]phenyl]pyrazin-2-yl]hydrazine (540 mg, 1.65 mmol) in THF (2 mL) was added to the above mixture. The mixture was stirred at 28° C. for 1 hour. Water (30 mL) was added, and the aqueous layer was extracted with EtOAc (30 mL×3). The combined organic layers were washed with brine (30 mL), dried over anhydrous Na$_2$SO$_4$, filtered, and concentrated to afford the product (790 mg, 1.63 mmol) as an oil. LCMS Rt=0.90 min in 1.5 min chromatography, 5-95AB, MS ESI calcd. for C$_{17}$H$_{17}$BrF$_5$N$_4$O$_2$ [M+H]$^+$ 485.0, found 484.8.

III-A33: 3-[bromo(difluoro)methyl]-6-[2-methyl-4-[1-(2,2,2-trifluoroethoxy)ethyl]phenyl]-[1,2,4]triazolo[4,3-a]pyrazine To a mixture of 2-bromo-2,2-difluoro-N'-[5-[2-methyl-4-[1-(2,2,2-trifluoroethoxy)ethyl]phenyl]pyrazin-2-yl]acetohydrazide (790 mg, 1.63 mmol) in toluene (10 mL) was added TsOH (84.46 mg, 0.49 mmol). The mixture was stirred at 125° C. for 15 hours. After cooling to room temperature, water (20 mL) was added, and the aqueous layer was extracted with EtOAc (20 mL×2). The combined organic phase was washed with brine (20 mL), dried over anhydrous Na$_2$SO$_4$, filtered, and concentrated. The crude product was purified by flash chromatography on silica gel (EtOAc in PE=0% to 15% to 20%) to give the product (180 mg, 0.39 mmol, 24% yield) as an oil. LCMS Rt=1.23 min in 2.0 min chromatography, 10-80AB, MS ESI calcd. for C$_{17}$H$_{15}$BrF$_5$N$_4$O [M+H]$^+$ 467.0, found 466.9.

III-A34: 3-[ethoxy(difluoro)methyl]-6-[2-methyl-4-[1-(2,2,2-trifluoroethoxy)ethyl]phenyl]-[1,2,4]triazolo[4,3-a]pyrazine To a solution of 3-[bromo(difluoro)methyl]-6-[2-methyl-4-[1-(2,2,2-trifluoroethoxy)ethyl]phenyl]-[1,2,4]triazolo[4,3-a]pyrazine (180 mg, 0.39 mmol) in ethanol (3 mL) were added AgBF$_4$ (225.18 mg, 1.16 mmol) and Na$_2$CO$_3$ (123.03 mg, 1.16 mmol). The mixture was stirred at 70° C. for 2.5 hours. Brine (40 mL) was added, and the aqueous layer was filtered through Celite. The filter cake was eluted with EtOAc (10×3 mL). The filtrate was separated, and the aqueous layer was extracted with EtOAc (20×3 mL). The combined organic layers were washed with brine (60 mL), dried over anhydrous Na$_2$SO$_4$, filtered, and concentrated. The crude product was purified by flash chromatography on silica gel (EtOAc in PE=0~20%) to afford the product (70 mg, 0.16 mmol, 42% yield) as an oil. LCMS Rt=0.93 min in 1.5 min chromatography, 5-95AB, MS ESI calcd. for C$_{19}$H$_{20}$F$_5$N$_4$O$_2$ [M+H]$^+$ 431.1, found 431.0.

Compounds III-9 & III-10: 3-[ethoxy(difluoro)methyl]-6-[2-methyl-4-[(1R)-1-(2,2,2-trifluoroethoxy)ethyl]phenyl]-[1,2,4]triazolo[4,3-a]pyrazine & 3-[ethoxy(difluoro)methyl]-6-[2-methyl-4-[(1S)-1-(2,2,2-trifluoroethoxy)ethyl]phenyl]-[1,2,4]triazolo[4,3-a]pyrazine Analytical SFC: (Chiralcel AD-3 150×4.6 mm I.D, 3 µm. Mobile phase: A: CO$_2$ B: ethanol (0.05% DEA). Gradient: from 5% to 40% of B in 5 min and from 40% to 5% of B in 0.5 min and hold 5% of B for 1.5 min. Flow rate: 2.5 mL/min. Column temperature: 35° C. ABPR: 1500 psi) showed two peaks at 2.02 min (49.82%) and 2.20 min (50.18%). 3-[ethoxy(difluoro)methyl]-6-[2-methyl-4-[1-(2,2,2-trifluoroethoxy)ethyl]phenyl]-[1,2,4]triazolo[4,3-a]pyrazine (70 mg, 0.16 mmol) was purified by SFC (DAICEL CHIRALCEL AD-H (250 mm×30 mm, 5 µm) A=CO$_2$ and B=0.1% NH$_3$H$_2$O-EtOH; 60 mL/min; 25% B, injections: 60) to afford the enantiomer 1, randomly assigned as 3-[ethoxy(difluoro)methyl]-6-[2-methyl-4-[(1R)-1-(2,2,2-trifluoroethoxy)ethyl]phenyl]-[1,2,4]triazolo[4,3-a]pyrazine (24.37 mg, 0.056 mmol, 34% yield) (Rt of Peak 1=2.07 min) and the enantiomer 2, randomly assigned as 3-[ethoxy(difluoro)methyl]-6-[2-methyl-4-[(1S)-1-(2,2,2-trifluoroethoxy)ethyl]phenyl]-[1,2,4]triazolo[4,3-a]pyrazine (28.47 mg, 0.064 mmol, 39% yield) (Rt of Peak 2=2.24 min) as oils. The stereochemistry of the compounds were randomly assigned.

Compound III-9: $^1$H NMR (400 MHz, CDCl$_3$) $\delta_H$=9.51 (s, 1H), 8.25 (s, 1H), 7.46 (d, 1H), 7.35-7.27 (m, 2H), 4.63 (q, 1H), 4.33 (q, 2H), 3.76-3.69 (m, 2H), 2.44 (s, 3H), 1.55 (d, 3H), 1.47 (t, 3H). LCMS Rt=1.22 min in 2.0 min chromatography, 10-80AB, MS ESI calcd. for C$_{19}$H$_{20}$F$_5$N$_4$O$_2$ [M+H]$^+$ 431.1, found 431.2.

Compound III-10: $^1$H NMR (400 MHz, CDCl$_3$) $\delta_H$=9.52 (s, 1H), 8.25 (s, 1H), 7.47 (d, 1H), 7.35-7.27 (m, 2H), 4.63 (q, 1H), 4.33 (q, 2H), 3.78-3.69 (m, 2H), 2.44 (s, 3H), 1.55 (d, 3H), 1.47 (t, 3H). LCMS Rt=1.22 min in 2.0 min chromatography, 10-80AB, MS ESI calcd. for C$_{19}$H$_{20}$F$_5$N$_4$O$_2$ [M+H]$^+$ 431.1, found 431.1.

Example III-7. Synthesis of Compound III-11: 3-(ethoxydifluoromethyl)-6-(4-((2,2,2-trifluoroethoxy)methyl)phenyl)-[1,2,4]triazolo[4,3-a]pyrazine

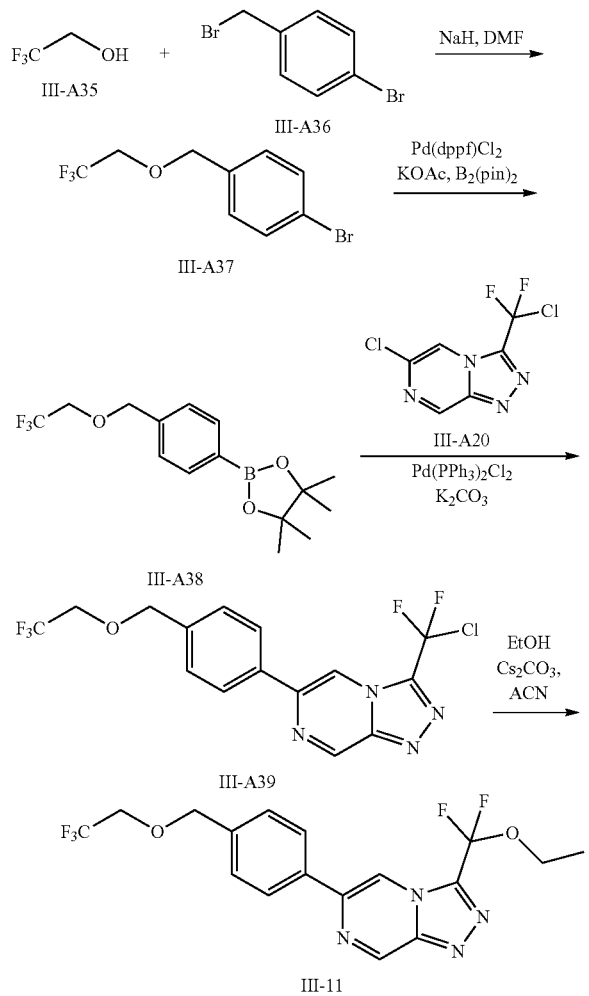

III-A37: 1-bromo-4-((2,2,2-trifluoroethoxy)methyl)benzene

To a stirred solution of NaH (300 mg, 7.5 mmol) in DMF (10.0 mL) was added 2,2,2-trifluoroethan-1-ol (500 mg, 5.0 mmol) at 0° C., and the resulting mixture was stirred for 15 minutes. To the reaction mixture was added 1-bromo-4-(bromomethyl)benzene (1.25 g, 5.0 mmol) in DMF (4.0 mL) dropwise. The reaction mixture was slowly warmed to room temperature and stirred for 1 hour. The reaction mixture was cooled to 10° C. and treated with ice water (20 mL). The reaction mixture was extracted with ethyl acetate (2×50 mL). The organic layer was washed with brine (30 mL), dried over anhydrous Na$_2$SO$_4$ and concentrated to afford 1-bromo-4-((2,2,2-trifluoroethoxy)methyl)benzene (1.15 g). It was used for the next step without further purification.

III-A38: 4,4,5,5-tetramethyl-2-(4-((2,2,2-trifluoroethoxy)methyl)phenyl)-1,3,2-dioxaborolane To a stirred solution of 1-bromo-4-((2,2,2-trifluoroethoxy)methyl)benzene (1.15 g, 4.2 mmol) and bis(pinacolato)diboron (1.39 g, 5.46 mmol) in 1,4-dioxane (12.0 mL) was added potassium acetate (1.59 g, 16.2 mmol). Pd(dppf)Cl$_2$·DCM (0.45 g, 0.55 mmol) was added to the reaction mixture under nitrogen atmosphere and heated at 85° C. for 4 hours. The reaction mixture was cooled to room temperature, filtered through Celite, and concentrated under reduced pressure. The crude product was purified by column chromatography on silica gel with 8% ethyl acetate/PE to afford 4,4,5,5-tetramethyl-2-(4-((2,2,2-trifluoroethoxy)methyl)phenyl)-1,3,2-dioxaborolane (1.18 g, 3.76 mmol, 89% yield) as a liquid. $^1$H NMR (400 MHz, CD$_3$OD) $\delta_H$=7.76 (d, 2H), 7.37 (d, 2H), 4.70 (s, 2H), 3.99-3.92 (m, 2H), 1.36 (s, 12H).

III-A39: 3-(chlorodifluoromethyl)-6-(4-((2,2,2-trifluoroethoxy)methyl)phenyl)-[1,2,4]triazolo[4,3-a]pyrazine To a stirred solution of 6-chloro-3-(chlorodifluoromethyl)-[1,2,4]triazolo[4,3-a]pyrazine (650 mg, 2.72 mmol) and 4,4,5,5-tetramethyl-2-(4-((2,2,2-trifluoroethoxy)methyl)phenyl)-1,3,2-dioxaborolane (1.12 g, 3.36 mmol) in 1,4-dioxane (9.0 mL) was added water (1.0 mL) and K$_2$CO$_3$ (751 mg, 5.44 mmol). Pd(PPh$_3$)$_2$Cl$_2$ (190 mg, 0.27 mmol) was added to the reaction mixture under nitrogen atmosphere and heated at 90° C. for 3 hours. The reaction mixture was cooled to room temperature, filtered through Celite, and concentrated under reduced pressure. The crude product was purified by column chromatography on silica gel with 30% ethyl acetate/PE to afford 3-(chlorodifluoromethyl)-6-(4-((2,2,2-trifluoroethoxy)methyl)phenyl)-[1,2,4]triazolo[4,3-a]pyrazine (195 mg, 0.49 mmol, 18% yield). LCMS: 393.0 (M+H), Rt 2.38 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min III-Compound 11: 3-(ethoxydifluoromethyl)-6-(4-((2,2,2-trifluoroethoxy)methyl)phenyl)-[1,2,4]triazolo[4,3-a]pyrazine To a stirred suspension of Cs$_2$CO$_3$ (970 mg, 2.98 mmol) in MeCN (2.0 mL) was added ethanol (0.58 mL, 9.93 mmol) at room temperature, and the resulting mixture was stirred for 15 minutes. To the reaction mixture was added 3-(chlorodifluoromethyl)-6-(4-((2,2,2-trifluoroethoxy)methyl)phenyl)-[1,2,4]triazolo[4,3-a]pyrazine (195 mg, 0.49 mmol) in MeCN (10.0 mL) dropwise, and the mixture was stirred for 6 hours. The reaction mixture was treated with water (50 mL) and extracted with ethyl acetate (2×40 mL). The organic layer was washed with brine (30 mL), dried over Na$_2$SO$_4$, and concentrated. The crude product was purified by preparative HPLC to afford 11 (30 mg, 0.07 mmol, 14% yield) as a solid. Prep-HPLC method: Rt 12.31; Column: X-Bridge C-18 (150×19 mm), 5.0 μm; 0.1% FA in water/acetonitrile; Flow Rate: 15.0 mL/min. HPLC: Rt 5.01 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 403.1 (M+H), Rt 2.53 min, 97.7%; Column: X-Bridge C8 (50×4.6 mm), 3.5 μm; Mobile Phase: A: 0.1% TFA in water:ACN (95:5), B: 0.1% TFA in ACN; Flow Rate: 1.5 mL/min. $^1$H NMR (400 MHz, DMSO-d$_6$) $\delta_H$=9.70 (d, 1H), 8.82 (d, 1H), 8.13 (d, 2H), 7.53 (d, 2H), 4.76 (s, 2H), 4.32 (q, 2H), 4.16 (q, 2H), 1.40 (t, 3H).

Example III-8. Synthesis of Compound III-12: 6-(4-(1,1-difluoro-2-methoxyethoxy)phenyl)-3-(trifluoromethyl)-[1,2,4]triazolo[4,3-a]pyrazine

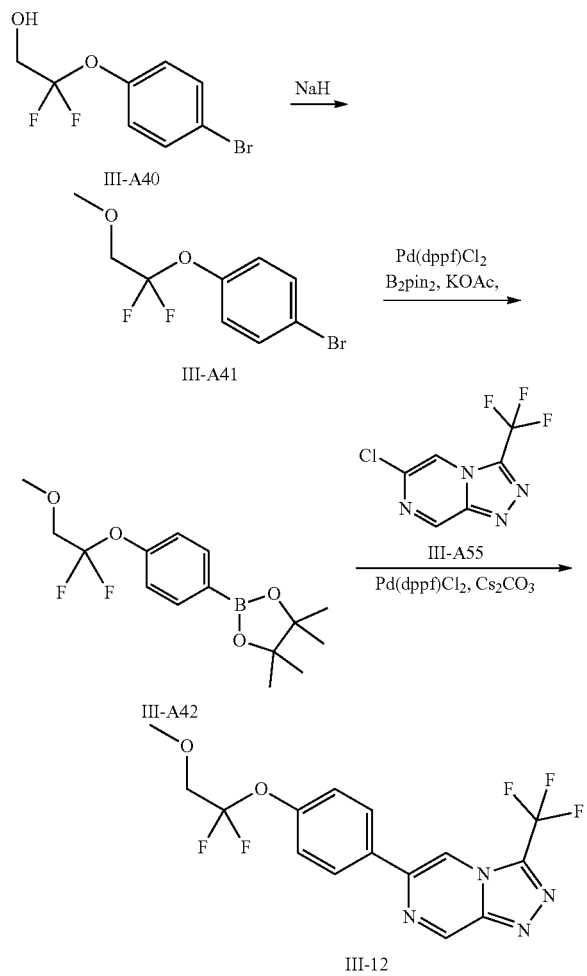

III-A41: 1-bromo-4-(1,1-difluoro-2-methoxyethoxy)benzene

To a stirred solution of 2-(4-bromophenoxy)-2,2-difluoroethan-1-ol (865 mg, 3.44 mmol) in THF (15.0 mL) was added NaH (60% in mineral oil, 0.28 g, 6.88 mmol) in small portions at 0° C. The reaction mixture was stirred for 20 minutes, and iodomethane (0.98 g, 6.88 mmol) in THF (1.0 mL) was added dropwise. The reaction mixture was slowly warmed to room temperature and stirred for 2 hours. The reaction mixture was cooled to 10° C., treated with ice water (30 mL), and extracted with ethyl acetate (2×30 mL). The organic layer was washed with brine (20 mL), dried over anhydrous Na$_2$SO$_4$ and concentrated. The crude product was purified by column chromatography on silica gel with 2% ethyl acetate/PE to afford 1-bromo-4-(1,1-difluoro-2-methoxyethoxy)benzene (860 mg, 3.24 mmol, 94% yield) as an oil. GCMS: 266.0 (M$^+$) and 268.0 (M+2), Rt 2.25 min.

III-A42: 2-(4-(1,1-difluoro-2-methoxyethoxy)phenyl)-4,4,5,5-tetramethyl-1,3,2-dioxaborolane To a stirred solution of 1-bromo-4-(1,1-difluoro-2-methoxyethoxy)benzene (860 mg, 3.24 mmol) and bis(pinacolato)diboron (1.07 g, 4.21 mmol) in 1,4-dioxane (15.0 mL) was added potassium acetate (636 mg, 6.48 mmol). Pd(dppf)Cl$_2$·DCM (344 mg, 0.42 mmol) was added to the reaction mixture under nitrogen atmosphere and heated at 85° C. for 4 hours. The reaction mixture was cooled to room temperature, filtered through Celite, and concentrated under reduced pressure. The crude product was purified by column chromatography on silica gel with 4% ethyl acetate/PE to afford 2-(4-(1,1-difluoro-2-methoxyethoxy)phenyl)-4,4,5,5-tetramethyl-1,3,2-dioxaborolane (605 mg, 1.93 mmol, 59% yield) as a liquid. GCMS: 314.1 (M$^+$), Rt 3.77 min

Compound III-12: 6-(4-(1,1-difluoro-2-methoxyethoxy)phenyl)-3-(trifluoromethyl)-[1,2,4]triazolo[4,3-a]pyrazine To a stirred solution of 6-chloro-3-(trifluoromethyl)-[1,2,4]triazolo[4,3-a]pyrazine (500 mg, 2.24 mmol) and 2-(4-(1,1-difluoro-2-methoxyethoxy)phenyl)-4,4,5,5-tetramethyl-1,3,2-dioxaborolane (562 mg, 1.79 mmol) in 1,4-dioxane (6.0 mL) was added water (0.5 mL) and Cs$_2$CO$_3$ (1.46 g, 4.49 mmol). Pd(dppf)Cl$_2$·DCM (183 mg, 0.22 mmol) was added to the reaction mixture under nitrogen atmosphere and heated at 90° C. for 3 hours. The reaction mixture was cooled to room temperature, filtered through Celite, and concentrated under reduced pressure. The crude reaction mixture was treated with water (30 mL) and extracted with ethyl acetate (2×30 mL). The organic layer was washed with brine (30 mL), dried over anhydrous Na$_2$SO$_4$ and concentrated. The crude product was purified by column chromatography on silica gel with 15% ethyl acetate/PE to afford III-12 (340 mg, 0.9 mmol, 50% yield) as a solid. HPLC: Rt 4.55 min; Column: X-Bridge C8 (50×4.6) mm, 3.5 µm; Mobile phase: A: 0.1% TFA in water, B: 0.1% TFA in ACN; Flow Rate: 2.0 mL/min. LCMS: 375.1 (M+H), Rt 2.25 min, 99.1%; Column: ZORBAX XDB C-18 (50×4.6 mm), 5.0 µm; Mobile Phase: A: 0.1% HCOOH in water:ACN (95:5), B: ACN; Flow Rate: 1.5 mL/min. $^1$H NMR (400 MHz, DMSO-d$_6$) $\delta_H$=9.77 (d, 1H), 9.03 (s, 1H), 8.24 (d, 2H), 7.39 (d, 2H), 3.96 (t, 2H), 3.47 (s, 3H).

Example III-9. Synthesis of Compound III-13: (R)-3-(difluoromethyl)-6-(6-((1,1,1-trifluoropropan-2-yl)oxy)pyridin-3-yl)-[1,2,4]triazolo[4,3-a]pyrazine

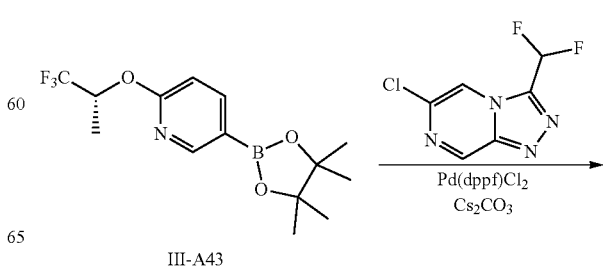

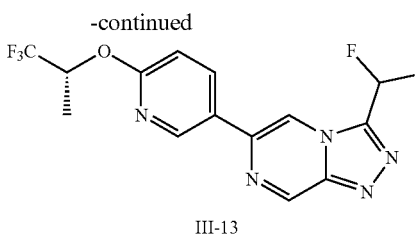

III-13

To a stirred solution of 6-chloro-3-(difluoromethyl)-[1,2,4]triazolo[4,3-a]pyrazine (150 mg, 0.73 mmol) and (R)-5-(4,4,5,5-tetramethyl-1,3,2-dioxaborolan-2-yl)-2-((1,1,1-trifluoropropan-2-yl)oxy)pyridine (256 mg, 0.81 mmol) in 1,4-dioxane (1.8 mL) was added water (0.2 mL) and Cs$_2$CO$_3$ (478 mg, 1.47 mmol). Pd(dppf)Cl$_2$·DCM (60 mg, 0.07 mmol) was added to the reaction mixture under nitrogen atmosphere and heated at 90° C. for 3 hours. The reaction mixture was cooled to room temperature, filtered through Celite, and concentrated under reduced pressure. The crude reaction mixture was treated with water (20 mL) and extracted with EtOAc (2×30 mL). The organic layer was washed with brine (20 mL), dried over Na$_2$SO$_4$ and concentrated. The crude product was purified by column chromatography on silica gel with 30% EtOAc/PE to afford III-13 (95 mg, 0.25 mmol, 34% yield) as a solid. HPLC: Rt 4.63 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 360.1 (M+H), Rt 2.34 min, 99.4%; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1$H NMR (400 MHz, DMSO-d$_6$) δ$_H$=9.69 (d, 1H), 9.23 (d, 1H), 8.93 (d, 1H), 8.49 (dd, 1H), 7.82 (t, 1H), 7.15 (d, 1H), 6.01-5.97 (m, 1H), 1.51 (d, 3H).

Example III-10. Syntheses of Compound III-14: (R)-6-(6-(1-cyclopropyl-2,2,2-trifluoroethoxy)pyridin-3-yl)-3-(trifluoromethyl)-[1,2,4]triazolo[4,3-a]pyrazine & Compound III-15: (S)-6-(6-(1-cyclopropyl-2,2,2-trifluoro ethoxy)pyridin-3-yl)-3-(trifluoromethyl)-[1,2,4]triazolo[4,3-a]pyrazine

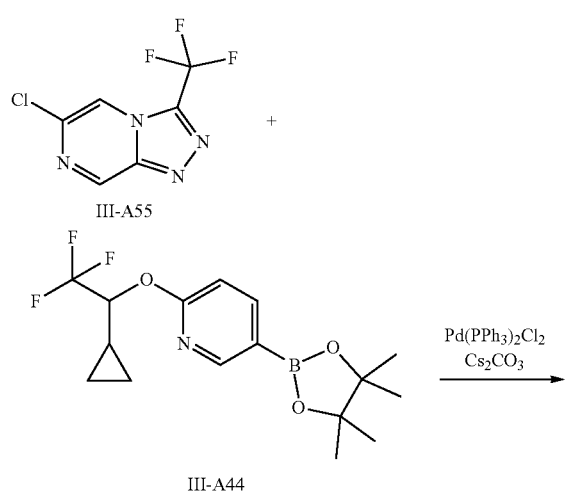

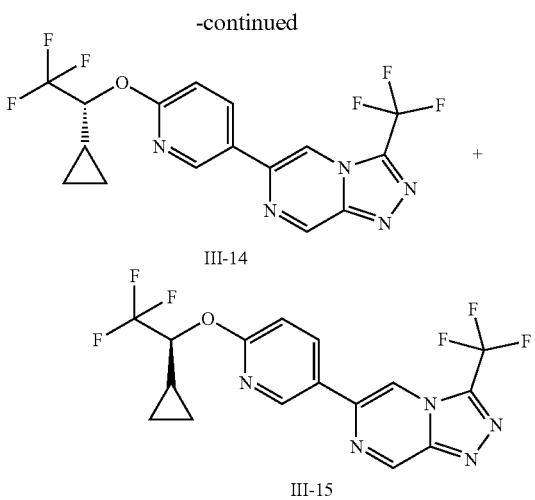

III-14

III-15

To a stirred solution of 6-chloro-3-(trifluoromethyl)-[1,2,4]triazolo[4,3-a]pyrazine (345 mg, 1.55 mmol) and 2-(1-cyclopropyl-2,2,2-trifluoroethoxy)-5-(4,4,5,5-tetramethyl-1,3,2-dioxaborolan-2-yl)pyridine (485 mg, 1.41 mmol) in 1,4-dioxane (9.0 mL) was added Cs$_2$CO$_3$ (918 mg, 2.82 mmol) and water (1.0 mL). Pd(dppf)Cl$_2$·DCM (115 mg, 0.14 mmol) was added to the reaction mixture under nitrogen atmosphere, and the mixture was heated at 90° C. for 3 hours. The reaction mixture was cooled to room temperature, filtered through Celite, and concentrated under reduced pressure. The crude product was purified by column chromatography on silica gel with 14% ethyl acetate/PE to afford racemic compound. The racemic mixture was separated by SFC purification to afford III-14 (20 mg, 0.05 mmol, 3.5% yield) and III-15 (15 mg, 0.036 mmol, 2.5% yield) as solids. Chiral method: SFC column: Lux C3; mobile phase: 90:10 (A:B), A=liquid CO$_2$, B=0.5% isopropyl amine in methanol; flow rate: 3.0 mL/min; wave length: 254 nm. The stereochemistry of III-14 and III-15 was randomly assigned.

Compound III-14: HPLC: Rt 5.38 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 404.1 (M+H), Rt 2.61 min, 95.1%; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 3.35 min, SFC column: Lux C3; mobile phase: 90:10 (A:B), A=liquid CO$_2$, B=0.5% isopropyl amine in methanol; flow rate: 3.0 mL/min; wave length: 254 nm. $^1$H NMR (400 MHz, CD$_3$OD) δ$_H$=9.61 (d, 1H), 8.89-8.88 (m, 2H), 8.46 (dd, 1H), 7.04 (dd, 1H), 5.54-5.50 (m, 1H), 1.37-1.26 (m, 1H), 0.80-0.75 (m, 1H), 0.68-0.63 (m, 3H).

Compound III-15: HPLC: Rt 5.38 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 404.0 (M+H), Rt 2.61 min, 98.2%; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 3.64 min, SFC column: Lux C3; mobile phase: 90:10 (A:B), A=liquid CO$_2$, B=0.5% isopropyl amine in methanol; flow rate: 3.0 mL/min; wave length: 254 nm. $^1$H NMR (400 MHz, CD$_3$OD): δ$_H$=9.61 (d, 1H), 8.89-8.88 (m, 2H), 8.46 (dd, 1H), 7.04 (dd, 1H), 5.55-5.48 (m, 1H), 1.37-1.28 (m, 1H), 0.80-0.75 (m, 1H), 0.68-0.63 (m, 3H).

Example III-11. Synthesis of Compound III-16: (S)-3-(difluoromethyl)-6-(6-((1,1,1-trifluoropropan-2-yl)oxy)pyridin-3-yl)-[1,2,4]triazolo[4,3-a]pyrazine

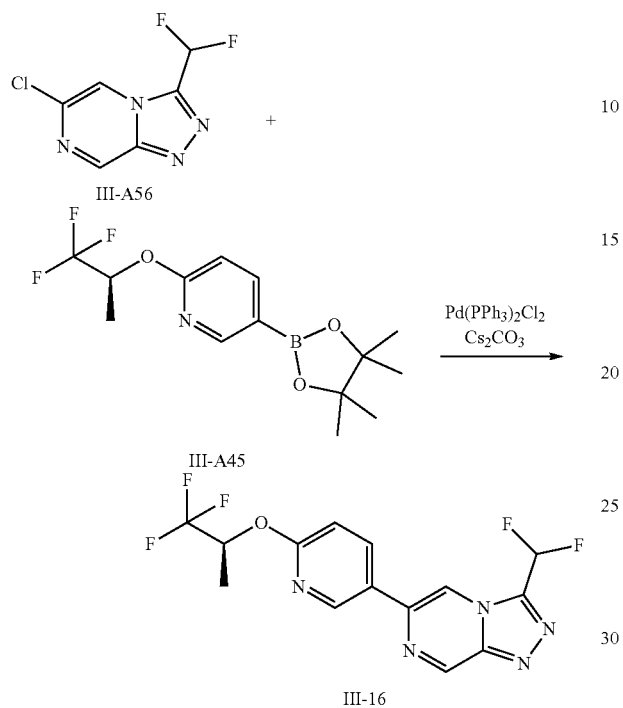

To a stirred solution of 6-chloro-3-(difluoromethyl)-[1,2,4]triazolo[4,3-a]pyrazine (150 mg, 0.73 mmol) and (S)-5-(4,4,5,5-tetramethyl-1,3,2-dioxaborolan-2-yl)-2-((1,1,1-trifluoropropan-2-yl)oxy)pyridine (245 mg, 0.77 mmol) in 1,4-dioxane (2.8 mL) was added $Cs_2CO_3$ (477 mg, 1.47 mmol) and water (0.40 mL). $Pd(dppf)Cl_2 \cdot DCM$ (60 mg, 0.07 mmol) was added to the reaction mixture under nitrogen atmosphere and heated at 90° C. for 3 h. The reaction mixture was cooled to room temperature and filtered through Celite. The crude reaction mixture was treated with water (30 mL) and extracted with ethyl acetate (2×50 mL). The organic layer was washed with brine (30 mL), dried over anhydrous $Na_2SO_4$ and concentrated. The crude product was purified by column chromatography on silica gel with 30% ethyl acetate/PE to afford III-16 (120 mg, 0.32 mmol, 44% yield) as a solid. HPLC: Rt 4.65 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 359.8 (M+H), Rt 2.34 min, 98.7%; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, $CD_3OD$) $\delta_H$=9.55 (d, 1H), 8.94-8.90 (m, 2H), 8.44 (dd, 1H), 7.60 (t, 1H), 7.03 (dd, 1H), 5.99-5.92 (m, 1H), 1.54 (d, 3H).

Example III-12. Syntheses of Compound III-17: 3-[difluoro(methoxy)methyl]-6-[4-[(1R)-1-(2,2,2-trifluoroethoxy)ethyl]phenyl]-[1,2,4]triazolo[4,3-a]pyrazine; Compound III-18: 3-[difluoro(methoxy)methyl]-6-[4-[(1S)-1-(2,2,2-trifluoroethoxy)ethyl]phenyl]-[1,2,4]triazolo[4,3-a]pyrazine; Compound III-19: 3-[ethoxy(difluoro)methyl]-6-[4-[(1R)-1-(2,2,2-trifluoroethoxy)ethyl]phenyl]-[1,2,4]triazolo[4,3-a]pyrazine; and Compound III-20: 3-[ethoxy(difluoro)methyl]-6-[4-[(1S)-1-(2,2,2-trifluoroethoxy)ethyl]phenyl]-[1,2,4]triazolo[4,3-a]pyrazine

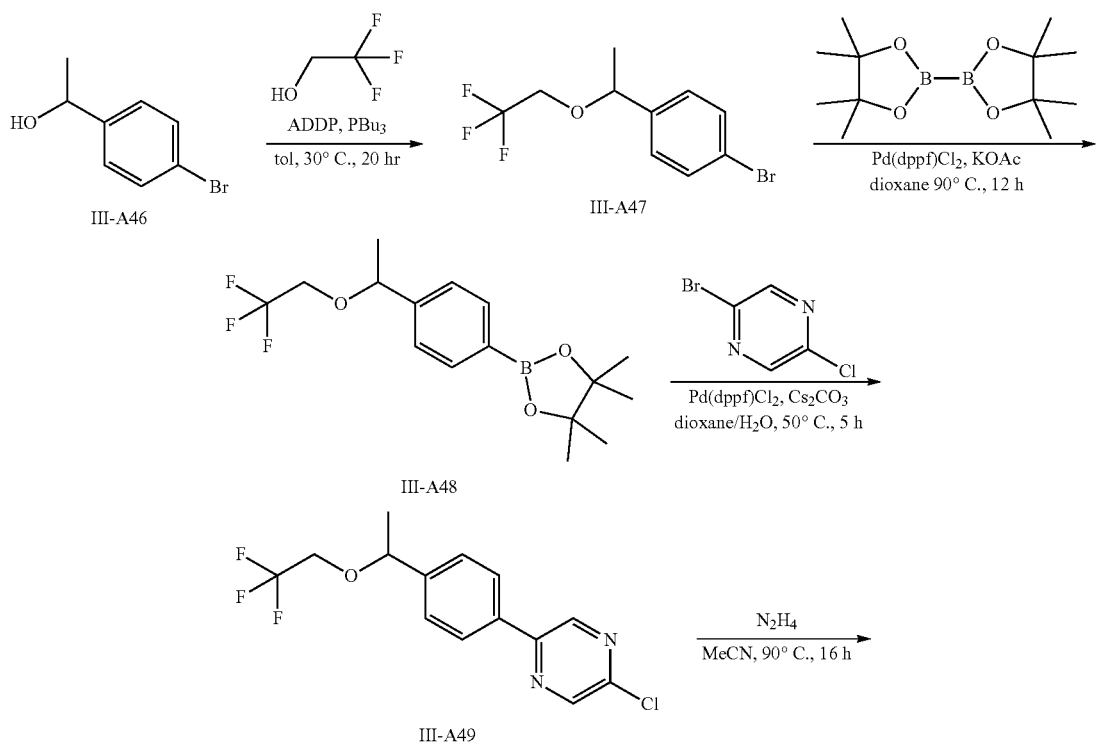

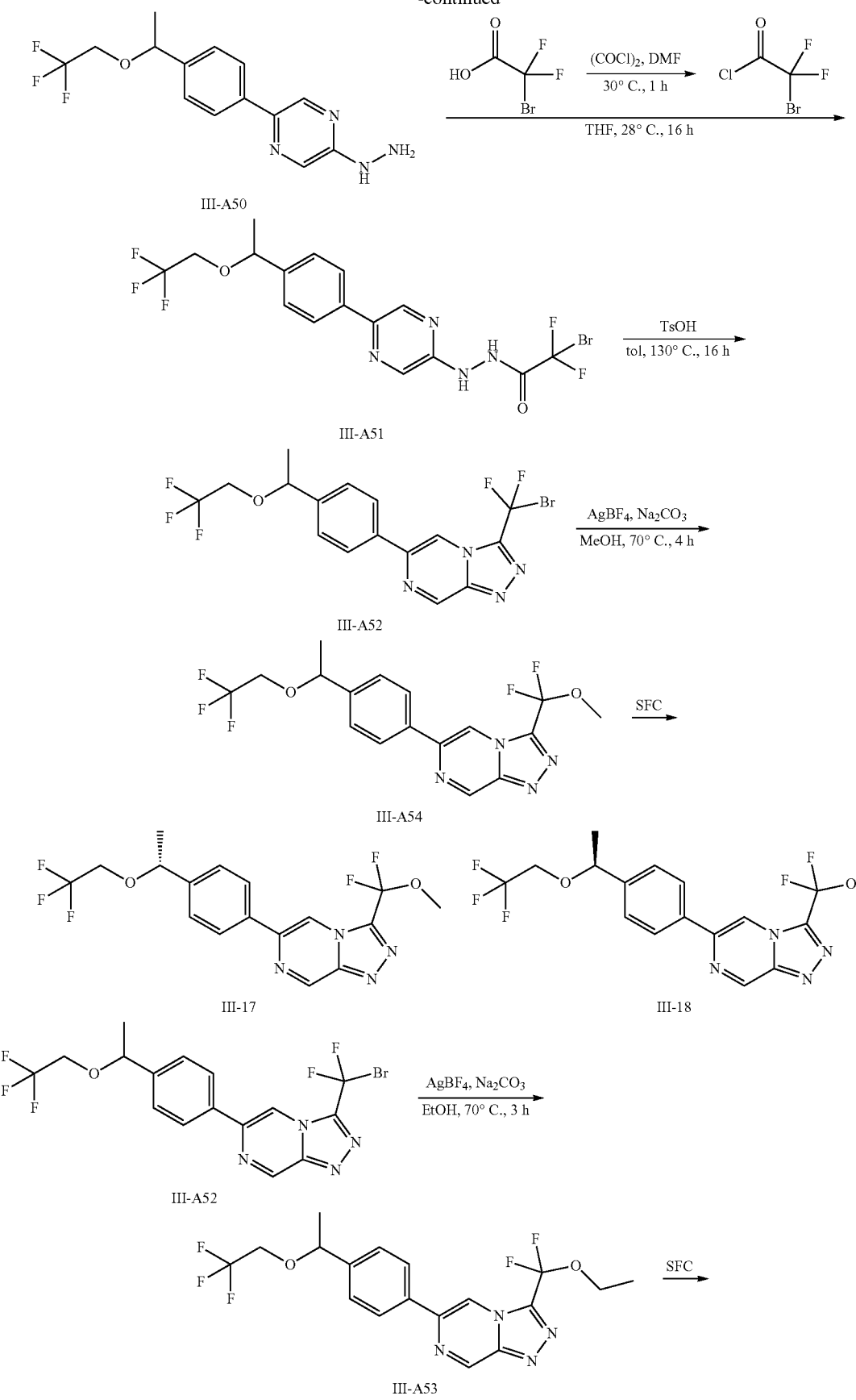

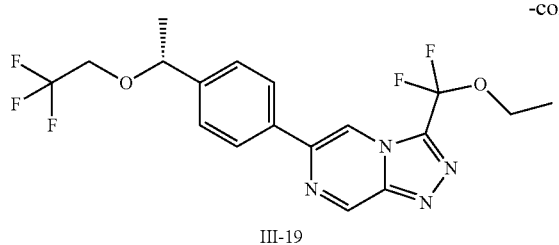

III-19

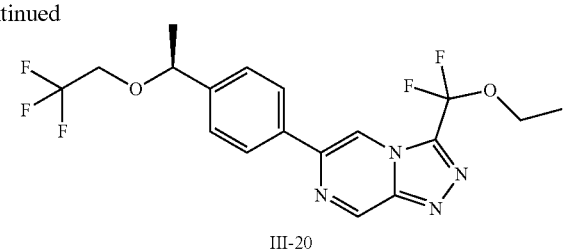

III-20

III-A47: 1-bromo-4-[1-(2,2,2-trifluoroethoxy)ethyl]benzene

To a solution of 1-(4-bromophenyl)ethanol (10.0 g, 49.74 mmol) in toluene (500 mL) were added tributylphosphine (15.09 g, 74.6 mmol) and 1,1-(azodicarbonyl)dipiperidine (18.82 g, 74.6 mmol) under $N_2$ at 30° C. The mixture was stirred at 30° C. for 30 min. Then 2,2,2-trifluoroethanol (9.95 g, 99.47 mmol) was added to the mixture. The mixture was stirred at 30° C. for 20 hours under $N_2$. The mixture was filtered, and the filter cake was washed with toluene (100 mL×2). The filtrate was concentrated under reduced pressure. The crude product was purified by flash chromatography on silica gel (DCM in PE 0~1%) to give the product (4.7 g, 16.60 mmol, 33% yield) as an oil. $^1$H NMR (400 MHz, CDCl$_3$) $\delta_H$=7.51 (d, 2H), 7.21 (d, 2H), 4.55 (q, 1H), 3.72-3.60 (m, 2H), 1.49 (d, 3H).

III-A48: 4,4,5,5-tetramethyl-2-[4-[1-(2,2,2-trifluoroethoxy)ethyl]phenyl]-1,3,2-dioxaborolane To a mixture of 1-bromo-4-[1-(2,2,2-trifluoroethoxy)ethyl]benzene (4.7 g, 16.60 mmol), 4,4,5,5-tetramethyl-2-(4,4,5,5-tetramethyl-1,3,2-dioxaborolan-2-yl)-1,3,2-dioxaborolane (4.64 g, 18.26 mmol), KOAc (3.26 g, 33.2 mmol) in 1,4-dioxane (50 mL) was stirred at 90° C. for 12 hours under $N_2$. After cooling to 25° C., the mixture was filtered, and the filtrate was concentrated. Water (50 mL) was added, and the aqueous layer was extracted with EtOAc (50 mL×3). The combined organic layers were washed with brine (50 mL), dried over anhydrous Na$_2$SO$_4$, filtered, and concentrated. The crude product was purified by flash chromatography on silica gel (DCM in PE=0-5%) to afford the product (4.2 g, 12.72 mmol, 77% yield) as an oil. $^1$H NMR (400 MHz, CDCl$_3$) $\delta_H$=7.83 (d, 2H), 7.33 (d, 2H), 4.59 (q, 1H), 3.72-3.58 (m, 2H), 1.50 (d, 3H), 1.35 (s, 12H).

III-A49: 2-chloro-5-[6-[1-(trifluoromethyl)propoxy]-3-pyridyl]pyrazine

To a solution of 4,4,5,5-tetramethyl-2-[4-[1-(2,2,2-trifluoroethoxy)ethyl]phenyl]-1,3,2-dioxaborolane (4.2 g, 12.72 mmol) in 1,4-dioxane (40 mL) and water (4 mL) were added 2-bromo-5-chloro-pyrazine (2.71 g, 13.99 mmol) and Cs$_2$CO$_3$ (8.29 g, 25.44 mmol). Then Pd(dppf)Cl$_2$ (931 mg, 1.27 mmol) was added to the above mixture. The mixture was stirred at 50° C. for 5 hours. The mixture was filtered, and the filtrate was concentrated. Water (50 mL) was added, and the aqueous layer was extracted with EtOAc (50 mL×3). The combined organic layers were washed with brine (50 mL), dried over anhydrous Na$_2$SO$_4$, filtered, and concentrated. The crude product was purified by flash chromatography on silica gel (EtOAc in PE 0 to 10%) to afford the product (3.4 g, 10.74 mmol, 84% yield) as a solid. $^1$H NMR (400 MHz, CDCl$_3$) $\delta_H$=8.80 (s, 1H), 8.65 (s, 1H), 8.01 (d, 2H), 7.48 (d, 2H), 4.65 (q, 1H), 3.78-3.65 (m, 2H), 1.55 (d, 3H).

III-A50: [5-[4-[1-(2,2,2-trifluoroethoxy)ethyl]phenyl]pyrazin-2-yl]hydrazine To a solution of 2-chloro-5-[4-[1-(2,2,2-trifluoroethoxy)ethyl]phenyl]pyrazine (3.4 g, 10.74 mmol) in MeCN (40 mL) was added hydrazine hydrate (5.37 g, 107.35 mmol). The mixture was stirred at 90° C. for 16 hours. Water (100 mL) was added and the aqueous layer was extracted with EtOAc (100 mL×3). The combined organic layers were washed with brine (100 mL), dried over anhydrous Na$_2$SO$_4$, filtered, and concentrated to afford the product (3.2 g, 10.2 mmol) as a solid. $^1$H NMR (400 MHz, DMSO-d$_6$) $\delta_H$=8.56 (s, 1H), 8.19 (s, 1H), 8.12 (s, 1H), 7.94 (d, 2H), 7.39 (d, 2H), 4.68 (q, 1H), 4.34 (brs, 2H), 4.02-3.93 (m, 1H), 3.90-3.77 (m, 1H), 1.43 (d, 3H).

III-A51: 2-bromo-2,2-difluoro-N'-[5-[4-[1-(2,2,2-trifluoroethoxy)ethyl]phenyl]pyrazin-2-yl]acetohydrazide To a solution of 2-bromo-2,2-difluoro-acetic acid (1.34 g, 7.69 mmol) in THF (20 mL) were added (COCl)$_2$ (0.79 mL, 9.22 mmol) and 5 drops of DMF. The mixture was stirred at 30° C. for 1 hour. A solution of [5-[4-[1-(2,2,2-trifluoroethoxy)ethyl]phenyl]pyrazin-2-yl]hydrazine (1.6 g, 5.12 mmol) in THF (5 mL) was added to the above mixture. The mixture was stirred at 28° C. for 16 hours. Water (30 mL) was added, and the aqueous layer was extracted with EtOAc (30 mL×3). The combined organic layers were washed with brine (30 mL), dried over anhydrous Na$_2$SO$_4$, filtered, and concentrated to afford the product (2.4 g, 5.12 mmol) as an oil. LCMS R$_t$=1.19 min in 2 min chromatography, 10-80AB, MS ESI calcd. for C$_{16}$H$_{15}$BrF$_5$N$_4$O$_2$ [M+H]$^+$ 471.0, found 471.0.

III-A52: 3-[bromo(difluoro)methyl]-6-[4-[1-(2,2,2-trifluoroethoxy)ethyl]phenyl]-[1,2,4]triazolo[4,3-a]pyrazine To a solution of 2-bromo-2,2-difluoro-N'-[5-[4-[1-(2,2,2-trifluoroethoxy)ethyl]phenyl]pyrazin-2-yl]acetohydrazide (2.4 g, 5.12 mmol) in toluene (5 mL) was added TsOH (264 mg, 1.53 mmol). The mixture was stirred at 130° C. for 16 hours. Water (20 mL) was added, and the aqueous layer was extracted with EtOAc (20 mL×3). The combined organic layers were washed with brine (20 mL), dried over anhydrous Na$_2$SO$_4$, filtered, and concentrated. The crude product was purified by flash chromatography on silica gel (EtOAc in PE 0 to 20%) to afford the product (240 mg, 0.53 mmol, 10% yield) as an oil. $^1$H NMR (400 MHz, CDCl$_3$) $\delta_H$=9.59

(s, 1H), 8.46 (s, 1H), 8.00 (d, 2H), 7.52 (d, 2H), 4.68 (q, 1H), 3.78-3.68 (m, 2H), 1.54 (d, 3H).

III-A54: 3-[difluoro(methoxy)methyl]-6-[4-[1-(2,2,2-trifluoroethoxy)ethyl]phenyl]-[1,2,4]triazolo[4,3-a]pyrazine To a solution of 3-[bromo(difluoro)methyl]-6-[4-[1-(2,2,2-trifluoroethoxy)ethyl]phenyl]-[1,2,4]triazolo[4,3-a]pyrazine (240 mg, 0.53 mmol) in methanol (3 mL) were added AgBF$_4$ (206.39 mg, 1.06 mmol) and Na$_2$CO$_3$ (113 mg, 1.06 mmol). The mixture was stirred at 70° C. for 4 hours. Brine (20 mL) was added, and the mixture was filtered. The aqueous layer was extracted with EtOAc (20 mL×3). The combined organic layers were washed with brine (20 mL), dried over anhydrous Na$_2$SO$_4$, filtered, and concentrated under reduced pressure. The crude product was purified by flash chromatography on silica gel (EtOAc in PE 0 to 20%) to afford the product (140 mg, 0.35 mmol, 65% yield) as an oil. LCMS R$_t$=0.99 min in 1.5 min chromatography, 5-95AB, MS ESI calcd. for C$_{17}$H$_{16}$F$_5$N$_4$O$_2$[M+H]$^+$ 403.1, found 403.0.

Compounds III-17 & III-18: 3-[difluoro(methoxy)methyl]-6-[4-[(1R)-1-(2,2,2-trifluoroethoxy)ethyl]phenyl]-[1,2,4]triazolo[4,3-a]pyrazine & 3-[difluoro(methoxy)methyl]-6-[4-[(1S)-1-(2,2,2-trifluoroethoxy)ethyl]phenyl]-[1,2,4]triazolo[4,3-a]pyrazine Analytical SFC: (Chiralpak AD-3 50×4.6 mm I.D, 3 μm. Mobile phase: A: CO$_2$, B: ethanol (0.05% DEA). Gradient: from 5% to 40% of B in 2 min and hold 40% of B for 1.2 min, then 5% of B for 0.8 min. Flow rate: 4 mL/min. Column temperature: 35° C. ABPR: 1500 psi) showed two peaks at 0.715 min (49.9%) and 0.795 min (50.1%). 3-[difluoro(methoxy)methyl]-6-[4-[1-(2,2,2-trifluoroethoxy)ethyl]phenyl]-[1,2,4]triazolo[4,3-a]pyrazine (140 mg, 0.35 mmol) was purified by SFC (DAICEL CHIRALCEL AD (250 mm×30 mm, 10 μm) A=CO$_2$ and B=0.1% NH$_3$H$_2$O-EtOH; 60 mL/min; 15% B, injections: 80) to afford the enantiomer 1, randomly assigned as 3-[difluoro(methoxy)methyl]-6-[4-[(1R)-1-(2,2,2-trifluoroethoxy)ethyl]phenyl]-[1,2,4]triazolo[4,3-a]pyrazine (40.95 mg, 0.10 mmol, 29% yield) (Rt of Peak 1=0.726 min) and the enantiomer 2, randomly assigned as 3-[difluoro(methoxy)methyl]-6-[4-[(1S)-1-(2,2,2-trifluoroethoxy)ethyl]phenyl]-[1,2,4]triazolo[4,3-a]pyrazine (56 mg, 0.14 mmol, 39% yield) (Rt of Peak 2=0.804 min) as solids.

Compound III-17: $^1$H NMR (400 MHz, CDCl$_3$) δ$_H$=9.52 (s, 1H), 8.47 (s, 1H), 7.97 (d, 2H), 7.50 (d, 2H), 4.74-4.63 (m, 1H), 3.97 (s, 3H), 3.82-3.63 (m, 2H), 1.55 (d, 3H). LCMS R$_t$=1.29 min in 2.0 min chromatography, 10-80AB, MS ESI calcd. for C$_{17}$H$_{16}$F$_5$N$_4$O$_2$[M+H]$^+$ 403.1, found 403.1.

Compound III-18: $^1$H NMR (400 MHz, CDCl$_3$) δ$_H$=9.51 (s, 1H), 8.47 (s, 1H), 7.97 (d, 2H), 7.50 (d, 2H), 4.74-4.63 (m, 1H), 3.96 (s, 3H), 3.82-3.63 (m, 2H), 1.55 (d, 3H). LCMS R$_t$=1.29 min in 2.0 min chromatography, 10-80AB, MS ESI calcd. for C$_{17}$H$_{16}$F$_5$N$_4$O$_2$[M+H]$^+$ 403.1, found 403.0.

A53: 3-[ethoxy(difluoro)methyl]-6-[4-[1-(2,2,2-trifluoroethoxy)ethyl]phenyl]-[1,2,4]triazolo[4,3-a]pyrazine Compounds III-19 & III-20: 3-[ethoxy(difluoro)methyl]-6-[4-[(1R)-1-(2,2,2-trifluoroethoxy)ethyl]phenyl]-[1,2,4]triazolo[4,3-a]pyrazine & 3-[ethoxy(difluoro)methyl]-6-[4-[(1S)-1-(2,2,2-trifluoroethoxy)ethyl]phenyl]-[1,2,4]triazolo[4,3-a]pyrazine To a solution of 3-[bromo(difluoro)methyl]-6-[4-[1-(2,2,2-trifluoroethoxy)ethyl]phenyl]-[1,2,4]triazolo[4,3-a]pyrazine (200 mg, 0.44 mmol) in ethanol (3 mL) were added AgBF$_4$ (258 mg, 1.33 mmol) and Na$_2$CO$_3$ (141 mg, 1.33 mmol). The mixture was stirred at 70° C. for 3 hours. Brine (20 mL) was added, and the suspension was filtered. The filtrate was extracted with EtOAc (20 mL×3). The combined organic layers were washed with brine (20 mL), dried over anhydrous Na$_2$SO$_4$, filtered, and concentrated. The crude product was purified by flash chromatography on silica gel (EtOAc in PE 0 to 15%) to afford the product (110 mg, 0.26 mmol, 60% yield) as an oil. LCMS R$_t$=1.24 min in 2 min chromatography, 10-80AB, MS ESI calcd. for C$_{18}$H$_{18}$F$_5$N$_4$O$_2$[M+H]$^+$ 417.1, found 417.1.

Analytical SFC: (Chiralpak AD-3 50×4.6 mm I.D, 3 μm. Mobile phase: A: CO$_2$, B: ethanol (0.05% DEA). Gradient: from 5% to 40% of B in 2 min and hold 40% of B for 1.2 min, then 5% of B for 0.8 min. Flow rate: 4 mL/min. Column temperature: 35° C. ABPR: 1500 psi) showed two peaks at 0.673 min (50.0%) and 0.740 min (50.0%). 3-[ethoxy(difluoro)methyl]-6-[4-[1-(2,2,2-trifluoroethoxy)ethyl]phenyl]-[1,2,4]triazolo[4,3-a]pyrazine (110 mg, 0.26 mmol) was purified by SFC (DAICEL CHIRALCEL AD-H (250 mm×30 mm, 5 μm) A=CO$_2$ and B=0.1% NH$_3$H$_2$O-EtOH; 60 mL/min; 15% B, injections: 70) to afford the enantiomer 1, randomly assigned as 3-[ethoxy(difluoro)methyl]-6-[4-[(1R)-1-(2,2,2-trifluoroethoxy)ethyl]phenyl]-[1,2,4]triazolo[4,3-a]pyrazine (15.93 mg, 0.038 mmol, 14% yield) (Rt of Peak 1=0.661 min) and the enantiomer 2, randomly assigned as 3-[ethoxy(difluoro)methyl]-6-[4-[(1S)-1-(2,2,2-trifluoroethoxy)ethyl]phenyl]-[1,2,4]triazolo[4,3-a]pyrazine (10.94 mg, 0.026 mmol, 10% yield) (Rt of Peak 2=0.727 min) as solids.

Compound III-19: $^1$H NMR (400 MHz, CDCl$_3$) δ$_H$=9.53 (s, 1H), 8.50 (s, 1H), 7.97 (d, 2H), 7.50 (d, 2H), 4.74-4.63 (m, 1H), 4.37 (q, 2H), 3.82-3.63 (m, 2H), 1.70-1.45 (m, 6H). LCMS R$_t$=1.32 min in 2.0 min chromatography, 10-80AB, MS ESI calcd. for C$_{18}$H$_{18}$F$_5$N$_4$O$_2$ [M+H]$^+$ 417.1, found 417.0.

Compound III-20: $^1$H NMR (400 MHz, CDCl$_3$) δ$_H$=9.53 (s, 1H), 8.50 (s, 1H), 7.97 (d, 2H), 7.50 (d, 2H), 4.74-4.63 (m, 1H), 4.37 (q, 2H), 3.82-3.63 (m, 2H), 1.70-1.45 (m, 6H). LCMS R$_t$=1.31 min in 2.0 min chromatography, 10-80AB, MS ESI calcd. for C$_{18}$H$_{18}$F$_5$N$_4$O$_2$ [M+H]$^+$ 417.1, found 417.0.

Example III-13: Syntheses of Intermediates

Synthesis of III-A20 (6-chloro-3-[chloro(difluoro)methyl]-[1,2,4]triazolo[4,3-a]pyrazine)

To a stirred solution of 2-chloro-N'-(5-chloropyrazin-2-yl)-2,2-difluoroacetohydrazide (6.0 mg, 23.34 mmol) in DCM (120 mL) was added trifluoromethanesulfonic anhydride (4.73 mL, 28.01 mmol) and 2-methoxypyridine (4.91 mL, 46.69 mmol) at 0° C. The reaction mixture was slowly warmed to room temperature and stirred for 2 hours. The reaction mixture was treated with 10% sodium bicarbonate solution (50 mL) and extracted with ethyl acetate (2×50 mL). The organic layer was washed with brine (50 mL), dried over Na$_2$SO$_4$ and concentrated. The crude product was purified by column chromatography on silica gel with 15% EtOAc/PE to afford the product (4.0 g, 16.5 mmol, 71% yield) as a solid. LCMS: 239.0 (M+H), Rt 1.66 min Column: ZORBAX XDB C-18 (50×4.6 mm), 3.5 µm Mobile Phase: A: 0.1% HCOOH in water:ACN (95:5), B: ACN; Flow Rate: 1.5 mL/min.

Synthesis of III-A43 ((R)-5-(4,4,5,5-tetramethyl-1,3,2-dioxaborolan-2-yl)-2-((1,1,1-trifluoropropan-2-yl)oxy)pyridine)

To a stirred solution of (R)-5-bromo-2-((1,1,1-trifluoropropan-2-yl)oxy)pyridine (3.1 g, 11.5 mmol) and bis(pinacolato)diboron (3.79 g, 14.92 mmol) in 1,4-dioxane (35.0 mL) was added potassium acetate (2.25 g, 22.96 mmol). Pd(dppf)Cl$_2$·DCM (1.41 g, 1.72 mmol) was added to the reaction mixture under nitrogen atmosphere, and the mixture was heated at 90° C. for 12 hours. The reaction mixture was cooled to room temperature, filtered through Celite, and concentrated under reduced pressure. The crude product was purified by column chromatography on silica gel with 6% ethyl acetate/PE to afford (R)-5-(4,4,5,5-tetramethyl-1,3,2-dioxaborolan-2-yl)-2-((1,1,1-trifluoropropan-2-yl)oxy)pyridine (2.8 g, 8.83 mmol, 76% yield) as a solid. LCMS: 318.0 (M+H), Rt 4.04 min; Column: ZORBAX Extend (50×4.6 mm), 5 µm; Mobile Phase: A: 10 mM Ammonium acetate in water, B: ACN; Flow Rate: 1.2 mL/min.

Synthesis of III-A44 (2-(1-cyclopropyl-2,2,2-trifluoroethoxy)-5-(4,4,5,5-tetramethyl-1,3,2-dioxaborolan-2-yl)pyridine)

To a stirred solution of 5-bromo-2-(1-cyclopropyl-2,2,2-trifluoroethoxy)pyridine (3.1 g, 10.47 mmol) and bis(pinacolato)diboron (3.46 g, 13.61 mmol) in 1,4-dioxane (30 mL) was added potassium acetate (1.72 g, 20.94 mmol). Pd(dppf)Cl$_2$·DCM (0.86 g, 1.05 mmol) was added to the reaction mixture under nitrogen atmosphere, and the mixture was heated at 90° C. for 3 hours. The reaction mixture was cooled to room temperature and filtered through Celite. The reaction mixture was treated with ice water (50 mL) and extracted with ethyl acetate (2×50 mL). The organic layer was washed with brine (30 mL), dried over anhydrous Na$_2$SO$_4$ and concentrated. The crude product was purified by column chromatography on silica gel with 4% ethyl acetate/PE to afford 2-(1-cyclopropyl-2,2,2-trifluoroethoxy)-5-(4,4,5,5-tetramethyl-1,3,2-dioxaborolan-2-yl)pyridine (3.2 g, 9.3 mmol, 89% yield). LCMS: 344.1 (M+H), Rt 3.18 min; Column: ZORBAX XDB C-18 (50×4.6 mm), 3.5 µm; Mobile Phase: A: 0.1% HCOOH in water:ACN (95:5), B: ACN; Flow Rate: 1.5 mL/min.

Synthesis of III-A45 ((S)-5-(4,4,5,5-tetramethyl-1,3,2-dioxaborolan-2-yl)-2-((1,1,1-trifluoropropan-2-yl)oxy)pyridine)

To a stirred solution of compound (S)-5-bromo-2-((1,1,1-trifluoropropan-2-yl)oxy)pyridine (0.5 g, 1.85 mmol) and bis(pinacolato)diboron (0.52 g, 2.04 mmol) in 1,4-dioxane (5.0 mL) was added potassium acetate (0.36 g, 3.7 mmol). Pd(dppf)Cl$_2$·DCM (0.15 g, 0.19 mmol) was added to the reaction mixture under nitrogen atmosphere and heated at 80° C. for 12 hours. The reaction mixture was cooled to room temperature, filtered through Celite, and concentrated under reduced pressure. The crude product was purified by column chromatography on silica gel with 10% ethyl acetate/PE to afford compound (S)-5-(4,4,5,5-tetramethyl-1,3,2-dioxaborolan-2-yl)-2-((1,1,1-trifluoropropan-2-yl)oxy)pyridine (302 mg, 0.95 mmol, 51% yield). LCMS: 318.1 (M+H), Rt 3.04 min; Column: ZORBAX XDB C-18 (50×4.6 mm), 3.5 µm; Mobile Phase: A: 0.1% HCOOH in water:ACN (95:5), B: ACN; Flow Rate: 1.5 mL/min.

Efficacy of Exemplary Compounds in the Modulation of Late Sodium Current (INaL)

Functional characterization of exemplary compounds to modulate INaL expressed by the NaV1.6 voltage-gated sodium channel was accomplished using the PatchXpress™ high throughput electrophysiology platform (Molecular Devices, Sunnyvale, CA). HEK-293 cells expressing recombinant, human NaV1.6 (hNaV1.6) were grown in DMEM/high-glucose Dulbecco's modified, 10% FBS, 2 mM sodium pyruvate, 10 mM HEPES and 400 µg/mL G418. Cells were grown to 50%-80% confluency prior to harvesting. Trypsinized cells were washed, allowed to recover for 1 hour and then resuspended in extracellular recording solution at a concentration of 1×106 cells/ml. The onboard liquid handling facility of the PatchXpress was used for dispensing cells and applying test compounds. NaV late currents were evoked by the application of 300 nM ATX-II. INaL was evoked by depolarizing pulses to 0 mV for 200 ms from a non-inactivating holding potential (e.g., −120 mV) at a frequency of 0.1 Hz. INaL amplitude and stability were determined by analyzing the mean current amplitude over the final 20 ms of the test pulse. Following steady state block with exemplary compounds (e.g., as described herein), a Na+ free solution containing an impermeant cation (e.g., Choline or NDMG) was added to confirm the identity of the sodium current. Percent steady-state inhibition of INaL was calculated as: [(INaL_compound)/(INaL_control)]*100, where INaL_compound and INaL_control represent INaL recorded in the presence or absence of compound, respectively.

Results from this assay relating to percent inhibition of INaL at hNaV1.6 (measured using a procedure similar to described above but using HEK-293 cells expressing recombinant, human NaV 1.6 (h NaV 1.6) at 1 µM are summarized in Table 1 below. In this table, "A" indicates inhibition of less than 30%; "B" indicates inhibition of between about 30% to about 70%; and "C" indicates inhibition of greater than 70%. "N/A" indicates not available.

TABLE 1

| Compound No. | NaV 1.6 Assay Data |
| --- | --- |
| I-1 | C |
| I-2 | B |
| I-3 | B |
| I-4 | B |
| I-5 | B |
| I-6 | B |
| I-7 | B |
| I-8 | B |
| I-9 | B |
| I-10 | B |
| I-11 | B |
| I-12 | B |
| I-13 | B |

TABLE 1-continued

| Compound No. | NaV 1.6 Assay Data |
| --- | --- |
| I-14 | B |
| I-15 | B |
| I-16 | B |
| I-17 | A |
| I-18 | B |
| I-19 | B |
| I-20 | B |
| I-21 | A |
| I-22 | A |
| I-23 | A |
| I-24 | A |
| II-1 | A |
| II-2 | A |
| II-3 | B |
| II-4 | A |
| II-5 | A |
| II-6 | A |
| II-7 | B |
| II-8 | B |
| II-9 | B |
| II-10 | C |
| II-11 | B |
| II-12 | C |
| II-13 | B |
| II-14 | B |
| II-15 | B |
| II-16 | N/A |
| III-1 | C |
| III-2 | C |
| III-3 | C |
| III-4 | B |
| III-5 | B |
| III-6 | B |
| III-7 | C |
| III-8 | C |
| III-9 | B |
| III-10 | A |
| III-11 | B |
| III-12 | B |
| III-13 | C |
| III-14 | B |
| III-15 | C |
| III-16 | C |
| III-17 | A |
| III-18 | A |
| III-19 | A |
| III-20 | B |

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of Formula (III-II):

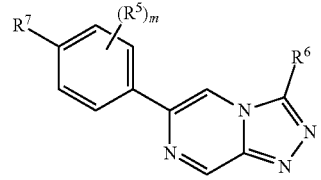

(III-II)

or a pharmaceutically acceptable salt or stereoisomer thereof, wherein:
   $R^5$ is halo, $C_{1-4}$ alkyl, or $C_{3-6}$ cycloalkyl, wherein the $C_{1-4}$ alkyl is optionally substituted with one $OC_{1-4}$ alkyl or $OC_{3-6}$ cycloalkyl substituent;
   $R^6$ is $C_{1-4}$ alkyl or $C_{1-4}$ haloalkyl, wherein the $C_{1-4}$ alkyl or $C_{1-4}$ haloalkyl is substituted with one $OR^c$ substituent;
   $R^7$ is a monocyclic $C_{3-6}$ cycloalkyl, wherein the $C_{3-6}$ cycloalkyl is substituted with one or more independently selected $R^a$ substituents;
   each $R^a$ is independently halo, $C_{1-4}$ alkyl, $C_{1-4}$ haloalkyl, $OC_{1-4}$ alkyl, or $OC_{1-4}$ haloalkyl;
   $R^c$ is $C_{1-4}$ alkyl or $C_{3-6}$ cycloalkyl, wherein the $C_{1-4}$ alkyl is optionally substituted with one $C_{3-6}$ cycloalkyl or phenyl substituent; and
   m is 0, 1, or 2.

2. The compound of claim 1, or a pharmaceutically acceptable salt or stereoisomer thereof, wherein $R^5$ is $C_{1-4}$ alkyl.

3. The compound of claim 2, or a pharmaceutically acceptable salt or stereoisomer thereof, wherein $R^5$ is $CH_3$.

4. The compound of claim 1, or a pharmaceutically acceptable salt or stereoisomer thereof, wherein $R^6$ is $C_{1-4}$ haloalkyl, wherein the $C_{1-4}$ haloalkyl is substituted with one $OR^c$ substituent.

5. The compound of claim 4, or a pharmaceutically acceptable salt or stereoisomer thereof, wherein $R^6$ is $CF_2OR^c$.

6. The compound of claim 1, or a pharmaceutically acceptable salt or stereoisomer thereof, wherein $R^7$ is cyclopropyl.

7. The compound of claim 1, or a pharmaceutically acceptable salt or stereoisomer thereof, wherein $R^c$ is $C_{1-4}$ alkyl.

8. The compound of claim 7, or a pharmaceutically acceptable salt or stereoisomer thereof, wherein $R^c$ is $CH_3$.

9. The compound of claim 1, or a pharmaceutically acceptable salt or stereoisomer thereof, wherein m is 1.

10. The compound of claim 1, or a stereoisomer thereof, wherein the compound, or stereoisomer thereof, is selected from the group consisting of:

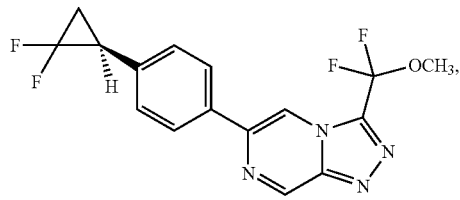

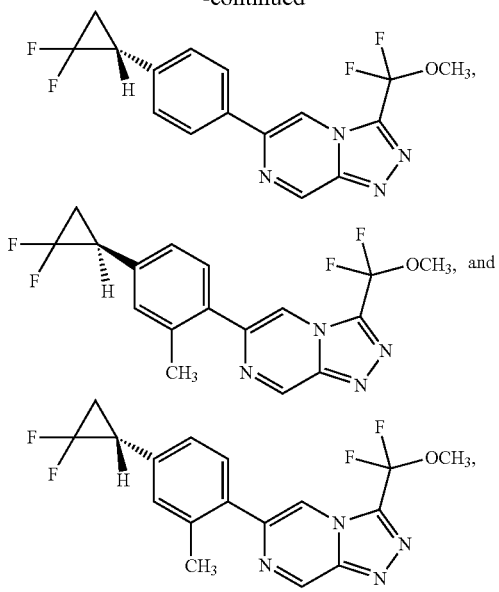

or a pharmaceutically acceptable salt thereof.

11. A pharmaceutical composition comprising a pharmaceutically acceptable carrier and a compound of claim 1, or a pharmaceutically acceptable salt or stereoisomer thereof.

12. A method for modulating sodium ion channel activity in a subject in need thereof, wherein the method comprises administering to the subject a therapeutically effective amount of a compound of claim 1, or a pharmaceutically acceptable salt or stereoisomer thereof.

13. The method of claim 12, wherein the subject has a condition relating to aberrant function of a sodium ion channel selected from the group consisting of a neurological disorder and a psychiatric disorder.

14. The method of claim 13, wherein the neurological disorder or psychiatric disorder is epilepsy or an epilepsy syndrome.

15. The method of claim 13, wherein the subject has a condition relating to aberrant function of a sodium ion channel selected from the group consisting of autosomal dominant nocturnal frontal lobe epilepsy, a benign familial neonatal-infantile seizure, cryptogenic pediatric partial epilepsy with a SCN3A mutation, Dravet syndrome, epileptic encephalopathy, focal epilepsy with a SCN3A mutation, generalized epilepsy with a febrile seizure, an infantile spasm, intractable childhood epilepsy with a generalized tonic-clonic seizure, a malignant migrating partial seizure of infancy, Rasmussen encephalitis, and sudden unexpected death in epilepsy (SUDEP).

16. The method of claim 15, wherein the Dravet syndrome is Dravet syndrome with a SCN1A mutation.

17. The method of claim 15, wherein the epileptic encephalopathy is selected from the group consisting of an epileptic encephalopathy with a SCN1A mutation, an epileptic encephalopathy with a SCN2A mutation, an epileptic encephalopathy with a SCN8A mutation, early infantile epileptic encephalopathy, KCNQ2 epileptic encephalopathy, KCNT1 epileptic encephalopathy, SCN2A epileptic encephalopathy, and SCN8A epileptic encephalopathy.

18. The method of claim 13, wherein the subject has a trigeminal autonomic cephalalgia.

19. The method of claim 18, wherein the trigeminal autonomic cephalalgia is selected from the group consisting of hemicrania continua, paroxysmal hemicrania, a long-lasting autonomic symptom with hemicrania, a short-lasting unilateral neuralgiform headache attack with a cranial autonomic symptom, and a short-lasting unilateral neuralgiform headache attack with conjunctival injection and tearing.

* * * * *